US009220746B2

(12) United States Patent
Clemmons et al.

(10) Patent No.: US 9,220,746 B2
(45) Date of Patent: Dec. 29, 2015

(54) COMPOUNDS AND METHODS FOR TREATING BONE DISORDERS AND CONTROLLING WEIGHT

(75) Inventors: David R. Clemmons, Chapel Hill, NC (US); Clifford J. Rosen, Freeport, ME (US)

(73) Assignees: The University of North Carolina at Chapel Hill, Chapel Hill, NC (US); Maine Medical Center, Scarborough, ME (US)

( * ) Notice: Subject to any disclaimer, the term of this patent is extended or adjusted under 35 U.S.C. 154(b) by 0 days.

(21) Appl. No.: 13/375,562

(22) PCT Filed: Jun. 4, 2010

(86) PCT No.: PCT/US2010/037390
§ 371 (c)(1),
(2), (4) Date: Feb. 27, 2012

(87) PCT Pub. No.: WO2010/141811
PCT Pub. Date: Dec. 9, 2010

(65) Prior Publication Data
US 2012/0149634 A1     Jun. 14, 2012

Related U.S. Application Data

(60) Provisional application No. 61/184,209, filed on Jun. 4, 2009.

(51) Int. Cl.
| | |
|---|---|
| A61K 38/10 | (2006.01) |
| A61K 38/08 | (2006.01) |
| A61P 19/08 | (2006.01) |
| A61P 19/10 | (2006.01) |
| C07K 7/08 | (2006.01) |
| C07K 7/06 | (2006.01) |
| A61K 38/04 | (2006.01) |

(52) U.S. Cl.
CPC .............. *A61K 38/10* (2013.01); *A61K 38/04* (2013.01); *A61K 38/08* (2013.01); *C07K 7/06* (2013.01); *C07K 7/08* (2013.01)

(58) Field of Classification Search
None
See application file for complete search history.

(56) References Cited

U.S. PATENT DOCUMENTS

| | | | | |
|---|---|---|---|---|
| 5,539,063 | A | * | 7/1996 | Hakimi et al. ............... 525/403 |
| 5,998,369 | A | * | 12/1999 | Khosla et al. ............... 424/10.1 |
| 7,504,374 | B2 | | 3/2009 | Marx et al. |
| 2004/0005579 | A1 | | 1/2004 | Birse et al. |

FOREIGN PATENT DOCUMENTS

| | | | |
|---|---|---|---|
| DE | 19757250 | * | 7/1999 |
| WO | WO 2005/014635 A2 | | 2/2005 |
| WO | WO 2006/034832 A2 | | 4/2006 |
| WO | WO 2006/102715 A1 | | 10/2006 |
| WO | WO 2008/019491 | | 2/2008 |
| WO | WO 2009/019254 | | 2/2009 |
| WO | WO 2009/059011 A2 | | 5/2009 |

OTHER PUBLICATIONS

Binkert et al., EMBO J., 1989, vol. 8(9):2497-2502.*
Heaney, R. P., Clin. Med. Res., 2003, vol. 1(2):93-99.*
Argente et al. "Multiple Endocrine Abnormalities of the Growth Hormone and Insulin-Like Growth Factor Axis in Prepubertal Children with Exogenous Obesity: Effect of Short- and Long-Term Weight Reduction" *J Clin Endocrinol Metab* 82:2076-2083 (1997).
Clemmons et al. "The Combination of Insulin-Like Growth Factor I and Insulin-Like Growth Factor-Binding Protein-3 Reduces Insulin Requirements in Insulin-Dependent Type 1 Diabetes: Evidence for in Vivo Biological Activity" *J Clin Endocrinol Metab* 85:1518-1524 (2000).
Fazeli et al. "Preadipocyte Factor-1 is Associated with Marrow Adiposity and Bone Mineral Density in Women with Anorexia Nervosa" *J Clin Endocrinol Metab* 95(1):407-413 (2010).
Fritton et al. "The Insulin-Like Growth Factor-1 Binding Protein Acid-labile Subunit Alters Mesenchymal Stromal Cell Fate" *The Journal of Biological Chemistry* 285(7):4709-4714 (2010).
Frystyk et al. "Circulating Levels of Free Insulin-Like Growth Factors in Obese Subjects: the Impact of Type 2 Diabetes" *Diabetes Metab Res Rev* 15:314-322 (1999).
Kawai et al. "A Circadian-Regulated Gene, Nocturnin, Promotes Adipogenesis by Stimulating PPAR-γ Nuclear Translocation" *PNAS* 107(23):10508-10513 (2010).
Kawai et al. "The Heparin-Binding Domain of IGFBP-2 Has Insulin-Like Growth Factor Binding-Independent Biologic Activity in the Growing Skeleton" *The Journal of Biological Chemistry* 286(16):14670-14680 (2011).
Khosla et al. "Use of Site Specific Antibodies to Characterize the Circulating Form of Big Insulin-Like Growth Factor II in Patients with Hepatitis C-Associated Osteosclerosis" *J Clin Endocrinol Metab* 87(8):3867-3870 (2002).
Maile et al. "An Essential Role for the Association of CD47 to SHPS-1 in Skeletal Remodeling" *Journal of Bone and Mineral Research* 26(9):2068-2081 (2011).
Nam et al. "Effect of Obesity on Total and Free Insulin-Like Growth Factor (IGF)-1, and Their Relationship to IGF-Binding Protein (BP)-1, IGFBP-2, IGFBP-3, Insulin, and Growth Hormone" *International Journal of Obesity* 21:355-359 (1997).

(Continued)

*Primary Examiner* — Xiaozhen Xie
(74) *Attorney, Agent, or Firm* — Myers Bigel Sibley & Sajovec, P.A.

(57) ABSTRACT

The present invention provides peptides and methods of their use in treating bone disorders and bone-related conditions and in treating obesity.

19 Claims, 16 Drawing Sheets

(56) References Cited

OTHER PUBLICATIONS

Sabin et al. "Dietary Monounsaturated Fat in Early Life Regulates IGFBP2: Implications for Fat Mass Accretion and Insulin Sensitivity" *Obesity* 19:2374-2381 (2011).

Touskova et al. "Serum Concentrations and Tissue Expression of Components of Insulin-Like Growth Factor-Axis in Females with Type 2 Diabetes Mellitus and Obesity: The Influence of Very-Low-Calorie Diet" *Molecular and Cellular Endocrinology* 361: 172-178 (2012).

Voskuil et al. Determinants of Circulating Insulin-Like Growth Factor (IGF)-I and IGF Binding Proteins 1-3 in Premenopausal Women: Physical Activity and Anthropometry (Netherlands) *Cancer Causes and Control* 12:951-958 (2001).

Wabitsch et al. "Insulin-Like Growth Factors and Their Binding Proteins Before and After Weight Loss and Their Associations with Hormonal and Metabolic Parameters in Obese Adolescent Girls" *Int J. Obes Relat Metab Disord.* 20(12):1073-1080 (1996) (Abstract Only).

Wheatcroft et al. "IGF-Dependent and IGF-Independent Actions of IGF-Binding Protein-1 and -2: Implications for Metabolic Homeostasis" *Trends in Endocrinology and Metabolism* 20(4):153-162 (2009).

Yakar et al. "Serum Complexes of Insulin-Like Growth Factor-1 Modulate Skeletal Integrity and Carbohydrate Metabolism" *FASEB J.* 23:709-719 (2009).

Breggia et al. "Global Deletion of IGFBP-2 Disrupts Hematopoiesis and Compromises Bone Marrow Engraftment in Lethally Irradiated Mice" Abstract of poster presented at the annual meeting of the Endocrine Society in San Diego, CA, Jun. 19-22, 2010.

Breggia et al. "IGFBP-2 from Mesenchymal Stromal Cells (MSCs) in the bone Marrow Niche Regulates Hematopoietic Stem Cell Proliferation and Marrow" Abstract of oral presentation at the annual ASBMR meeting in Toronto, Ontario, Canada, Oct. 15-19, 2010.

Breggia et al. "The Heparin Binding Domain of IGFBP-2 is an Important Regulator of Murine Hematopoiesis and Human Stem Cell Proliferation" Abstract of oral presentation at the annual ASBMR meeting in San Diego, CA, Sep. 16-20, 2011.

Breggia et al. " The Heparin Binding Domain of IGFBP-2 Increases Proliferation of Human Hematopoietic Stem Cells In Vitro" *Endocr Rev* 32:P1-138 (Jun. 2011) (Abstract).

International Search Report and Written Opinion of International Application No. PCT/US2010/037390, mailed Dec. 3, 2010 (14 pages).

Hoeflich et al. "Growth Inhibition in Giant Growth Hormone Transgenic Mice by Overexpression of Insulin-Like Growth Factor-Binding Protein-2" *Endocrinology* 142(5):1889-1898 (2001).

Huynh et al. "Insulin-Like Growth Factor-Binding Protein 2 Secreted by a Tumorigenic Cell Line Supports Ex Vivo Expansion of Mouse Hematopoietic Stem Cells" *Stem Cells* 26(6):1628-1635 (2008).

Amin et al. "High Serum IGFBP-2 is Predictive of Increased Bone Turnover in Aging Men and Women" *Journal of Bone and Mineral Research* 22(6):799-807 (2007).

Arai et al. "Binding of Insulin-Like Growth Factor (IGF) I or II to IGF-Binding Protein-2 Enables it to Bind to Heparin and Extracellular Matrix" *Endocrinology* 137(11):4571-4575 (1996).

Ballen et al. "The National Marrow Donor Program 20 Years of Unrelated Donor Hematopoietic Cell Transplantation" *Biology of Blood and Marrow Transplantation* 14:2-7 (2008).

Bendall et al. "IGF and FGF Cooperatively Establish the Regulatory Stem Cell Niche of Pluripotent Human Cells In Vitro" *Nature* 448:1015-1021 (2007).

Bennett et al. "Regulation of Osteoblastogenesis and Bone Mass by Wnt10b" *PNAS* 102(9):3324-3329 (2005).

Bhattacharya et al. "Purified Hematopoietic Stem Cell Engraftment of Rare Niches Corrects Severe Lymphoid Deficiencies Without Host Conditioning" *JEM* 203(1):73-85 (2006).

Calvi et al. "Osteoblastic Cells Regulate the Haematopoietic Stem Cell Niche" *Nature* 425:841-846 (2003).

Clawson et al. "Differential Expression of Insulin-Like Growth Factor Binding Proteins in Murine Hematopoietic Stromal Cell Lines" *Molecular and Cellular Endocrinology* 120:59-66 (1996).

Cohen et al. "Elevated Levels of Insulin-Like Growth Factor-Binding Protein-2 in the Serum of Prostate Cancer Patients" *Journal of Clinical Endocrinology and Metabolism* 76(4):1031-1035 (1993).

Conover et al. "Subcutaneous Administration of Insulin-Like Growth Factor (IGF)-II/IGF Binding Protein-2 Complex Stimulates Bone Formation and Prevents Loss of Bone Mineral Density in a Rat Model of Disuse Osteoporosis" *Growth Hormone & IGF Research* 12:178-183 (2002).

Czechowicz et al. "Efficient Transplantation Via Antibody-Based Clearance of Hematopoietic Stem Cell Niches" *Science* 318:1296-1299 (2007).

Dawczynski et al. "Changes of Serum Growth Factors (IGF-I,-II and IFGBP-2,-3) Prior to and After Stem Cell Transplantation in Children with Acute Leukemia" *Bone Marrow Transplantation* 32:411-415 (2003).

Dawczynski et al. "Elevated Serum Insulin-Like Growth Factor Binding Protein-2 is Associated With a High Relapse Risk After Hematopoietic Stem Cell Transplantation in Childhood AML" *Bone Marrow Transplantation* 37:589-594 (2006).

Delaney et al. "Notch-Mediated Expansion of Human Cord Blood Progenitor Cells Capable of Rapid Myeloid Reconstitution" *Nature Medicine* 16(2):232-237 (2010).

Demambro et al. "Gender-Specific Changes in Bone Turnover and Skeletal Architecture in *Igfbp*-2-Null Mice" *Endocrinology* 149(5):2051-2061 (2008).

Desbois-Mouthon et al. "Insulin and IGF-1 Stimulate the β-Catenin Pathway Through Two Signalling Cascades Involving GSK-3β Inhibition and Ras Activation" *Oncogene* 20:252-259 (2001).

Duan et al. "Insulin-Like Growth Factor Binding Protein 2 is a Growth Inhibitory Protein Conserved in Zebrafish" *PNAS* 96(26):15274-15279 (1999).

Eckstein et al. "Insulin-Like Growth Factor-Binding Protein-2 (IGFBP-2) Overexpression Negatively Regulates Bone Size and Mass, but not Density, in the Absence and Presence of Growth Hormone/IGF-I Excess in Transgenic Mice" *Anat Embryol* 206:139-148 (2002).

Eminli et al. "Differentiation Stage Determines Potential of Hematopoietic Cells for Reprogramming into Induced Pluripotent Stem Cells" *Nature Genetics* 41(9):968-976 (2009).

Fang et al. "Phosphorylation of β-Catenin by AKT Promotes β-Catenin Transcriptional Activity" *The Journal of Biological Chemistry* 282(15):11221-11229 (2007).

Firth et al. "Cellular Actions of the Insulin-Like Growth Factor Binding Proteins" *Endocrine Reviews* 23(6):824-854 (2002).

Forsberg et al. "Hematopoietic Stem Cells *Expression Profiling and Beyond"* Stem Cell Reviews* 2:23-30 (2006).

Frisch et al. "Hematopoietic Niche and Bone Meet" *Curr Opin Support Palliat Care* 2:211-217 (2008).

Frisch et al. "In Vivo Prostaglandin $E_2$ Treatment Alters the Bone Marrow Microenvironment and Preferentially Expands Short-Term Hematopoietic Stem Cells" *Blood* 114(19):4054-4063 (2009).

Fu et al. "Promotion of Cancer Cell Migration *An Insulin-Like Growth Factor (IGF)-Independent Action of IGF-Binding Protein-6" Journal of Biological Chemistry* 282(31):22298-22306 (2007).

Fujita et al. "Runx2 Induces Osteoblast and Chondrocyte Differentiation and Enhances Their Migration by Coupling with PI3K-Akt Signaling" *The Journal of Cell Biology* 166(1):8595 (2004).

Gesta et al. "Developmental Origin of Fat: Tracking Obesity to its Source" *Cell* 131:242-256 (2007).

Glass et al. "Molecular Bases of the Regulation of Bone Remodeling by the Canonical Wnt Signaling Pathway" *Current Topics in Developmental Biology* 73:43-84 (2006).

Glass et al. "Canonical Wnt Signaling in Differentiated Osteoblasts Controls Osteoclast Differentiation" *Developmental Cell* 8:751-764 (2005).

Haug et al. "N-Cadherin Expression Level Distinguishes Reserved Versus Primed States of Hematopoietic Stem Cells" *Cell Stem Cell* 2:367-379 (2008).

He et al. "PTEN-Deficient Intestinal Stem Cells Initiate Intestinal Polyposis" *Nature Genetics* 39(2):189-198 (2007).

(56) References Cited

OTHER PUBLICATIONS

Hedbacker et al. "Antidiabetic Effects of IGFBP2, a Leptin-Regulated Gene" *Cell Metabolism* 11:11-22 (2010).
Hoeflich et al. "Insulin-Like Growth Factor-Binding Protein 2 in Tumorigenesis: Protector or Promoter?" *Cancer Research* 61:8601-8610 (2001).
Hoeflich et al. "Mutation of the RGD Sequence Does Not Affect Plasma Membrane Association and Growth Inhibitory Effects of Elevated IGFBP-2 In Vivo" *FEBS Letters* 523:63-67 (2002).
Hu et al. "Serum Insulin-Like Growth Factor-1 Binding Proteins 1 and 2 and Mortality in Older Adults: The Health, Aging, and Body Composition Study" *J Am Geriatr Soc* 57:1213-1218 (2009).
Huynh et al. "Insulin-Like Growth Factor-Binding Protein 2 Secreted by a Tumorigenic Cell Line Supports Ex Vivo Expansion of Mouse Hematopoietic Stem Cells" *Stem Cells* 26:1628-1635 (2008).
Hwa et al. "The Insulin-Like Growth Factor-Binding Protein (IGFBP) Superfamily*" *Endocrine Reviews* 20(6):761-787 (1999).
Jenq et al. "Allogeneic Haematopoietic Stem Cell Transplantation: Individualized Stem Cell and Immune Therapy of Cancer" *Nat Rev Cancer* 10:213-221 (2010).
Jin et al. "Wnt and Beyond Wnt: Multiple Mechanisms Control the Transcriptional Property of β-Catenin" *Cellular Signalling* 20:1697-1704 (2008).
Jones et al. "Insulin-Like Growth Factors and Their Binding Proteins: Biological Actions*" *Endocr Rev* 16(1):3-34 (1995).
Kawai et al. "Insulin-Like Growth Factor-I and Bone: Lessons from Mice and Men" *Pediatr Nephrol* 24:1277-1285 (2009).
Kawai et al. "Growth Hormone Stimulates Adipogenesis of 3T3-L1 Cells Through Activation of the Stat5A/5B-PPARγ Pathway" *Journal of Molecular Endocrinology* 38:19-34 (2007).
Kearns et al. "Receptor Activator of Nuclear Factor κB Ligand and Osteoprotegerin Regulation of Bone Remodeling in Health and Disease" *Endocrine Reviews* 29(2):155-192 (2008).
Khosla et al. "Insulin-Like Growth Factor System Abnormalities in Hepatitis C-Associated Osteosclerosis" *J. Clin. Invest.* 101(10):2165-2173 (1998).
Kuznetsov et al. "The Interplay of Osteogenesis and Hematopoiesis: Expression of a Constitutively Active PTH/PTHrP Receptor in Osteogenic Cells Perturbs the Establishment of Hematopoiesis in Bone and of Skeletal Stem Cells in the Bone, Marrow" *The Journal of Cell Biology* 167(6):1113-1122 (2004).
Levitt et al. "PTEN-Induction in U251 Glioma Cells Decreases the Expression of Insulin-Like Growth Factor Binding Protein-2" *Biochemical and Biophysical Research Communications* 336:1056-1061 (2005).
Liu et al. "Mice Carrying Null Mutations of the Genes Encoding Insulin-Like Growth Factor I (*Igf-1*) and Type 1 IGF Receptor (*Igf1r*)" *Cell* 75:59-72 (1993).
Liu et al. "Functional Interaction Between Peroxisome Proliferator-Activated Receptor γ and β-Catenin" *Molecular and Cellular Biology* 26(15):5827-5837 (2006).
Liu et al. "Lifelong Accumulation of Bone in Mice Lacking Pten in Osteoblasts" *PNAS* 104(7):2259-2264 (2007).
Maile et al. "Modulation of Integrin Antagonist Signaling by Ligand Binding of the Heparin-Binding Domain of Vitronectin to the αVβ3 Integrin" *J. Cell. Biochem.* 105:437-446 (2008).
Mehrian-Shai et al. "Insulin Growth Factor-Binding Protein 2 is Candidate Biomarker for PTEN Status and PI3K/Akt Pathway Activation in Glioblastoma and Prostate Cancer" *PNAS* 104(13):5563-5568 (2007).
Mukherjee et al. "Akt Promotes BMP2-Mediated Osteoblast Differentiation and Bone Development" *Journal of Cell Science* 122:716-726 (2009).
Mukherjee et al. "Insulin-Like Growth Factor-Binding Protein-5 Inhibits Osteoblast Differentiation and Skeletal Growth by Blocking Insulin-Like Growth Factor Actions" *Molecular Endocrinology* 22(5):1238-1250 (2008).
Palermo et al. "Potentiating Role of IGFBP-2 on IGF-II Stimulated Alkaline Phosphatase Activity in Differentiating Osteoblasts" *Am J Physiol Endocrinol Metab* 286:E648-E657 (2004).

Peng et al. "Dwarfism, Impaired Skin Development, Skeletal Muscle Atrophy, Delayed Bone Development, and Impeded Adipogenesis in Mice Lacking Akt1 and Akt2" *Genes Dev* 17:1352-1365 (2003).
Perks et al. "IGF-II and IGFBP-2 Differentially Regulate PTEN in Human Breast Cancer Cells" *Oncogene* 26:5966-5972 (2007).
Playford et al. "Insulin-Like Growth Factor 1 Regulates the Location, Stability, and Transcriptional Activity of β-Catenin" *PNAS* 97(22):12103-12108 (2000).
Pulte et al. "Trends in Survival After Diagnosis with Hematologic Malignancy in Adolescence or Young Adulthood in the United States, 1981-2005" *Cancer* 115:4973-4979 (2009).
Rosen et al. "Congenic Mice with Low Serum IGF-I Have Increased Body Fat, Reduced Bone Mineral Density, and an Altered Osteoblast Differentiation Program" *Bone* 35:1046-1058 (2004).
Ross et al. "Inhibition of Adipogenesis by Wnt Signaling" *Science* 289:950-953 (2000).
Russo et al. "Insulin-Like Growth Factor Binding Protein-2 Binds to Cell Surface Proteoglycans in the Rat Brain Olfactory Bulb" *Endocrinology* 138(11):4858-4867 (1997).
Russo et al. "Basic Fibroblast Growth Factor Induces Proteolysis of Secreted and Cell Membrane-Associated Insulin-Like Growth Factor Binding Protein-2 in Human Neuroblastoma Cells" *Endocrinology* 140(7):3082-3090 (1999).
Russo et al. "Insulin-Like Growth Factor Binding Protein-2 Binding to Extracellular Matrix Plays a Critical Role in Neuroblastoma Cell Proliferation, Migration, and Invasion" *Endocrinology* 146(10):4445-4455 (2005).
Sakata et al. "Skeletal Unloading Induces Resistance to Insulin-Like Growth Factor-I (IGF-I) by Inhibiting Activation of the IGF-I Signaling Pathways" *J Bone Miner Res* 19(3):436-446 (2003).
Schutt et al. "Integrin-Mediated Action of Insulin-Like Growth Factor Binding Protein-2 in Tumor Cells" *Journal of Molecular Endocrinology* 32:859-868 (2004).
Shoba et al. "Inhibition of Phosphatidylinositol 3-Kinase and p70S6 Kinase Blocks Osteogenic Protein-1 Induction of Alkaline Phosphatase Activity in Fetal Rat Calvaria Cells" *Journal of Cellular Biochemistry* 88:1247-1255 (2003).
Song et al. "IIp45, an Insulin-Like Growth Factor Binding Protein 2 (IGFBP-2) Binding Protein, Antagonizes IGFBP-2 Stimulation of Glioma Cell Invasion" *PNAS* 100(24):13970-13975 (2003).
Taurin et al. "Phosphorylation of β-Catenin by Cyclic AMP-Dependent Protein Kinase" *The Journal of Biological Chemistry* 281(15):9971-9976 (2006).
Wang et al. "Role of IGF-I Signaling in Regulating Osteoclastogenesis" *J Bone Miner Res* 21(9):1350-1358 (2006).
Wang et al. "An Interaction Between Insulin-Like Growth Factor-Binding Protein 2 (IGFBP2) and Integrin α5 is Essential for IGFBP2-Induced Cell Mobility" *The Journal of Biological Chemistry* 281(20):14085-14091 (2006).
Wheatcroft et al. "IGF-Binding Protein-2 Protects Against the Development of Obesity and Insulin Resistance" *Diabetes* 56:285-294 (2007).
Wilson et al. "Bone-Marrow Haematopoietic-Stem-Cell Niches" *Nat Rev Immunol* 6:93-106 (2006).
Wood et al. "Selective Alterations in Organ Sizes in Mice with a Targeted Disruption of the Insulin-Like Growth Factor Binding Protein-2 Gene" *Molecular Endocrinology* 14(9):1472-1482 (2000).
Yakar et al. "Circulating Levels of IGF-1 Directly Regulate Bone Growth and Density" *J. Clin. Invest.* 110(6):771-781 (2002).
Zhang et al. "Osteoblast-Specific Knockout of the Insulin-Like Growth Factor (IGF) Receptor Gene Reveals an Essential Role of IGF Signaling in Bone Matrix Mineralization" *The Journal of Biological Chemistry* 277(46):44005-44012 (2002).
Zhang et al. "Angiopoietin-Like 5 and IGFBP2 Stimulate Ex Vivo Expansion of Human Cord Blood Hematopoietic Stem Cells as Assayed by NOD/SCID Transplantation" *Blood* 111(7):3415-3423 (2008).
Zhao et al. "Targeted Overexpression of Insulin-Like Growth Factor I to Osteoblasts of Transgenic Mice: Increased Trabecular Bone vol. Without Increased Osteoblast Proliferation*" *Endocrinology* 141(7):2674-2682 (2000).

(56) References Cited

OTHER PUBLICATIONS

Zia et al. "Monoclonal Antibody αIR-3 Inhibits Non-Small Cell Lung Cancer Growth In Vitro and In Vivo" *Journal of Cellular Biochemistry Supplement* 24:269-275 (1996).
Demambro V.E. et al., "OR13,5 IGFBP-2 null mice develop obesity and insulin resistance with aging", *Growth Hormone and IGF Research*, vol. 18, Sep. 2008, p. S26.
Demambro V.E. et al., "Serum IGFBP-2 (IGF binding protein-2) Is a Marker of Bone Turnover; In Vivo Evidence from the IGFBP-2 Null Male Mouse", ASBMR 29th Annual Meeting, *Journal of Bone and Mineral Research*, Sep. 2007, S71.
European Search Report Corresponding to European Application No. 10 78 4143; Dated: Feb. 1, 2013; 15 Pages.
Mark Silke et al., "Diversity of human insulin-like growth factor (IGF) binding protein-2 fragments in plasma: Primary structure, IGF-Binding properties, and disulfide bonding pattern", *Biochemistry*, 2005, vol. 44, No. 9, 3644-3652.

\* cited by examiner

VON KOSSA STAINING
IGFBP2+/+      IGFBP2-/-

ALP STAINING

IGFBP2+/+

IGFBP2-/-

COBs

ALP STAINING

CONTROL   PEG-HBD

BMSCs

ALIZARIN RED STAINING

CONTROL   PEG-HBD

ALIZARIN RED STAINING

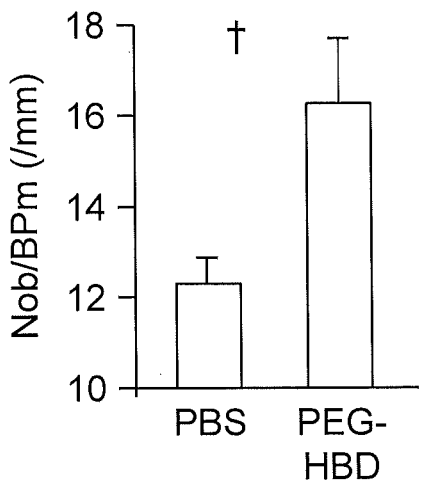
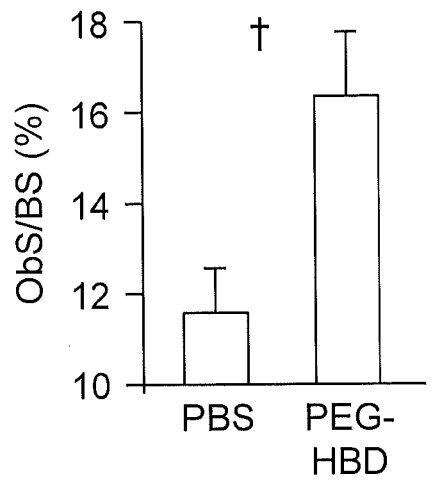
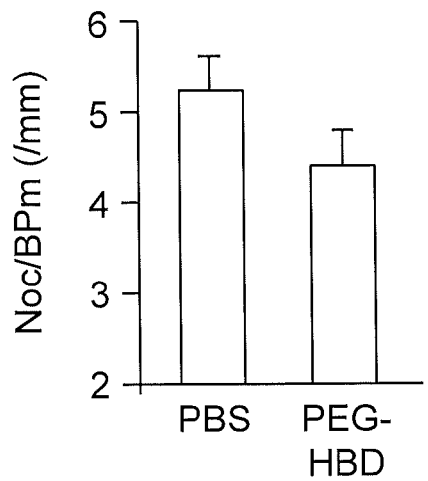
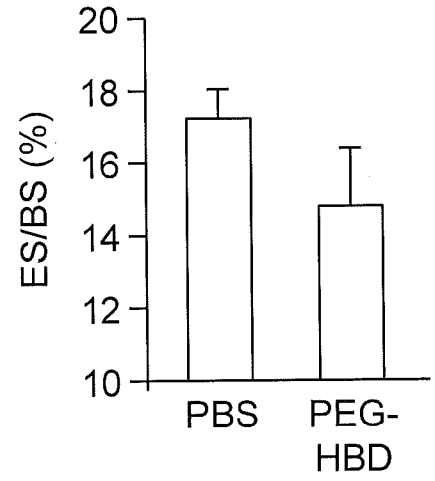
FIG. 4C
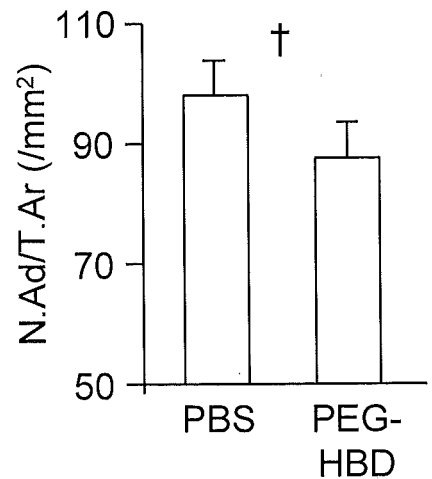
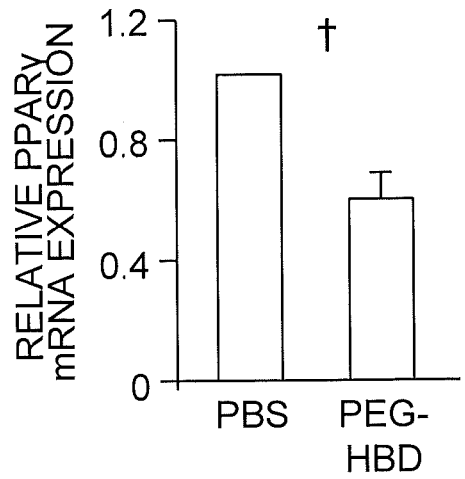
FIG. 4D      FIG. 4E

COMPOUNDS AND METHODS FOR TREATING BONE DISORDERS AND CONTROLLING WEIGHT

STATEMENT OF PRIORITY

This application is a 35 U.S.C. §371 national phase application of International Application Serial No. PCT/US2010/037390, filed Jun. 4, 2010, which claims the benefit, under 35 U.S.C. §119(e), of U.S. Provisional Application No. 61/184,209, filed Jun. 4, 2009, the contents of each of which are incorporated by reference herein in their entireties.

STATEMENT OF GOVERNMENT SUPPORT

This invention was made with government support under Grant Nos. AG002331 and HL056580 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. §1.821, entitled 5470-528_ST25.txt, 2,135,089 bytes in size, generated on Apr. 22, 2013 and filed via EFS-Web, is provided in lieu of a paper copy. This Sequence Listing is hereby incorporated by reference into the specification for its disclosures.

FIELD OF THE INVENTION

The present invention concerns peptides, pharmaceutical formulations containing the same, and methods of use thereof in controlling weight, treating bone disorders and improving bone marrow reconstitution.

BACKGROUND OF THE INVENTION

Insulin-like growth factor binding protein-2 (IGFBP-2) is a 36,000 dalton protein that is a member of the IGFBP family. There are six forms of high affinity IGF binding proteins. In addition to binding the insulin-like growth factors I and II and acting as transport proteins, these proteins have been shown to have some actions that are independent of their ability to bind to IGFs.

IGFBP-2 is the second most abundant binding protein in serum. It circulates in concentrations in humans that vary between 100-600 ng/ml. Protein concentrations are high during fetal life and at birth and fall progressively during childhood and adolescence. There is a slight rise, an approximately 25% increase that occurs between 60-80 years. Serum concentrations of IGFBP-2 are regulated by hormones and nutrients. Fasting causes a significant increase in IGFBP-2 and feeding (particularly feeding protein) restores concentrations to normal. Concentrations are also suppressed by administration of insulin or growth hormone, and are increased by insulin-like growth factor-I. This is probably due in part to suppression of growth hormone and insulin, both of which are suppressed by administering IGF-I.

Proteolytic cleavage of IGFBP-2 results in small fragments that include the heparin binding domain (HBD). A small molecule containing the HBD present in the linker region of IGFBP-2 has been synthesized. Of the two HBDs in this molecule, the one synthesized is unique to IGFBP-2 and is not represented in other IGFBPs.

The present invention overcomes previous shortcomings in the art by providing peptides of IFGBP-2 and methods of their use in treating bone disorders, controlling weight and improving bone marrow reconstitution.

SUMMARY OF THE INVENTION

A first aspect of the invention is a compound comprising, consisting of or consisting essentially of the IGFBP-2 fragment KHHLGLEEPKKLR (SEQ ID NO:1), KHHLGLEEPKK (SEQ ID NO:2), HLGLEEPKKLR (SEQ ID NO:3), analogs thereof, prodrug of any thereof, or pharmaceutically acceptable salts of any thereof (all hereinafter sometimes referred to as "active compounds" or "active agents").

A second aspect of the invention is a composition comprising an active compound as described herein, which can be in combination with a pharmaceutically acceptable carrier, and optionally including at least one (e.g., 1, 2, 3, 4, 5, 6, 7, 8, 9, 10. etc.) additional active agent such as a bone resorption inhibitor or a weight control agent.

A further aspect of the invention is a method for inducing deposition and maturation of bone in a subject having a compromised bone condition, comprising administering the subject an active compound in an amount effective to induce deposition and maturation of bone in the subject. The method may further comprise concurrently administering a bone resorption inhibitor to the subject in an effective amount.

An additional aspect of the invention is a method for enhancing bone formation and inhibiting bone resorption simultaneously in a subject in need thereof, comprising administering to the subject an active compound in an amount effective to enhance bone formation and inhibit bone resorption simultaneously in said subject.

A further aspect of the invention is a method for controlling body weight in a subject in need thereof, comprising administering the subject an active compound as described herein in an amount effective to control body weight. The method may further comprise concurrently administering the subject an additional weight control agent.

Another aspect of the invention is a method for improving bone marrow reconstitution in a subject in need thereof, comprising administering to said subject an active compound of this invention in an amount effective to improve bone marrow reconstitution.

A further aspect of the invention is the use of an active compound as described herein for carrying out a method as described herein, and/or for the preparation of a medicament for carrying out a method as described herein.

The present invention is explained in greater detail below.

DETAILED DESCRIPTION OF THE INVENTION

Figure 1A:
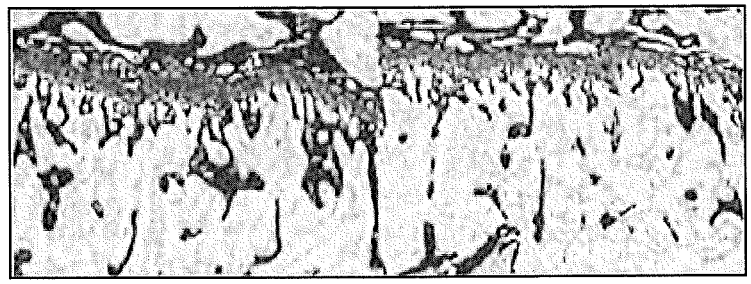
FIG. 1. The heparin-binding domain of IGFBP2 enhances osteoblastogenesis in vitro. a. Von Kossa staining was performed using tibia from 8 weeks old Igfbp2$^{+/+}$ and Igfbp2$^{-/-}$ male mouse. b. Calvarial osteoblasts (COBs) were harvested from day 7 old male Igfbp2$^{+/+}$ and Igfbp2$^{-/-}$ male mouse, and treated with osteogenic media in the presence of 2.5% FCS. At day 7, alkaline phosphatase (ALP) staining was performed. c and d. COBs and Bone marrow stromal cells (BMSCs) from Igfbp2$^{-/-}$ mouse were treated with osteogenic media with pegylated heparin-binding domain peptide (PEG-HBD) in the presence of 10% FCS. ALP staining (day 7) and Alizarin Red staining (day 14) were performed (c). RNA was isolated at day 14 from BMSCs and expression of ALP, osteocalcin (OC) and Runx2 was analyzed by real-time PCR. Figures shown represent at least 3 independent experiments (n=3). Statistical difference was analyzed by student's test. *; p<0.05.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all United States patents, patent publications and non-patent documents cited herein are incorporated herein by reference in their entirety.

The present invention is based on the discovery that peptides of IGFBP-2, (e.g., the heparin binding domain (HBD)) can be employed in methods of treating bone disorders, methods of weight control and methods of improving bone marrow reconstitution.

Thus, in certain embodiments, the present invention provides a method for enhancing bone formation (i.e., increasing the amount of new bone that is laid down) and inhibiting bone resorption (i.e., reducing the amount of bone that is dissolved) simultaneously in a subject in need thereof, comprising administering to the subject an active compound of this invention in an amount effective to enhance bone formation and inhibit bone resorption simultaneously in said subject. Nonlimiting examples of subjects for whom such treatment would be indicated and/or beneficial include women (e.g., post-menopausal; premenopausal) with osteoporosis or low bone mass, men with osteoporosis or low bone mass, subjects with a healing fracture, subjects undergoing prolonged immobilization, subjects who have been or are immobilized for a prolonged period, subjects likely to undergo or experience prolonged immobilization, subjects with estrogen deficiency, etc., as would be known in the art.

Also provided herein is a method for inducing deposition and maturation of bone in a subject in need thereof (e.g., a subject having a compromised bone condition), comprising administering to the subject an active compound of this invention in an amount effective to induce deposition and maturation of bone in the subject. The methods of this invention may further comprise concurrently administering a bone resorption inhibitor to the subject in an effective amount.

In some embodiments, a compromised bone condition is at a targeted site of the subject. The site may be an intervertebral space, a facet joint, a site of a bone fracture, bones of the mouth, chin and jaw, or an implant site.

Also provided herein is a method for improving bone marrow reconstitution in a subject in need thereof, comprising administering to said subject an active compound of this invention in an amount effective to improve bone marrow reconstitution (i.e., restoring (e.g., partially or fully) bone marrow cells in a subject, which can be, for example, a subject having chemotherapy, radiation or other treatments that deplete bone marrow cells. For example, a subject undergoing chemotherapy with or without radiation would benefit from more rapid restoration of cells in the bone marrow in order to prevent opportunistic infections. A subject of these methods can also be a subject having or suspected of having a hematologic disorder (e.g., aplastic anemia; myelodysplasia) that depletes bone marrow cells. Such an improvement or enhancement or increase in bone marrow reconstitution is in comparison to a subject to whom the active compound has not been administered.

In some embodiments, the methods of this invention can be employed in methods of ex vivo expansion of stem cells, carried out according to protocols known in the art. Thus, the present invention provides a method of expanding stem cells ex vivo, comprising contacting the compound of this invention with stem cells from a subject, wherein said stem cells are maintained under conditions whereby they are reintroduced into the subject.

For example in some ex vivo embodiments, the stem cells are obtained from a subject, e.g., a human, e.g., from peripheral blood, umbilical cord blood, or bone marrow, and the stem cells are contacted with the compound of this invention outside the body of the subject. Ex vivo embodiments include obtaining stem cells from a subject and culturing the cells for a period of time prior to use (e.g., for transplantation). In some embodiments, after contact with the compound, the cells are delivered to a subject, e.g., the same subject from which the cells were isolated (autologous donation) or a different subject (non-autologous (e.g., syngeneic or allogeneic) donation).

Nonlimiting examples of a subject for whom these methods would be indicated or beneficial include a subject having or who has had chemotherapy, a subject having or who has had radiation, a subject having aplastic anemia, a subject having myelodysplasia, and any combination thereof.

Administration of the compound or composition of this invention may be by any suitable route, including intrathecal injection, subcutaneous, cutaneous, oral, intravenous, intraperitoneal, intramuscular injection, in an implant, in a matrix, in a gel, or any combination thereof.

A bone condition that can be treated according methods of this invention may be one or more of broken bones, bone defects, bone transplant, bone grafts, bone cancer, joint replacements, joint repair, fusion, facet repair, bone degeneration, dental implants and repair, bone marrow deficits and other conditions associated with bone and boney tissue. Bone defects may be a gap, deformation and/or a nonunion fracture in a bone.

Bone degeneration may be due to osteopenia or osteoporosis (e.g. the patient is afflicted with geriatric or senile osteoporosis, with post-menopausal osteoporosis, etc.), or due to dwarfism.

Joint replacements that may be treated include vertebral, knee, hip, tarsal, phalangeal, elbow, ankle and/or other articulating joints or replacements thereof. Joint repairs include, but are not limited to, vertebral, knee, hip, tarsal, phalangeal, elbow, ankle, and sacroiliac joint repairs.

A further aspect of the invention is a method for controlling body weight in a subject in need thereof, comprising administering the subject an active compound as described herein in an amount effective to control body weight. The method may further comprise concurrently administering the subject an additional weight control agent.

In some embodiments, the subject is obese.

In some embodiments, the compound is administered in an amount effective to reduce weight gain or induce weight loss (or particularly fat loss) in the subject.

In some embodiments, the compound is administered in an amount effective to reduce the body mass index of the subject.

In some embodiments the subject has a body mass index of 25 or 30 kg/m$^2$ or above.

In some embodiments, the administering is continued for a period of at least 16 or 24 weeks, and/or until the individual has achieved at least 5% weight loss or the individual's body mass index is reduced to less than 25 kg/m$^2$.

In some embodiments, the active compound is administered in an amount effective to inhibit fat cell differentiation (e.g., inhibiting fat cell precursor differentiation into mature adipocytes) in the subject.

Some embodiments further comprise concurrently administering the subject an additional weight control agent.

The therapeutically effective dosage of any specific active compound of this invention will vary from compound to compound, and patient to patient, and will depend, among other things, upon the effect or result to be achieved, the condition of the patient and the route of delivery. In some embodiments, a dosage from about 0.001 (i.e., 1 ug/kg), 0.05, 0.1, 0.2, 0.3, 0.4, 0.5, 0.6, 0.7, 0.8, 0.9 or 1.0 mg/kg, up to about 30, 40 or 50 mg/kg (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/kg), or more, may be used.

A. Definitions

"Subjects" as used herein are generally human subjects and includes, but is not limited to, post-menopausal subjects. The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric. In some embodiments the subjects are post-menopausal female subjects, or subjects afflicted with senile osteoporosis. Subjects may also include animal subjects, particularly mammalian subjects such as canines, felines, bovines, caprines, equines, ovines, porcines, rodents (e.g. rats and mice), lagomorphs, primates (including non-human primates), etc., for veterinary medicine or pharmaceutical drug development purposes.

"Treat," "treating" or "treatment" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Concurrently administering" or "concurrently administer" as used herein means that the two or more compounds or compositions are administered closely enough in time to produce a combined effect (that is, concurrently may be simultaneously, or it may be two or more events occurring within a short time period before or after each other, e.g., sequentially). Simultaneous concurrent administration may be carried out by mixing the compounds prior to administration, or by administering the compounds at the same point in time but at different anatomic sites and/or by using different routes of administration.

"Bone resorption inhibitor" as used herein may be any suitable bone resorption inhibitor, including but not limited to a bisphosphonate, a selective estrogen receptor modulator, calcitonin, a vitamin D analog, and a calcium salt. See, e.g., U.S. Pat. No. 7,507,715. Numerous such compounds are known. See, e.g., U.S. Pat. Nos. 7,018,982; 6,723,696; 6,284,730; and 5,039,669.

"Weight control agent" as used herein includes any additional weight control active agent, including but not limited to appetite suppressants such as sibutramine, phentermine, diethylpropion, phendimetrazine, etc.; lipase inhibitors such as orilstat; antidepressants such as bupropion; anti-seizure agents such as topiramate, zonisamide, and metformin, etc.

"Capping group" as used herein includes, but is not limited to, acetyl, benzoyl, formyl, trifluoroacetyl, benzyloxycarbonyl, tert-butyloxycarbonyl, biphenylylisopropyloxycarbonyl, triphenylmethyl, o-nitrobenzenesulfenyl, and diphenylphosphinyl. The capping groups may consist of such groups as $R^{10}CO-$, $R^{10}-O-CO-$, $R^{10}-PO-$, $R^{10}-SO_2-$ and arylalkyl-; where $R^{10}$ is selected from the group consisting of H, alkyl, alkenyl, alkynyl, aryl, and arylalkyl.

"Linking group" or "linker" as used herein includes non-amino acid linking groups such as are known in the art (see, e.g., U.S. Pat. Nos. 7,468,418; 7402,652; and 7,351,797) or variations thereof that will be apparent to those skilled in the art.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 1 to 4 carbon atoms.

"Alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 1 to 4 carbon atoms.

The alkyl, alkenyl, and alkynyl groups of the invention can be substituted or unsubstituted and are either unless otherwise specified. When substituted the alkyl, alkenyl or alkynyl groups of the invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, "Aryl" as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, "Arylalkyl," as used herein, refers to an aryl group, as defined herein, appended to the parent molecular moiety through an alkenyl group, as defined herein. Representative examples of arylalkenyl include, but are not limited to, 2-phenylethenyl, 3-phenylpropen-2-yl, 2-naphth-2-ylethenyl, and the like, which may be substituted or unsubstituted as noted above.

"Polyalkylene oxides" as used herein are known (see, e.g., U.S. Pat. No. 7,462,687) and include poly(ethylene glycol) or "PEG". Additional examples may contain hetero atoms such as S or N, and are typically linear polyalkylene oxides such as: O—(CH$_2$CH$_2$O)$_x$—, —O—C(O)CH$_2$—O—(CH$_2$CH$_2$O)$_x$—CH$_2$C(O)—O—, —NRCH$_2$CH$_2$-O—(CH$_2$CH$_2$O)$_x$—CH$_2$CH$_2$NR—, and —SHCH$_2$CH$_2$—O—(CH$_2$CH$_2$O)$_x$—CH$_2$CH$_2$SH—, wherein R is H or loweralkyl (preferably methyl), and x is an integer that provides or yields a total number average molecular weight for the molecule of from about 1,000, 2,000, 3,000, 4,000, 5,000, 6,000, 7,000, 8,000, 9,000, 10,000, 15,000, 20,000, 30,000, 40,000, 50,000, 60,000, 70,000, 80,000, 90,000 or 100,000 daltons or more.

"Analog" as used herein is a peptide that has the physiological activity of the parent compound thereof, and that includes one or more (e.g., two, three, four, five or six or more) amino acids different from the amino acid sequence of a naturally occurring parent peptide. Such an analog preferably has at least about 70% of the physiological activity of the parent peptide. Such different amino acids may be additions, substitutions, deletions, or combinations thereof, including addition of non-natural side-chain groups and backbone links. Modifications of peptides to produce analogs thereof are known. See, e.g., U.S. Pat. No. 7,323,543; see also U.S. Pat. Nos. 7,482,171; 7,459,152; and 7,393,919.

B. Active Compounds

The single letter code for amino acids as used herein is: A (Ala), C (Cys), D (Asp), E (Glu), F (Phe), G (Gly), H(His), I (Ile), K (Lys), L (Leu), M (Met), N (Asn), P (Pro), Q (Gln), R (Arg), S (Ser), T (Thr), V (Val), W (Trp), and Y (Tyr)).

Active compounds of the present invention are, in general, compounds (from amino or N terminus to carboxy or C terminus) of Formula I (SEQ ID NO:4):

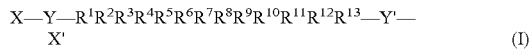

(I)

wherein:

X is present or absent and when present is a capping group, a polyalkylene oxide (e.g., a poly(ethylene glycol), "PEG"), or a peptide consisting of from 2 to 6 or 10 additional amino acids (of any type), which peptide is optionally terminated by a capping group or polyalkylene oxide;

Y is present or absent and when present is a linking group;

$R^1$ is present or absent and when present is a positively charged (at pH 6.0) amino acid, which can be an amino acid selected from the group consisting of K, R and H;

$R^2$ is present or absent and when present is a positively charged (at pH 6.0) amino acid, which can be an amino acid selected from the group consisting of K, R and H;

$R^3$ is any amino acid and in some embodiments is a positively charged (at pH 6.0) amino acid, which can be an amino acid selected from the group consisting of K, R and H;

$R^4$ is any amino acid and in some embodiments is an amino acid with a nonpolar side chain, which can be an amino acid selected from the group consisting of L, I or V;

$R^5$ is any amino acid and in some embodiments is G;

$R^6$ is any amino acid and in some embodiments is an amino acid with a nonpolar side chain, which can be an amino acid selected from the group consisting of L, I and V;

$R^7$ is any amino acid and in some embodiments is an amino acid selected from the group consisting of E and N;

$R^8$ is any amino acid and in some embodiments is an amino acid selected from the group consisting of E and N;

$R^9$ is any amino acid and in some embodiments is P;

$R^{10}$ is a positively charged (at pH 6.0) amino acid, which can be an amino acid selected from the group consisting of K, R and H;

$R^{11}$ is a positively charged (at pH 6.0) amino acid, which can be an amino acid selected from the group consisting of K, R and H;

$R^{12}$ is present or absent and when present is any amino acid and in some embodiments is an amino acid with a nonpolar side chain, which can be an amino acid selected from the group consisting of L, I or V;

$R^{13}$ is present or absent and when present is a positively charged (at pH 6.0) amino acid, which can be an amino acid selected from the group consisting of K, R and H;

Y' is present or absent and when present is a linking group; and

X' is present or absent and when present is a capping group, a polyalkylene oxide (e.g., PEG), or a peptide consisting of from 2 to 6 or 10 additional amino acids, which peptide is optionally terminated by a capping group or polyalkylene oxide.

Also provided herein is a pharmaceutically acceptable salt of the compound of Formula I.

Amino acids in peptides of the present invention may be in the D or L configuration: e.g., all D; all L; some D and some L in any combination.

In some embodiments, X is preferably a polyalkylene oxide, or a peptide consisting of from 2 to 6 or 10 additional amino acids, which peptide is terminated by polyalkylene oxide.

Nonlimiting examples of an active agent of this invention include KHHLGLEEPKKLR (SEQ ID NO:1), KHHL-GLEEPKK (SEQ ID NO:2), HLGLEEPKKLR (SEQ ID NO:3), analogs thereof, prodrug of any thereof, or pharmaceutically acceptable salts of any thereof.

Illustrative examples of the foregoing include, but are not limited to the peptides listed in Table 7 herein.

Additional examples of compounds of the present invention include all of the foregoing compounds, where the first one or two N-terminal amino acids are deleted.

Additional examples of compounds of the present invention include all of the foregoing compounds, with one, two or three additional C-terminal amino acids of any type coupled thereto.

Additional examples of compounds of the present invention include all of the foregoing compounds, with a 10,000 to 30,000 molecular weight of poly(ethylene glycol) (or "PEG") moiety coupled to either the N or C terminus thereof.

"Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the monoalkylether of the polyalkylene glycol. Thus, in various embodiments of this invention, the polyalkylene glycol in the compositions of this invention can be, but is not limited to, polyethylene glycol, polypropylene glycol, polybutylene glycol, and any combination thereof.

In certain embodiments, the polyalkylene glycol of the composition is polyethylene glycol or "PEG." The term "PEG subunit" refers to a single polyethylene glycol unit, i.e., —($CH_2CH_2O$)—.

In some embodiments, the polyalkylene glycol (e.g., PEG) can be non-polydispersed, monodispersed, substantially monodispersed, purely monodispersed, or substantially purely monodispersed.

"Monodispersed" is used to describe a mixture of compounds wherein about 100 percent of the compounds in the mixture have the same molecular weight.

"Substantially monodispersed" is used to describe a mixture of compounds wherein at least about 95 percent of the compounds in the mixture have the same molecular weight.

"Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

"Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

C. Pharmaceutical Formulations

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The present invention is illustrated in the following non-limiting examples.

EXAMPLES

Initial studies showed that when some cell types were exposed to IGFBP-2, it could enhance the ability of IGF-I to stimulate DNA synthesis and growth. In contrast other labs showed that high concentrations of the native protein often inhibited the ability of IGF-I to stimulate growth.

The studies described herein have focused on IGF independent actions of IGFBP-2 that are independent of its ability to inhibit IGF-I binding to its receptor and inhibit growth. Specifically it has been shown in mice in which the IGFBP-2 gene had been deleted that they had reduced bone turnover as reflected by histologic examination of the bones following tetracycline labeling and that cortical thickness and trabecular thickness were also reduced as evidenced by DEXA scanning, PIXI scanning and microCT analysis. A molecular explanation for this phenomenon was provided by the observation that both aortic smooth muscle and bone cells removed from these animals showed high concentrations of the growth inhibitor PTEN and that exogenous addition of IGFBP-2 or the 13 amino acid peptide described herein could suppress PTEN concentrations, thus leading to enhanced activation of the PI-3 kinase/AKT pathway which is necessary for growth stimulation. Other workers have also suggested that IGFBP-2 may stimulate stem cells. Lodish and Zhang demonstrated that IGFBP-2 was a potent stem cell growth factor and could stimulate hematopoetic stem cell reconstitution after bone marrow ablation with radiation therapy. These investigators did not investigate whether any fragments of IGFBP-2 or any portions of the protein had this property.

Example 1

Peptide Sequences

The amino acid sequence of a 13 amino acid peptide of the invention is as follows:

```
KHHLGLEEPKKLR.          (SEQ ID NO: 1)
```

The amino acid sequence of an 11 amino acid peptide of the present invention (a fragment of SEQ ID NO: 1 that retains biological activity) is as follows:

```
KHHLGLEEPKK.            (SEQ ID NO: 2)
```

The amino acid sequence of an 11 amino acid peptide of the present invention (a fragment of SEQ ID NO: 1 that retains biological activity) is as follows:

```
HLGLEEPKKLR             (SEQ ID NO: 3)
```

Variations on the foregoing sequences that are biologically active include substitutions that can be made for the K or H in positions 1, 2, and 3 (positions referring to SEQ ID NO: 1) with arginine or lysine, and which retain activity. Similarly, substitutions can be made for L at position 4 and 6 with I or V. Substitutions can be made at positions 7 or 8, for either E, with N. Substitutions can be made at positions 10 and 11 with either H or R. Substitutions can be made at position 12 with L for I or V, and at position 13 for R with K or H.

The rationale for picking this particular region of the IGFBP-2 protein was primarily based on certain factors. The first is its charge density; that is, the peptide contains 6 basic residues in 13 positions and 2 acidic residues. This gives it an extremely high charge density. Secondly, it is flanked by a polyproline sequence, which indicates it is held in rigid position by the parent protein. Third, this sequence is unique for IGFBP-2. The IGFBP family contains 6 members that have a high degree of sequence conservation at the N terminus and C terminus of the proteins. However, the mid region of each protein shows sequence divergence. This 13 amino acid sequence is completely unique for IGFBP-2 and is not contained in any of the other 6 IGF binding proteins. The importance of this is that knockout of IGFBP-2 in mice gives a unique phenotype: low bone turnover and high fat mass. Knockout of any of the other 5 IGF binding proteins does not give this phenotype. Therefore, it was hypothesized that there was a region within IGBP-2 that accounted for these effects.

Example 2

Preparation of Pegylated Peptide

The 13 amino acid peptide of SEQ ID NO: 1 described herein was prepared by solid phase synthesis, purified by HPLC, and then assessed for purity using mass spectrometry. Poly(ethylene glycol) ("PEG") was purchased from JenKem Technology USA (2033 W. McDermott Dr., Suite 320 #188, Allen, Tex. 75013-4675). 10.3 mg of the peptide was dissolved in 1.0 ml of 50 mM sodium phosphate pH 6.5. 406 mg of methoxyPEG propinaldehyde molecular weight 20 kDa was dissolved in 4 ml of 50 mM sodium phosphate. 120 ul of a 1M solution of sodium cyanoborhydride, tetrahydrofuran (Aldridge) was added to the solution of PEG. 1 ml of peptide was then added to the PEG solution, followed by additional 1 ml of sodium phosphate. The reaction mixture was then rotated in a 15 ml conical tube for 24 hours at 4° C. Following incubation, Tris base was added to a final concentration of 6.8 mM to block unreacted sites. N-terminal peglyation was verified by SDS-PAGE followed by Coumassie staining, which yielded a molecular weight that was consistent with 1 PEG molecule added per molecule of peptide. The compound was also analyzed by immunoblotting using an antibody that had been specifically prepared against the 13 amino acid sequence. The electrophoretic mobility of the Coumassie stained protein and the immunoblotted protein were identical, indicating that the immunoreactive peptide had been pegylated.

Example 3

Fat Cell Assays

In some assays, fat cell data were obtained by using the cell line 3T3L1, which is used to study fat cell differentiation. These cells are grown as fat cell precursors. These cells are maintained in Hams F12 with fetal calf serum and 15 mM glutamine. To stimulate them to enter the fat cell differentiation pathway, isomethylbutylxanine, dexamethasone and insulin are added using concentrations of 0.5 mM IBMX 16.7 nM insulin and 0.1 uM dexamethasone. In some cases 100 ng/ml IGF-I was added instead of insulin. Three days after the addition, differentiation into adipocytes is apparent and is detected by oil red O staining.

To determine the effects of the peptide of SEQ ID NO:1, it was added at concentrations of 20 ng/ml, 200 ng/ml and 2 ug/ml. A detectable inhibition of adipocyte differentiation, as determined by a decrease in the number of oil red O positive cells, was detected using 20 ng/ml of peptide. The response was maximal at 200 ng/ml and not increased further by adding 2 mcg/ml. Wildtype IGFBP-2 was tested in parallel and was found to also inhibit adipocyte differentiation using concentrations between 50-500 ng/ml.

For oil red O staining, a stock solution of 0.5 ml/100 ml isoproponol is prepared. 60 ml of solution is mixed with 40 ml of water and allowed to sit at room temperature for an hour and then filtered. The media is aspirated from the adipocyte cultures and cells are fixed in 1% formaldehyde. Formaldehyde is aspirated and the oil red O solution is added in an amount necessary to cover the cells, which are then left at room temperature for one hour. The stain is then removed and the plates are washed with distilled water and dried. Typically 60-70% of the cells stain positive after 3 days.

The maximum effect of the peptide was to inhibit differentiation to a level wherein <20% of the cells were positive. These findings were reconfirmed using primary mouse preadipocytes. 35-50 day old mice were killed and inguinal fat pads were removed aseptically. Fat tissue was washed and dissolved in Hanks basic salt solution containing 0.1% glucose and 2 mg/ml collagenase, (type 3 Worthington) and 4% BSA. Following 15 min digestion at 37°, the tissue was separated by dispersion and pipetting and then filtered through an 80 micron sterile nylon filter. The cells were then plated in DMEM F12 containing 10% fetal calf serum and then centrifuged at 700×g to separate the stromal vascular cells from the adipocytes, which float. The supernatant was discarded and the cell pellet which contained the stromal vascular cells was resuspended in DMEM F12 with 10% FCS and plated at a density of 15,000 cells/cm$^2$. The medium was aspirated 24 hr later and fresh medium was replaced every 3 days until the cells reached 80-90% confluence. Differentiation was induced by adding serum free medium containing 25 mM glucose, 10 ug/ml transferin, 10 nM T3, 10-7 dexamethasone, 5 ug/ml HDL and 16.7 nM insulin. This was added to cultures that were between 30-50% confluent. Medium was replaced every 3 days until fat droplets were observed, usually 6-8 days. They were then confirmed by oil Red O staining as described previously. The peptide was tested at concentrations between 2 ng and 2 ug/ml and native IGFBP-2 protein between 50-500 ng/ml. The IGFBP-2 had been purified from cellular conditioned medium and was determined to be homogenous by amino acid sequence analysis.

Example 4

Measurement of Osteoclast Differentiation

The method for osteoclast differentiation is as follows: Balb/c mice in which the IGFBP-2 gene had been deleted (see V. DeMambro et al, *Endocrinology*, 149(5): 2051-2061 (2007)) were anesthetized and sacrificed using cervical dislocation. The femurs from each mouse were dissected free of soft tissue and the bone marrow aspirated by needle puncture. Cells were removed sterile and resuspended in DMEM with 10% fetal calf serum. The cells were centrifuged at 700×g and the cell pellet resuspended in medium and plated in 24 well plates at a concentration of 5000 cells/cm$^2$. The plates that are used are low adherence plates that have no additives to facilitate cell adherence. Under these conditions macrophages will adhere while other cells will not. The media is supplemented with mCSF 20 ng/ml. After 3 days the cells are removed from the plate and the adherent macrophages are exposed to fresh media containing 10% FBS and mCSF. This is repeated again after 3 days and then after an additional 3 days cells are trypsinized and replated in fresh plates at $6\times10^4$ cells/cm. At this time RANK ligand, 50 ng/ml, is added, although in some experiments concentrations as low as 10 ng/ml were utilized. Medium is changed at 3 and 6 days and on day 7 cells are stained for tartrate resistant acid phosphatase, a marker of osteoclast differentiation. IGFBP-2 was added at concentrations between 50 ng/ml and 500 mcg/ml. The peptide was added at 20 or 200 ng/ml.

The results showed that the cells would not differentiate into osteoclasts without addition of the peptide or native IGFBP-2. Additionally, in the presence of the peptide, the serum concentration could be lowered to as low as 0.5% and osteoclast differentiation was still detected. Additionally, if 2% serum was utilized, mCSF could be deleted from the medium and RANK ligand lowered to as low at 30 ng/ml. However it was not possible to remove IGFBP-2. That is, cultures maintained without IGFBP-2 or the peptide did not differentiate into osteoclasts.

For tartrate resistant acid phosphatase staining, a 1% solution is prepared and incubated with the cells for 30 min at room temperature. Cultures are then washed and cell number determined by manual counting. In some experiments the pegylated 13 amino acid peptide was compared to the nonpegylated peptide and found to have equal biologic activity.

Example 5

Measurement of Osteoblast Differentiation

For measurement of osteoblast differentiation, the cells are also derived from the same bone marrow aspirates. However in some experiments they were derived from calvaria obtained from newborn animals. Cells are plated in 6 well plates at $20\times10^6$ cells/well in alpha MEM with 10% fetal bovine serum. Media was changed on day 1 and 3. At day 3 the cells received differentiation medium, which is alpha-MEM containing 10% fetal calf serum, 8 mM glycerol phosphate and 50 ug/ml ascorbic acid. Media subsequently is changed every 2 days until termination of the experiment, generally at 18 days. In some experiments fetal calf serum concentration was lowered to either 5% or 2%. IGFBP-2 200 ng/ml was added to some cultures or the IGFBP-2 peptide at concentrations between 2 ng/ml and 2 mcg/ml. To determine osteoblast differentiation, the cells were fixed with 4% paraformaldehyde and then stained for alkaline phosphatase. The cells were then counterstained with von kossa stain to detect mineralization. In some experiments the pegylated 13 amino acid peptide was compared to the nonpegylated peptide and found to have equal biologic activity.

Example 6

Bone Growth and Mineralization Studies

This system uses an ex vivo explant system, therefore it is a transition between cultured cells and in vivo experiments. The bone forming tissue is removed directly from a mouse and then grown in organ culture for several days. The test additives can be added directly to the medium at any concentration in order to test for biological activity. The method is as follows: mouse metatarsal bones were isolated from newborn mice between days 0 and 3 after birth using the dissecting microscope. The middle three metatarsals were used for all experiments. Three metatarsals were incubated per well in a 24 well tissue culture dish in DMEM containing 0.5% bovine serum, 0.5M ascorbic acid, 1 mM beta glycerol phosphate at 37° C. The medium was replaced one day later and the metatarsals are cultured for up to 10 days. Growth was measured by quantitative increase in size, both length and width of the bones using an inverted phase microscope with a built in micrometer scaling bar for measurements. Mineralization was assessed by the addition of calcein (500 ng/ml) to the medium for 2 hrs prior to tissue fixation. Fluorescent images were captured using a digital camera attached to an inverted microscope and quantifying calcein fluorescence under the appropriate weight length stimulus. Bone and cartilage histology were measured by fixing the bones in 4% PFA overnight and storing at 70% ethanol, followed by parafilm embedding sectioning and staining. Sections were stained with H&E, Alizaran red or alkaline phosphatase. For analysis of proteins, the tissue was homogenized in Laemmli sample buffer and gels were run using standard SDS polyacrylamide gel electrophoresis and western blotting.

Results demonstrated that addition of either intact IGFBP-2 or the IGFBP-2 peptide at a concentration of 20-200 ng/ml stimulated bone growth and calcification in metatarsals derived from the IGFBP-2-/- mice. The peptide also had a modest additional stimulatory effect on metatarsals from normal, but the percent increase was much greater in the metatarsals derived from the IGFBP-2 null animals.

Example 7

In Vivo Rescue of the Bone Phenotype in IGFBP-2-/- Mice

IGFBP-2-/- mice have reduced bone mineral density, reduced cortical and trabecular thickness and reduced bone turnover, both formation and resorption. To determine if the 13 amino acid peptide was active systemically, a pegylated preparation was prepared in order to extend halflife. This preparation was then injected into the mice. Mice between the ages of 16 and 20 weeks were utilized. These mice are known to have a major bone phenotype. The peptide was injected at a dose of 50 mcg of peptide plus conjugate, that is the total molecular weight of PEG plus the peptide, which is approximately 23,000 molecular weight was injected intraperitoneally five days per week for three weeks. Six mice were injected in each group. The major measure of bone density is the bone volume over total volume as calculated by micro CT analysis. This measures the amount of total bone within a given space. Control animals receive PBS injections.

The BV/TV values were as follows: For the normal mice, the value of the volume occupied by bone was 0.22 (22%); for the mice, with the IGFBP-2 gene deletion, the value was 0.12; and for mice that received the peptide, it was 0.18. Therefore, injection of the peptide rescued the bone phenotype to within 70% of normal even though these mice had gone the first 6 weeks of life without exposure to this protein. Measurement of the cortical thickness also showed that it was substantially increased by administration of the peptide. Analysis of the bones biochemically showed that PTEN was downregulated. Therefore it appears that the peptide is fully capable of rescuing a bone phenotype in a whole animal model.

Example 8

The Heparin Binding Domain of IGFBP2 is Anabolic to the Skeleton and Works Through a Mechanism that is Independent of IGF-I Binding Mice.

Generation of the original mixed background strain, B6; 129-Igfbp2<tm1Jep>, which are refer to Igfbp2$^{-/-}$ mice, has been described previously[10,52]. The original mice were backcrossed onto C57BL/6J background for at least 10 generations. All in vivo and ex vivo experimental studies were performed using male mice. All the animal studies were reviewed and approved by the Institutional Animal Care and Use Committee of Maine Medical Center Research Institute. Mice had free access to water and diet for the duration of the study. Colony environmental conditions included 14:10 hour light:dark cycles.

Cell Culture.

Neonatal calvarial osteoblasts were collected from 7-10 day old mice as previously described[53]. Briefly, calvariae were digested 5 times with collagenase P and Trypsin. Cells released from digests 2 through 5 were collected as primary calvarial osteoblasts, and maintained in DMEM supplemented with 10% FCS and non-essential amino acids. Osteoblastogenesis of primary calvarial osteoblasts was carried out by treating cells with 4 mM β-glycerophosphate and 50 μg/ml ascorbic acid in αMEM. Bone marrow stromal cells (BMSCs) were harvested from femurs and tibias of 8 weeks old mice as described previously[10]. Osteoblastogenesis of BMSCs was induced by the treatment with osteogenic media consisting of αMEM containing 10% FCS, 8 mM β-glycerophosphate, and 50 μg/ml ascorbic acid.

Metacarpal Culture.

Metacarpals were isolated from Igfbp2$^{-/-}$ mice at 1-day old and incubated in DMEM containing 0.5% BSA, 50 μg/ml ascorbic acid and 1 mM β-glycerol phosphate for 10 days[54]. Stimulants were added to culture media from day 1. At day 10, metacarpals were incubated in media containing calcein (500 ng/ml) for 2 hours for staining of calcium deposition, and images were obtained. Then, bones were fixed with 4% PFA, embedded in paraffin, and processed for Alcian blue and von Kossa double staining.

Real-Time PCR.

Total RNA was prepared using RNeasy Mini Kit (Qiagen) and treated with DNase (Qiagen). cDNA was generated using a random hexamer and reverse transcriptase (Superscript III, Invitrogen) according to the manufacturer's instructions. Quantification of mRNA expression was carried out using an iQ SYBR Green Supermix in a iQ5 thermal cycler and detection system (Bio-Rad). 18S rRNA or Gapdh was used as an internal standard control gene for all quantification.

Western Blot Analysis.

To prepare whole cell lysates, cells were solubilized in RIPA buffer[55]. For cytosolic fraction, cells were solubilized with hypotonic buffer containing protease and phosphatase inhibitors (10 mM Tris, 0.2 mM $MgCl_2$, pH 7.4) and kept on ice for 10 min. Cell lysates were mixed with sucrose buffer (final concentration; 25 mM Sucrose, 0.1 mM EDTA) and centrifuged at 20,000×g for 1 hour. Supernatant was used as cytosolic fraction. To prepare the membrane fraction, cells were solubilized with PBS containing protease and phosphatase inhibitors. The lysates were frozen at −80° C. for 1 h and thawed at room temperature. After three cycles, they were centrifuged at 13,000×g for 25 min. The pellet was suspended with membrane protein isolation buffer (20 mM Tris-HCl; 150 mM NaCl; 1 mM EDTA; 1 mM EGTA; and 1% Triton X-100, pH 7.5) containing protease and phosphatase inhibitors. Protein concentration was assessed by BCA protein assay kit (Thermo Scientific) and equal amounts of sample were separated by SDS-PAGE and transferred electrophoretically to nitrocellulose membranes. Membranes were blocked in 5% BSA in Tris-buffered saline. Thereafter, the membranes were immunoblotted with anti-PTEN (Cell signaling, #9559), anti-Akt (Cell signaling, #9272), anti-pSer473-Akt (Cell signaling, #9271), anti-β-catenin (BD Transduction Laboratories, 610153), anti-pSer552-β-catenin (Cell signaling, #9566P), or anti-α-actin (Santa Cruz, sc-47778), and developed with horseradish peroxidase-coupled anti mouse or rabbit IgG antibodies, followed by enhancement with SuperSignal West Dura Extended Duration Substrate Antibodies (Pierce Chemical Co.).

Generation of Heparin-Binding Domain Peptide.

The synthetic peptide containing the mouse homologue of the heparin binding domain (AA246-249) and 9 additional amino acids of mouse IGFBP-2, $^{237}$KHLSLEEPKKLRP$^{250}$ (SEQ ID NO:8753, referred to as HBD-peptide), and control peptide for HBD-peptide (AALSLEEPAALAP; SEQ ID NO:8754) were synthesized by the Protein Chemistry Core Facility at the University of North Carolina at Chapel Hill. The synthetic peptide for heparin-binding domain of IGFBP-5 ($^{201}$(RKGFYKRKQCKPSRGKRK$^{218}$; SEQ ID NO:8755) was generated in the same way. Purity and sequence confirmation were determined by mass spectrometry. The IGFBP-2 HBP-peptide was pegylated as follows: 10 mg of peptide was mixed with 380 ug of methoxy PEG maleimide (20000 kDa)(1:3 molar ratio peptide to PEG) (Jenkem Biotechnology) in 4.0 ml of 0.05M $NaH_2PO_4$, pH 7.0. Following an overnight incubation at 4° C., cysteine was added to a final concentration of 17 mM to block unreacted sites. To remove the nonpegylated peptide and cysteine the mixture was desalted using a Zebra Desalt spin column (Thermo Scientific) following the manufacturer's instructions. Pegylation was verified by SDS-PAGE analysis with Coomassie staining.

In Vivo Treatment of Igfbp2$^{-/-}$ Mice with Pegylated Heparin-Binding Peptide (PEG-HBD-Peptide).

Igfbp2$^{+/+}$ and Igfbp2$^{-/-}$ mice were administered with PBS or PEG-HBD-peptide (50 μg/day) intraperitoneally 5 times per week from 6 to 9 weeks of age. Dual-energy x-ray absorptiometry was performed before the initiation of treatment. Mice were injected with 20 mg/kg calcein intraperitoneally 7 days and 2 days before sample collection.

Dual-Energy x-Ray Absorptiometry (DXA).

Dual-energy x-ray absorptiometry (DXA) for whole body and femoral areal bone mineral density (aBMD) and body composition exclusive of the head were performed using the PIXImus (GE-Lunar)[10]. The PIXImus was calibrated daily with a mouse phantom provided by the manufacturer.

MicroCT.

Microarchitecture of distal trabecular bone and midshaft cortical bone was analyzed with femurs and vertebrae (L5) by MicroCT (MicroCT40)[10]. Approximately 100 slices were measured just proximal to the distal growth plate, with an isotropic pixel size of 12 μm and slice thickness of 12 μm. Midshaft cortical bone thickness was analysis in a similar fashion using approximately 18 slices obtained at the exact midpoint of the femur.

Bone Histomorphometry.

In vivo histomorphometry differences were analyzed between Igfbp2$^{-/-}$ mice treated with PBS or PEG-HBD-peptide at 9 weeks of age, Mice were injected with 20 mg/kg calcein intraperitoneally 7 days and 2 days before sample collection. Femurs were analyzed as described previously[10].

Femoral Biomechanics.

Femoral biomechanical properties were compared by three-point bending between Igfbp2$^{-/-}$ mice treated with PBS or PEG-HBD-peptide at 9 weeks of age. Load was applied at a constant rate (0.05 mm/sec) until failure. Failure load (newtons), bending stiffness (newtons per millimeter), and work-to-failure (newton-millimeters) from the load-displacement curve were measured and the apparent elastic modulus (megapascal) and ultimate strength (gigapascal) were measured using the relevant midfemoral cross-sectional geometry measured from μCT.

Statistical Analysis.

All data are expressed as the mean±Standard Error of the Mean (SEM). Results were analyzed for statistically significant differences using Student's t-test or ANOVA followed by Bonferroni multiple comparison post hoc test. The glucose tolerance test was analyzed using repeat measures ANOVA. Statistical significance was set at $p<0.05$.

The Heparin-Binding Domain of IGFBP-2 Stimulates In Vitro Osteoblastogenesis.

Figure 1B:
Figure 1C:
Figure 1C:
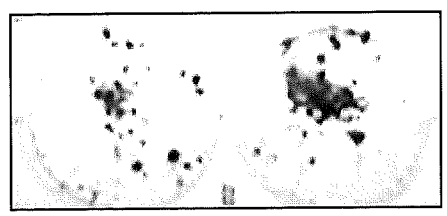
Figure 1D:
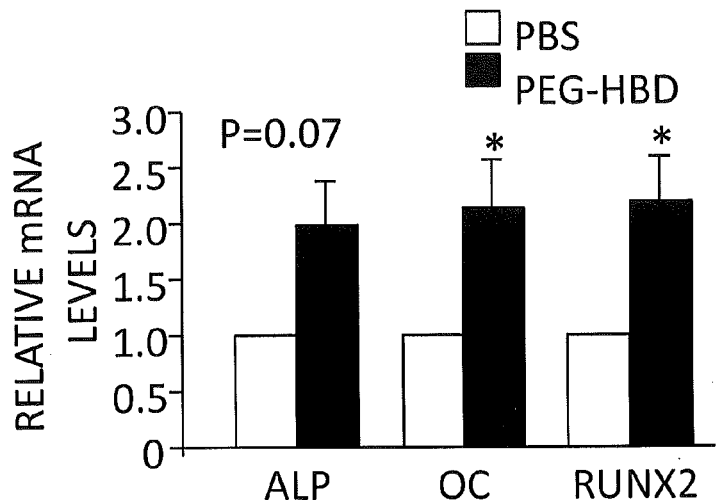
Figure 7:
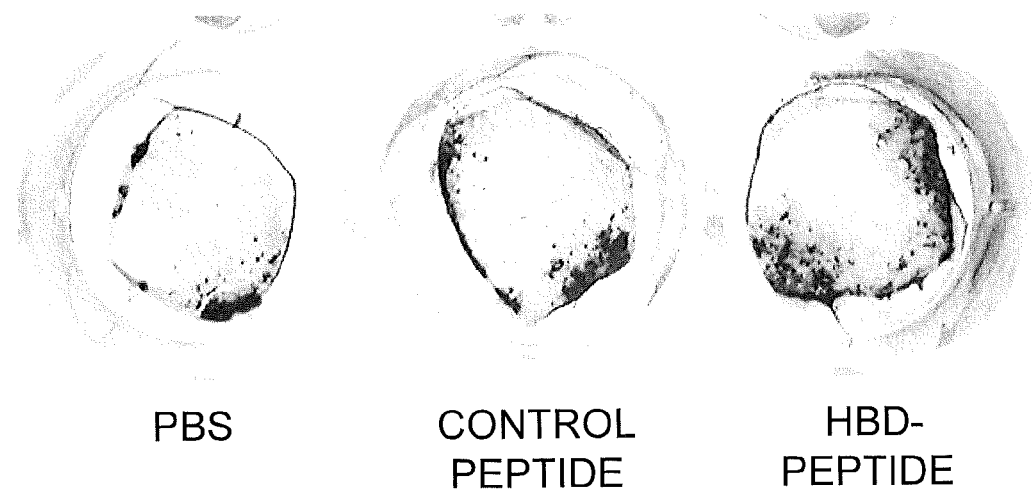
FIG. 7. Control peptide for heparin-binding domain peptide does not have any anabolic effects on in vitro osteoblastogenesis. Igfbp2$^{-/-}$ calvarial osteoblasts (COBs) were cultured with osteogenic media with PBS, control peptide (2 µg/ml) or heparin binding domain peptide (HBD-peptide) (2 µg/ml). Osteoblastogenesis was evaluated by Alizarin Red staining.
Figure 8A:
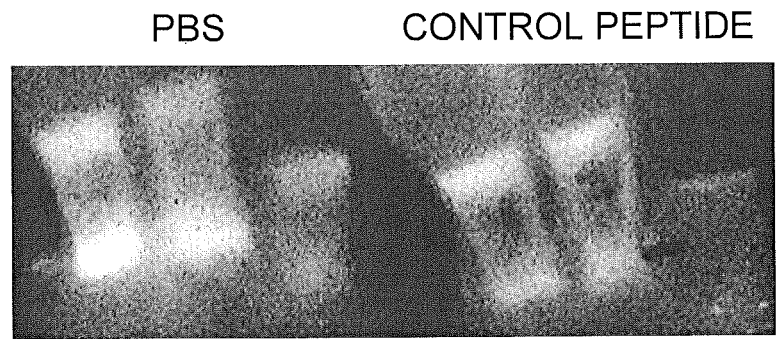
FIG. 8. Control peptide for heparin binding domain peptide does not have any anabolic effects on metacarpals ex vivo. Metacarpals were collected from day 1 male Igfbp2$^{+/+}$ mouse, and cultured in DMEM (1 g/L of glucose) containing 1 mM β-glycerophosphate and 50 µg/ml ascorbic acid. Either PBS or control peptide (2 µg/ml) was added to the media. At day 10, bones were treated with 500 ng/ml of calcein for two hours. Calcein incorporated area was visualized (a) and longitudinal length of incorporated area was quantified (b). Metacarpals were fixed with 4% PFA and subjected to Alcian blue and von Kossa double staining (c). Length and width of metacarpals were quantified (d). Values were expressed as the mean±SEM (n=3). Statistical significance was analyzed by Student's t-test. ns; not significant.
Figure 8B:
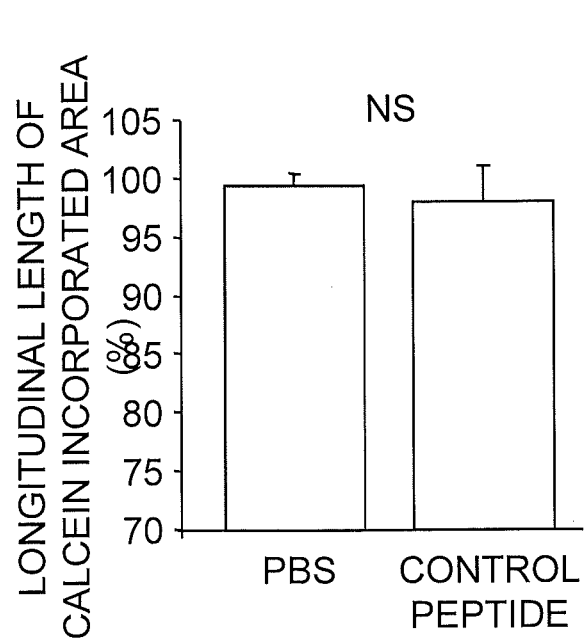
Figure 8C:
Figure 8D:
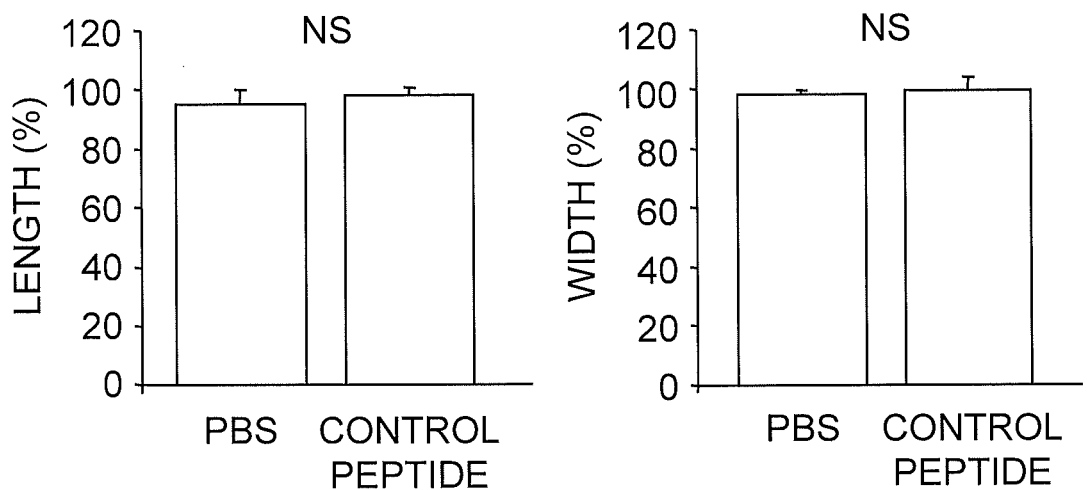

It has been reported previously that Igfbp2$^{-/-}$ mice exhibited an osteopenic phenotype with low bone formation and impaired osteoblastogenesis in bone marrow stromal cells (BMSCs) from Igfbp2$^{-/-}$ mice compared to wild-type cells (FIG. 1a)[10]. Consistent with this, Igfbp2-deficient calvarial osteoblasts (COBs) exhibited impaired alkaline phosphatase (ALP) activity during osteoblastogenesis compared to wild-type cells (FIG. 1b). To investigate whether the heparin-binding domain (HBD) of IGFBP-2 has an anabolic effect on the skeleton, a small molecule (the HBD-peptide), which contains the HBD of IGFBP-2, was generated and tested for its effect on osteoblastogenesis in vitro. To confirm that the effect of HBD-peptide was specific, a control peptide was also made and analyzed for its effect on osteogenesis. The control peptide did not enhance mineralization of Igfbp2$^{-/-}$ COBs compared to PBS-treated cells, whereas the HBD-peptide was fully active (FIG. 7). To prolong the half-life of the small molecule such that it was feasible to undertake in vivo studies, pegylation of the HBD-peptide was performed (PEG-HBD). Igfbp2$^{-/-}$ COBs and BMSCs were cultured in osteogenic media (i.e., ascorbic acid and β-glycerol phosphate) in the presence of the PEG-HBD. PEG-HBD strongly enhanced osteogenesis of COBs and BMSCs as measured by alkaline phosphatase and Alizarin Red staining (FIG. 1c). Consistent with this, ALP, Runx2 and osteocalcin (OC) expression were enhanced in BMSCs treated with PEG-HBD compared to control treated cells (FIG. 1d).

The Heparin-Binding Domain of IGFBP-2 Stimulates Periosteal Expansion of Metacarpals Ex Vivo.

Figure 2A:
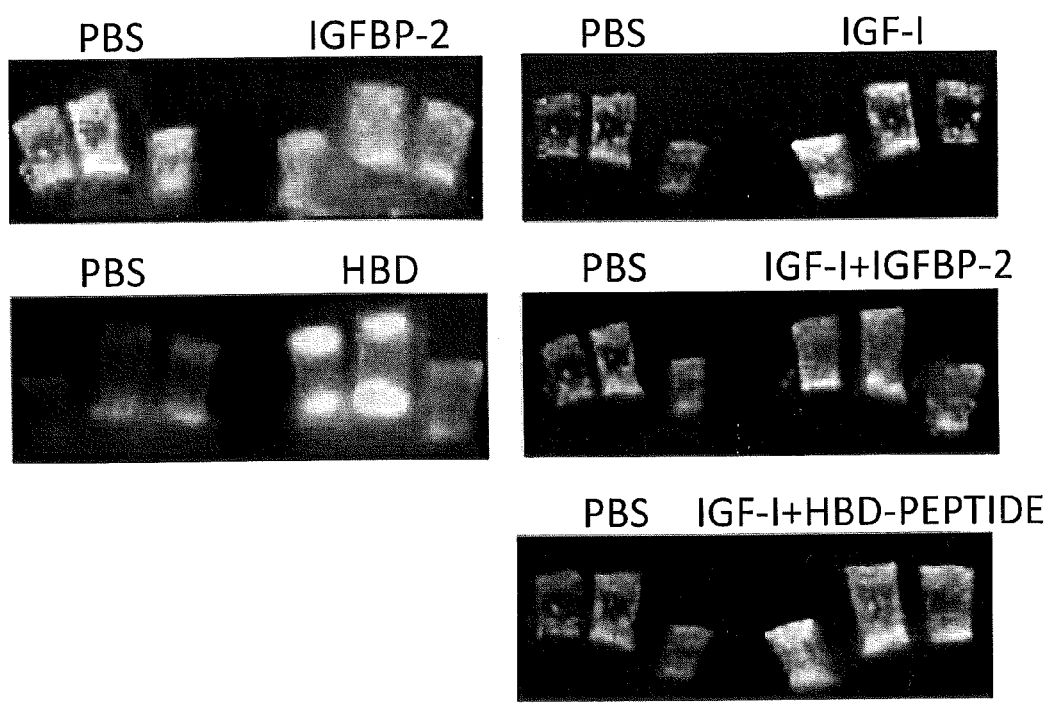
FIG. 2. The heparin binding domain of IGFBP2 enhances periosteal expansion of metacarpals ex vivo. Metacarpals were collected from day 1 male mouse, and treated with osteogenic media with IGFBP2 (200 ng/ml) or the heparin-binding domain peptide (HBD-peptide) (2 µg/ml) in the presence or absence of IGF-1 (20 ng/ml) for 10 days. Bones were labeled with calcein (500 ng/ml) and calcein incorporated area was visualized (a) and longitudinal length of calcein incorporated area was quantified (b). Alcian blue and Von Kossa double staining was performed (c) and length and width of metacarpals were quantified (d). Statistical difference was analyzed by ANOVA followed by Bonferroni post-hoc test. Figures shown represent at least 3 independent experiments. Values are expressed as the mean±SEM (n=3-4). $^a$; <0.05 vs PBS, $^b$; <0.01 vs PBS, $^c$; <0.001 vs PBS, $^d$; <0.01 vs HBD, $^e$; <0.05 vs IGF-I, $^f$; <0.05 vs HBD.
Figure 2B:
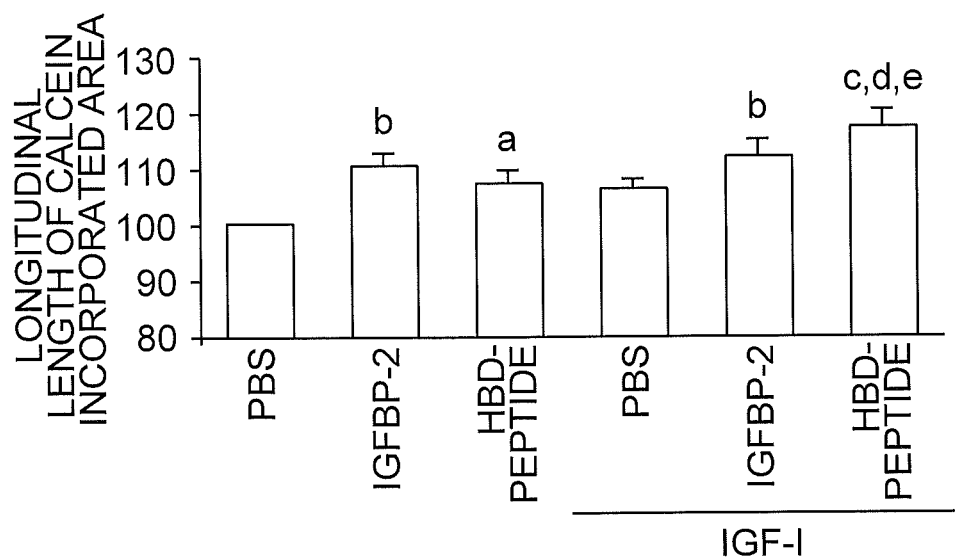
Figure 2C:
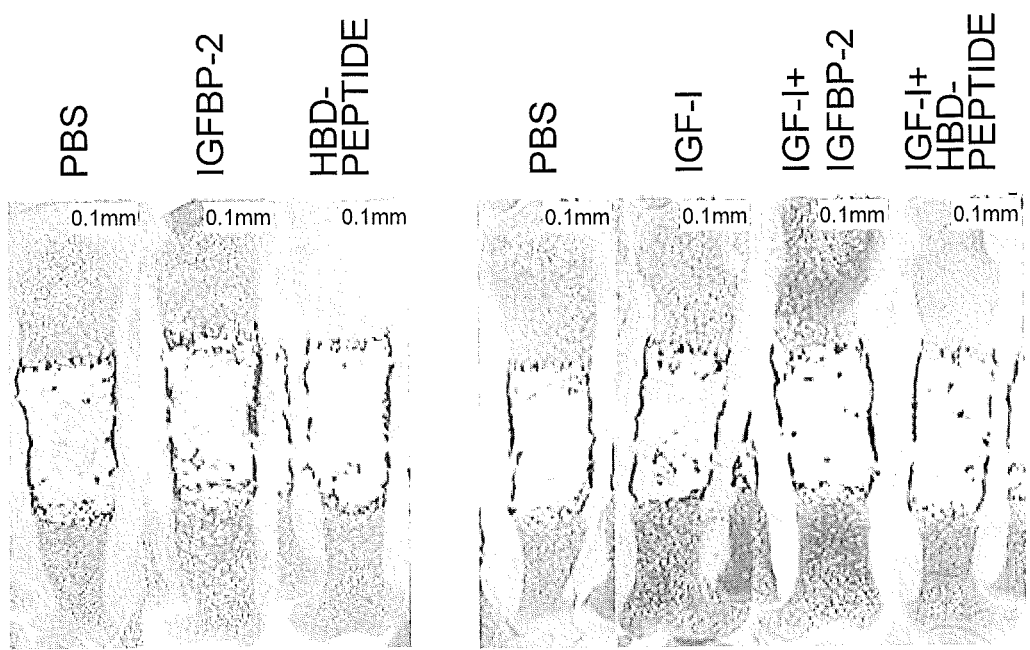
Figure 2D:
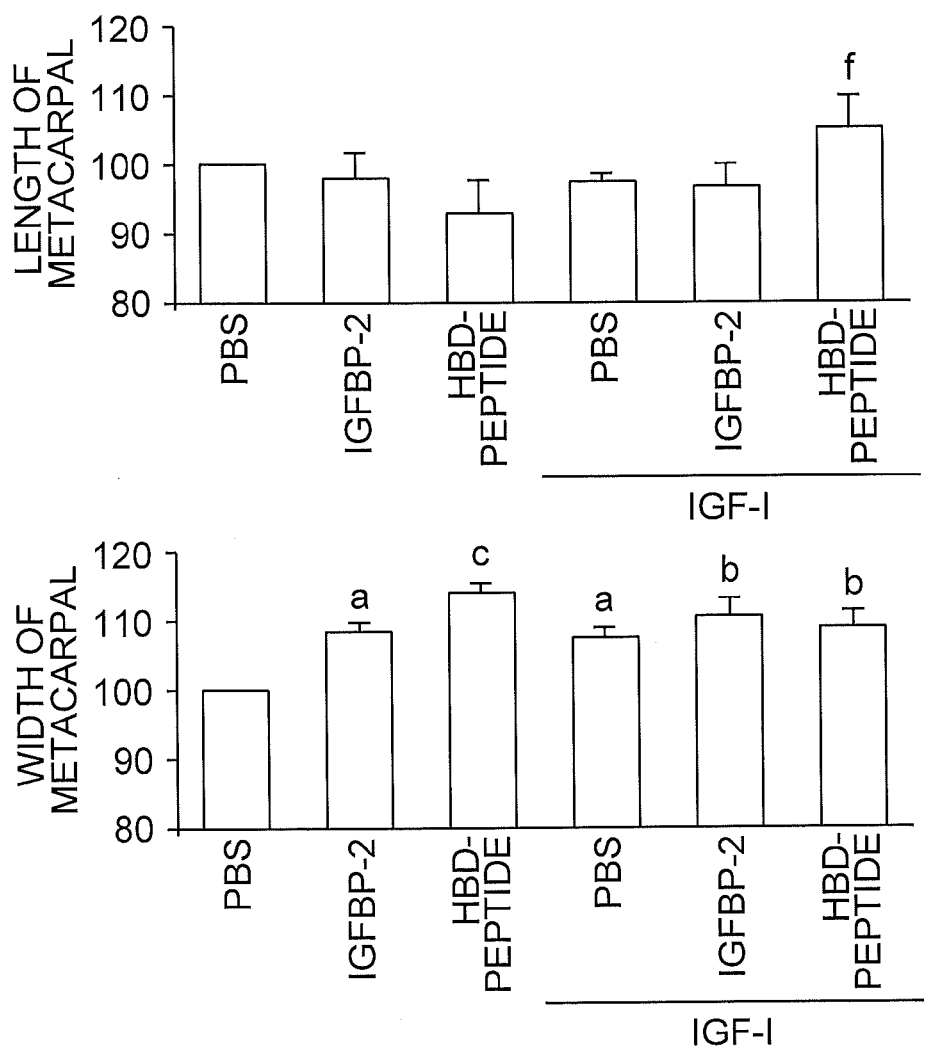

To further understand the anabolic effect of the HBD on the skeleton, metacarpals from 1 day old mouse were collected and incubated with osteogenic media in the absence of fetal calf serum and analyzed for the effects of HBD-peptide on skeletal growth. Bone accrual was evaluated by the longitudinal length of calcein incorporated area as well as width and length of metacarpals. The control peptide had no effect on calcein incorporated area, and length and width of metacarpals was comparable to the metacarpals treated with PBS. Hence PBS was used as the subsequent control for further studies (FIG. 8). As shown in FIG. 2a, IGFBP-2 and HBD-peptide significantly enhanced calcein incorporated area of metacarpals (FIGS. 2a and b). IGF-I also stimulated expansion of calcein incorporated area to a similar extent as IGFBP-2 and HBD-peptide (FIGS. 2a and b). When metacarpal bones were treated with IGF-I together with the HBD-peptide the metacarpals displayed further enhancement of calcein incorporated area. In addition, IGFBP-2 and HBD-peptide also increased the width of metacarpals, implying that IGFBP-2 has an important role in periosteal expansion (FIGS. 2c and d).

The Heparin-Binding Domain of IGFBP-5 does not have an Anabolic Effect on the Skeleton In Vitro and Ex Vivo.

Figure 3A:
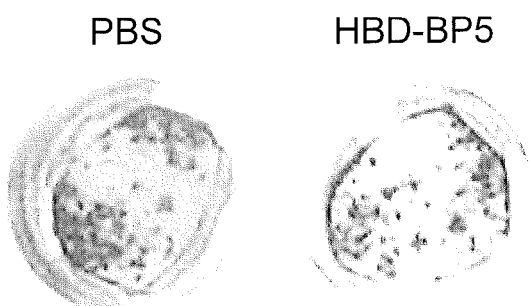
FIG. 3. The heparin binding domain of IGFBP5 does not show any effect on in vitro osteoblastogenesis or periosteal expansion of metacarpals ex vivo. Primary calvarial osteoblasts were collected from male Igfbp2$^{-/-}$ male mouse and treated with osteogenic media with or without the heparin-binding domain of IGFBP-5 (HBD-BP5) (2 µg/ml). Osteoblastogenesis was evaluated by Alizarin Red staining (a). Metacarpals were collected from day 1 male mouse, and treated with osteogenic media with or without HBD-BP5 (2 µg/ml) for 10 days (b and c). Bones were labeled with calcein (500 ng/ml) and calcein incorporated area was visualized (a). Longitudinal length of calcein incorporated area was quantified (b and c). Alcian blue and Von Kossa double staining was performed (d) and length and width of metacarpals were quantified (e). Figures shown represent at least 3 independent experiments. Values are expressed as the mean±SEM. Statistical difference was analyzed by Student's t-test (n=3-4).
Figure 3B:
Figure 3E:
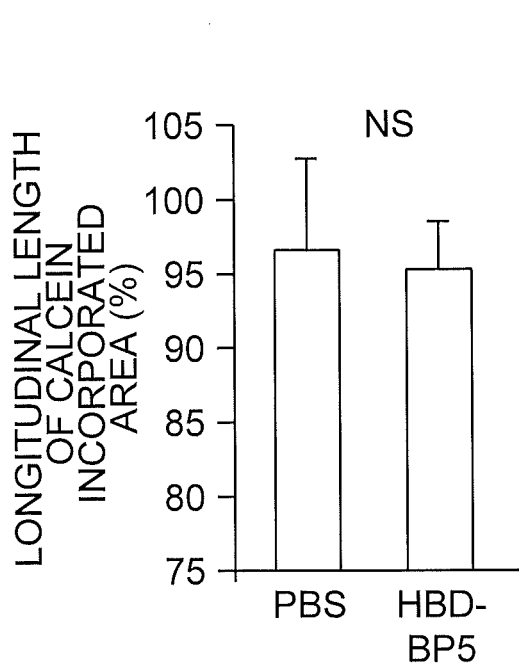
Figure 3E:
Figure 3E:
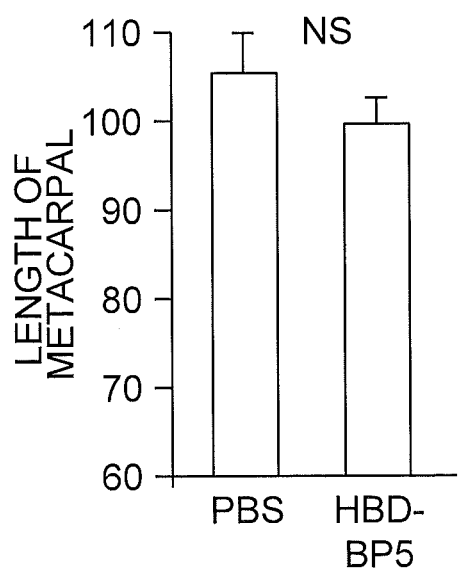
Figure 3E:
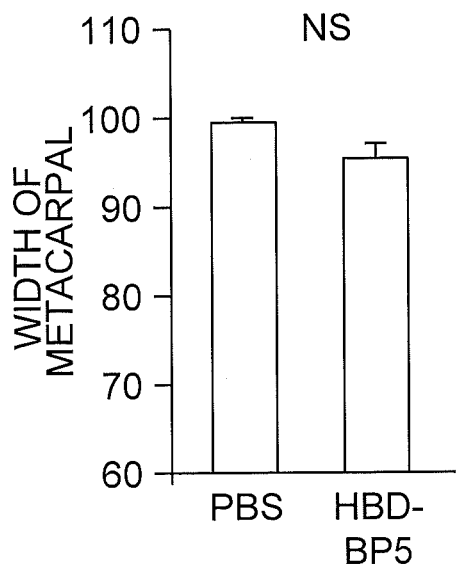

Because other IGFBPs possess HBD regions as well as IGFBP-2, analyses were carried out to determine whether the osteogenic effect of the HBD peptide is specific for this region in IGFBP-2 or whether the HBD domain in other forms of IGFBPs also had this effect. For this purpose a peptide was prepared that contained the HBD region in IGFBP-5 (HBD-BP5) and its effect on osteoblastogenesis was determined. Igfbp2-deficient COBs were cultured in the presence of HBD-BP5 and it was determined that HBD-BP5 did not show any enhancement of mineralization compared to PBS-treated cell (FIG. 3a). Second, metacarpals were collected and treated with osteogenic media with or without HBD-BP5. HBD-BP5 did not have any effect on calcein incorporated area or length and width of metacarpals. These data indicate that the effect of the HBD on skeletal acquisition is likely specific to IGFBP-2.

The Heparin-Binding Domain of IGFBP-2 Rescues the Osteopenic Phenotype of Igfbp2$^{-/-}$ Mice In Vivo by Improving Skeletal Micro-Architecture.

Figure 4A:
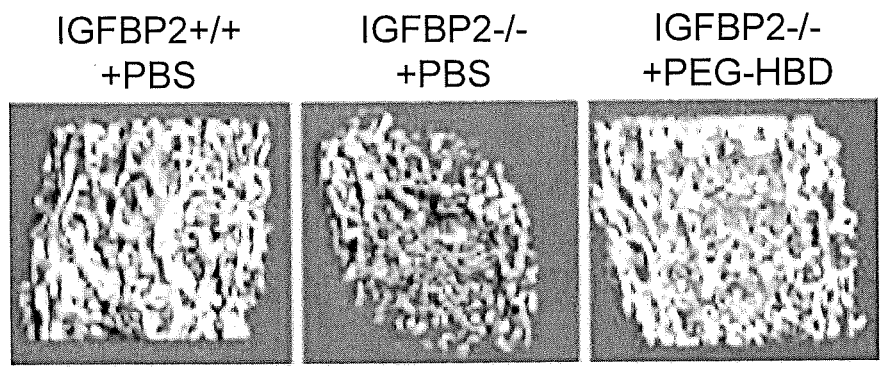
FIG. 4. The heparin-binding domain of IGFBP2 partially rescues osteopenic phenotype of Igfbp2$^{-/-}$ mice. Igfbp2$^{-/-}$ mice were treated with PBS or pegylated heparin-binding domain (PEG-HBD) from 6 to 9 weeks of age. MicroCT image of distal femur (a). Parameters by three-point bending study were shown (b). Osteoblast number/bone perimeter (Nob/BPm), osteoblast surface/bone surface (ObS/BS), osteoclast number/bone parameter (Noc/BPm) and erosion surface/bone surface (ES/BS) were determined by histomorphometry (n=5) (c). Adipocyte number (N.Ad) was counted just proximal to the distal growth plate of femur and normalized by the total area (T.Ar) (n=6) (d). Igfbp2$^{-/-}$ calvarial osteoblasts (COBs) were treated with PBS or PEG-HBD for 24 hours in serum-free media. Expression of Pparg was analyzed by real-time PCR (n=3) (e). Serum levels of Trap5b were analyzed by ELISA (Immunodiagnostics Inc.) (n=6-9) (f). Igfbp2$^{-/-}$ COBs were treated with or without PEG-HBD for 2 hours (g), Igfbp2$^{-/-}$ BMSCs were cultured with osteogenic media with PBS or PEG-HBD for 2 weeks (h). Expression of Opg and Rankl was analyzed by real-time PCR (n=3) (g and h). Figures shown represent at least 3 independent experiments. Values are expressed as the mean±SEM. Statistical difference was analyzed by Student's t-test *; <0.001, **; <0.01, $^†$; <0.05, $^{††}$; <0.06.
Figure 4B:
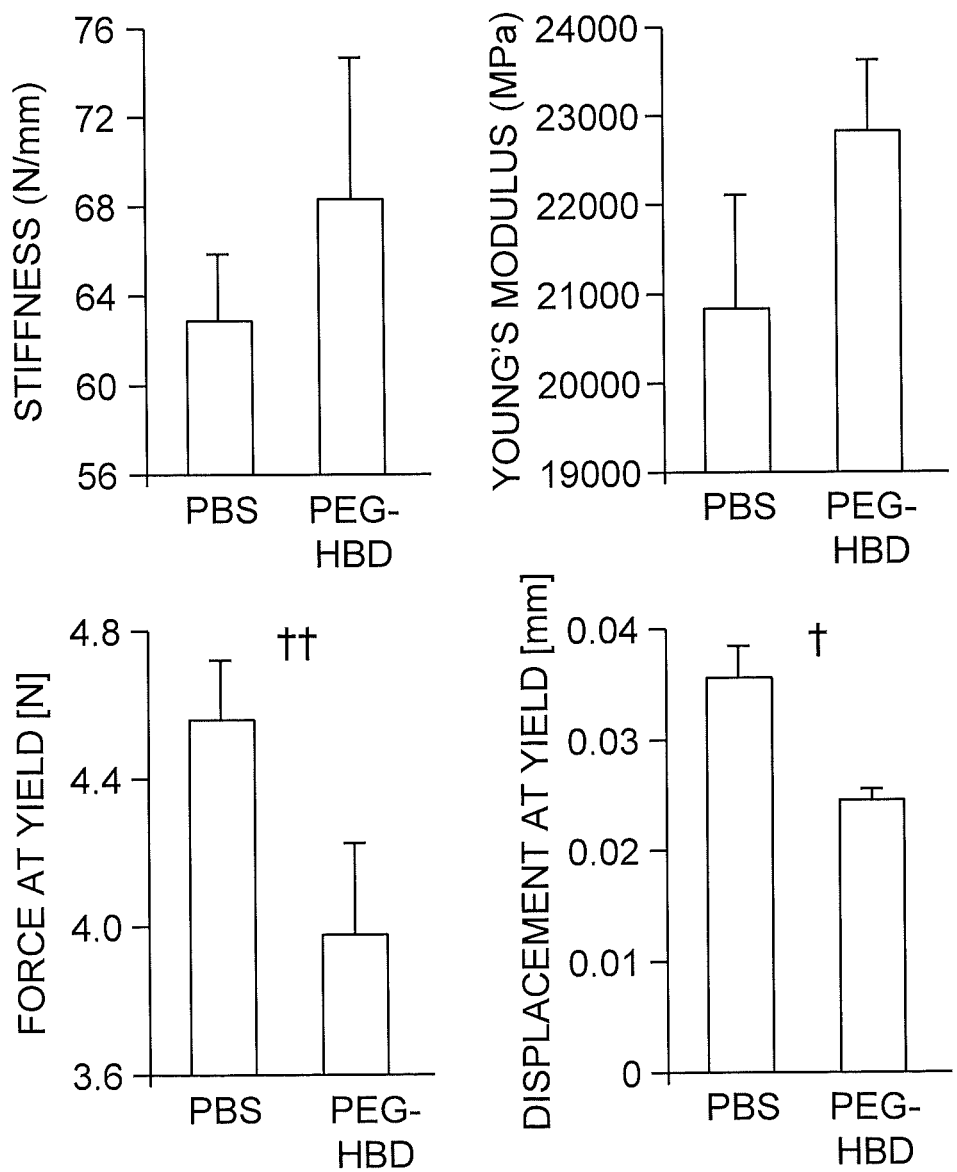

Based on these in vitro and ex vivo observations studies were conducted to determine if the HBD-peptide could rescue the osteopenic phenotype of Igfbp2$^{-/-}$ mice. For this purpose, Igfbp2$^{-/-}$ mice were treated with PBS or PEG-HBD. Based on the half-life analysis of PEG-HBD (data not shown), 50 μg of PEG-HBD were administered 5 times per week for 3 weeks in mice from 6 to 9 weeks of age. Whole-body areal bone mineral density (aBMD) and bone mineral content (aBMC)/body weight (BW) analyzed by DXA were not different before initiation of treatment between Igfbp2$^{-/-}$ mice treated with PBS or PEG-HBD (Table 3). As expected due to normal growth and consolidation, Igfbp2$^{+/+}$ mice treated with PBS showed increased trabecular bone volume by microCT compared to Igfbp2$^{-/-}$ mice treated with PBS. Treatment with the PEG-HBD enhanced whole body aBMD and aBMC/BW in Igfbp2$^{-/-}$ mice (Table 4) although it did not reach statistical significance. On the other hand, microCT analysis revealed an increase in trabecular bone volume both in the distal femur and L5 vertebrae of Igfbp2$^{-/-}$ mice treated with PEG-HBD vs PBS-treated Igfbp2$^{-/-}$ mice. This was accompanied by increased trabecular thickness (FIG. 4a, Table 1, Table 5). Cortical thickness at the midshaft of the femur was not affected by administration of PEG-HBD, but total area analyzed at the level of the femur midshaft was increased in Igfbp2$^{-/-}$ mice treated with PEG-HBD compared to PBS-treated Igfbp2$^{-/-}$ mice. This is consistent with an effect of PEG-HBD on periosteal expansion in a manner similar to what was demonstrated in the ex vivo metacarpal assay (Table 1 and FIG. 2). The skeletal architectural changes were associated with a similar trend in bone strength. In the three point bending studies of the femur, Igfbp2$^{-/-}$ mice treated with PEG-HBD had slightly higher bone stiffness and estimated Young's Modulus compared to PBS treated null mice (FIG. 4b). Furthermore, force at yield and displacement-at-yield were lower in the PEG-HBD treated animals compared to controls (FIG. 4b).

Histomorphometric analysis revealed that osteoblast number per bone perimeter was significantly increased, whereas osteoclast number per bone perimeter exhibited a decrease in Igfbp2$^{-/-}$ mice treated with PEG-HBD vs PBS-treated Igfbp2$^{-/-}$ mice (FIG. 4c, Table 6). Interestingly, the number of bone marrow adipocytes was reduced in Igfbp2$^{-/-}$ mice treated with PEG-HBD, although PEG-HBD did not have a direct effect on whole body adiposity (FIG. 4d, Tables 3 and 4). The increase in osteoblast number of the Igfbp2$^{-/-}$ mice treated with PEG-HBD coincident with the reduction in marrow adipocytes implies that allocation of mesenchymal stem cells may be altered towards the osteogenic lineage in mice treated with PEG-HBD. Consistent with this, Pparg expression was reduced in COBs treated with PEG-HBD (FIG. 4e).

Figure 4F:
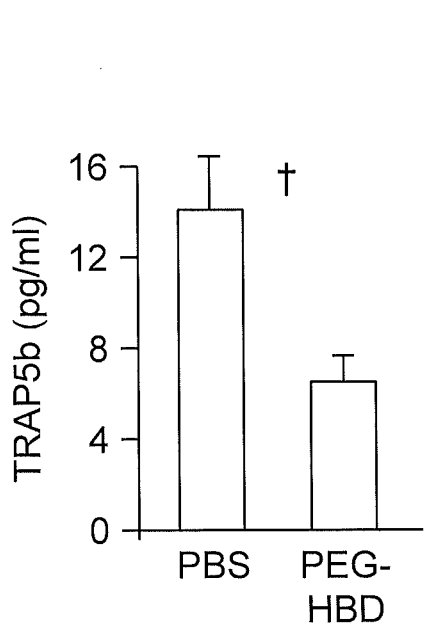
Figure 4G:
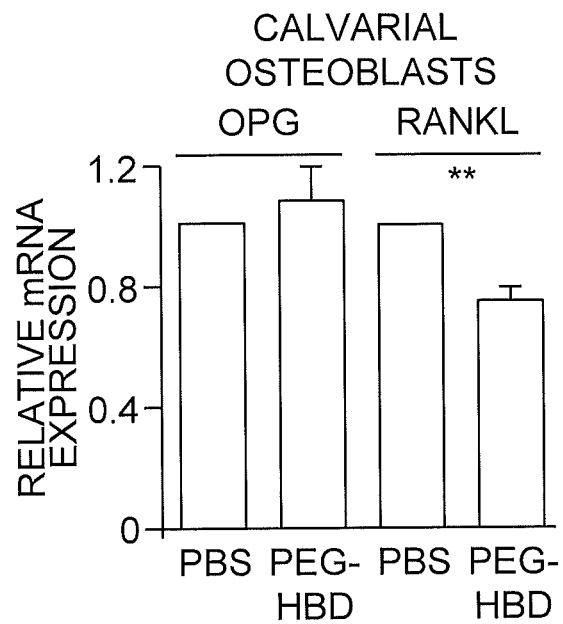
Figure 4H:
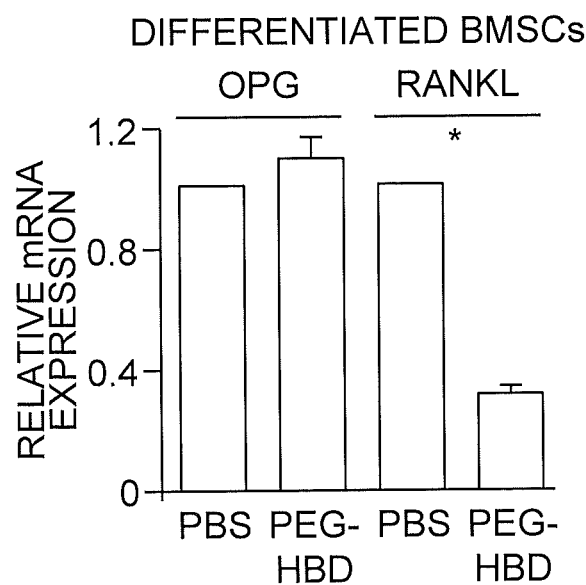

In respect to the reduction in osteoclast number seen on histomorphometry from PEG-HBD treated mice, serum TRAP5b levels were also significantly decreased in Igfbp2$^{-/-}$ mice treated with PEG-HBD (FIG. 4f). To investigate the mechanism whereby PEG-HBD affects osteoclasts, bone marrow stromal cells from Igfbp2$^{-/-}$ mice were cultured and osteoclastogenesis was induced in the presence or absence of the HBD. PEG-HBD did not have a direct effect on osteoclastogenesis (data not shown). Second, Igfbp2$^{-/-}$ COBs and BMSCs were collected and treated with PEG-HBD. PEG-HBD did not affect Opg expression, but it markedly suppressed Rankl expression (FIGS. 4g and h). These data imply that PEG-HBD reduces osteoclastogenesis indirectly through down-regulation of Rankl expression in osteoblasts.

The Heparin-Binding Domain of IGFBP-2 Suppresses PTEN Expression and Stimulates IGF-I/Akt Signaling.

Figure 5A:
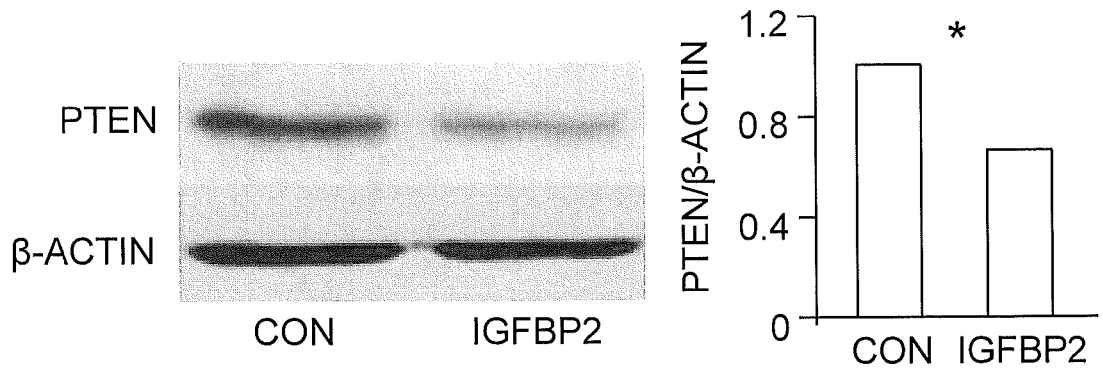
FIG. 5. The heparin-binding domain of IGFBP2 suppresses PTEN expression. a and b, Igfbp2$^{-/-}$ calvarial osteoblasts (COBs) were isolated, and treated with PBS, IGFBP-2 or pegylated heparin-binding domain peptide (PEG-HBD) in MEMα containing 0.1% BSA overnight. Whole cell lysate was collected and expression of PTEN and α-actin was analyzed by Western blot analysis. Expression levels of PTEN were quantified by normalizing to the expression levels of α-actin. c and d. COBs pre-incubated with PBS, IGFBP-2 or PEG-HBD overnight were treated with IGF-I (100 ng/ml) for 15 minutes. Whole cell lysate was collected and expression of pSer473-Akt and Akt was analyzed by Western blot analysis. Expression levels of pSer473-Akt were quantified by normalizing to the expression levels of Akt. Figures shown represent at least 3 independent experiments. Values are expressed as the mean±SEM (n=3-4). Statistical difference was analyzed by Student's t-test. *; <0.001, **; <0.01, $^†$; <0.05.
Figure 5B:
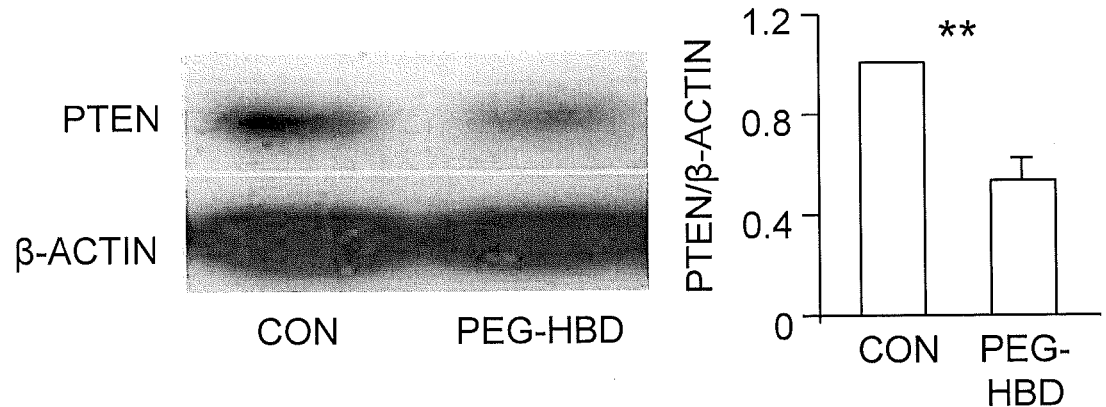
Figure 5C:
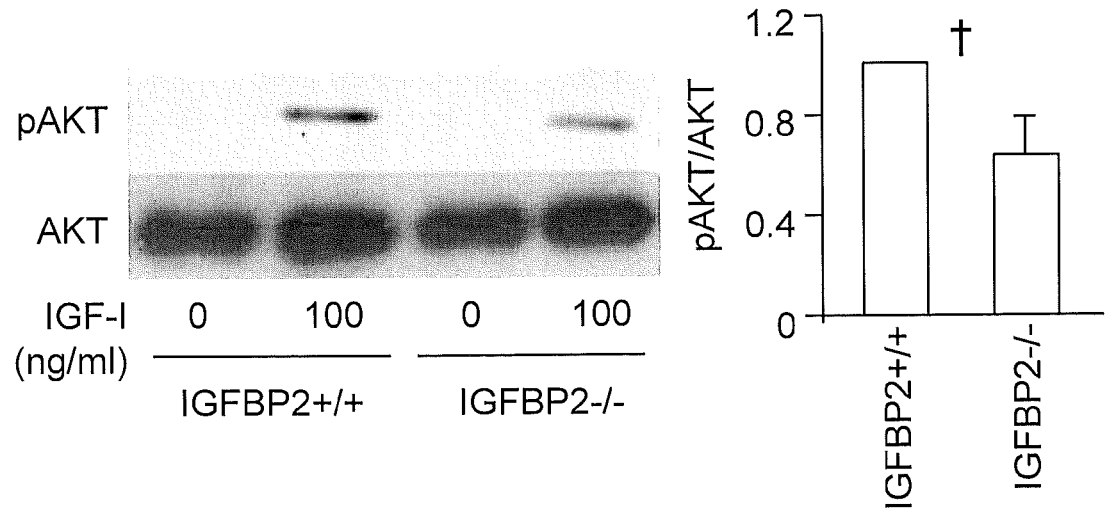
Figure 5D:
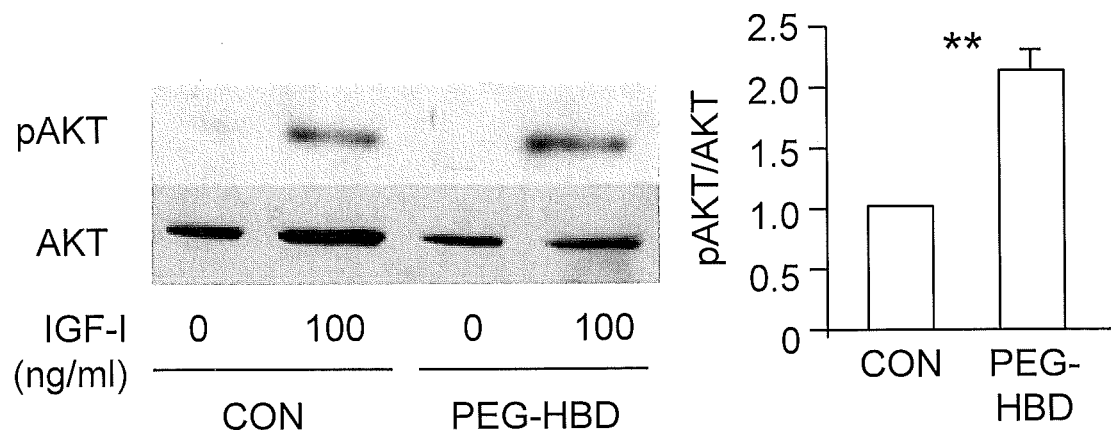
Figure 9A:
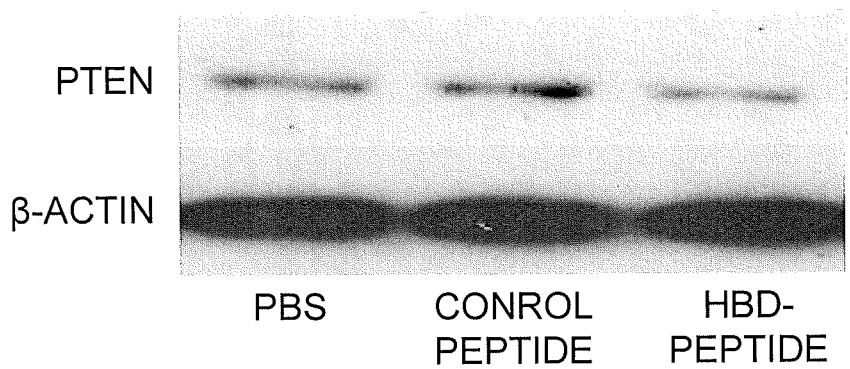
FIG. 9. Control peptide for heparin-binding domain peptide does not suppress PTEN expression in Igfbp2$^{+/+}$ calvarial osteoblasts. Igfbp2$^{+/+}$ calvarial osteoblasts were treated with PBS, control peptide, or heparin-binding domain peptide (HBD-peptide) overnight, and whole cell lysate was collected. PTEN expression was analyzed using western blot analysis (a), and quantitative analysis was performed (b). Values were expressed as the mean±SEM (n=3). Statistical significance was analyzed by ANOVA followed by Bonferroni post-hoc test. $^a$; p<0.01 vs. PBS, $^b$; p<0.01 vs. control peptide.
Figure 9B:
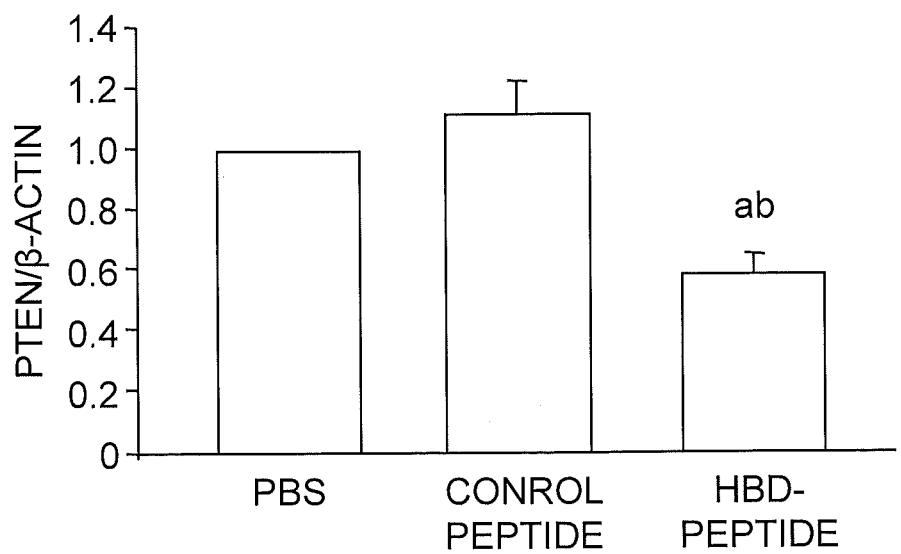

There is evidence of a negative association between IGFBP-2 and PTEN expression in human cancer cells such as glioblastoma and prostate cancer[18-21]. In addition, PTEN expression has beef shown to be enhanced in Igfbp2 deficient osteoblasts[10]. These findings led to the speculation that IGFBP-2 negatively regulates PTEN expression and enhances IGF-I signaling in osteoblasts. First analyses were carried out to determine whether IGFBP-2 suppressed PTEN expression using primary Igfbp2$^{-/-}$ COBs. It was found that full-length IGFBP-2 markedly suppressed PTEN expression in these cells (FIG. 5a). The control peptide had no effect on PTEN expression (FIG. 9), but much like IGFBP-2, PEG-HBD also induced a reduction in PTEN expression (FIG. 5b). Second, analyses were carried out to determine whether the reduction in PTEN expression resulted in enhanced IGF-I/Akt signaling. Western blot analysis for phosphorylation of Akt at serine 473 (pSer473-Akt) revealed that IGF-I stimulated Akt activation was impaired in Igfbp2$^{-/-}$ COBs compared to Igfbp2$^{+/+}$ COBs (FIG. 5c). Furthermore, pSer473-Akt was enhanced in Igfbp2$^{-/-}$ COBs treated with PEG-HBD vs PBS-treated controls (FIG. 5d). These data indicate that IGFBP-2 enhances IGF-I stimulated/Akt activation by suppressing PTEN expression in part through the HBD.

The Heparin-Binding Domain of IGFBP-2 Stimulates IGF-I Induced Cytosolic β-Catenin Accumulation and Ser552 Phosphorylation of β-Catenin.

Figure 6A:
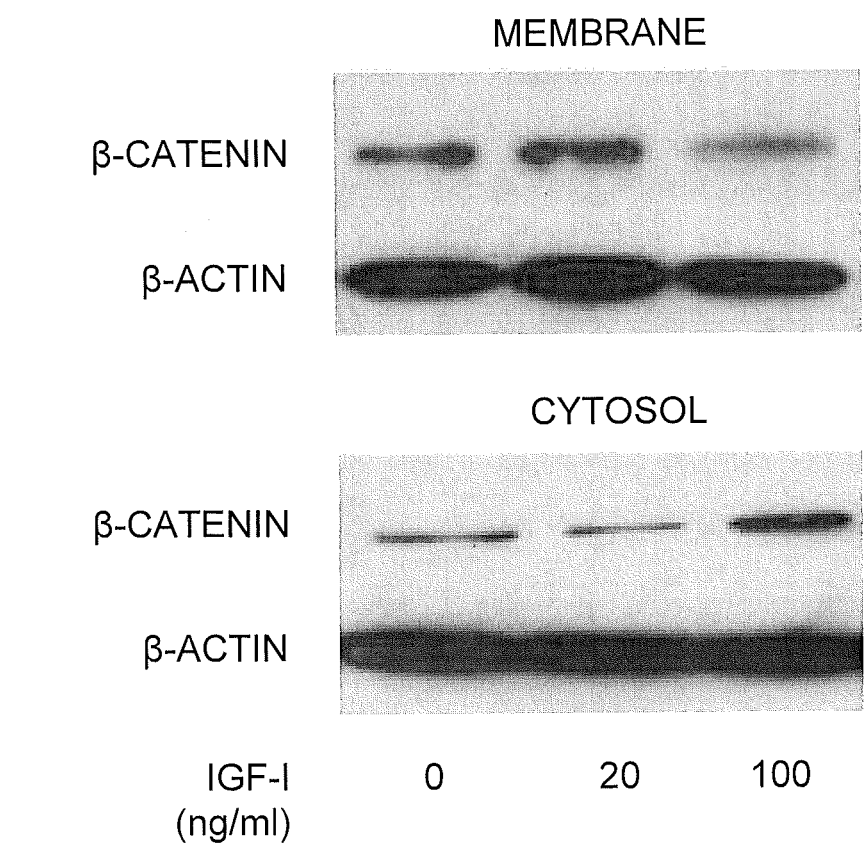
FIG. 6. The heparin-binding domain of IGFBP-2 stimulates cytosolic accumulation and Ser552 phosphorylation of β-catenin by IGF-I. a, MC3T3-E1 cells were serum-starved over-night and treated with IGF-I at the indicated concentration for 6 hours. Expression of β-catenin and α-actin was analyzed by Western blot analysis with membrane and cytosolic fraction. b, Igfbp2$^{-/-}$ calvarial osteoblasts (COBs) were serum-starved over-night with PBS or pegylated heparin-binding domain peptide (PEG-HBD) and then treated with IGF-I (100 ng/ml) for 6 hours. Expression of β-catenin was analyzed by Western blot analysis with cytosolic fraction and quantified by normalizing to α-actin (n=3). c, MC3T3-E1 cells were serum-starved over-night and treated with IGF-I (100 ng/ml) for 15 min. Expression of pSer552-β-catenin, β-catenin, pSer473-Akt, Akt and α-actin was analyzed by Western blot analysis with whole cell lysates. d, Igfbp2$^{-/-}$ COBs were serum-starved over-night with PBS or PEG-HBD and then treated with IGF-I (100 ng/ml) for 15 min. Expression of pSer552-β-catenin was analyzed by Western blot analysis with whole cell lysates and quantified by normalizing to β-catenin (n=3). Figures shown represent at least 3 independent experiments. Values are expressed as the mean±SEM. Statistical difference was analyzed by Student's t-test. *; <0.001, **; <0.01, $^†$; <0.05.
Figure 6B:
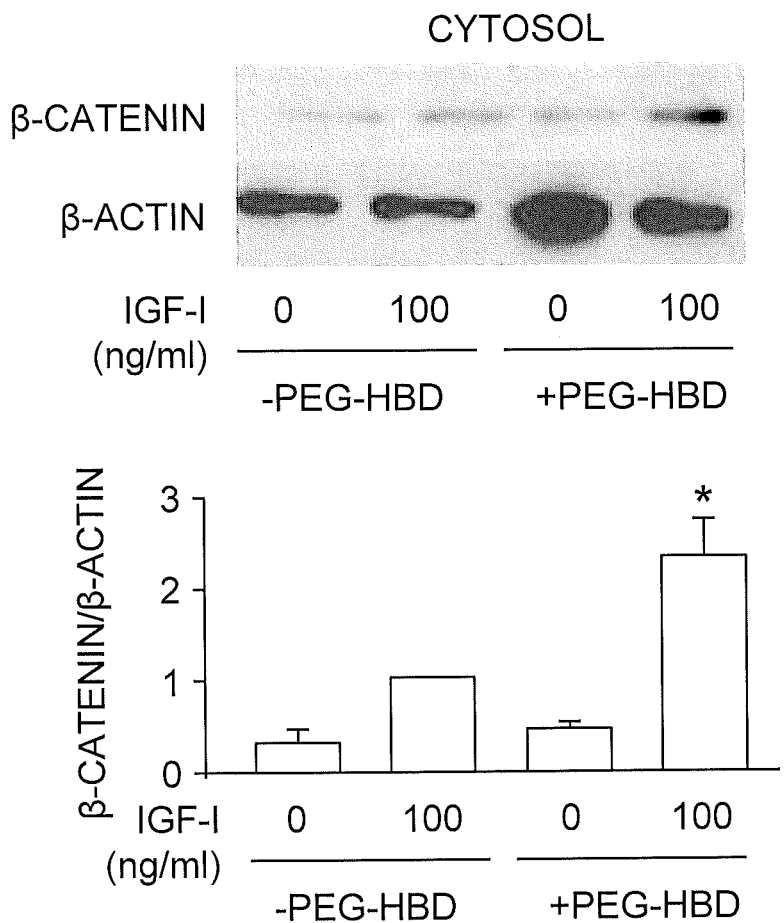
Figure 6C:
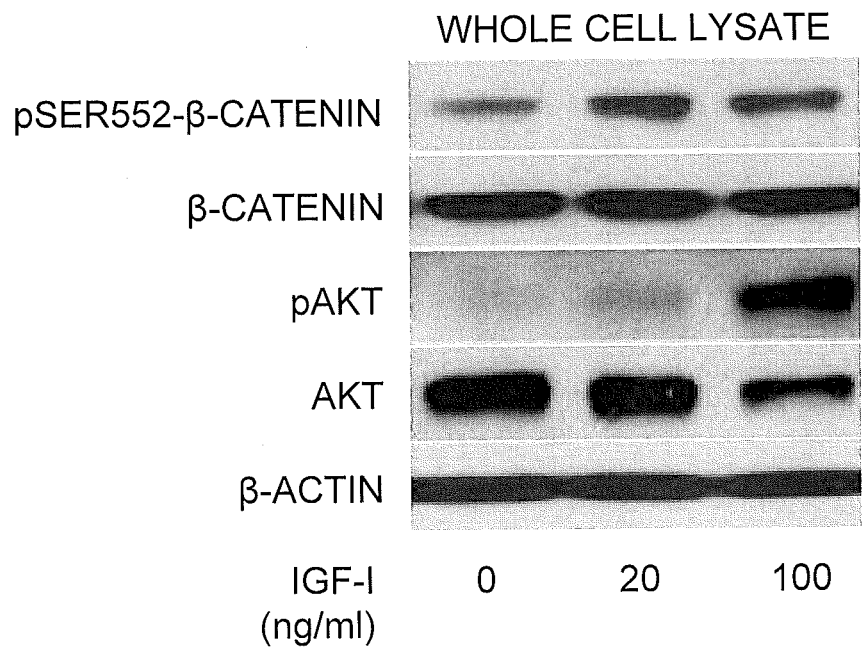
Figure 6D:
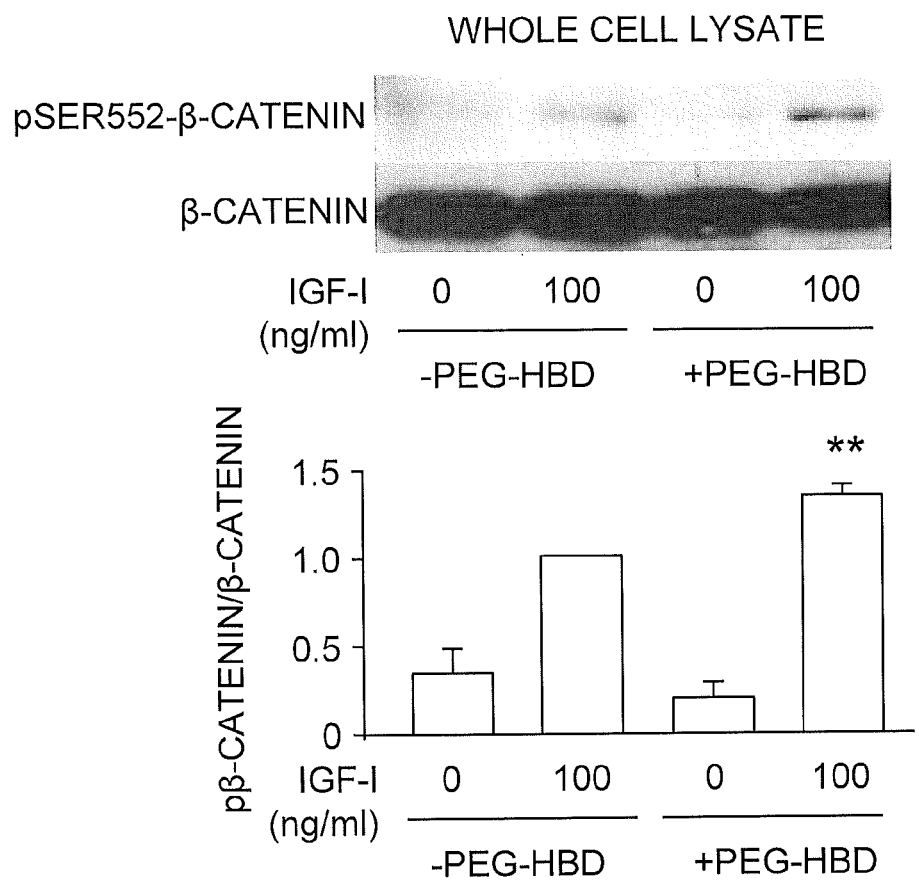

Several lines of evidence demonstrate cross-talk between IGF-I signaling and β-catenin signaling in tumor cell lines[24-27]. Thus, it was hypothesized that IGF-I signaling stimulated β-catenin signaling and that HBD-peptide could enhance β-catenin signaling by suppressing PTEN expression in osteoblastic cells. Analyses were first carried out to determine whether IGF-I affects β-catenin accumulation in the cytosol of osteoblastic cells. Western blot analysis revealed that IGF-I reduced membrane-bound β-catenin expression and enhanced cytosolic accumulation of β-catenin in MC3T3-E1 cells (FIG. 6a). In addition, cytosolic accumulation of β-catenin in response to IGF-I was enhanced in Igfbp2$^{-/-}$ COBs treated with PEG-HBD compared to PBS-treated control cells (FIG. 6b). This suggests that the HBD-peptide is involved in IGF-I/β-catenin signaling possibly by suppressing PTEN expression. Serine 552 (Ser552) phosphorylation of β-catenin, which can be induced by Akt has been shown to be important for dissociation of β-catenin from membrane and re-localization to cytoplasm and nucleus[28-30]. Based on this observation, studies were conducted to determine whether IGF-I stimulated Ser552 phosphorylation in β-catenin and if the HBD-peptide facilitates this response in osteoblastic cells. As shown in FIG. 6c and d, IGF-I stimulated β-catenin phosphorylation on Ser552, and this response was enhanced in cells treated with PEG-HBD. Because activation of β-catenin is important for bone formation, the osteogenic effect of the HBD-peptide might be mediated by IGF-I β-catenin signaling in osteoblasts.

This study provides evidence that the heparin-binding domain of IGFBP-2 may be critical for the anabolic actions of IGFBP-2 on bone. The determination that the HBD suppresses PTEN expression in osteoblasts provides one mechanism by which IGFBP-2 could regulate cell fate. However, sorting the IGF-I dependent and independent activities of intact IGFBP-2 is challenging. IGF-I signaling is a prerequisite for skeletal acquisition and modulation of this signaling pathway results in alterations in skeletal homeostasis[17,34-40]. Therefore, an anabolic effect of the HBD on the skeleton could in part be mediated by enhancement of IGF-1-induced activation of the PI3K/Akt pathway as a result of PTEN suppression. In addition, the increase in osteoblast number in HBD-treated Igfbp2$^{-/-}$ mice could also be due to this mechanistic change since enhanced PI3K/Akt signaling in osteoblasts is involved in cell proliferation. In fact, Liu et al. showed that loss of PTEN in osteoblasts in vivo resulted in very high bone mass and increased osteoblast number[17].

Although the HBD rescued the low osteoblast number in Igfbp2$^{-/-}$ mice, osteoclast number was further diminished by administration of HBD. This observation is consistent with the observed increase in bone mass but suggests that bone turnover is not accelerated by HBD treatment. Indeed, mineral apposition rate and bone formation rate showed minimal changes in Igfbp2$^{-/-}$ mice treated with HBD. In contrast to the HBD, IGF-I signaling has been shown to directly stimulate osteoclastogenesis, and prior data suggest that physiological levels of IGFBP-2 in the skeletal microenvironment are required for osteoclastogenesis[41]. It is possible that IGFBP-2 acts to maintain IGF-I concentrations within the pericellular niche but that the HBD, which lacks the IGF-I binding domain, may play a distinct role by inhibiting bone resorption when supraphysiologic concentrations are administered. Since the HBD does not directly suppress osteoclast differentiation in vitro, the underlying mechanism whereby the HBD decreases bone resorption is likely indirect and due to decreased Rankl expression in osteoblasts. Expression of Rankl is regulated by numerous factors including the Wnt/β-catenin signaling pathway[42]. Glass et al. reported that mice expressing the stabilized form of β-catenin exhibit increased trabecular bone volume with a reduction in osteoclast number primarily caused by an increased Opg/Rankl ratio[43]. Consistent with this, targeted deletion of β-catenin in osteoblasts resulted in low bone mass with increased bone resorption[43]. Thus, stabilization of β-catenin in osteoblasts increases bone mass not only by increasing Wnt mediated activation but also through suppression of bone resorption.

A reduction in PTEN expression has been shown to be associated with increased O-catenin in signaling. Inactivation of GSK3β (glycogen synthase kinase 3) by Akt has been proposed to be the key pathway by which Akt activation enhances β-catenin stabilization, whereas several lines of evidence demonstrate the important role of Ser 552 phosphorylation in β-catenin activation[28-30]. β-catenin is directly phosphorylated by Akt and Ser552 phosphorylation is important for cytosolic and nuclear accumulation of β-catenin, resulting in increased β-catenin transcriptional activity[28]. He et al reported that loss of PTEN resulted in an excess of intestinal stem cells by stimulating β-catenin activity in part through Ser 552 phosphorylation[29]. The current study demonstrated that IGF-I enhanced β-catenin accumulation in cytoplasm and phosphorylated ser552 of β-catenin in osteoblastic cells, and this response was further enhanced by the HBD. Taken together, these lines of evidence suggest that enhanced activation of β-catenin signaling may contribute to both increased bone formation and decreased bone resorption in Igfbp2$^{-/-}$ mice treated with PEG-HBD.

In the PEG-HBD treated Igfbp2$^{-/-}$ mice, osteoblast number was increased and this was accompanied by reduced number of marrow adipocytes. Mesenchymal cell allocation is an important step in regulating bone mass and marrow adiposity. Numerous factors are involved in this process including Wnt/β-catenin signaling and the transcription factor, PPAR-gamma[44]. Activation of Wnt/β-catenin signaling favors osteoblastogenesis over adipogenesis in part by either sequestering PPAR-gamma or suppressing PPAR-gamma transcriptional activity[45-47]. Because HBD enhances β-catenin stability that is induced by IGF-I, the switch of mesenchymal cells towards the osteogenic lineage might explain the increased osteoblasts and reduced adipocytes in bone marrow from Igfbp2$^{-/-}$ mice treated with PEG-HBD.

Nevertheless, the mechanism by which the HBD suppresses PTEN expression has not been defined. One possibility resides in the binding of HBD with the integrin receptor. Maile et al. reported that the heparin-binding domain of vitronectin bound to a cystein loop region of β3 integrin and modulated αVβ3 integrin signaling in smooth muscle cells[48]. Furthermore, Perks et al. reported that PTEN down-regulation by IGFBP-2 might be mediated by an integrin receptor, although they did not demonstrate an interaction between IGFBP-2 and a specific integrin receptor or whether the HBD was involved in this interaction[20].

The presence of an RGD sequence motif in the C-terminus of IGFBP-2 has led to speculation that IGFBP-2 could bind to an integrin, independent of its IGF-binding[3]. Schutt et al. reported that IGFBP-2 binding to the cell surface was mediated through α5β1 integrin, and blocked by RGD-containing peptide in Ewing sarcoma and breast cancer cell lines[49]. Wang et al. also showed that IGFBP-2 interacted with α5 integrin through an RGD motif in a human glioblastoma cell line[50]. In contrast to these reports, Russo et al. and Pereira et al. independently reported that IGFBP-2 binding to extracellular matrix was independent of RGD sequences in neuroblastoma cells and breast cancer cells. In addition, Hoeflich et al. showed that the RGD motif is not involved in IGFBP-2 binding to plasma membrane in multiple organs[51]. Thus, the functional role of the RGD motif in Igfbp2$^{-/-}$ mice remains controversial and further studies are needed.

Results using a supraphysiologic concentration of the HBD cannot be used to reach a definitive conclusion regarding the role of physiologic concentrations of IGFBP-2 in bone acquisition. However, it does suggest that this binding protein has unique properties that might explain the high circulating levels of IGFBP-2 during periods of rapid growth such as the first year of life and during puberty. In summary, these studies show that the HBD in IGFBP-2 has an anabolic effect on the skeleton and this effect is partially mediated by the suppression of PTEN expression and involves activation of β-catenin signaling. These lines of evidence provide new insights regarding the physiologic role of IGFBP-2 in bone and suggest that a small molecule such as the HBD-peptide could have potential as a pharmacological intervention for the treatment of osteoporosis.

REFERENCES FOR EXAMPLE 8

1. Hwa, V., Oh, Y. & Rosenfeld, R. G. The insulin-like growth factor-binding protein (IGFBP) superfamily. *Endocr Rev* 20, 761-87 (1999).
2. Jones, J. I. & Clemmons, D. R. Insulin-like growth factors and their binding proteins: biological actions. *Endocr Rev* 16, 3-34 (1995).
3. Firth, S. M. & Baxter, R. C. Cellular actions of the insulin-like growth factor binding proteins. *Endocr Rev* 23, 824-54 (2002).
4. Hu, D. et al. Serum insulin-like growth factor-1 binding proteins 1 and 2 and mortality in older adults: the Health, Aging, and Body Composition Study. *J Am Geriatr Soc* 57, 1213-8 (2009).
5. Hedbacker, K. et al. Antidiabetic effects of IGFBP2, a leptin-regulated gene. *Cell Metab* 11, 11-22.
6. Wheatcroft, S. B. et al. IGF-binding protein-2 protects against the development of obesity and insulin resistance. *Diabetes* 56, 285-94 (2007).
7. Hoeflich, A. et al. Growth inhibition in giant growth hormone transgenic mice by overexpression of insulin-like growth factor-binding protein-2. *Endocrinology* 142, 1889-98 (2001).
8. Conover, C. A. et al. Subcutaneous administration of insulin-like growth factor (IGF)-II/IGF binding protein-2 complex stimulates bone formation and prevents loss of bone mineral density in a rat model of disuse osteoporosis. *Growth Horm IGF Res* 12, 178-83 (2002).
9. Khosla, S. et al. Insulin-like growth factor system abnormalities in hepatitis C-associated osteosclerosis. Potential insights into increasing bone mass in adults. *J Clin Invest* 101, 2165-73 (1998).
10. DeMambro, V. E. et al. Gender-specific changes in bone turnover and skeletal architecture in igfbp-2-null mice. *Endocrinology* 149, 2051-61 (2008).
11. Arai, T., Busby, W., Jr. & Clemmons, D. R. Binding of insulin-like growth factor (IGF) I or II to IGF-binding protein-2 enables it to bind to heparin and extracellular matrix. *Endocrinology* 137, 4571-5 (1996).
12. Russo, V. C., Bach, L. A., Fosang, A. J., Baker, N. L. & Werther, G. A. Insulin-like growth factor binding protein-2 binds to cell surface proteoglycans in the rat brain olfactory bulb. *Endocrinology* 138, 4858-67 (1997).
13. Russo, V. C., Rekaris, G., Baker, N. L., Bach, L. A. & Werther, G. A. Basic fibroblast growth factor induces proteolysis of secreted and cell membrane-associated insulin-like growth factor binding protein-2 in human neuroblastoma cells. *Endocrinology* 140, 3082-90 (1999).
14. Russo, V. C. et al. Insulin-like growth factor binding protein-2 binding to extracellular matrix plays a critical role in neuroblastoma cell proliferation, migration, and invasion. *Endocrinology* 146, 4445-55 (2005).
15. Duan, C., Ding, J., Li, Q., Tsai, W. & Pozios, K. Insulin-like growth factor binding protein 2 is a growth inhibitory protein conserved in zebrafish. *Proc Natl Acad Sci USA* 96, 15274-9 (1999).
16. Kawai, M. & Rosen, C. J. Insulin-like growth factor-I and bone: lessons from mice and men. *Pediatr Nephrol* 24, 1277-85 (2009).
17. Liu, X. et al. Lifelong accumulation of bone in mice lacking Pten in osteoblasts. *Proc Natl Acad Sci USA* 104, 2259-64 (2007).
18, Cohen, P. et al. Elevated levels of insulin-like growth factor-binding protein-2 in the serum of prostate cancer patients. *J Clin Endocrinol Metab* 76, 1031-5 (1993).
19. Mehrian-Shai, R. et al. Insulin growth factor-binding protein 2 is a candidate biomarker for PTEN status and PI3K/Akt pathway activation in glioblastoma and prostate cancer. *Proc Natl Acad Sci USA* 104, 5563-8 (2007).

20. Perks, C. M., Vernon, E. G., Rosendahl, A. H., Tonge, D. & Holly, J. M. IGF-II and IGFBP-2 differentially regulate PTEN in human breast cancer cells. *Oncogene* 26, 5966-72 (2007).
21. Levitt, R. J., Georgescu, M. M. & Pollak, M. PTEN-induction in U251 glioma cells decreases the expression of insulin-like growth factor binding protein-2. *Biochem Biophys Res Commun* 336, 1056-61 (2005).
22. Sakata, T. et al. Skeletal unloading induces resistance to insulin-like growth factor-I (IGF-I) by inhibiting activation of the IGF-I signaling pathways. *J Bone Miner Res* 19, 436-46 (2004).
23. Shoba, L. N. & Lee, J. C. Inhibition of phosphatidylinositol 3-kinase and p70S6 kinase blocks osteogenic protein-1 induction of alkaline phosphatase activity in fetal rat calvaria cells. *J Cell Biochem* 88, 1247-55 (2003).
24. Jin, T., George Fantus, I. & Sun, J. Wnt and beyond Wnt: multiple mechanisms control the transcriptional property of beta-catenin. *Cell Signal* 20, 1697-704 (2008).
25. Desbois-Mouthon, C. et al. Insulin and IGF-1 stimulate the beta-catenin pathway through two signalling cascades involving GSK-3beta inhibition and Ras activation. *Oncogene* 20, 252-9 (2001).
26. Playford, M. P., Bicknell, D., Bodmer, W. F. & Macaulay, V. M. Insulin-like growth factor 1 regulates the location, stability, and transcriptional activity of beta-catenin. *Proc Natl Acad Sci USA* 97, 12103-8 (2000).
27. Amin, S. et al. High serum IGFBP-2 is predictive of increased bone turnover in aging men and women. *J Bone Miner Res* 22, 799-807 (2007).
28. Fang, D. et al. Phosphorylation of beta-catenin by AKT promotes beta-catenin transcriptional activity. *J Biol Chem* 282, 11221-9 (2007).
29. He, X. C. et al. PTEN-deficient intestinal stem cells initiate intestinal polyposis. *Nat Genet.* 39, 189-98 (2007).
30. Taurin, S., Sandbo, N., Qin, Y., Browning, D. & Dulin, N. O. Phosphorylation of beta-catenin by cyclic AMP-dependent protein kinase. *J Biol Chem* 281, 9971-6 (2006).
31. Glass, D. A., 2nd & Karsenty, G. Molecular bases of the regulation of bone remodeling by the canonical Wnt signaling pathway. *Curr Top Dev Biol* 73, 43-84 (2006).
32. Eckstein, F. et al. Insulin-like growth factor-binding protein-2 (IGFBP-2) overexpression negatively regulates bone size and mass, but not density, in the absence and presence of growth hormone/IGF-I excess in transgenic mice. *Anat Embryol (Berl)* 206, 139-48 (2002).
33. Palermo, C. et al. Potentiating role of IGFBP-2 on IGF-II-stimulated alkaline phosphatase activity in differentiating osteoblasts. *Am J Physiol Endocrinol Metab* 286, E648-57 (2004).
34. Fujita, T. et al. Runx2 induces osteoblast and chondrocyte differentiation and enhances their migration by coupling with PI3K-Akt signaling. *J Cell Biol* 166, 85-95 (2004).
35. Peng, X. D. et al. Dwarfism, impaired skin development, skeletal muscle atrophy, delayed bone development, and impeded adipogenesis in mice lacking Akt1 and Akt2. *Genes Dev* 17, 1352-65 (2003).
36. Liu, J. P., Baker, J., Perkins, A. S., Robertson, E. J. & Efstratiadis, A. Mice carrying null mutations of the genes encoding insulin-like growth factor I (Igf-1) and type 1 IGF receptor (Igf1r). *Cell* 75, 59-72 (1993).
37. Yakar, S. et al. Circulating levels of IGF-1 directly regulate bone growth and density. *J Clin Invest* 110, 771-81 (2002).
38. Zhang, M. et al. Osteoblast-specific knockout of the insulin-like growth factor (IGF) receptor gene reveals an essential role of IGF signaling in bone matrix mineralization. *J Biol Chem* 277, 44005-12 (2002).
39. Zhao, G, et al. Targeted overexpression of insulin-like growth factor I to osteoblasts of transgenic mice: increased trabecular bone volume without increased osteoblast proliferation. *Endocrinology* 141, 2674-82 (2000).
40. Mukherjee, A. & Rotwein, P. Akt promotes BMP2-mediated osteoblast differentiation and bone development. *J Cell Sci* 122, 716-26 (2009).
41. Wang, Y. et al. Role of IGF-I signaling in regulating osteoclastogenesis. *J Bone Miner Res* 21, 1350-8 (2006).
42. Kearns, A. E., Khosla, S. & Kostenuik, P. J. Receptor activator of nuclear factor kappaB ligand and osteoprotegerin regulation of bone remodeling in health and disease. *Endocr Rev* 29, 155-92 (2008).
43. Glass, D. A., 2nd et al. Canonical Wnt signaling in differentiated osteoblasts controls osteoclast differentiation. *Dev Cell* 8, 751-64 (2005).
44. Gesta, S., Tseng, Y. H. & Kahn, C. R. Developmental origin of fat: tracking obesity to its source. *Cell* 131, 242-56 (2007).
45. Liu, J., Wang, H., Zuo, Y. & Farmer, S. R. Functional interaction between peroxisome proliferator-activated receptor gamma and beta-catenin. *Mol Cell Biol* 26, 5827-37 (2006).
46. Bennett, C. N. et al. Regulation of osteoblastogenesis and bone mass by Wnt10b. *Proc Natl Acad Sci USA* 102, 3324-9 (2005).
47. Ross, S. E. et al. Inhibition of adipogenesis by Wnt signaling. *Science* 289, 950-3 (2000).
48. Maile, L. A. et al. Modulation of integrin antagonist signaling by ligand binding of the heparin-binding domain of vitronectin to the alphaVbeta3 integrin. *J Cell Biochem* 105, 437-46 (2008).
49. Schutt, B. S., Langkamp, M., Rauschnabel, U., Ranke, M. B. & Elmlinger, M. W. Integrin-mediated action of insulin-like growth factor binding protein-2 in tumor cells. *J Mol Endocrinol* 32, 859-68 (2004).
50. Wang, G. K., Hu, L., Fuller, G. N. & Zhang, W. An interaction between insulin-like growth factor-binding protein 2 (IGFBP2) and integrin alpha5 is essential for IGFBP2-induced cell mobility. *J Biol Chem* 281, 14085-91 (2006).
51. Hoeflich, A. et al. Mutation of the RGD sequence does not affect plasma membrane association and growth inhibitory effects of elevated IGFBP-2 in vivo. *FEBS Lett* 523, 63-7 (2002).
52. Wood, T. L., Rogler, L. E., Czick, M. E., Schuller, A. G. & Pintar, J. E. Selective alterations in organ sizes in mice with a targeted disruption of the insulin-like growth factor binding protein-2 gene. *Mol Endocrinol* 14, 1472-82 (2000).
53. Rosen, C. J. et al. Congenic mice with low serum IGF-I have increased body fat, reduced bone mineral density, and an altered osteoblast differentiation program. *Bone* 35, 1046-58 (2004).
54. Mukherjee, A. & Rotwein, P. Insulin-like growth factor-binding protein-5 inhibits osteoblast differentiation and skeletal growth by blocking insulin-like growth factor actions. *Mol Endocrinol* 22, 1238-50 (2008).
55. Kawai, M. et al. Growth hormone stimulates adipogenesis of 3T3-L1 cells through activation of the Stat5A/5B-PPARgamma pathway. *J Mol Endocrinol* 38, 19-34 (2007).

Example 9

Efficacy of the Peptide in Inhibiting Fat Accumulation

A variety of data in the literature support that IGFBP-2 inhibits fat accumulation. These data include studies in which IGFBP-2 was overexpressed in mice; that is transgenic mice that produced excessive IGFBP-2 were created. These animals had decreased fat mass. Importantly when they were fed a high fat diet which normally induces glucose intolerance, they maintained normal glucose tolerance compared to control mice that were fed the same high fat diet and developed hyperglycemia. This suggests that IGFBP-2 protects against insulin resistance. In contrast the mice in which the IGFBP-2 gene was deleted had the opposite phenotype; that is they were significantly fatter than control mice. After 24 weeks the IGFBP-2 knockout mice weighed 37±1.5 gm whereas control animals weighed 32±1.3 gm. After 52 weeks this difference was maintained. This is a highly significant difference in total body weight. More importantly when fat mass was analyzed by DEXA scanning almost the entire difference in body weight was due to a difference in fat mass. At 26 weeks the percent body fat in the control mice was 16.1±1.4% fat whereas in the knockout mice it was 24.2±1.1%. Again this is a highly significant difference and indicates that much of the difference in weight was due to a difference in fat. Glucose tolerance testing showed that the IGFBP-2 gene deletion mice had glucose intolerance and were less sensitive to the administration of insulin. This indicates that the increased fat mass caused increased resistance to the hormone insulin. Blood insulin levels were higher in the IGFBP-2 knockout mice showing they had insulin resistance which resulted in high serum insulin concentrations. This has been shown by others to be an important risk factor for cardiovascular disease.

Further experiments have been carried out in which the knockout mice and control animals have been administered the mouse homologue of the heparin binding peptide. The peptide was administered to 8 animals in each group. The 6 week treatment data are provided in Table 2. The knockout animals weighed 30.4±1.5 gm whereas the control animals weighed 25.2±1.1 gm. The knockout animals that received the active peptide weighed 24.9±1.3 gm. This clearly indicated that administration of peptide which was given at a dose of 50 mcg administered intraperitoneally three days per week was effective in preventing weight gain. More importantly when absolute fat mass was analyzed by MRI, highly significant differences were also present. The knockout mice had 6.21±0.76 grams of fat. The control mice had 3.82±0.67 grams and the knockout mice administered the heparin binding peptide had 3.67±0.36 grams. Again these are highly significant differences. Glucose tolerance tests were also performed in these animals and showed that the knockout animals have impaired glucose tolerance and this was significantly improved with administration of the peptide and not significantly different from control mice.

Example 10

Global Deletion of IGFBP-2 Disrupts Hematopoiesis and Compromises Bone Marrow Engraftment in Lethally Irradiated Mice Studies were carried out to determine if global deletion of IGFBP2 (BP2) might disrupt steady-state hematopoiesis and interfere with the engraftment of bone marrow donor cells. Peripheral blood and spleen cells from male (M) and female (F) WT and BP2−/− mice were first analyzed by flow cytometry for the major white blood cell (WBC) populations. In peripheral blood, BP2−/−F-mice had significantly lower CD3+ T cells compared to WT-F and BP2−/− M (p=0.02) while BP2−/−M had significantly increased CD3+ T cells (p=0.03), CD19+ B cells (p=0.00), F480+ macrophages (p=0.00), CD11b+ monocytes (p=0.00) and LY6G+ neutrophils (p=0.02) compared to both WT-M and BP2−/−F. Intraperitoneal injection of IGFBP-2 heparin binding domain (HBD) peptide reduced the percentage of macrophages (p=0.01) and neutrophils (p=0.02) in peripheral blood of BP2−/− M compared to PBS injected controls. BP2−/−F splenic CD3+ T cells were increased (p=0.0) and CD19+ B cells were decreased (p=0.05) compared to WT-F, WT-M and BP2−/−M. There was a significant increase in B220+ B cell progenitor cells in the spleens of BP2−/− M compared to WT-M but no difference in the percentages of all other mature WBC populations. Bone marrow transplants into lethally irradiated WT and BP2−/− male recipients were next performed. In non-competitive transplants, the efficiency of donor engraftment was the same for both strains as ≥75% of the repopulating cells in both WT and BP2−/− were of donor origin (Ly5.1+). In competitive repopulation transplants, support donor cells from LY5.1+ mice were mixed with competitor donor cells from either WT or BP2−/− in 2:3 and 1:3 ratios and transplanted into strain specific recipients. At 8 weeks post transplant, WT recipients in which ⅔ of the donor cells were WT (LY5.2+), 75% of bone marrow cells were of WT origin (LY5.2+) while in BP2−/− recipients in which ⅔ of the donor cells were from BP2−/− (LY5.2+) only 56% of bone marrow cells were LY5.2+ at 8 weeks post transplant representing 20% less (p=0.01) engraftment of BP2−/− donor cells compared to WT. These data confirm that IGFBP2 may be an important regulator of the hematopoietic stem cell niche.

Example 11

IGFBP-2 from Mesenchymal Stromal Cells (MSCs) in the Bone Marrow Niche Regulates Hematopoietic Stem Cell Proliferation and Marrow Engraftment IGFBP2 (BP2) is one of 6 IGF binding proteins that shuttles IGFs to their respective receptors. PTH has been shown to induce IGFBP2 synthesis in calvarial osteoblasts and global deletion of BP2 results in small spleens, very low bone formation, impaired bone resorption and increased marrow adiposity. In vitro, bone marrow from bp2−/− mice show impaired recruitment of both osteoblasts and osteoclasts. BP2 null males also have a hematopoietic phenotype in which increased percentages of lymphoid and myeloid subpopulations are found in both the peripheral blood and spleen. Studies were conducted to determine if BP2 serves a critical role as a proliferative factor in the bone marrow niche. Using RNA from purified mouse mesenchymal stem cells (Stem Cell Technologies), it was first determined that BP2 gene expression levels were 6-8 times higher than in purified B or T cells. Non competitive bone marrow transplants (BMT) were performed by transplanting LY 5.1+ donor cells into lethally irradiated WT and bp2−/− recipients. Donor engraftment was not different between strains as shown by greater than 70% donor cells present in the peripheral blood of recipient mice from both strains. However, in competitive repopulation transplantation using same strain donor-recipient pairs, bp2−/− donor cells engrafted bp2−/− recipient bone marrow 30% less efficiently (P=0.01) than WT transplants. In addition, there were significantly fewer mature lymphoid (CD3, CD19) and myeloid (CD11b, LY6G and F480) cells in the peripheral blood of bp2−/− recipients (p≤0.05). In response to administration of a single component of the IGFBP2 molecule, the heparin binding domain (HBD), to bp2−/− mice, trabecular bone mass was rescued and osteoblast number increased. Importantly, in vivo administration of the HBD suppressed the percentages of mature monocytes, macrophages and neutrophils in the peripheral circulation, comparable to those found in WT mice. Taken together these data demonstrate that BP2, which is synthesized by MSCs and inducible by PTH, is a potent regulator of hematopoiesis and may specifically control stem cell fate in an IGF binding independent manner within the marrow niche. Niche regulation by IGFBP2 may be therapeutically important to clinical bone marrow transplantation which is currently the only treatment option for many hematologic and solid tissue malignancies.

Example 12

Regulation of Hematopoietic Stem Cells by the Heparin Binding Domain of IGFBP-2

The following studies are described to determine the role of IGFBP-2, through its heparin binding domain, in enhancing the success of bone marrow transplantation by stimulating hematopoietic bone marrow repopulation.

Rationale.

Hematopoietic stem cell transplantation is used primarily in the treatment of hematopoietic cancers (leukemias and lymphomas), following high dose chemotherapy for non hematopoietic malignancies. It is also used for diseases involving genetic or acquired bone marrow failure, such as aplastic anemia and autoimmune diseases. Positive transplant outcomes are dependent upon (1) retrieval of sufficient numbers of hematopoietic stem cells (HSCs) from donor bone marrow, cord blood or peripheral blood and (2) successful homing of HSCs to the recipient's bone marrow[1]. IGFBP-2 has been shown to be a necessary factor for the in vitro proliferation of both human and murine hematopoietic stem cells[2,3]. Consistent with this result, it has been found that global deletion of IGFBP-2 in mice results in compromised repopulation of the bone marrow following lethal irradiation. A peptide unique to the heparin binding domain (HBD) of IGFBP-2 has been synthesized and it has been demonstrated that this peptide has the ability to increase osteoblast and bone marrow stromal cell numbers in vitro and to enhance bone formation in vivo independently of IGF signaling. These studies investigate the role of the HBD of IGFBP-2 in hematopoietic stem cell transplantation, a critical component of therapeutic anti-cancer regimens.

Significance.

Successful bone marrow transplantation is an important therapeutic option for both hematologic and solid tissue neoplasms. For example, a major advance in treating multiple myeloma has been the transplantation of bone marrow hematopoietic stem cells (HSCs). Propagation of HSCs prior to transplant increases the likelihood of successful engraftment and re-establishment of steady state hematopoiesis[4]. IGFBP-2 has been shown to be a potent stimulus for the in vitro proliferation of mouse and human hematopoietic stem cells[2,3]. However, the mechanism responsible for this effect is unknown. Recent studies have established the importance of IGFBP-2 for successful in vivo bone marrow transplantation as well as its capacity to stimulate mesenchymal stromal cell (MSC) differentiation. The studies described herein are intended to elucidate the pathways through which IGFBP-2 increases HSC proliferation and enhances establishment of the hematopoietic stem cell niche. As HSC transplantation is widely used as a therapy for both hematopoietic and non hematopoietic malignancies, these studies should have broad therapeutic implications.

Background.

The potential of the stem cell niche to respond to stress and injury requires not only HSCs but also bone forming osteoblasts[5,6]. Insulin-Like Growth Factor Binding Protein 2 (IGFBP-2) is one of six IGF binding proteins (IGFBP 1-6) that regulates the bioavailability of the proliferative growth factors IGF-I and IGF-II. Studies have established the importance of IGFBP-2 in regulating osteoblast proliferation and differentiation[7]. Preliminary evidence suggests that IGFBP-2 can act independently of IGF, but the mechanisms underlying these actions have yet to be investigated. For example, cell mobility in glioblastoma appears to be mediated by the binding of IGFBP-2 to the integrin α5 receptor via the Arg-Gly-Asp (RGD) domain[8]. In addition, proteolytic cleavage of IGFBP2 results in small fragments that include the heparin binding domain (HBD). When the HBD binds to the extracellular matrix, it can stimulate the proliferation and metastatic behavior of neuroblastoma cells[9]. A small molecule containing the HBD present in the linker region of IGFBP-2 has been synthesized. Of the two HBDs in this molecule, the one synthesized is unique to IGFBP-2 and is not represented in other IGFBPs. This peptide is studied for its effect on HSC proliferation, migration, and bone marrow homing with the ultimate goal of defining the usefulness of the HBD as an adjuvant for HSC transplantation therapies.

Data in Support of Proposed Investigation.

Figure 10:
FIG. 10. The HBD of IGFBP-2 increased cell proliferation of osteoblasts and bone marrow stromal cells as compared to full length (FL) IGFBP-2 (BP2) and control peptide and as seen by increased alkaline phosphatase and alizarin red staining, respectively.
Figure 10:
Figure 11:
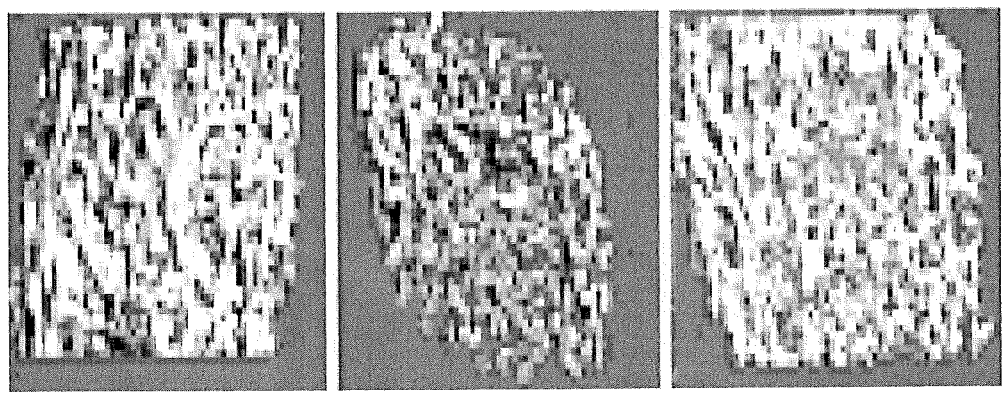
FIG. 11. The HBD of IGBP-2 rescued the low bone mass phenotype of Igfbp2$^{-/-}$ mice in vivo, as shown by μCT analysis.

In the context of bone formation, the IGF independent actions of IGFBP-2 were investigated using a synthesized peptide of the HBD contained in the linker region of IGFBP-2. This peptide is distinct from the other IGF binding proteins. In vitro, the HBD peptide rescued the low bone mineralization phenotype of Igfbp2−/− bone marrow stromal cells and calvarial osteoblasts (FIG. 10) and stimulated periosteal expansion and growth in ex vivo explants of Igfbp2−/− metacarpals. In vivo, the HBD peptide rescued the low bone mass phenotype of Igfbp2−/− mice, as seen by increased osteoblast number, restored bone mass, and improved bone strength (FIG. 11).

Figure 12:
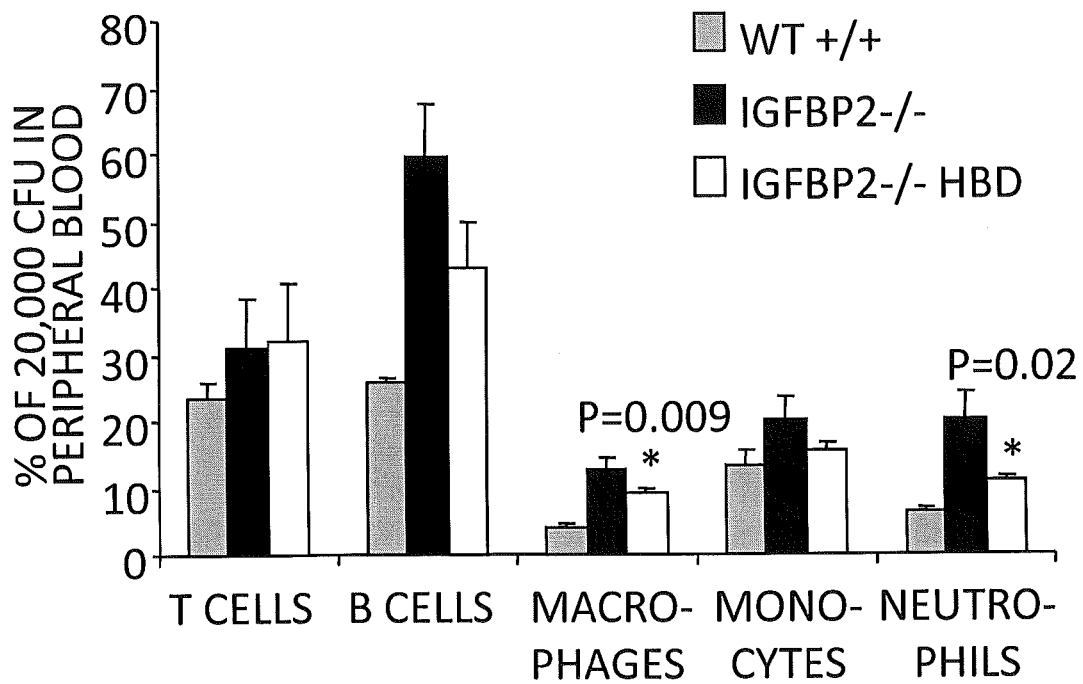
FIG. 12. HBD reversed the increased lymphoid and myeloid hematopoietic phenotype of Igfbp2$^{-/-}$ mice.
Figure 13:
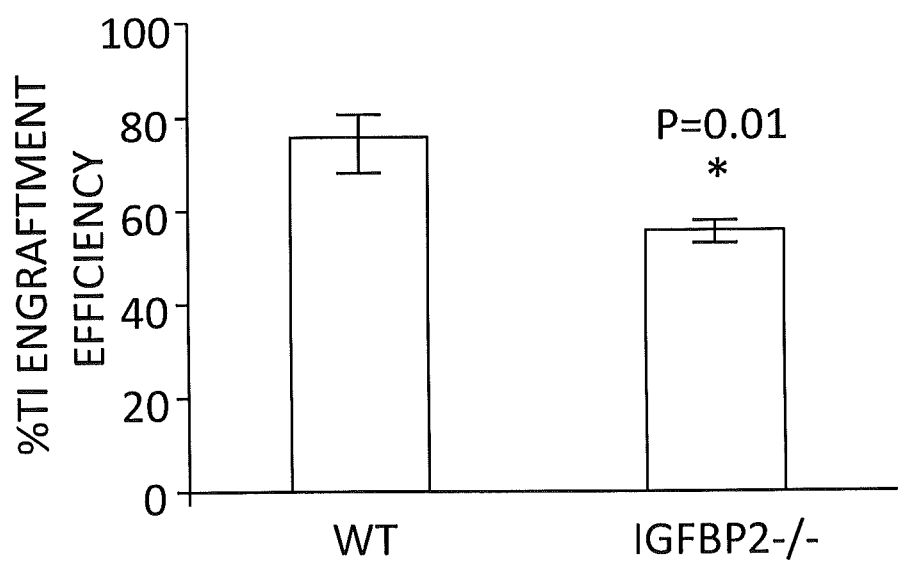
FIG. 13. In competitive re-population bone marrow transplants, Igfbp2$^{-/-}$ bone marrow donor cells repopulated the bone marrow of same-strain recipients with 30% less efficiency than Igfbp2$^{+/+}$ donor cells.

In addition to its actions on mesenchymal cells, IGFBP-2 has been shown to be a necessary factor for the in vitro proliferation of murine and human hematopoietic stem cells. Global deletion of IGFBP-2 results in altered hematopoiesis such that the peripheral blood and spleen of Igfbp2−/− mice contain significantly increased B lymphocytes and myeloid lineage cells. In vivo administration of the HBD reduced the number of differentiated lymphoid and myeloid cells to the baseline percentages of PBS injected controls (FIG. 12). Furthermore, in competitive repopulation bone marrow transplants, Igfbp2−/− donor cells failed to efficiently repopulate the bone marrow of same strain recipients (FIG. 13).

Taken together, these findings indicate that the HBD may be an important component of IGFBP-2 signaling to enhance cell proliferation and suppress differentiation in HSCs. The studies described herein are to determine if the growth promoting effects of IGFBP-2 on HSCs are mediated through the HBD and are independent of the actions of IGF-I.

Investigation of the Effect of the IGFBP-2 Heparin Binding Domain Peptide (HBD) on Hematopoietic Stem Cell Proliferation and Differentiation In Vitro.

Rationale:

Increasing the number of long term (LT) HSCs in donor bone marrow cell preparations prior to bone marrow transplantation improves transplantation outcomes. In vitro, IGFBP-2 acts to increase the proliferation of HSCs, but the mechanism underlying this effect is unknown. IGFBP-2 has been shown to act independently of IGF-1 signaling via the RGD and HBD domains. Using a synthesized HBD peptide unique to IGFBP-2, the ability of the HBD to increase the proliferation of human and murine HSCs and maintain the HSCs in an undifferentiated state will be tested. To delineate IGFBP-2 independent effects, the HBD will be tested in vitro on mouse HSCs collected from both Igfbp2−/− and Igfbp2+/+ mice.

Design and Methods:

The Igfbp2−/− mouse was created by Dr. John Pintar in the 1990s and then backcrossed to B6 by Dr. Terri Wood in the early 2000s. These mice were obtained from Dr. Wood and they continued to be backcrossed to C57BL6 at The Jackson Laboratory. The HBD peptide and scrambled control peptide are provided by David Clemmons, MD, at UNC Chapel Hill. To extend the short half-life, the HBD has been pegylated. In vitro experiments have demonstrated that HBD and the pegylated HBD are identical in their ability to stimulate osteoblast proliferation and differentiation. Human HSCs isolated from cord blood will be purchased from Stem Cell Technologies and cultured in Methocult stem cell media, according to the manufacturer's instructions. Murine bone marrow stromal cells (BMSC) will be recovered from the femurs of Igfbp2−/− and Igfbp2+/+ mice. BMSC will be stained with fluorescently conjugated antibodies and HSCs isolated using the FACSAria cell sorter. HSCs will be defined as $Lin^- CD34^- Sca-1^+ Kit^+ Flk-2^-$. Twenty HSCs from each strain will be cultured in StemSpan serum free media (Stem Cell Technologies) supplemented with heparin, stem cell factor, thrombopoietin, and FGF-1, as previously reported[3]. HBD, full length IGFBP-2, or scrambled control peptide will be added to cell cultures at predetermined concentrations and for optimized exposure time. At day 10 of culture, cell proliferation for test specimens and controls will be quantified by the uptake of $H^3$ Thymidine as counts of radioactivity per minute using the L56500 Liquid Scintillation Counter. Results will be expressed as the average of triplicate tests. Cells will also be analyzed by flow cytometry to determine percentages of short term (ST) and long term (LT) hematopoietic stem cells as defined by $CD34^+ Sca-1^+ Thy1.1^{+/lo} c-kit^+ lin^- CD135^- Slamf1/CD150^+ CD11b^{lo}$ and $CD34^- Sca-1^+ Thy1.1^{+/lo} c-kit^+ lin^- CD135^- Slamf1/CD150^+$ respectively. To confirm that HSCs remain undifferentiated in culture, percentages of differentiated cells will also be determined by flow cytometry using antibodies to lineage specific markers including Ter119 (erythrocytes) LY6G (Gr-1, myeloid), CD3 (T cell), CD19 (B cell) and CD11b (Mac-1, macrophage). Percentages will be based on collection of 20,000 events using the FACSCalibur flow cytometer. Cell culture experiments will be repeated three times. Analysis of variance (ANOVA) will be used to assess differences across groups. The confidence interval will be set at 95% ($p \leq 0.05$).

Investigation of Whether the Effects of the HBD on Hematopoietic Stem Cells are Independent of IGF Signaling.

Rationale.

IGF-I is a growth promoter for both normal and malignant cells. Elevated serum levels of IGFBP-2 are recognized as a poor prognostic indicator in recurrent metastatic disease and in childhood acute myelogenous leukemia following hematopoietic stem cell transplantation[10,11]. It is, therefore, important to determine if the effects of IGFBP-2 on HSC expansion in vitro are independent of IGF signaling and whether there is synergy between IGF and IGFBP-2 with respect to cell signaling.

Design and Methods:

HSCs will be cultured from murine bone marrow stromal cells, as described herein. IGF signaling will be inhibited by blocking the IGF receptor using the alpha IR-3 antibody in murine HSC cultures. The alpha IR-3 antibody used in these experiments has been published as effectively blocking IGF signaling in a variety of cell types, including murine hematopoietic stem cells[12]. In these experiments, successful blocking of the IGF receptor will be assessed by adding IGF 1 to cell cultures and measuring cell proliferation by $H^3$ Thymidine uptake. Following confirmation of receptor blocking, HBD, scrambled peptide and full length IGFBP-2 will be added to HSC cultures, and cell proliferation quantified by H3 Thymidine uptake. Data will be analyzed by ANOVA as described herein.

Investigation of What Signaling Events are Initiated in Hematopoietic Stem Cells by the HBD of IGFBP-2.

Rationale.

HBD has been shown to increase osteoblast proliferation by decreasing PTEN expression and increasing AKT phosphorylation. The mechanisms by which IGFBP-2 increases HSC proliferation have not been determined. Osteoblasts and hematopoietic cells reside together in close proximity in the bone marrow, and many cell signaling pathways are common to both the bone and hematopoietic niches. To determine the signaling events activated by the HBD, gene expression profiling will be performed on HSC cell cultures with and without the HBD, scrambled peptide, and full length IGFBP-2. Through PCR gene arrays, the contribution of cell proliferation and/or inhibition of apoptosis to HSC expansion will be determined.

Design and Methods:

HSCs will be exposed to HBD, full length IGFBP-2, and a scrambled peptide, as described herein. RNA will be extracted from cultured HSCs on day 10 of culture. cDNA will be prepared using the RT2 First Strand Kit (SABiosciences, Frederick, Md.), according to the manufacturer's directions. A small aliquot (i.e., 25 ul) of the experimental cocktail consisting of cDNA, Syber Green RT2 qPCR Master Mix (SABiosciences) will be added to each well of the PCR array in a 96 well plate format (SABiosciences). PCR amplification will be performed using the Bio-Rad iQ5 thermocycler at the following settings: one cycle for 10 minutes at 95° C., followed by 40 cycles of 15 seconds each at 95° C. and 40 cycles of one minute each at 60° C. Baseline and threshold values will be determined manually. The ΔΔCt (delta threshold change) will be calculated for each gene using the SABiosciences PCR Array Data Analysis Web Portal (http://www.SABiosciences.com). A fold change greater than 1 between the experimental ΔCt (delta threshold change) and the control ΔCt will be considered up-regulation of the gene. A fold change less than 1 will be considered down-regulation of the gene. Ct values above 35 will be considered negative. PCR arrays will be performed for apoptosis, hematopoietic stem cells and hematopoiesis, and the PI3K-Akt, Wnt, MAP Kinase and Insulin signaling pathways.

Investigation of the Effect of the HBD of IGFBP-2 on Bone Marrow Transplantation in Vivo.

Determination of Whether the HSCs are Expanded In Vitro Using the HBD of IGFBP-2 Functional in Bone Marrow Transplantation.

Rationale:

While it is important that HSCs remain undifferentiated prior to transplant, successful transplantation is dependent upon a sufficient number of HSCs homing to the bone marrow and differentiating first into progenitor cells and eventually into mature and functional erythrocytes and white blood cells. The ability of the HSCs expanded in vitro by the HBD peptide to repopulate the bone marrow and to maintain steady state hematopoiesis when transplanted into lethally irradiated recipient mice will be tested.

Design and Methods:

Murine HSCs collected from Igfbp2+/+ mice and expanded in vitro by the HBD peptide will be transplanted into Igfbp2+/+ mice. HSCs from human cord blood also expanded by the HBD peptide will be transplanted into non-obese, diabetic, severe combined immunodeficient (NOD/SCID) mice, a strain commonly used for transplantation studies of human bone marrow cells. Recipient mice will receive a lethal dose (10 Gy for IGFBP2+/+) or sublethal dose (3.5 Gy for NOD/SCID) of irradiation by exposure to a Cesium source using the J.L Shepherd 143-45 Irradiator in two sessions and with 4 hours between sessions. Human and murine HSCs will be expanded in culture for 10 days, counted, and resuspended in PBS at a concentration of $10 \times 10^6$ cells/mL. 30 uL of donor HSCs will be transplanted into the retro orbitus of recipient mice. At 8 weeks post transplant, peripheral blood of recipient mice will be tested for successful bone marrow engraftment by determining the percentage of LY5.2+ murine donor cells and CD45/71+ human donor cells by flow cytometry in Igfbp2+/+ and NOD/SCID mice respectively. The presence of ≥80% donor cells will be indicative of successful engraftment. Recipient mice will be sacrificed at 16 weeks post transplant. Percentages of the major blood cell populations will be determined in peripheral blood by flow cytometry using conjugated antibodies to Ter 119 (erythrocytes), LY6G (Gr-1, myeloid), CD3 (T cell), CD19 (B cell), and CD11b (Mac-1, macrophage). As a functional test of successful engraftment and an assessment of the self renewal potential of transplanted HSCs, bone marrow cells will be collected from one femur of recipient mice at 16 weeks post transplant and used as the donor cells for a second set of transplant recipients. These second set recipients will be monitored as described for the original transplants. Three mice for each test and control condition will be transplanted, and transplants will be performed in at least 2 independent experiments for an N=6 for each experimental condition. ANOVA will be used to analyze differences between groups as previously described. Investigation of Whether the HBD Increases the Efficiency of Bone Marrow Repopulation Following Myeloablation in Igfbp2−/− Mice.

Rationale.

It has been shown that global deletion of IGFBP-2 in Igfbp2−/− bone marrow transplant recipients does not preclude successful engraftment of IGFBP-2 positive donor cells. However, as seen in competitive repopulation transplant experiments, donor cells from Igfbp2−/− mice engraft 30% less efficiently when compared with Igfbp2+/+ donor cells. Taken together, these data implicate IGFBP-2 as an important regulator of HSC homing to the bone marrow and a contributor to establish HSCs within the hematopoietic stem cell niche. Both of these steps are required for successful transplantation. The goal in these experiments is to rescue the decreased engraftment efficiency of Igfbp2−/− donor cells by co-administering HBD peptide to Igfbp2−/− transplant recipients. These experiments will serve as a functional test of the ability of the HBD to improve engraftment of bone marrow cells.

Design and Methods:

The LY5.1/LY5.2 gene system will be used in competitive experiments to repopulate the bone marrow and distinguish donor engrafted bone marrow cells from recipient endogenous bone marrow cells. The B6.SJL-Ptprc$^a$pepc$^b$/BoyJ mouse strain (LY5.1 positive) will be used as the source of competitor bone marrow donor cells. All recipient mice will be LY5.2 positive. Donor and recipient mice will be male and 8 weeks of age at the time of transplant. To obtain donor bone marrow cells, mice will be sacrificed, and the femurs will be recovered aseptically. Bone marrow cells will be collected, washed, and resuspended in phosphate buffered saline (PBS) at a concentration of $0.3 \times 10^6$ cells per 30 uL injection volume. For competitive repopulation transplants, LY5.1+ donor cells are mixed with LY5.2+ (Igfbp2−/− or Igfbp2+/+) donor cells at 1:0 (100% LY5.1 donor cells, positive control), 1:3 and 1:6 ratios. The HBD peptide, scrambled peptide, or full length IGFBP2 will be added to donor cell preparations at a concentration optimized in previous in vivo experiments (50 ug/30 uL). Recipient mice will be irradiated lethally and transplanted, as described herein. At 8 weeks post transplant, percentages of LY5.1 positive and LY5.2 positive engrafted donor cells will be determined in peripheral blood by flow cytometry. Transplant recipients will be sacrificed at 16 weeks post transplant, and white blood cell populations analyzed by flow cytometry. HSCs present in the bone marrow will be quantified and sorted using the FACSAria cell sorter. Sorted cells will be cultured and the number of colony forming units determined in a standard colony forming cell culture assay (Stem Cell Technologies). In addition, functionality of transplanted HSCs will be assessed by a second set of transplants, which will be performed as described herein. Three mice for each test and control condition will be transplanted, and transplants will be performed in at least 2 independent experiments for an N=6 for each experimental condition. ANOVA will be used to assess statistical significance between group means of test (Igfbp2−/−) and control (Igfbp2+/+) recipients. The confidence interval will be set at ≤0.05.

REFERENCE LIST FOR EXAMPLE 12

1. Jenq, R. R. & van den Brink, M. R. Allogeneic haematopoietic stem cell transplantation: individualized stem cell and immune therapy of cancer. *Nat Rev Cancer* 10, 213-21.
2. Huynh, H. et al. Insulin-like growth factor-binding protein 2 secreted by a tumorigenic cell line supports ex vivo expansion of mouse hematopoietic stem cells. *Stem Cells* 26, 1628-35 (2008).
3. Zhang, C. C., Kaba, M., Iizuka, S., Huynh, H. & Lodish, H. F. Angiopoietin-like 5 and IGFBP2 stimulate ex vivo expansion of human cord blood hematopoietic stem cells as assayed by NOD/SCID transplantation. Blood 111, 3415-23 (2008).
4. Pulte, D., Gondos, A. & Brenner, H. Trends in survival after diagnosis with hematologic malignancy in adolescence or young adulthood in the United States, 1981-2005. Cancer 115, 4973-9 (2009).
5. Calvi, L. M. et al. Osteoblastic cells regulate the haematopoietic stem cell niche. Nature 425, 841-6 (2003).
6. Wilson, A. & Trumpp, A. Bone-marrow haematopoietic-stem-cell niches. Nat Rev Immunol 6, 93-106 (2006).
7. DeMambro, V. E. et al. Gender-specific changes in bone turnover and skeletal architecture in igfbp-2-null mice. Endocrinology 149, 2051-61 (2008).
8. Song, S. W. et al. IIp45, an insulin-like growth factor binding protein 2 (IGFBP-2) binding protein, antagonizes IGFBP-2 stimulation of glioma cell invasion. Proc Natl Acad Sci USA 100, 13970-5 (2003).
9. Russo, V. C. et al. Insulin-like growth factor binding protein-2 binding to extracellular matrix plays a critical role in neuroblastoma cell proliferation, migration, and invasion. Endocrinology 146, 4445-55 (2005).

10. Dawczynski, K. et al. Elevated serum insulin-like growth factor binding protein-2 is associated with a high relapse risk after hematopoietic stem cell transplantation in childhood AML. Bone Marrow Transplant 37, 589-94 (2006).
11. Dawczynski, K., Kauf, E. & Zintl, F. Changes of serum growth factors (IGF-I, -II and IGFBP-2, -3) prior to and after stem cell transplantation in children with acute leukemia. Bone Marrow Transplant 32, 411-5 (2003).
12. Zia, F. et al. Monoclonal antibody alpha IR-3 inhibits non-small cell lung cancer growth in vitro and in vivo. J Cell Biochem Suppl 24, 269-75 (1996).
13. Frisch, B. J., Porter, R. L. & Calvi, L. M. Hematopoietic niche and bone meet. Curr Opin Support Palliat Care 2, 211-7 (2008).
14. Kuznetsov, S. A. et al. The interplay of osteogenesis and hematopoiesis: expression of a constitutively active PTH/PTHrP receptor in osteogenic cells perturbs the establishment of hematopoiesis in bone and of skeletal stem cells in the bone marrow. J Cell Biol 167, 1113-22 (2004).
15. Ballen, K. K.; King, R. J.; Chitphakdithai, P.; Bolan, C. D., Jr.; Agura, E.; Hartzman, R. J.; Kennan, N. A., The national marrow donor program 20 years of unrelated donor hematopoietic cell transplantation. *Biol Blood Marrow Transplant* 2008, 14, (9 Suppl), 2-7.
16. Bendall, S. C.; Stewart, M. H.; Menendez, P.; George, D.; Vijayaragavan, K.; Werbowetski-Ogilvie, T.; Ramos-Mejia, V.; Rouleau, A.; Yang, J.; Bosse, M.; Lajoie, G.; Bhatia, M., IGF and FGF cooperatively establish the regulatory stem cell niche of pluripotent human cells in vitro. *Nature* 2007, 448, (7157), 1015-21.
17. Bhattacharya, D.; Rossi, D. J.; Bryder, D.; Weissman, I. L., Purified hematopoietic stem cell engraftment of rare niches corrects severe lymphoid deficiencies without host conditioning. *J Exp Med* 2006, 203, (1), 73-85.
18. Clawson, T. F.; Lee, W. H.; Yoder, M. C., Differential expression of insulin-like growth factor binding proteins in murine hematopoietic stromal cell lines. *Mol Cell Endocrinol* 1996, 120, (1), 59-66.
19. Czechowicz, A.; Kraft, D.; Weissman, I. L.; Bhattacharya, D., Efficient transplantation via antibody-based clearance of hematopoietic stem cell niches. *Science* 2007, 318, (5854), 1296-9.
20. Delaney, C.; Heimfeld, S.; Brashem-Stein, C.; Voorhies, H.; Manger, R. L.; Bernstein, I. D., Notch-mediated expansion of human cord blood progenitor cells capable of rapid myeloid reconstitution. *Nat Med* 16, (2), 232-6.
21. Eminli, S.; Foudi, A.; Stadtfeld, M.; Maherali, N.; Ahfeldt, T.; Mostoslaysky, G.; Hock, H.; Hochedlinger, K., Differentiation stage determines potential of hematopoietic cells for reprogramming into induced pluripotent stem cells. *Nat Genet.* 2009, 41, (9), 968-76.
22. Forsberg, E. C.; Bhattacharya, D.; Weissman, I. L., Hematopoietic stem cells: expression profiling and beyond. *Stem Cell Rev* 2006, 2, (1), 23-30.
23. Frisch, B. J.; Porter, R. L.; Gigliotti, B. J.; Olm-Shipman, A. J.; Weber, J. M.; O'Keefe, R. J.; Jordan, C. T.; Calvi, L. M., In vivo prostaglandin E2 treatment alters the bone marrow microenvironment and preferentially expands short-term hematopoietic stem cells. *Blood* 2009, 114, (19), 4054-63.
24. Fu, P.; Thompson, J. A.; Bach, L. A., Promotion of cancer cell migration: an insulin-like growth factor (IGF)-independent action of IGF-binding protein-6. *J Biol Chem* 2007, 282, (31), 22298-306.
25. Haug, J. S.; He, X. C.; Grindley, J. C.; Wunderlich, J. P.; Gaudenz, K.; Ross, J. T.; Paulson, A.; Wagner, K. P.; Xie, Y.; Zhu, R.; Yin, T.; Perry, J. M.; Hembree, M. J.; Redenbaugh, E. P.; Radice, G. L.; Seidel, C.; Li, L., N-cadherin expression level distinguishes reserved versus primed states of hematopoietic stem cells. *Cell Stem Cell* 2008, 2, (4), 367-79.
26. Hoeflich, A.; Reisinger, R.; Lahm, H.; Kiess, W.; Blum, W. F.; Kolb, H. J.; Weber, M. M.; Wolf, E., Insulin-like growth factor-binding protein 2 in tumorigenesis: protector or promoter? *Cancer Res* 2001, 61, (24), 8601-10.

The foregoing is illustrative of the present invention, and is not to be construed as limiting thereof. The invention is defined by the following claims, with equivalents of the claims to be included therein.

TABLE 1

MicroCT analysis of femurs from IGFBP2$^{+/+}$ and IGFBP2$^{-/-}$ treated with PBS or PEG-HBD-peptide

| | IGFBP2$^{+/+}$ PBS N = 8 | IGFBP2$^{-/-}$ PBS N = 12 | IGFBP2$^{-/-}$ PEG-HBD N = 6 |
|---|---|---|---|
| Midshaft | | | |
| Cortical thickness | 0.198 ± 0.007 | 0.197 ± 0.003 | 0.200 ± 0.006 |
| Bone area | 0.889 ± 0.047 | 0.868 ± 0.018 | 0.903 ± 0.024 |
| Total area | 1.970 ± 0.062 | 1.955 ± 0.036 | 2.076 ± 0.031[a] |
| Bone area/Total area | 0.449 ± 0.011 | 0.444 ± 0.006 | 0.435 ± 0.014 |
| Distal Femur | | | |
| Bone volume/Total volume | 0.143 ± 0.017 | 0.095 ± 0.007[b] | 0.125 ± 0.012[c] |
| Trabecular number | 4.86 ± 0.16 | 429 ± 0.09[b] | 4.47 ± 0.15 |
| Trabecular thickness | 0.047 ± 0.003 | 0.041 ± 0.001 | 0.048 ± 0.002[d] |
| Trabecular spacing | 0.200 ± 0.007 | 0.230 ± 0.005[b] | 0.221 ± 0.008 |

PEG-HBD; pegylated heparin-binding domain
Values are expressed as the mean ± SEM.
[a] $p < 0.05$ vs IGFBP2$^{-/-}$ with PBS
[b] $p < 0.01$ vs IGFBP2$^{+/+}$ with PBS
[c] $p < 0.05$ vs IGFBP2$^{-/-}$ with PBS
[d] $p < 0.01$ vs IGFBP2$^{-/-}$ with PBS

TABLE 2

IGFBP-2 Heparin Binding Peptide Reduces Fat Mass

| Treatment Group | Number of mice | Body Weight (gms) | Fat Mass (gms) |
|---|---|---|---|
| IGFBP-2 −/− + placebo | 8 | 30.4 ± 1.5 | 6.21 ± 0.76 |
| IGFBP-2 −/− + HBD | 8 | 24.9 ± 1.3 | 3.67 ± 0.36 |
| IGFBP-2 +/+ | 8 | 25.2 ± 1.1 | 3.82 ± 0.67 |

TABLE 3

Body composition of Igfbp2$^{-/-}$ mice before treatment with PBS or PEG-HBD.

| | Igfbp2$^{-/-}$ PBS | Igfbp2$^{-/-}$ PEG-HBD |
|---|---|---|
| Whole-body BMD | 0.0378 ± 0.0009 | 0.0382 + 0.0008 |
| Whole-body BMC/Body weight | 0.0115 ± 0.0004 | 0.0119 ± 0.0006 |
| % body fat | 10.4 ± 0.52 | 9.8 ± 0.62 |

PEG-RBD; pegylated heparin-binding domain
BMD; bone mineral density
BMC; bone mineral content
BW; body weight

TABLE 4

Body composition of Igfbp2⁻/⁻ mice after treatment with PBS or PEG-HBD.

|  | Igfbp2⁻/⁻ PBS | Igfbp2⁻/⁻ PEG-HBD |
|---|---|---|
| Whole-body BMD | 0.0445 ± 0.0006 | 0.0459 ± 0.0004 |
| Whole-body BMC/BW | 0.0138 ± 0.0004 | 0.0147 ± 0.0005 |
| % body fat | 10.4 ± 0.70 | 10.4 ± 1.02 |
| Epidydymal fat weight/BW (mg/g) | 12.2 ± 0.51 | 12.2 ± 0.67 |

PEG-HBD; pegylated heparin-binding domain
BMD; bone mineral density
BMC; bone mineral content
BW; body weight

TABLE 5

MicroCT analysis of vertebrae (L5) from IGFBP2⁺/⁺ and IGFBP2⁻/⁻ treated with PBS or PEG-HBD

|  | IGFBP2⁺/⁺ PBS N = 7 | IGFBP2⁻/⁻ PBS N = 9 | IGFBP2⁻/⁻ PEG-HBD N = 6 |
|---|---|---|---|
| Bone volume/Total volume | 0.314 ± 0.020 | 0.278 ± 0.010 | 0.305 ± 0.012 |
| Trabecular number | 6.15 ± 0.36 | 5.77 ± 0.11 | 5.70 ± 0.10 |
| Trabecular thickness | 0.052 ± 0.002 | 0.049 ± 0.001 | 0.054 ± 0.002[a] |
| Trabecular spacing | 0.155 ± 0.009 | 0.160 ± 0.004 | 0.161 ± 0.004 |

PEG-HBD; pegylated heparin-binding domain
Values are expressed as the mean ± SEM.
[a] $p < 0.05$ vs IGFBP2⁻/⁻ with PBS

TABLE 6

Histomorphometric analysis of femur from IGFBP2⁻/⁻ mice treated with PBS or PEG-HBD.

|  | IGFBP2⁻/⁻ PBS N = 5 | IGFBP2⁻/⁻ PEG-HBD N = 5 |
|---|---|---|
| OS/BS (%) | 238 ± 1.11 | 3.56 ± 0.44 |
| ObS/BS (%) | 11.5 ± 1.03 | 16.26 ± 1.42[a] |
| Nob/BPm (/mm) | 12.31 ± 0.52 | 16.3 ± 1.4[a] |
| ES/BS (%) | 17.11 ± 0.93 | 14.79 ± 01.58 |
| OcS/BS (%) | 11.02 ± 0.87 | 9.14 ± 0.90 |
| Noc/BPm (/mm) | 5.19 ± 0.37 | 4.37 ± 0.39 |
| MAR (μm/day) | 0.873 ± 0.0078 | 0.91 ± 0.0453 |
| BFR/BSd (μm3/μm2/day) | 0.0796 ± 0.0164 | 0.080 ± 0.0191 |

PEG-HBD; pegylated heparin-binding domain, OS; osteoid surface, BS; bone surface, ObS; osteoblast surface, Nob; osteoblast number, BPm; bone perimeter, ES; erosion surface, OcS; osteoclast surface, Noc; osteoclast number, MAR; mineral apposition rate, BFR; bone formation rate
Values are expressed as the mean ± SEM
[a] $p < 0.05$ vs IGFBP2⁻/⁻ with PBS

TABLE 7

SEQ ID NO. shown to left of sequence (cont'd)

| 5. | KHHLGLEEPKK; |
|---|---|
| 6. | RHHLGLEEPKK; |
| 7. | HHHLGLEEPKK; |
| 8. | KKHLGLEEPKK; |
| 9. | RKHLGLEEPKK; |
| 10. | HKHLGLEEPKK; |

TABLE 7-continued

SEQ ID NO. shown to left of sequence (cont'd)

| 11. | KRHLGLEEPKK; |
|---|---|
| 12. | RRHLGLEEPKK; |
| 13. | HRHLGLEEPKK; |
| 14. | KHKLGLEEPKK; |
| 15. | RHKLGLEEPKK; |
| 16. | HHKLGLEEPKK; |
| 17. | KKKLGLEEPKK; |
| 18. | RKKLGLEEPKK; |
| 19. | HKKLGLEEPKK; |
| 20. | KRKLGLEEPKK; |
| 21. | RRKLGLEEPKK; |
| 22. | HRKLGLEEPKK; |
| 23. | KHRLGLEEPKK; |
| 24. | RHRLGLEEPKK; |
| 25. | HHRLGLEEPKK; |
| 26. | KKRLGLEEPKK; |
| 27. | RKRLGLEEPKK; |
| 28. | HKRLGLEEPKK; |
| 29. | KRRLGLEEPKK; |
| 30. | RRRLGLEEPKK; |
| 31. | HRRLGLEEPKK; |
| 32. | KHHIGLEEPKK; |
| 33. | RHHIGLEEPKK; |
| 34. | HHHIGLEEPKK; |
| 35. | KKHIGLEEPKK; |
| 36. | RKHIGLEEPKK; |
| 37. | HKHIGLEEPKK; |
| 38. | KRHIGLEEPKK; |
| 39. | RRHIGLEEPKK; |
| 40. | HRHIGLEEPKK; |
| 41. | KHKIGLEEPKK; |
| 42. | RHKIGLEEPKK; |
| 43. | HHKIGLEEPKK; |
| 44. | KKKIGLEEPKK; |
| 45. | RKKIGLEEPKK; |
| 46. | HKKIGLEEPKK; |
| 47. | KRKIGLEEPKK; |
| 48. | RRKIGLEEPKK; |
| 49. | HRKIGLEEPKK; |

TABLE 7-continued

SEQ ID NO. shown to left of sequence(cont'd)

| SEQ ID NO. | Sequence |
|---|---|
| 50. | KHRIGLEEPKK; |
| 51. | RHRIGLEEPKK; |
| 52. | HHRIGLEEPKK; |
| 53. | KKRIGLEEPKK; |
| 54. | RKRIGLEEPKK; |
| 55. | HKRIGLEEPKK; |
| 56. | KRRIGLEEPKK; |
| 57. | RRRIGLEEPKK; |
| 58. | HRRIGLEEPKK; |
| 59. | KHHVGLEEPKK; |
| 60. | RHHVGLEEPKK; |
| 61. | HHHVGLEEPKK; |
| 62. | KKHVGLEEPKK; |
| 63. | RKHVGLEEPKK; |
| 64. | HKHVGLEEPKK; |
| 65. | KRHVGLEEPKK; |
| 66. | RRHVGLEEPKK; |
| 67. | HRHVGLEEPKK; |
| 68. | KHKVGLEEPKK; |
| 69. | RHKVGLEEPKK; |
| 70. | HHKVGLEEPKK; |
| 71. | KKKVGLEEPKK; |
| 72. | RKKVGLEEPKK; |
| 73. | HKKVGLEEPKK; |
| 74. | KRKVGLEEPKK; |
| 75. | RRKVGLEEPKK; |
| 76. | HRKVGLEEPKK; |
| 77. | KHRVGLEEPKK; |
| 78. | RHRVGLEEPKK; |
| 79. | HHRVGLEEPKK; |
| 80. | KKRVGLEEPKK; |
| 81. | RKRVGLEEPKK; |
| 82. | HKRVGLEEPKK; |
| 83. | KRRVGLEEPKK; |
| 84. | RRRVGLEEPKK; |
| 85. | HRRVGLEEPKK; |
| 86. | KHHLGIEEPKK; |
| 87. | RHHLGIEEPKK; |
| 88. | HHHLGIEEPKK; |
| 89. | KKHLGIEEPKK; |
| 90. | RKHLGIEEPKK; |
| 91. | HKHLGIEEPKK; |
| 92. | KRHLGIEEPKK; |
| 93. | RRHLGIEEPKK; |
| 94. | HRHLGIEEPKK; |
| 95. | KHKLGIEEPKK; |
| 96. | RHKLGIEEPKK; |
| 97. | HHKLGIEEPKK; |
| 98. | KKKLGIEEPKK; |
| 99. | RKKLGIEEPKK; |
| 100. | HKKLGIEEPKK; |
| 101. | KRKLGIEEPKK; |
| 102. | RRKLGIEEPKK; |
| 103. | HRKLGIEEPKK; |
| 104. | KHRLGIEEPKK; |
| 105. | RHRLGIEEPKK; |
| 106. | HHRLGIEEPKK; |
| 107. | KKRLGIEEPKK; |
| 108. | RKRLGIEEPKK; |
| 109. | HKRLGIEEPKK; |
| 110. | KRRLGIEEPKK; |
| 111. | RRRLGIEEPKK; |
| 112. | HRRLGIEEPKK; |
| 113. | KHHIGIEEPKK; |
| 114. | RHHIGIEEPKK; |
| 115. | HHHIGIEEPKK; |
| 116. | KKHIGIEEPKK; |
| 117. | RKHIGIEEPKK; |
| 118. | HKHIGIEEPKK; |
| 119. | KRHIGIEEPKK; |
| 120. | RRHIGIEEPKK; |
| 121. | HRHIGIEEPKK; |
| 122. | KHKIGIEEPKK; |
| 123. | RHKIGIEEPKK; |
| 124. | HHKIGIEEPKK; |
| 125. | KKKIGIEEPKK; |
| 126. | RKKIGIEEPKK; |
| 127. | HKKIGIEEPKK; |

TABLE 7-continued

SEQ ID NO. shown to left of sequence(cont'd)

| SEQ ID NO. | Sequence |
|---|---|
| 128. | KRKIGIEEPKK; |
| 129. | RRKIGIEEPKK; |
| 130. | HRKIGIEEPKK; |
| 131. | KHRIGIEEPKK; |
| 132. | RHRIGIEEPKK; |
| 133. | HHRIGIEEPKK; |
| 134. | KKRIGIEEPKK; |
| 135. | RKRIGIEEPKK; |
| 136. | HKRIGIEEPKK; |
| 137. | KRRIGIEEPKK; |
| 138. | RRRIGIEEPKK; |
| 139. | HRRIGIEEPKK; |
| 140. | KHHVGIEEPKK; |
| 141. | RHHVGIEEPKK; |
| 142. | HHHVGIEEPKK; |
| 143. | KKHVGIEEPKK; |
| 144. | RKHVGIEEPKK; |
| 145. | HKHVGIEEPKK; |
| 146. | KRHVGIEEPKK; |
| 147. | RRHVGIEEPKK; |
| 148. | HRHVGIEEPKK; |
| 149. | KHKVGIEEPKK; |
| 150. | RHKVGIEEPKK; |
| 151. | HHKVGIEEPKK; |
| 152. | KKKVGIEEPKK; |
| 153. | RKKVGIEEPKK; |
| 154. | HKKVGIEEPKK; |
| 155. | KRKVGIEEPKK; |
| 156. | RRKVGIEEPKK; |
| 157. | HRKVGIEEPKK; |
| 158. | KHRVGIEEPKK; |
| 159. | RHRVGIEEPKK; |
| 160. | HHRVGIEEPKK; |
| 161. | KKRVGIEEPKK; |
| 162. | RKRVGIEEPKK; |
| 163. | HKRVGIEEPKK; |
| 164. | KRRVGIEEPKK; |
| 165. | RRRVGIEEPKK; |
| 166. | HRRVGIEEPKK; |
| 167. | KHHLGVEEPKK; |
| 168. | RHHLGVEEPKK; |
| 169. | HHHLGVEEPKK; |
| 170. | KKHLGVEEPKK; |
| 171. | RKHLGVEEPKK; |
| 172. | HKHLGVEEPKK; |
| 173. | KRHLGVEEPKK; |
| 174. | RRHLGVEEPKK; |
| 175. | HRHLGVEEPKK; |
| 176. | KHKLGVEEPKK; |
| 177. | RHKLGVEEPKK; |
| 178. | HHKLGVEEPKK; |
| 179. | KKKLGVEEPKK; |
| 180. | RKKLGVEEPKK; |
| 181. | HKKLGVEEPKK; |
| 182. | KRKLGVEEPKK; |
| 183. | RRKLGVEEPKK; |
| 184. | HRKLGVEEPKK; |
| 185. | KHRLGVEEPKK; |
| 186. | RHRLGVEEPKK; |
| 187. | HHRLGVEEPKK; |
| 188. | KKRLGVEEPKK; |
| 189. | RKRLGVEEPKK; |
| 190. | HKRLGVEEPKK; |
| 191. | KRRLGVEEPKK; |
| 192. | RRRLGVEEPKK; |
| 193. | HRRLGVEEPKK; |
| 194. | KHHIGVEEPKK; |
| 195. | RHHIGVEEPKK; |
| 196. | HHHIGVEEPKK; |
| 197. | KKHIGVEEPKK; |
| 198. | RKHIGVEEPKK; |
| 199. | HKHIGVEEPKK; |
| 200. | KRHIGVEEPKK; |
| 201. | RRHIGVEEPKK; |
| 202. | HRHIGVEEPKK; |
| 203. | KHKIGVEEPKK; |
| 204. | RHKIGVEEPKK; |
| 205. | HHKIGVEEPKK; |

TABLE 7-continued

| SEQ ID NO. | shown to left of sequence(cont'd) |
|---|---|
| 206. | KKKIGVEEPKK; |
| 207. | RKKIGVEEPKK; |
| 208. | HKKIGVEEPKK; |
| 209. | KRKIGVEEPKK; |
| 210. | RRKIGVEEPKK; |
| 211. | HRKIGVEEPKK; |
| 212. | KHRIGVEEPKK; |
| 213. | RHRIGVEEPKK; |
| 214. | HHRIGVEEPKK; |
| 215. | KKRIGVEEPKK; |
| 216. | RKRIGVEEPKK; |
| 217. | HKRIGVEEPKK; |
| 218. | KRRIGVEEPKK; |
| 219. | RRRIGVEEPKK; |
| 220. | HRRIGVEEPKK; |
| 221. | KHHVGVEEPKK; |
| 222. | RHHVGVEEPKK; |
| 223. | HHHVGVEEPKK; |
| 224. | KKHVGVEEPKK; |
| 225. | RKHVGVEEPKK; |
| 226. | HKHVGVEEPKK; |
| 227. | KRHVGVEEPKK; |
| 228. | RRHVGVEEPKK; |
| 229. | HRHVGVEEPKK; |
| 230. | KHKVGVEEPKK; |
| 231. | RHKVGVEEPKK; |
| 232. | HHKVGVEEPKK; |
| 233. | KKKVGVEEPKK; |
| 234. | RKKVGVEEPKK; |
| 235. | HKKVGVEEPKK; |
| 236. | KRKVGVEEPKK; |
| 237. | RRKVGVEEPKK; |
| 238. | HRKVGVEEPKK; |
| 239. | KHRVGVEEPKK; |
| 240. | RHRVGVEEPKK; |
| 241. | HHRVGVEEPKK; |
| 242. | KKRVGVEEPKK; |
| 243. | RKRVGVEEPKK; |
| 244. | HKRVGVEEPKK; |

TABLE 7-continued

| SEQ ID NO. | shown to left of sequence(cont'd) |
|---|---|
| 245. | KRRVGVEEPKK; |
| 246. | RRRVGVEEPKK; |
| 247. | HRRVGVEEPKK; |
| 248. | KHHLGLNEPKK; |
| 249. | RHHLGLNEPKK; |
| 250. | HHHLGLNEPKK; |
| 251. | KKHLGLNEPKK; |
| 252. | RKHLGLNEPKK; |
| 253. | HKHLGLNEPKK; |
| 254. | KRHLGLNEPKK; |
| 255. | RRHLGLNEPKK; |
| 256. | HRHLGLNEPKK; |
| 257. | KHKLGLNEPKK; |
| 258. | RHKLGLNEPKK; |
| 259. | HHKLGLNEPKK; |
| 260. | KKKLGLNEPKK; |
| 261. | RKKLGLNEPKK; |
| 262. | HKKLGLNEPKK; |
| 263. | KRKLGLNEPKK; |
| 264. | RRKLGLNEPKK; |
| 265. | HRKLGLNEPKK; |
| 266. | KHRLGLNEPKK; |
| 267. | RHRLGLNEPKK; |
| 268. | HHRLGLNEPKK; |
| 269. | KKRLGLNEPKK; |
| 270. | RKRLGLNEPKK; |
| 271. | HKRLGLNEPKK; |
| 272. | KRRLGLNEPKK; |
| 273. | RRRLGLNEPKK; |
| 274. | HRRLGLNEPKK; |
| 275. | KHHIGLNPKK; |
| 276. | RHHIGLNEPKK; |
| 277. | HHHIGLNEPKK; |
| 278. | KKHIGLNEPKK; |
| 279. | RKHIGLNEPKK; |
| 280. | HKHIGLNEPKK; |
| 281. | KRHIGLNEPKK; |
| 282. | RRHIGLNEPKK; |
| 283. | HRHIGLNEPKK; |

TABLE 7-continued

SEQ ID NO. shown to left of sequence(cont'd)

| SEQ ID NO. | Sequence |
|---|---|
| 284. | KHKIGLNEPKK; |
| 285. | RHKIGLNEPKK; |
| 286. | HHKIGLNEPKK; |
| 287. | KKKIGLNEPKK; |
| 288. | RKKIGLNEPKK; |
| 289. | HKKIGLNEPKK; |
| 290. | KRKIGLNEPKK; |
| 291. | RRKIGLNEPKK; |
| 292. | HRKIGLNEPKK; |
| 293. | KHRIGLNEPKK; |
| 294. | RHRIGLNEPKK; |
| 295. | HHRIGLNEPKK; |
| 296. | KKRIGLNEPKK; |
| 297. | RKRIGLNEPKK; |
| 298. | HKRIGLNEPKK; |
| 299. | KRRIGLNEPKK; |
| 300. | RRRIGLNEPKK; |
| 301. | HRRIGLNEPKK; |
| 302. | KHHVGLNEPKK; |
| 303. | RHHVGLNEPKK; |
| 304. | HHHVGLNEPKK; |
| 305. | KKHVGLNEPKK; |
| 306. | RKHVGLNEPKK; |
| 307. | HKHVGLNEPKK; |
| 308. | KRHVGLNEPKK; |
| 309. | RRHVGLNEPKK; |
| 310. | HRHVGLNEPKK; |
| 311. | KHKVGLNEPKK; |
| 312. | RHKVGLNEPKK; |
| 313. | HHKVGLNEPKK; |
| 314. | KKKVGLNEPKK; |
| 315. | RKKVGLNEPKK; |
| 316. | HKKVGLNEPKK; |
| 317. | KRKVGLNEPKK; |
| 318. | RRKVGLNEPKK; |
| 319. | HRKVGLNEPKK; |
| 320. | KHRVGLNEPKK; |
| 321. | RHRVGLNEPKK; |
| 322. | HHRVGLNEPKK; |
| 323. | KKRVGLNEPKK; |
| 324. | RKRVGLNEPKK; |
| 325. | HKRVGLNEPKK; |
| 326. | KRRVGLNEPKK; |
| 327. | RRRVGLNEPKK; |
| 328. | HRRVGLNEPKK; |
| 329. | KHHLGINEPKK; |
| 330. | RHHLGINEPKK; |
| 331. | HHHLGINEPKK; |
| 332. | KKHLGINEPKK; |
| 333. | RKHLGINEPKK; |
| 334. | HKHLGINEPKK; |
| 335. | KRHLGINEPKK; |
| 336. | RRHLGINEPKK; |
| 337. | HRHLGINEPKK; |
| 338. | KHKLGINEPKK; |
| 339. | RHKLGINEPKK; |
| 340. | HHKLGINEPKK; |
| 341. | KKKLGINEPKK; |
| 342. | RKKLGINEPKK; |
| 343. | HKKLGINEPKK; |
| 344. | KRKLGINEPKK; |
| 345. | RRKLGINEPKK; |
| 346. | HRKLGINEPKK; |
| 347. | KHRLGINEPKK; |
| 348. | RHRLGINEPKK; |
| 349. | HHRLGINEPKK; |
| 350. | KKRLGINEPKK; |
| 351. | RKRLGINEPKK; |
| 352. | HKRLGINEPKK; |
| 353. | KRRLGINEPKK; |
| 354. | RRRLGINEPKK; |
| 355. | HRRLGINEPKK; |
| 356. | KHHIGIENPKK; |
| 357. | RHHIGINEPKK; |
| 358. | HHHIGINEPKK; |
| 359. | KKHIGINEPKK; |
| 360. | RKHIGINEPKK; |
| 361. | HKHIGINEPKK; |

TABLE 7-continued

SEQ ID NO. shown to left of sequence(cont'd)

| SEQ ID NO. | Sequence |
|---|---|
| 362. | KRHIGINEPKK; |
| 363. | RRHIGINEPKK; |
| 364. | HRHIGINEPKK; |
| 365. | KHKIGINEPKK; |
| 366. | RHKIGINEPKK; |
| 367. | HHKIGINEPKK; |
| 368. | KKKIGINEPKK; |
| 369. | RKKIGINEPKK; |
| 370. | HKKIGINEPKK; |
| 371. | KRKIGINEPKK; |
| 372. | RRKIGINEPKK; |
| 373. | HRKIGINEPKK; |
| 374. | KHRIGINEPKK; |
| 375. | RHRIGINEPKK; |
| 376. | HHRVGINEPKK; |
| 377. | KKRIGINEPKK; |
| 378. | RKRIGINEPKK; |
| 379. | HKRIGINEPKK; |
| 380. | KRRIGINEPKK; |
| 381. | RRRIGINEPKK; |
| 382. | HRRIGINEPKK; |
| 383. | KHHVGINEPKK; |
| 384. | RHHVGINEPKK; |
| 385. | HHHVGINEPKK; |
| 386. | KKHVGINEPKK; |
| 387. | RKHVGINEPKK; |
| 388. | HKHVGINEPKK; |
| 389. | KRHVGINEPKK; |
| 390. | RRHVGINEPKK; |
| 391. | HRHVGINEPKK; |
| 392. | KHKVGINEPKK; |
| 393. | RHKVGINEPKK; |
| 394. | HKKVGINEPKK; |
| 395. | KKKVGINEPKK; |
| 396. | RKKVGINEPKK; |
| 397. | HKKVGINEPKK; |
| 398. | KRKVGINEPKK; |
| 399. | RRKVGINEPKK; |
| 400. | HRKVGINEPKK; |
| 401. | KHRVGINEPKK; |
| 402. | RHRVGINEPKK; |
| 403. | HHRVGINEPKK; |
| 404. | KKRVGINEPKK; |
| 405. | RKRVGINEPKK; |
| 406. | HKRVGINEPKK; |
| 407. | KRRVGINEPKK; |
| 408. | RRRVGINEPKK; |
| 409. | HRRVGINEPKK; |
| 410. | KHHLGVNEPKK; |
| 411. | RHHLGVNEPKK; |
| 412. | HHHLGVNEPKK; |
| 413. | KKHLGVNEPKK; |
| 414. | RKHLGVNEPKK; |
| 415. | HKHLGVNEPKK; |
| 416. | KRHLGVNEPKK; |
| 417. | RRHLGVNEPKK; |
| 418. | HRHLGVNEPKK; |
| 419. | KHKLGVNEPKK; |
| 420. | RHKLGVNEPKK; |
| 421. | HHKLGVNEPKK; |
| 422. | KKKLGVNEPKK; |
| 423. | RKKLGVNEPKK; |
| 424. | HKKLGVNEPKK; |
| 425. | KRKLGVNEPKK; |
| 426. | RRKLGVNEPKK; |
| 427. | HRKLGVNEPKK; |
| 428. | KHRLGVNEPKK; |
| 429. | RHRLGVNEPKK; |
| 430. | HHRLGVNEPKK; |
| 431. | KKRLGVNEPKK; |
| 432. | RKRLGVNEPKK; |
| 433. | HKRLGVNEPKK; |
| 434. | KRRLGVNEPKK; |
| 435. | RRRLGVNEPKK; |
| 436. | HRRLGVNEPKK; |
| 437. | KHHIGVNEPKK; |
| 438. | RHHIGVNEPKK; |
| 439. | HHHIGVNEPKK; |

TABLE 7-continued

SEQ ID NO. shown to left of sequence(cont'd)

| SEQ ID NO. | Sequence |
|---|---|
| 440. | KKHIGVNEPKK; |
| 441. | RKHIGVNEPKK; |
| 442. | HKHIGVNEPKK; |
| 443. | KRHIGVNEPKK; |
| 444. | RRHIGVNEPKK; |
| 445. | HRHIGVNEPKK; |
| 446. | KHKIGVNEPKK; |
| 447. | RHKIGVNEPKK; |
| 448. | HHKIGVNEPKK; |
| 449. | KKKIGVNEPKK; |
| 450. | RKKIGVNEPKK; |
| 451. | HKKIGVNEPKK; |
| 452. | KRKIGVNEPKK; |
| 453. | RRKIGVNEPKK; |
| 454. | HRKIGVNEPKK; |
| 455. | KHRIGVNEPKK; |
| 456. | RHRIGVNEPKK; |
| 457. | HHRIGVNEPKK; |
| 458. | KKRIGVNEPKK; |
| 459. | RKRIGVNEPKK; |
| 460. | HKRIGVNEPKK; |
| 461. | KRRIGVNEPKK; |
| 462. | RRRIGVNEPKK; |
| 463. | HRRIGVNEPKK; |
| 464. | KHHVGVNEPKK; |
| 465. | RHHVGVNEPKK; |
| 466. | HHHVGVNEPKK; |
| 467. | KKHVGVNEPKK; |
| 468. | RKHVGVNEPKK; |
| 469. | HKHVGVNEPKK; |
| 470. | KRHVGVNEPKK; |
| 471. | RRHVGVNEPKK; |
| 472. | HRHVGVNEPKK; |
| 473. | KHKVGVNEPKK; |
| 474. | RHKVGVNEPKK; |
| 475. | HHKVGVNEPKK; |
| 476. | KKKVGVNEPKK; |
| 477. | RKKVGVNEPKK; |
| 478. | HKKVGVNEPKK; |
| 479. | KRKVGVNEPKK; |
| 480. | RRKVGVNEPKK; |
| 481. | HRKVGVNEPKK; |
| 482. | KHRVGVNEPKK; |
| 483. | RHRVGVNEPKK; |
| 484. | HHRVGVNEPKK; |
| 485. | KKRVGVNEPKK; |
| 486. | RKRVGVNEPKK; |
| 487. | HKRVGVNEPKK; |
| 488. | KRRVGVNEPKK; |
| 489. | RRRVGVNEPKK; |
| 490. | HRRVGVNEPKK; |
| 491. | KHHLGLENPKK; |
| 492. | RHHLGLENPKK; |
| 493. | HHHLGLENPKK; |
| 494. | KKHLGLENPKK; |
| 495. | RKHLGLENPKK; |
| 496. | HKHLGLENPKK; |
| 497. | KRHLGLENPKK; |
| 498. | RRHLGLENPKK; |
| 499. | HRHLGLENPKK; |
| 500. | KHKLGLENPKK; |
| 501. | RHKLGLENPKK; |
| 502. | HHKLGLENPKK; |
| 503. | KKKLGLENPKK; |
| 504. | RKKLGLENPKK; |
| 505. | HKKLGLENPKK; |
| 506. | KRKLGLENPKK; |
| 507. | RRKLGLENPKK; |
| 508. | HRKLGLENPKK; |
| 509. | KHRLGLENPKK; |
| 510. | RHRLGLENPKK; |
| 511. | HHRLGLENPKK; |
| 512. | KKRLGLENPKK; |
| 513. | RKRLGLENPKK; |
| 514. | HKRLGLENPKK; |
| 515. | KRRLGLENPKK; |
| 516. | RRRLGLENPKK; |
| 517. | HRRLGLENPKK; |

TABLE 7-continued

SEQ ID NO. shown to left of sequence (cont'd)

| SEQ ID NO. | Sequence |
|---|---|
| 518. | KHHIGLENPKK; |
| 519. | RHHIGLENPKK; |
| 520. | HHHIGLENPKK; |
| 521. | KKHIGLENPKK; |
| 522. | RKHIGLENPKK; |
| 523. | HKHIGLENPKK; |
| 524. | KRHIGLENPKK; |
| 525. | RRHIGLENPKK; |
| 526. | HRHIGLENPKK; |
| 527. | KHKIGLENPKK; |
| 528. | RHKIGLENPKK; |
| 529. | HHKIGLENPKK; |
| 530. | KKKIGLENPKK; |
| 531. | RKKIGLENPKK; |
| 532. | HKKIGLENPKK; |
| 533. | KRKIGLENPKK; |
| 534. | RRKIGLENPKK; |
| 535. | HRKIGLENPKK; |
| 536. | KHRIGLENPKK; |
| 537. | RHRIGLENPKK; |
| 538. | HHRIGLENPKK; |
| 539. | KKRIGLENPKK; |
| 540. | RKRIGLENPKK; |
| 541. | HKRIGLENPKK; |
| 542. | KRRIGLENPKK; |
| 543. | RRRIGLENPKK; |
| 544. | HRRIGLENPKK; |
| 545. | KHHVGLENPKK; |
| 546. | RHHVGLENPKK; |
| 547. | HHHVGLENPKK; |
| 548. | KKHVGLENPKK; |
| 549. | RKHVGLENPKK; |
| 550. | HKHVGLENPKK; |
| 551. | KRHVGLENPKK; |
| 552. | RRHVGLENPKK; |
| 553. | HRHVGLENPKK; |
| 554. | KHKVGLENPKK; |
| 555. | RHKVGLENPKK; |
| 556. | HHKVGLENPKK; |
| 557. | KKKVGLENPKK; |
| 558. | RKKVGLENPKK; |
| 559. | HKKVGLENPKK; |
| 560. | KRKVGLENPKK; |
| 561. | RRKVGLENPKK; |
| 562. | HRKVGLENPKK; |
| 563. | KHRVGLENPKK; |
| 564. | RHRVGLENPKK; |
| 565. | HHRVGLENPKK; |
| 566. | KKRVGLENPKK; |
| 567. | RKRVGLENPKK; |
| 568. | HKRVGLENPKK; |
| 569. | KRRVGLENPKK; |
| 570. | RRRVGLENPKK; |
| 571. | HRRVGLENPKK; |
| 572. | KHHLGIENPKK; |
| 573. | RHHLGIENPKK; |
| 574. | HHHLGIENPKK; |
| 575. | KKHLGIENPKK; |
| 576. | RKHLGIENPKK; |
| 577. | HKHLGIENPKK; |
| 578. | KRHLGIENPKK; |
| 579. | RRHLGIENPKK; |
| 580. | HRHLGIENPKK; |
| 581. | KHKLGIENPKK; |
| 582. | RHKLGIENPKK; |
| 583. | HHKLGIENPKK; |
| 584. | KKKLGIENPKK; |
| 585. | RKKLGIENPKK; |
| 586. | HKKLGIENPKK; |
| 587. | KRKLGIENPKK; |
| 588. | RRKLGIENPKK; |
| 589. | HRKLGIENPKK; |
| 590. | KHRLGIENPKK; |
| 591. | RHRLGIENPKK; |
| 592. | HHRLGIENPKK; |
| 593. | KKRLGIENPKK; |
| 594. | RKRLGIENPKK; |
| 595. | HKRLGIENPKK; |

TABLE 7-continued

| SEQ ID NO. | shown to left of sequence (cont'd) |
|---|---|
| 596. | KRRLGIENPKK; |
| 597. | RRRLGIENPKK; |
| 598. | HRRLGIENPKK; |
| 599. | KHHIGIENPKK; |
| 600. | RHHIGIENPKK; |
| 601. | HHHIGIENPKK; |
| 602. | KKHIGIENPKK; |
| 603. | RKHIGIENPKK; |
| 604. | HKHIGIENPKK; |
| 605. | KRHIGIENPKK; |
| 606. | RRHIGIENPKK; |
| 607. | HRHIGIENPKK; |
| 608. | KHKIGIENPKK; |
| 609. | RHKIGIENPKK; |
| 610. | HHKIGIENPKK; |
| 611. | KKKIGIENPKK; |
| 612. | RKKIGIENPKK; |
| 613. | HKKIGIENPKK; |
| 614. | KRKIGIENPKK; |
| 615. | RRKIGIENPKK; |
| 616. | HRKIGIENPKK; |
| 617. | KHRIGIENPKK; |
| 618. | RHRIGIENPKK; |
| 619. | HHRIGIENPKK; |
| 620. | KKRIGIENPKK; |
| 621. | RKRIGIENPKK; |
| 622. | HKRIGIENPKK; |
| 623. | KRRIGIENPKK; |
| 624. | RRRIGIENPKK; |
| 625. | HRRIGIENPKK; |
| 626. | KHHVGIENPKK; |
| 627. | RHHVGIENPKK; |
| 628. | HHHVGIENPKK; |
| 629. | KKHVGIENPKK; |
| 630. | RKHVGIENPKK; |
| 631. | HKHVGIENPKK; |
| 632. | KRHVGIENPKK; |
| 633. | RRHVGIENPKK; |
| 634. | HRHVGIENPKK; |
| 635. | KHKVGIENPKK; |
| 636. | RHKVGIENPKK; |
| 637. | HHKVGIENPKK; |
| 638. | KKKVGIENPKK; |
| 639. | RKKVGIENPKK; |
| 640. | HKKVGIENPKK; |
| 641. | KRKVGIENPKK; |
| 642. | RRKVGIENPKK; |
| 643. | HRKVGIENPKK; |
| 644. | KHRVGIENPKK; |
| 645. | RHRVGIENPKK; |
| 646. | HHRVGIENPKK; |
| 647. | KKRVGIENPKK; |
| 648. | RKRVGIENPKK; |
| 649. | HKRVGIENPKK; |
| 650. | KRRVGIENPKK; |
| 651. | RRRVGIENPKK; |
| 652. | HRRVGIENPKK; |
| 653. | KHHLGVENPKK; |
| 654. | RHHLGVENPKK; |
| 655. | HHHLGVENPKK; |
| 656. | KKHLGVENPKK; |
| 657. | RKHLGVENPKK; |
| 658. | HKHLGVENPKK; |
| 659. | KRHLGVENPKK; |
| 660. | RRHLGVENPKK; |
| 661. | HRHLGVENPKK; |
| 662. | KHKLGVENPKK; |
| 663. | RHKLGVENPKK; |
| 664. | HHKLGVENPKK; |
| 665. | KKKLGVENPKK; |
| 666. | RKKLGVENPKK; |
| 667. | HKKLGVENPKK; |
| 668. | KRKLGVENPKK; |
| 669. | RRKLGVENPKK; |
| 670. | HRKLGVENPKK; |
| 671. | KHRLGVENPKK; |
| 672. | RHRLGVENPKK; |
| 673. | HHRLGVENPKK; |

TABLE 7-continued

SEQ ID NO. shown to left of sequence(cont'd)

| SEQ ID NO. | Sequence |
|---|---|
| 674. | KKRLGVENPKK; |
| 675. | RKRLGVENPKK; |
| 676. | HKRLGVENPKK; |
| 677. | KRRLGVENPKK; |
| 678. | RRRLGVENPKK; |
| 679. | HRRLGVENPKK; |
| 680. | KHHIGVENPKK; |
| 681. | RHHIGVEEPKK; |
| 682. | HHHIGVENPKK; |
| 683. | KKHIGVENPKK; |
| 684. | RKHIGVENPKK; |
| 685. | HKHIGVENPKK; |
| 686. | KRHIGVENPKK; |
| 687. | RRHIGVENPKK; |
| 688. | HRHIGVENPKK; |
| 689. | KHKIGVENPKK; |
| 690. | RHKIGVENPKK; |
| 691. | HHKIGVENPKK; |
| 692. | KKKIGVENPKK; |
| 693. | RKKIGVENPKK; |
| 694. | HKKIGVENPKK; |
| 695. | KRKIGVENPKK; |
| 696. | RRKIGVENPKK; |
| 697. | HRKIGVENPKK; |
| 698. | KHRIGVENPKK; |
| 699. | RHRIGVENPKK; |
| 700. | HHRIGVENPKK; |
| 701. | KKRIGVENPKK; |
| 702. | RKRIGVENPKK; |
| 703. | HKRIGVENPKK; |
| 704. | KRRIGVENPKK; |
| 705. | RRRIGVENPKK; |
| 706. | HRRIGVENPKK; |
| 707. | KHHVGVENPKK; |
| 708. | RHHVGVENPKK; |
| 709. | HHHVGVENPKK; |
| 710. | KKHVGVENPKK; |
| 711. | RKHVGVENPKK; |
| 712. | HKHVGVENPKK; |
| 713. | KRHVGVENPKK; |
| 714. | RRHVGVENPKK; |
| 715. | HRHVGVENPKK; |
| 716. | KHKVGVENPKK; |
| 717. | RHKVGVENPKK; |
| 718. | HHKVGVENPKK; |
| 719. | KKKVGVENPKK; |
| 720. | RKKVGVENPKK; |
| 721. | HKKVGVENPKK; |
| 722. | KRKVGVENPKK; |
| 723. | RRKVGVEEPKK; |
| 724. | HRKVGVENPKK; |
| 725. | KHRVGVENPKK; |
| 726. | RHRVGVENPKK; |
| 727. | HHRVGVENPKK; |
| 728. | KKRVGVENPKK; |
| 729. | RKRVGVENPKK; |
| 730. | HKRVGVENPKK; |
| 731. | KRRVGVENPKK; |
| 732. | RRRVGVENPKK; |
| 733. | HRRVGVENPKK; |
| 734. | KHHLGLNNPKK; |
| 735. | RHHLGLNNPKK; |
| 736. | HHHLGLNNPKK; |
| 737. | KKHLGLNNPKK; |
| 738. | RKHLGLNNPKK; |
| 739. | HKHLGLNNPKK; |
| 740. | KRHLGLNNPKK; |
| 741. | RRHLGLNNPKK; |
| 742. | HRHLGLNNPKK; |
| 743. | KHKLGLNNPKK; |
| 744. | RHKLGLNNPKK; |
| 745. | HHKLGLNNPKK; |
| 746. | KKKLGLNNPKK; |
| 747. | RKKLGLNNPKK; |
| 748. | HKKLGLNNPKK; |
| 749. | KRKLGLNNPKK; |
| 750. | RRKLGLNNPKK; |
| 751. | HRKLGLNNPKK; |

TABLE 7-continued

SEQ ID NO. shown to left of sequence(cont'd)

| SEQ ID NO. | Sequence |
|---|---|
| 752. | KHRLGLNNPKK; |
| 753. | RHRLGLNNPKK; |
| 754. | HHRLGLNNPKK; |
| 755. | KKRLGLNNPKK; |
| 756. | RKRLGLNNPKK; |
| 757. | HKRLGLNNPKK; |
| 758. | KRRLGLNNPKK; |
| 759. | RRRLGLNNPKK; |
| 760. | HRRLGLNNPKK; |
| 761. | KHHIGLNNPKK; |
| 762. | RHHIGLNNPKK; |
| 763. | HHHIGLNNPKK; |
| 764. | KKHIGLNNPKK; |
| 765. | RKHIGLNNPKK; |
| 766. | HKHIGLNNPKK; |
| 767. | KRHIGLNNPKK; |
| 768. | RRHIGLNNPKK; |
| 769. | HRHIGLNNPKK; |
| 770. | KHKIGLNNPKK; |
| 771. | RHKIGLNNPKK; |
| 772. | HHKIGLNNPKK; |
| 773. | KKKIGLNNPKK; |
| 774. | RKKIGLNNPKK; |
| 775. | HKKIGLNNPKK; |
| 776. | KRKIGLNNPKK; |
| 777. | RRKIGLNNPKK; |
| 778. | HRKIGLNNPKK; |
| 779. | KHRIGLNNPKK; |
| 780. | RHRIGLNNPKK; |
| 781. | HHRIGLNNPKK; |
| 782. | KKRIGLNNPKK; |
| 783. | RKRIGLNNPKK; |
| 784. | HKRIGLNNPKK; |
| 785. | KRRIGLNNPKK; |
| 786. | RRRIGLNNPKK; |
| 787. | HRRIGLNNPKK; |
| 788. | KHHVGLNNPKK; |
| 789. | RHHVGLNNPKK; |
| 790. | HHHVGLNNPKK; |
| 791. | KKHVGLNNPKK; |
| 792. | RKHVGLNNPKK; |
| 793. | HKHVGLNNPKK; |
| 794. | KRHVGLNNPKK; |
| 795. | RRHVGLNNPKK; |
| 796. | HRHVGLNNPKK; |
| 797. | KHKVGLNNPKK; |
| 798. | RHKVGLNNPKK; |
| 799. | HHKVGLNNPKK; |
| 800. | KKKVGLNNPKK; |
| 801. | RKKVGLNNPKK; |
| 802. | HKKVGLNNPKK; |
| 803. | KRKVGLNNPKK; |
| 804. | RRKVGLNNPKK; |
| 805. | HRKVGLNNPKK; |
| 806. | KHRVGLNNPKK; |
| 807. | RHRVGLNNPKK; |
| 808. | HHRVGLNNPKK; |
| 809. | KKRVGLNNPKK; |
| 810. | RKRVGLNNPKK; |
| 811. | HKRVGLNNPKK; |
| 812. | KRRVGLNNPKK; |
| 813. | RRRVGLNNPKK; |
| 814. | HRRVGLNNPKK; |
| 815. | KHHLGINNPKK; |
| 816. | RHHLGINNPKK; |
| 817. | HHHLGINNPKK; |
| 818. | KKHLGINNPKK; |
| 819. | RKHLGINNPKK; |
| 820. | HKHLGINNPKK; |
| 821. | KRHLGINNPKK; |
| 822. | RRHLGINNPKK; |
| 823. | HRHLGINNPKK; |
| 824. | KHKLGINNPKK; |
| 825. | RHKLGINNPKK; |
| 826. | HHKLGINNPKK; |
| 827. | KKKLGINNPKK; |
| 828. | RKKLGINNPKK; |
| 829. | HKKLGINNPKK; |

TABLE 7-continued

SEQ ID NO. shown to left of sequence (cont'd)

| SEQ ID NO. | Sequence |
|---|---|
| 830. | KRKLGINNPKK; |
| 831. | RRKLGINNPKK; |
| 832. | HRKLGINNPKK; |
| 833. | KHRLGINNPKK; |
| 834. | RHRLGINNPKK; |
| 835. | HHRLGLNNPKK; |
| 836. | KKRLGINNPKK; |
| 837. | RKRLGINNPKK; |
| 838. | HKRLGINNPKK; |
| 839. | KRRLGINNPKK; |
| 840. | RRRLGINNPKK; |
| 841. | HRRLGINNPKK; |
| 842. | KHHIGIENPKK; |
| 843. | RHHIGINNPKK; |
| 844. | HHHIGINNPKK; |
| 845. | KKHIGINNPKK; |
| 846. | RKHIGINNPKK; |
| 847. | HKHIGINNPKK; |
| 848. | KRHIGINNPKK; |
| 849. | RRHIGINNPKK; |
| 850. | HRHIGINNPKK; |
| 851. | KHKIGINNPKK; |
| 852. | RHKIGINNPKK; |
| 853. | HHKIGINNPKK; |
| 854. | KKKIGINNPKK; |
| 855. | RKKIGINNPKK; |
| 856. | HKKIGINNPKK; |
| 857. | KRKIGINNPKK; |
| 858. | RRKIGINNPKK; |
| 859. | HRKIGINNPKK; |
| 860. | KHRIGINNPKK; |
| 861. | RHRIGINNPKK; |
| 862. | HHRIGINNPKK; |
| 863. | KKRIGINNPKK; |
| 864. | RKRIGINNPKK; |
| 865. | HKRIGINNPKK; |
| 866. | KRRIGINNPKK; |
| 867. | RRRIGINNPKK; |
| 868. | HRRIGINNPKK; |
| 869. | KHHVGINNPKK; |
| 870. | RHHVGINNPKK; |
| 871. | HHHVGINNPKK; |
| 872. | KKHVGINNPKK; |
| 873. | RKHVGINNPKK; |
| 874. | HKHVGINNPKK; |
| 875. | KRHVGINNPKK; |
| 876. | RRHVGINNPKK; |
| 877. | HRHVGINNPKK; |
| 878. | KHKVGINNPKK; |
| 879. | RHKVGINNPKK; |
| 880. | HHKVGINNPKK; |
| 881. | KKKVGINNPKK; |
| 882. | RKKVGINNPKK; |
| 883. | HKKVGINNPKK; |
| 884. | KRKVGINNPKK; |
| 885. | RRKVGINNPKK; |
| 886. | HRKVGINNPKK; |
| 887. | KHRVGINNPKK; |
| 888. | RHRVGINNPKK; |
| 889. | HHRVGINNPKK; |
| 890. | KKRVGINNPKK; |
| 891. | RKRVGINNPKK; |
| 892. | HKRVGINNPKK; |
| 893. | KRRVGINNPKK; |
| 894. | RRRVGINNPKK; |
| 895. | HRRVGINNPKK; |
| 896. | KHHLGVNNPKK; |
| 897. | RHHLGVNNPKK; |
| 898. | HHHLGVNNPKK; |
| 899. | KKHLGVNNPKK; |
| 900. | RKHLGVNNPKK; |
| 901. | HKHLGVNNPKK; |
| 902. | KRHLGVNNPKK; |
| 903. | RRHLGVNNPKK; |
| 904. | HRHLGVNNPKK; |
| 905. | KHKLGVNNPKK; |
| 906. | RHKLGVNNPKK; |
| 907. | HHKLGVNNPKK; |

TABLE 7-continued

SEQ ID NO. shown to left of sequence(cont'd)

| | |
|---|---|
| 908. | KKKLGVNNPKK; |
| 909. | RKKLGVNNPKK; |
| 910. | HKKLGVNNPKK; |
| 911. | KRKLGVNNPKK; |
| 912. | RRKLGVNNPKK; |
| 913. | HRKLGVNNPKK; |
| 914. | KHRLGVNNPKK; |
| 915. | RHRLGVNNPKK; |
| 916. | HHRLGVNNPKK; |
| 917. | KKRLGVNNPKK; |
| 918. | RKRLGVNNPKK; |
| 919. | HKRLGVNNPKK; |
| 920. | KRRLGVNNPKK; |
| 921. | RRRLGVNNPKK; |
| 922. | HRRLGVNNPKK; |
| 923. | KHHIGVNNPKK; |
| 924. | RHHIGVNNPKK; |
| 925. | HHHIGVNNPKK; |
| 926. | KKHIGVNNPKK; |
| 927. | RKHIGVNNPKK; |
| 928. | HKHIGVNNPKK; |
| 929. | KRHIGVNNPKK; |
| 930. | RRHIGVNNPKK; |
| 931. | HRHIGVNNPKK; |
| 932. | KHKIGVNNPKK; |
| 933. | RHKIGVNNPKK; |
| 934. | HHKIGVNNPKK; |
| 935. | KKKIGVNNPKK; |
| 936. | RKKIGVNNPKK; |
| 937. | HKKIGVNNPKK; |
| 938. | KRKIGVNNPKK; |
| 939. | RRKIGVNNPKK; |
| 940. | HRKIGVNNPKK; |
| 941. | KHRIGVNNPKK; |
| 942. | RHRIGVNNPKK; |
| 943. | HHRIGVNNPKK; |
| 944. | KKRIGVNNPKK; |
| 945. | RKRIGVNNPKK; |
| 946. | HKRIGVNNPKK; |

TABLE 7-continued

SEQ ID NO. shown to left of sequence(cont'd)

| | |
|---|---|
| 947. | KRRIGVNNPKK; |
| 948. | RRRIGVNNPKK; |
| 949. | HRRIGVNNPKK; |
| 950. | KHHVGVNNPKK; |
| 951. | RHHVGVNNPKK; |
| 952. | HHHVGVNNPKK; |
| 953. | KKHVGVNNPKK; |
| 954. | RKHVGVNNPKK; |
| 955. | HKHVGVNNPKK; |
| 956. | KRHVGVNNPKK; |
| 957. | RRHVGVNNPKK; |
| 958. | HRHVGVNNPKK; |
| 959. | KHKVGVNNPKK; |
| 960. | RHKVGVNNPKK; |
| 961. | HHKVGVNNPKK; |
| 962. | KKKVGVNNPKK; |
| 963. | RKKVGVNNPKK; |
| 964. | HKKVGVNNPKK; |
| 965. | KRKVGVNNPKK; |
| 966. | RRKVGVNNPKK; |
| 967. | HRKVGVNNPKK; |
| 968. | KHRVGVNNPKK; |
| 969. | RHRVGVNNPKK; |
| 970. | HHRVGVNNPKK; |
| 971. | KKRVGVNNPKK; |
| 972. | RKRVGVNNPKK; |
| 973. | HKRVGVNNPKK; |
| 974. | KRRVGVNNPKK; |
| 975. | RRRVGVNNPKK; |
| 976. | HRRVGVNNPKK; |
| 977. | KHHLGLEEPKR; |
| 978. | RHHLGLEEPKR; |
| 979. | HHHLGLEEPKR; |
| 980. | KKHLGLEEPKR; |
| 981. | RKHLGLEEPKR; |
| 982. | HKHLGLEEPKR; |
| 983. | KRHLGLEEPKR; |
| 984. | RRHLGLEEPKR; |
| 985. | HRHLGLEEPKR; |

TABLE 7-continued

SEQ ID NO. shown to left of sequence (cont'd)

| SEQ ID NO. | Sequence |
|---|---|
| 986. | KHKLGLEEPKR; |
| 987. | RHKLGLEEPKR; |
| 988. | HHKLGLEEPKR; |
| 989. | KKKLGLEEPKR; |
| 990. | RKKLGLEEPKR; |
| 991. | HKKLGLEEPKR; |
| 992. | KRKLGLEEPKR; |
| 993. | RRKLGLEEPKR; |
| 994. | HRKLGLEEPKR; |
| 995. | KHRLGLEEPKR; |
| 996. | RHRLGLEEPKR; |
| 997. | HHRLGLEEPKR; |
| 998. | KKRLGLEEPKR; |
| 999. | RKRLGLEEPKR; |
| 1000. | HKRLGLEEPKR; |
| 1001. | KRRLGLEEPKR; |
| 1002. | RRRLGLEEPKR; |
| 1003. | HRRLGLEEPKR; |
| 1004. | KHHIGLEEPKR; |
| 1005. | RHHIGLEEPKR; |
| 1006. | HHHIGLEEPKR; |
| 1007. | KKHIGLEEPKR; |
| 1008. | RKHIGLEEPKR; |
| 1009. | HKHIGLEEPKR; |
| 1010. | KRHIGLEEPKR; |
| 1011. | RRHIGLEEPKR; |
| 1012. | HRHIGLEEPKR; |
| 1013. | KHKIGLEEPKR; |
| 1014. | RHKIGLEEPKR; |
| 1015. | HHKIGLEEPKR; |
| 1016. | KKKIGLEEPKR; |
| 1017. | RKKIGLEEPKR; |
| 1018. | HKKIGLEEPKR; |
| 1019. | KRKIGLEEPKR; |
| 1020. | RRKIGLEEPKR; |
| 1021. | HRKIGLEEPKR; |
| 1022. | KHRIGLEEPKR; |
| 1023. | RHRIGLEEPKR; |
| 1024. | HHRIGLEEPKR; |
| 1025. | KKRIGLEEPKR; |
| 1026. | RKRIGLEEPKR; |
| 1027. | HKRIGLEEPKR; |
| 1028. | KRRIGLEEPKR; |
| 1029. | RRRIGLEEPKR; |
| 1030. | HRRIGLEEPKR; |
| 1031. | KHHVGLEEPKR; |
| 1032. | RHHVGLEEPKR; |
| 1033. | HHHVGLEEPKR; |
| 1034. | KKHVGLEEPKR; |
| 1035. | RKHVGLEEPKR; |
| 1036. | HKHVGLEEPKR; |
| 1037. | KRHVGLEEPKR; |
| 1038. | RRHVGLEEPKR; |
| 1039. | HRHVGLEEPKR; |
| 1040. | KHKVGLEEPKR; |
| 1041. | RHKVGLEEPKR; |
| 1042. | HHKVGLEEPKR; |
| 1043. | KKKVGLEEPKR; |
| 1044. | RKKVGLEEPKR; |
| 1045. | HKKVGLEEPKR; |
| 1046. | KRKVGLEEPKR; |
| 1047. | RRKVGLEEPKR; |
| 1048. | HRKVGLEEPKR; |
| 1049. | KHRVGLEEPKR; |
| 1050. | RHRVGLEEPKR; |
| 1051. | HHRVGLEEPKR; |
| 1052. | KKRVGLEEPKR; |
| 1053. | RKRVGLEEPKR; |
| 1054. | HKRVGLEEPKR; |
| 1055. | KRRVGLEEPKR; |
| 1056. | RRRVGLEEPKR; |
| 1057. | HRRVGLEEPKR; |
| 1058. | KHHLGIEEPKR; |
| 1059. | RHHLGIEEPKR; |
| 1060. | HHHLGIEEPKR; |
| 1061. | KKHLGIEEPKR; |
| 1062. | RKHLGIEEPKR; |
| 1063. | HKHLGIEEPKR; |

TABLE 7-continued

SEQ ID NO. shown to left of sequence(cont'd)

| SEQ ID NO. | Sequence |
|---|---|
| 1064. | KRHLGIEEPKR; |
| 1065. | RRHLGIEEPKR; |
| 1066. | HRHLGIEEPKR; |
| 1067. | KHKLGIEEPKR; |
| 1068. | RHKLGIEEPKR; |
| 1069. | HHKLGIEEPKR; |
| 1070. | KKKLGIEEPKR; |
| 1071. | RKKLGIEEPKR; |
| 1072. | HKKLGIEEPKR; |
| 1073. | KRKLGIEEPKR; |
| 1074. | RRKLGIEEPKR; |
| 1075. | HRKLGIEEPKR; |
| 1076. | KHRLGIEEPKR; |
| 1077. | RHRLGIEEPKR; |
| 1078. | HHRLGIEEPKR; |
| 1079. | KKRLGIEEPKR; |
| 1080. | RKRLGIEEPKR; |
| 1081. | HKRLGIEEPKR; |
| 1082. | KRRLGIEEPKR; |
| 1083. | RRRLGIEEPKR; |
| 1084. | HRRLGIEEPKR; |
| 1085. | KHHIGIEEPKR; |
| 1086. | RHHIGIEEPKR; |
| 1087. | HHHIGIEEPKR; |
| 1088. | KKHIGIEEPKR; |
| 1089. | RKHIGIEEPKR; |
| 1090. | HKHIGIEEPKR; |
| 1091. | KRHIGIEEPKR; |
| 1092. | RRHIGIEEPKR; |
| 1093. | HRHIGIEEPKR; |
| 1094. | KHKIGIEEPKR; |
| 1095. | RHKIGIEEPKR; |
| 1096. | HHKIGIEEPKR; |
| 1097. | KKKIGIEEPKR; |
| 1098. | RKKIGIEEPKR; |
| 1099. | HKKIGIEEPKR; |
| 1100. | KRKIGIEEPKR; |
| 1101. | RRKIGIEEPKR; |
| 1102. | HRKIGIEEPKR; |
| 1103. | KHRIGIEEPKR; |
| 1104. | RHRIGIEEPKR; |
| 1105. | HHRIGIEEPKR; |
| 1106. | KKRIGIEEPKR; |
| 1107. | RKRIGIEEPKR; |
| 1108. | HKRIGIEEPKR; |
| 1109. | KRRIGIEEPKR; |
| 1110. | RRRIGIEEPKR; |
| 1111. | HRRIGIEEPKR; |
| 1112. | KHHVGIEEPKR; |
| 1113. | RHHVGIEEPKR; |
| 1114. | HHHVGIEEPKR; |
| 1115. | KKHVGIEEPKR; |
| 1116. | RKHVGIEEPKR; |
| 1117. | HKHVGIEEPKR; |
| 1118. | KRHVGIEEPKR; |
| 1119. | RRHVGIEEPKR; |
| 1120. | HRHVGIEEPKR; |
| 1121. | KHKVGIEEPKR; |
| 1122. | RHKVGIEEPKR; |
| 1123. | HHKVGIEEPKR; |
| 1124. | KKKVGIEEPKR; |
| 1125. | RKKVGIEEPKR; |
| 1126. | HKKVGIEEPKR; |
| 1127. | KRKVGIEEPKR; |
| 1128. | RRKVGIEEPKR; |
| 1129. | HRKVGIEEPKR; |
| 1130. | KHRVGIEEPKR; |
| 1131. | RHRVGIEEPKR; |
| 1132. | HHRVGIEEPKR; |
| 1133. | KKRVGIEEPKR; |
| 1134. | RKRVGIEEPKR; |
| 1135. | HKRVGIEEPKR; |
| 1136. | KRRVGIEEPKR; |
| 1137. | RRRVGIEEPKR; |
| 1138. | HRRVGIEEPKR; |
| 1139. | KHHLGVEEPKR; |
| 1140. | RHHLGVEEPKR; |
| 1141. | HHHLGVEEPKR; |

TABLE 7-continued

SEQ ID NO. shown to left of sequence(cont'd)

| | |
|---|---|
| 1142. | KKHLGVEEPKR; |
| 1143. | RKHLGVEEPKR; |
| 1144. | HKHLGVEEPKR; |
| 1145. | KRHLGVEEPKR; |
| 1146. | RRHLGVEEPKR; |
| 1147. | HRHLGVEEPKR; |
| 1148. | KHKLGVEEPKR; |
| 1149. | RHKLGVEEPKR; |
| 1150. | HHKLGVEEPKR; |
| 1151. | KKKLGVEEPKR; |
| 1152. | RKKLGVEEPKR; |
| 1153. | HKKLGVEEPKR; |
| 1154. | KRKLGVEEPKR; |
| 1155. | RRKLGVEEPKR; |
| 1156. | HRKLGVEEPKR; |
| 1157. | KHRLGVEEPKR; |
| 1158. | RHRLGVEEPKR; |
| 1159. | HHRLGVEEPKR; |
| 1160. | KKRLGVEEPKR; |
| 1161. | RKRLGVEEPKR; |
| 1162. | HKRLGVEEPKR; |
| 1163. | KRRLGVEEPKR; |
| 1164. | RRRLGVEEPKR; |
| 1165. | HRRLGVEEPKR; |
| 1166. | KHHIGVEEPKR; |
| 1167. | RHHIGVEEPKR; |
| 1168. | HHHIGVEEPKR; |
| 1169. | KKHIGVEEPKR; |
| 1170. | RKHIGVEEPKR; |
| 1171. | HKHIGVEEPKR; |
| 1172. | KRHIGVEEPKR; |
| 1173. | RRHIGVEEPKR; |
| 1174. | HRHIGVEEPKR; |
| 1175. | KHKIGVEEPKR; |
| 1176. | RHKIGVEEPKR; |
| 1177. | HHKIGVEEPKR; |
| 1178. | KKKIGVEEPKR; |
| 1179. | RKKIGVEEPKR; |
| 1180. | HKKIGVEEPKR; |
| 1181. | KRKIGVEEPKR; |
| 1182. | RRKIGVEEPKR; |
| 1183. | HRKIGVEEPKR; |
| 1184. | KHRIGVEEPKR; |
| 1185. | RHRIGVEEPKR; |
| 1186. | HHRIGVEEPKR; |
| 1187. | KKRIGVEEPKR; |
| 1188. | RKRIGVEEPKR; |
| 1189. | HKRIGVEEPKR; |
| 1190. | KRRIGVEEPKR; |
| 1191. | RRRIGVEEPKR; |
| 1192. | HRRIGVEEPKR; |
| 1193. | KHHVGVEEPKR; |
| 1194. | RHHVGVEEPKR; |
| 1195. | HHHVGVEEPKR; |
| 1196. | KKHVGVEEPKR; |
| 1197. | RKHVGVEEPKR; |
| 1198. | HKHVGVEEPKR; |
| 1199. | KRHVGVEEPKR; |
| 1200. | RRHVGVEEPKR; |
| 1201. | HRHVGVEEPKR; |
| 1202. | KHKVGVEEPKR; |
| 1203. | RHKVGVEEPKR; |
| 1204. | HHKVGVEEPKR; |
| 1205. | KKKVGVEEPKR; |
| 1206. | RKKVGVEEPKR; |
| 1207. | HKKVGVEEPKR; |
| 1208. | KRKVGVEEPKR; |
| 1209. | RRKVGVEEPKR; |
| 1210. | HRKVGVEEPKR; |
| 1211. | KHRVGVEEPKR; |
| 1212. | RHRVGVEEPKR; |
| 1213. | HHRVGVEEPKR; |
| 1214. | KKRVGVEEPKR; |
| 1215. | RKRVGVEEPKR; |
| 1216. | HKRVGVEEPKR; |
| 1217. | KRRVGVEEPKR; |
| 1218. | RRRVGVEEPKR; |
| 1219. | HRRVGVEEPKR; |

TABLE 7-continued

SEQ ID NO. shown to left of sequence(cont'd)

| | |
|---|---|
| 1220. | KHHLGLNEPKR; |
| 1221. | RHHLGLNEPKR; |
| 1222. | HHHLGLNEPKR; |
| 1223. | KKHLGLNEPKR; |
| 1224. | RKHLGLNEPKR; |
| 1225. | HKHLGLNEPKR; |
| 1226. | KRHLGLNEPKR; |
| 1227. | RRHLGLNEPKR; |
| 1228. | HRHLGLNEPKR; |
| 1229. | KHKLGLNEPKR; |
| 1230. | RHKLGLNEPKR; |
| 1231. | HHKLGLNEPKR; |
| 1232. | KKKLGLNEPKR; |
| 1233. | RKKLGLNEPKR; |
| 1234. | HKKLGLNEPKR; |
| 1235. | KRKLGLNEPKR; |
| 1236. | RRKLGLNEPKR; |
| 1237. | HRKLGLNEPKR; |
| 1238. | KHRLGLNEPKR; |
| 1239. | RHRLGLNEPKR; |
| 1240. | HHRLGLNEPKR; |
| 1241. | KKRLGLNEPKR; |
| 1242. | RKRLGLNEPKR; |
| 1243. | HKRLGLNEPKR; |
| 1244. | KRRLGLNEPKR; |
| 1245. | RRRLGLNEPKR; |
| 1246. | HRRLGLNEPKR; |
| 1247. | KHHIGLNPKR; |
| 1248. | RHHIGLNEPKR; |
| 1249. | HHHIGLNEPKR; |
| 1250. | KKHIGLNEPKR; |
| 1251. | RKHIGLNEPKR; |
| 1252. | HKHIGLNEPKR; |
| 1253. | KRHIGLNEPKR; |
| 1254. | RRHIGLNEPKR; |
| 1255. | HRHIGLNEPKR; |
| 1256. | KHKIGLNEPKR; |
| 1257. | RHKIGLNEPKR; |
| 1258. | HHKIGLNEPKR; |

TABLE 7-continued

SEQ ID NO. shown to left of sequence(cont'd)

| | |
|---|---|
| 1259. | KKKIGLNEPKR; |
| 1260. | RKKIGLNEPKR; |
| 1261. | HKKIGLNEPKR; |
| 1262. | KRKIGLNEPKR; |
| 1263. | RRKIGLNEPKR; |
| 1264. | HRKIGLNEPKR; |
| 1265. | KHRIGLNEPKR; |
| 1266. | RHRIGLNEPKR; |
| 1267. | HHRIGLNEPKR; |
| 1268. | KKRIGLNEPKR; |
| 1269. | RKRIGLNEPKR; |
| 1270. | HKRIGLNEPKR; |
| 1271. | KRRIGLNEPKR; |
| 1272. | RRRIGLNEPKR; |
| 1273. | HRRIGLNEPKR; |
| 1274. | KHHVGLNEPKR; |
| 1275. | RHHVGLNEPKR; |
| 1276. | HHHVGLNEPKR; |
| 1277. | KKHVGLNEPKR; |
| 1278. | RKHVGLNEPKR; |
| 1279. | HKHVGLNEPKR; |
| 1280. | KRHVGLNEPKR; |
| 1281. | RRHVGLNEPKR; |
| 1282. | HRHVGLNEPKR; |
| 1283. | KHKVGLNEPKR; |
| 1284. | RHKVGLNEPKR; |
| 1285. | HHKVGLNEPKR; |
| 1286. | KKKVGLNEPKR; |
| 1287. | RKKVGLNEPKR; |
| 1288. | HKKVGLNEPKR; |
| 1289. | KRKVGLNEPKR; |
| 1290. | RRKVGLNEPKR; |
| 1291. | HRKVGLNEPKR; |
| 1292. | KHRVGLNEPKR; |
| 1293. | RHRVGLNEPKR; |
| 1294. | HHRVGLNEPKR; |
| 1295. | KKRVGLNEPKR; |
| 1296. | RKRVGLNEPKR; |
| 1297. | HKRVGLNEPKR; |

TABLE 7-continued

SEQ ID NO. shown to left of sequence(cont'd)

| | |
|---|---|
| 1298. | KRRVGLNEPKR; |
| 1299. | RRRVGLNEPKR; |
| 1300. | HRRVGLNEPKR; |
| 1301. | KHHLGINEPKR; |
| 1302. | RHHLGINEPKR; |
| 1303. | HHHLGINEPKR; |
| 1304. | KKHLGINEPKR; |
| 1305. | RKHLGINEPKR; |
| 1306. | HKHLGINEPKR; |
| 1307. | KRHLGINEPKR; |
| 1308. | RRHLGINEPKR; |
| 1309. | HRHLGINEPKR; |
| 1310. | KHKLGINEPKR; |
| 1311. | RHKLGINEPKR; |
| 1312. | HHKLGINEPKR; |
| 1313. | KKKLGINEPKR; |
| 1314. | RKKLGINEPKR; |
| 1315. | HKKLGINEPKR; |
| 1316. | KRKLGINEPKR; |
| 1317. | RRKLGINEPKR; |
| 1318. | HRKLG1NEPKR; |
| 1319. | KHRLGINEPKR; |
| 1320. | RHRLGINEPKR; |
| 1321. | HHRLGINEPKR; |
| 1322. | KKRLGINEPKR; |
| 1323. | RKRLGINEPKR; |
| 1324. | HKRLGINEPKR; |
| 1325. | KRRLGINEPKR; |
| 1326. | RRRLGINEPKR; |
| 1327. | HRRLGINEPKR; |
| 1328. | KHHIGIENPKR; |
| 1329. | RHHIGINEPKR; |
| 1330. | HHHIGINEPKR; |
| 1331. | KKHIGINEPKR; |
| 1332. | RKHIGINEPKR; |
| 1333. | HKHIGINEPKR; |
| 1334. | KRHIGINEPKR; |
| 1335. | RRHIGINEPKR; |
| 1336. | HRHIGINEPKR; |
| 1337. | KHKIGINEPKR; |
| 1338. | RHKIGINEPKR; |
| 1339. | HHKIGINEPKR; |
| 1340. | KKKIGINEPKR; |
| 1341. | RKKIGINEPKR; |
| 1342. | HKKIGINEPKR; |
| 1343. | KRKIGINEPKR; |
| 1344. | RRKIGINEPKR; |
| 1345. | HRKIGINEPKR; |
| 1346. | KHRIGINEPKR; |
| 1347. | RHRIGINEPKR; |
| 1348. | HHRIGINEPKR; |
| 1349. | KKRIGINEPKR; |
| 1350. | RKRIGINEPKR; |
| 1351. | HKRIGINEPKR; |
| 1352. | KRRIGINEPKR; |
| 1353. | RRRIGINEPKR; |
| 1354. | HRRIGINEPKR; |
| 1355. | KHHVGINEPKR; |
| 1356. | RHHVGINEPKR; |
| 1357. | HHHVGINEPKR; |
| 1358. | KKHVGINEPKR; |
| 1359. | RKHVGINEPKR; |
| 1360. | HKHVGINEPKR; |
| 1361. | KRHVGINEPKR; |
| 1362. | RRHVGINEPKR; |
| 1363. | HRHVGINEPKR; |
| 1364. | KHKVGINEPKR; |
| 1365. | RHKVGINEPKR; |
| 1366. | HHKVGINEPKR; |
| 1367. | KKKVGINEPKR; |
| 1368. | RKKVGINEPKR; |
| 1369. | HKKVGINEPKR; |
| 1370. | KRKVGINEPKR; |
| 1371. | RRKVGINEPKR; |
| 1372. | HRKVGINEPKR; |
| 1373. | KHRVGINEPKR; |
| 1374. | RHRVGINEPKR; |
| 1375. | HHRVGINEPKR; |

TABLE 7-continued

SEQ ID NO. shown to left of sequence(cont'd)

| | |
|---|---|
| 1376. | KKRVGINEPKR; |
| 1377. | RKRVGINEPKR; |
| 1378. | HKRVGINEPKR; |
| 1379. | KRRVGINEPKR; |
| 1380. | RRRVGINEPKR; |
| 1381. | HRRVGINEPKR; |
| 1382. | KHHLGVNEPKR; |
| 1383. | RHHLGVNEPKR; |
| 1384. | HHHLGVNEPKR; |
| 1385. | KKHLGVNEPKR; |
| 1386. | RKHLGVNEPKR; |
| 1387. | HKHLGVNEPKR; |
| 1388. | KRHLGVNEPKR; |
| 1389. | RRHLGVNEPKR; |
| 1390. | HRHLGVNEPKR; |
| 1391. | KHKLGVNEPKR; |
| 1392. | RKRLGVNEPKR; |
| 1393. | HHKLGVNEPKR; |
| 1394. | KKKLGVNEPKR; |
| 1395. | RKKLGVNEPKR; |
| 1396. | HKKLGVNEPKR; |
| 1397. | KRKLGVNEPKR; |
| 1398. | RRKLGVNEPKR; |
| 1399. | HRKLGVNEPKR; |
| 1400. | KHRLGVNEPKR; |
| 1401. | RHRLGVNEPKR; |
| 1402. | HHRLGVNEPKR; |
| 1403. | KKRLGVNEPKR; |
| 1404. | RKRLGVNEPKR; |
| 1405. | HKRLGVNEPKR; |
| 1406. | KRRLGVNEPKR; |
| 1407. | RRRLGVNEPKR; |
| 1408. | HRRLGVNEPKR; |
| 1409. | KHHIGVNEPKR; |
| 1410. | RHHIGVNEPKR; |
| 1411. | HHHIGVNEPKR; |
| 1412. | KKHIGVNEPKR; |
| 1413. | RKHIGVNEPKR; |
| 1414. | HKHIGVNEPKR; |

TABLE 7-continued

SEQ ID NO. shown to left of sequence(cont'd)

| | |
|---|---|
| 1415. | KRHIGVNEPKR; |
| 1416. | RRHIGVNEPKR; |
| 1417. | HRHIGVNEPKR; |
| 1418. | KHKIGVNEPKR; |
| 1419. | RHKIGVNEPKR; |
| 1420. | HHKIGVNEPKR; |
| 1421. | KKKIGVNEPKR; |
| 1422. | RKKIGVNEPKR; |
| 1423. | HKKIGVNEPKR; |
| 1424. | KRKIGVNEPKR; |
| 1425. | RRKIGVNEPKR; |
| 1426. | HRKIGVNEPKR; |
| 1427. | KHRIGVNEPKR; |
| 1428. | RHRIGVNEPKR; |
| 1429. | HHRIGVNEPKR; |
| 1430. | KKRIGVNEPKR; |
| 1431. | RKRIGVNEPKR; |
| 1432. | HKRIGVNEPKR; |
| 1433. | KRRIGVNEPKR; |
| 1434. | RRRIGVNEPKR; |
| 1435. | HRRVGVNEPKR; |
| 1436. | KHHVGVNEPKR; |
| 1437. | RHHVGVNEPKR; |
| 1438. | HHHVGVNEPKR; |
| 1439. | KKHVGVNEPKR; |
| 1440. | RKHVGVNEPKR; |
| 1441. | HKHVGVNEPKR; |
| 1442. | KRHVGVNEPKR; |
| 1443. | RRHVGVNEPKR; |
| 1444. | HRHVGVNEPKR; |
| 1445. | KHKVGVNEPKR; |
| 1446. | RHKVGVNEPKR; |
| 1447. | HHKVGVNEPKR; |
| 1448. | KKKVGVNEPKR; |
| 1449. | RKKVGVNEPKR; |
| 1450. | HKKVGVNEPKR; |
| 1451. | KRKVGVNEPKR; |
| 1452. | RRKVGVNEPKR; |
| 1453. | HRKVGVNEPKR; |

TABLE 7-continued

| SEQ ID NO. shown to left of sequence(cont'd) | |
|---|---|
| 1454. | KHRVGVNEPKR; |
| 1455. | RHRVGVNEPKR; |
| 1456. | HHRVGVNEPKR; |
| 1457. | KKRVGVNEPKR; |
| 1458. | RKRVGVNEPKR; |
| 1459. | HKRVGVNEPKR; |
| 1460. | KRRVGVNEPKR; |
| 1461. | RRRVGVNEPKR; |
| 1462. | HRRVGVNEPKR; |
| 1463. | KHHLGLENPKR; |
| 1464. | RHHLGLENPKR; |
| 1465. | HHHLGLENPKR; |
| 1466. | KKHLGLENPKR; |
| 1467. | RKHLGLENPKR; |
| 1468. | HKHLGLENPKR; |
| 1469. | KRHLGLENPKR; |
| 1470. | RRHLGLENPKR; |
| 1471. | HRHLGLENPKR; |
| 1472. | KHKLGLENPKR; |
| 1473. | RHKLGLENPKR; |
| 1474. | HHKLGLENPKR; |
| 1475. | KKKLGLENPKR; |
| 1476. | RKKLGLENPKR; |
| 1477. | HKKLGLENPKR; |
| 1478. | KRKLGLENPKR; |
| 1479. | RRKLGLENPKR; |
| 1480. | HRKLGLENPKR; |
| 1481. | KHRLGLENPKR; |
| 1482. | RHRLGLENPKR; |
| 1483. | HHRLGLENPKR; |
| 1484. | KKRLGLENPKR; |
| 1485. | RKRLGLENPKR; |
| 1486. | HKRLGLENPKR; |
| 1487. | KRRLGLENPKR; |
| 1488. | RRRLGLENPKR; |
| 1489. | HRRLGLENPKR; |
| 1490. | KHHIGLENPKR; |
| 1491. | RHHIGLENPKR; |
| 1492. | HHHIGLENPKR; |

TABLE 7-continued

| SEQ ID NO. shown to left of sequence(cont'd) | |
|---|---|
| 1493. | KKHIGLENPKR; |
| 1494. | RKHIGLENPKR; |
| 1495. | HKHIGLENPKR; |
| 1496. | KRHIGLENPKR; |
| 1497. | RRHVGLENPKR; |
| 1498. | HRHIGLENPKR; |
| 1499. | KHKIGLENPKR; |
| 1500. | RHKIGLENPKR; |
| 1501. | HHKIGLENPKR; |
| 1502. | KKKIGLENPKR; |
| 1503. | RKKIGLENPKR; |
| 1504. | HKKIGLENPKR; |
| 1505. | KRKVGLENPKR; |
| 1506. | RRKIGLENPKR; |
| 1507. | HRKIGLENPKR; |
| 1508. | KHRIGLENPKR; |
| 1509. | RHRIGLENPKR; |
| 1510. | HHRIGLENPKR; |
| 1511. | KKRIGLENPKR; |
| 1512. | RKRIGLENPKR; |
| 1513. | HKRIGLENPKR; |
| 1514. | KRRIGLENPKR; |
| 1515. | RRRIGLENPKR; |
| 1516. | HRRIGLENPKR; |
| 1517. | KHHVGLENPKR; |
| 1518. | RHHVGLENPKR; |
| 1519. | HHHVGLENPKR; |
| 1520. | KKHVGLENPKR; |
| 1521. | RKHVGLENPKR; |
| 1522. | HKHVGLENPKR; |
| 1523. | KRHVGLENPKR; |
| 1524. | RRHVGLENPKR; |
| 1525. | HRHVGLENPKR; |
| 1526. | KHKVGLENPKR; |
| 1527. | RHKVGLENPKR; |
| 1528. | HHKVGLENPKR; |
| 1529. | KKKVGLENPKR; |
| 1530. | RKKVGLENPKR; |
| 1531. | HKKVGLENPKR; |

TABLE 7-continued

SEQ ID NO. shown to left of sequence(cont'd)

| | |
|---|---|
| 1532. | KRKVGLENPKR; |
| 1533. | RRKVGLENPKR; |
| 1534. | HRKVGLENPKR; |
| 1535. | KHRVGLENPKR; |
| 1536. | RHRVGLENPKR; |
| 1537. | HHRVGLENPKR; |
| 1538. | KKRVGLENPKR; |
| 1539. | RKRVGLENPKR; |
| 1540. | HKRVGLENPKR; |
| 1541. | KRRVGLENPKR; |
| 1542. | RRRVGLENPKR; |
| 1543. | HRRVGLENPKR; |
| 1544. | KHHLGIENPKR; |
| 1545. | RHHLGIENPKR; |
| 1546. | HHHLGIENPKR; |
| 1547. | KKHLGIENPKR; |
| 1548. | RKHLGIENPKR; |
| 1549. | HKHLGIENPKR; |
| 1550. | KRHLGIENPKR; |
| 1551. | RRHLGIENPKR; |
| 1552. | HRHLGIENPKR; |
| 1553. | KHKLGIENPKR; |
| 1554. | RHKLGIENPKR; |
| 1555. | HHKLGIENPKR; |
| 1556. | KKKLGIENPKR; |
| 1557. | RKKLGIENPKR; |
| 1558. | HKKLGIENPKR; |
| 1559. | KRKLGIENPKR; |
| 1560. | RRKLGIENPKR; |
| 1561. | HRKLGIENPKR; |
| 1562. | KHRLGIENPKR; |
| 1563. | RHRLGIENPKR; |
| 1564. | HHRLGIENPKR; |
| 1565. | KKRLGIENPKR; |
| 1566. | RKRLGIENPKR; |
| 1567. | HKRLGIENPKR; |
| 1568. | KRRLGIENPKR; |
| 1569. | RRRLGIENPKR; |
| 1570. | HRRLGIENPKR; |

TABLE 7-continued

SEQ ID NO. shown to left of sequence(cont'd)

| | |
|---|---|
| 1571. | KHHIGIENPKR; |
| 1572. | RHHIGIENPKR; |
| 1573. | HHHIGIENPKR; |
| 1574. | KKHIGIENPKR; |
| 1575. | RKHIGIENPKR; |
| 1576. | HKHIGIENPKR; |
| 1577. | KRHIGIENPKR; |
| 1578. | RRHIGIENPKR; |
| 1579. | HRHIGIENPKR; |
| 1580. | KHKIGIENPKR; |
| 1581. | RHKIGIENPKR; |
| 1582. | HHKIGIENPKR; |
| 1583. | KKKIGIENPKR; |
| 1584. | RKKIGIENPKR; |
| 1585. | HKKIGIENPKR; |
| 1586. | KRKIGIENPKR; |
| 1587. | RRKIGIENPKR; |
| 1588. | HRKIGIENPKR; |
| 1589. | KHRIGIENPKR; |
| 1590. | RHRIGIENPKR; |
| 1591. | HHRIGIENPKR; |
| 1592. | KKRIGIENPKR; |
| 1593. | RKRIGIENPKR; |
| 1594. | HKRIGIENPKR; |
| 1595. | KRRIGIENPKR; |
| 1596. | RRRIGIENPKR; |
| 1597. | HRRIGIENPKR; |
| 1598. | KHHVGIENPKR; |
| 1599. | RHHVGIENPKR; |
| 1600. | HHHVGIENPKR; |
| 1601. | KKHVGIENPKR; |
| 1602. | RKHVGIENPKR; |
| 1603. | HKHVGIENPKR; |
| 1604. | KRHVGIENPKR; |
| 1605. | RRHVGIENPKR; |
| 1606. | HRHVGIENPKR; |
| 1607. | KHKVGIENPKR; |
| 1608. | RHKVGIENPKR; |
| 1609. | HHKVGIENPKR; |

TABLE 7-continued

SEQ ID NO. shown to left of sequence(cont'd)

| SEQ ID NO. | Sequence |
|---|---|
| 1610. | KKKVGIENPKR; |
| 1611. | RKKVGIENPKR; |
| 1612. | HKKVGIENPKR; |
| 1613. | KRKVGIENPKR; |
| 1614. | RRKVGIENPKR; |
| 1615. | HRKVGIENPKR; |
| 1616. | KHRVGIENPKR; |
| 1617. | RHRVGIENPKR; |
| 1618. | HHRVGIENPKR; |
| 1619. | KKRVGIENPKR; |
| 1620. | RKRVGIENPKR; |
| 1621. | HKRVGVENPKR; |
| 1622. | KRRVGIENPKR; |
| 1623. | RRRVGIENPKR; |
| 1624. | HRRVGIENPKR; |
| 1625. | KHHLGVENPKR; |
| 1626. | RHHLGVENPKR; |
| 1627. | HHHLGVENPKR; |
| 1628. | KKHLGVENPKR; |
| 1629. | RKHLGVENPKR; |
| 1630. | HKHLGVENPKR; |
| 1631. | KRHLGVENPKR; |
| 1632. | RRHLGVENPKR; |
| 1633. | HRHLGVENPKR; |
| 1634. | KHKLGVENPKR; |
| 1635. | RHKLGVENPKR; |
| 1636. | HHKLGVENPKR; |
| 1637. | KKKLGVENPKR; |
| 1638. | RKKLGVENPKR; |
| 1639. | HKKLGVENPKR; |
| 1640. | KRKLGVENPKR; |
| 1641. | RRKLGVENPKR; |
| 1642. | HRKLGVENPKR; |
| 1643. | KHRLGVENPKR; |
| 1644. | RHRLGVENPKR; |
| 1645. | HHRLGVENPKR; |
| 1646. | KKRLGVENPKR; |
| 1647. | RKRLGVENPKR; |
| 1648. | HKRLGVENPKR; |
| 1649. | KRRLGVENPKR; |
| 1650. | RRHLGVENPKR; |
| 1651. | HRRLGVENPKR; |
| 1652. | KHHIGVENPKR; |
| 1653. | RHHIGVEEPKR; |
| 1654. | HHHIGVENPKR; |
| 1655. | KKHIGVENPKR; |
| 1656. | RKHIGVENPKR; |
| 1657. | HKHIGVENPKR; |
| 1658. | KRHIGVENPKR; |
| 1659. | RRHVGVENPKR; |
| 1660. | HRHIGVENPKR; |
| 1661. | KHKIGVENPKR; |
| 1662. | RHKIGVENPKR; |
| 1663. | HHKIGVENPKR; |
| 1664. | KKKIGVENPKR; |
| 1665. | RKKIGVENPKR; |
| 1666. | HKKIGVENPKR; |
| 1667. | KRKIGVENPKR; |
| 1668. | RRKIGVENPKR; |
| 1669. | HRKIGVENPKR; |
| 1670. | KHRIGVENPKR; |
| 1671. | RHRIGVENPKR; |
| 1672. | HHRIGVENPKR; |
| 1673. | KKRIGVENPKR; |
| 1674. | RKRIGVENPKR; |
| 1675. | HKRIGVENPKR; |
| 1676. | KRRIGVENPKR; |
| 1677. | RRRIGVENPKR; |
| 1678. | HRRIGVENPKR; |
| 1679. | KHHVGVENPKR; |
| 1680. | RHHVGVENPKR; |
| 1681. | HHHVGVENPKR; |
| 1682. | KKHVGVENPKR; |
| 1683. | RKHVGVENPKR; |
| 1684. | HKHVGVENPKR; |
| 1685. | KRHVGVENPKR; |
| 1686. | RRHVGVENPKR; |
| 1687. | HRHVGVENPKR; |

TABLE 7-continued

| SEQ ID NO. shown to left of sequence(cont'd) | |
|---|---|
| 1688. | KHKVGVENPKR; |
| 1689. | RHKVGVENPKR; |
| 1690. | HHKVGVENPKR; |
| 1691. | KKKVGVENPKR; |
| 1692. | RKKVGVENPKR; |
| 1693. | HKKVGVENPKR; |
| 1694. | KRKVGVENPKR; |
| 1695. | RRKVGVEEPKR; |
| 1696. | HRKVGVENPKR; |
| 1697. | KHRVGVENPKR; |
| 1698. | RHRVGVENPKR; |
| 1699. | HHRVGVENPKR; |
| 1700. | KKRVGVENPKR; |
| 1701. | RKRVGVENPKR; |
| 1702. | HKRVGVENPKR; |
| 1703. | KRRVGVENPKR; |
| 1704. | RRRVGVENPKR; |
| 1705. | HRRVGVENPKR; |
| 1706. | KHHLGLNNPKR; |
| 1707. | RHHLGLNNPKR; |
| 1708. | HHHLGLNNPKR; |
| 1709. | KKHLGLNNPKR; |
| 1710. | RKHLGLNNPKR; |
| 1711. | HKHLGLNNPKR; |
| 1712. | KRHLGLNNPKR; |
| 1713. | RRHLGLNNPKR; |
| 1714. | HRHLGLNNPKR; |
| 1715. | KHKLGLNNPKR; |
| 1716. | RHKLGLNNPKR; |
| 1717. | HHKLGLNNPKR; |
| 1718. | KKKLGLNNPKR; |
| 1719. | RKKLGLNNPKR; |
| 1720. | HKKLGLNNPKR; |
| 1721. | KRKLGLNNPKR; |
| 1722. | RRKLGLNNPKR; |
| 1723. | HRKLGLNNPKR; |
| 1724. | KHRLGLNNPKR; |
| 1725. | RHRLGLNNPKR; |
| 1726. | HHRLGLNNPKR; |
| 1727. | KKRLGLNNPKR; |
| 1728. | RKRLGLNNPKR; |
| 1729. | HKRLGLNNPKR; |
| 1730. | KRRLGLNNPKR; |
| 1731. | RRRLGLNNPKR; |
| 1732. | HRRLGLNNPKR; |
| 1733. | KHHIGLNNPKR; |
| 1734. | RHHIGLNNPKR; |
| 1735. | HHHIGLNNPKR; |
| 1736. | KKHIGLNNPKR; |
| 1737. | RKHIGLNNPKR; |
| 1738. | HKHIGLNNPKR; |
| 1739. | KRHIGLNNPKR; |
| 1740. | RRHIGLNNPKR; |
| 1741. | HRHIGLNNPKR; |
| 1742. | KHKIGLNNPKR; |
| 1743. | RHKIGLNNPKR; |
| 1744. | HHKIGLNNPKR; |
| 1745. | KKKIGLNNPKR; |
| 1746. | RKKIGLNNPKR; |
| 1747. | HKKIGLNNPKR; |
| 1748. | KRKIGLNNPKR; |
| 1749. | RRKIGLNNPKR; |
| 1750. | HRKIGLNNPKR; |
| 1751. | KHRIGLNNPKR; |
| 1752. | RHRIGLNNPKR; |
| 1753. | HHRIGLNNPKR; |
| 1754. | KKRIGLNNPKR; |
| 1755. | RKRIGLNNPKR; |
| 1756. | HKRIGLNNPKR; |
| 1757. | KRRIGLNNPKR; |
| 1758. | RRRIGLNNPKR; |
| 1759. | HRRIGLNNPKR; |
| 1760. | KHHVGLNNPKR; |
| 1761. | RHHVGLNNPKR; |
| 1762. | HHHVGLNNPKR; |
| 1763. | KKHVGLNNPKR; |
| 1764. | RKHVGLNNPKR; |
| 1765. | HKHVGLNNPKR; |

TABLE 7-continued

SEQ ID NO. shown to left of sequence(cont'd)

| SEQ ID NO. | Sequence |
|---|---|
| 1766. | KRHVGLNNPKR; |
| 1767. | RRHVGLNNPKR; |
| 1768. | HRHVGLNNPKR; |
| 1769. | KHKVGLNNPKR; |
| 1770. | RHKVGLNNPKR; |
| 1771. | HHKVGLNNPKR; |
| 1772. | KKKVGLNNPKR; |
| 1773. | RKKVGLNNPKR; |
| 1774. | HKKVGLNNPKR; |
| 1775. | KRKVGLNNPKR; |
| 1776. | RRKVGLNNPKR; |
| 1777. | HRKVGLNNPKR; |
| 1778. | KHRVGLNNPKR; |
| 1779. | RHRVGLNNPKR; |
| 1780. | HHRVGLNNPKR; |
| 1781. | KKRVGLNNPKR; |
| 1782. | RKRVGLNNPKR; |
| 1783. | HKRVGLNNPKR; |
| 1784. | KRRVGLNNPKR; |
| 1785. | RRRVGLNNPKR; |
| 1786. | HRRVGLNNPKR; |
| 1787. | KHHLGINNPKR; |
| 1788. | RHHLGINNPKR; |
| 1789. | HHHLGINNPKR; |
| 1790. | KKHLGINNPKR; |
| 1791. | RKHLGINNPKR; |
| 1792. | HKHLGINNPKR; |
| 1793. | KRHLGINNPKR; |
| 1794. | RRHLGINNPKR; |
| 1795. | HRHLGINNPKR; |
| 1796. | KHKLGINNPKR; |
| 1797. | RHKLGINNPKR; |
| 1798. | HHKLGINNPKR; |
| 1799. | KKKLGINNPKR; |
| 1800. | RKKLGINNPKR; |
| 1801. | HKKLGINNPKR; |
| 1802. | KRKLGINNPKR; |
| 1803. | RRKLGINNPKR; |
| 1804. | HRKLGINNPKR; |
| 1805. | KHRLGINNPKR; |
| 1806. | RHRLGINNPKR; |
| 1807. | HHRLGINNPKR; |
| 1808. | KKRLGINNPKR; |
| 1809. | RKRLGINNPKR; |
| 1810. | HKRLGINNPKR; |
| 1811. | KRRLGINNPKR; |
| 1812. | RRRLGINNPKR; |
| 1813. | HRRLGINNPKR; |
| 1814. | KHHIGIENPKR; |
| 1815. | RHHIGINNPKR; |
| 1816. | HHHIGINNPKR; |
| 1817. | KKHIGINNPKR; |
| 1818. | RKHIGINNPKR; |
| 1819. | HKHIGINNPKR; |
| 1820. | KRHIGINNPKR; |
| 1821. | RRHIGINNPKR; |
| 1822. | HRHIGINNPKR; |
| 1823. | KHKIGINNPKR; |
| 1824. | RHKIGINNPKR; |
| 1825. | HHKIGINNPKR; |
| 1826. | KKKIGINNPKR; |
| 1827. | RKKIGINNPKR; |
| 1828. | HKKIGINNPKR; |
| 1829. | KRKIGINNPKR; |
| 1830. | RRKIGINNPKR; |
| 1831. | HRKIGINNPKR; |
| 1832. | KHRIGINNPKR; |
| 1833. | RHRIGINNPKR; |
| 1834. | HHRIGINNPKR; |
| 1835. | KKRIGINNPKR; |
| 1836. | RKRIGINNPKR; |
| 1837. | HKRIGINNPKR; |
| 1838. | KRRIGINNPKR; |
| 1839. | RRRIGINNPKR; |
| 1840. | HRRIGINNPKR; |
| 1841. | KHHVGINNPKR; |
| 1842. | RHHVGINNPKR; |
| 1843. | HHHVGINNPKR; |

TABLE 7-continued

SEQ ID NO. shown to left of sequence(cont'd)

| | |
|---|---|
| 1844. | KKHVGINNPKR; |
| 1845. | RKHVGINNPKR; |
| 1846. | HKHVGINNPKR; |
| 1847. | KRRVGINNPKR; |
| 1848. | RRHVGINNPKR; |
| 1849. | HRHVGINNPKR; |
| 1850. | KHKVGINNPKR; |
| 1851. | RHKVGINNPKR; |
| 1852. | HHKVGINNPKR; |
| 1853. | KKKVGINNPKR; |
| 1854. | RKKVGINNPKR; |
| 1855. | HKKVGINNPKR; |
| 1856. | KRKVGINNPKR; |
| 1857. | RRKVGINNPKR; |
| 1858. | HRKVGINNPKR; |
| 1859. | KHRVGINNPKR; |
| 1860. | RHRVGINNPKR; |
| 1861. | HHRVGINNPKR; |
| 1862. | KKRVGINNPKR; |
| 1863. | RKRVGINNPKR; |
| 1864. | HKRVGINNPKR; |
| 1865. | KRRVGINNPKR; |
| 1866. | RRRVGINNPKR; |
| 1867. | HRRVGINNPKR; |
| 1868. | KHHLGVNNPKR; |
| 1869. | RHHLGVNNPKR; |
| 1870. | HHHLGVNNPKR; |
| 1871. | KKHLGVNNPKR; |
| 1872. | RKHLGVNNPKR; |
| 1873. | HKHLGVNNPKR; |
| 1874. | KRHLGVNNPKR; |
| 1875. | RRHLGVNNPKR; |
| 1876. | HRHLGVNNPKR; |
| 1877. | KHKLGVNNPKR; |
| 1878. | RHKLGVNNPKR; |
| 1879. | HHKLGVNNPKR; |
| 1880. | KKKLGVNNPKR; |
| 1881. | RKKLGVNNPKR; |
| 1882. | HKKLGVNNPKR; |

TABLE 7-continued

SEQ ID NO. shown to left of sequence(cont'd)

| | |
|---|---|
| 1883. | KRKLGVNNPKR; |
| 1884. | RRKLGVNNPKR; |
| 1885. | HRKLGVNNPKR; |
| 1886. | KHRLGVNNPKR; |
| 1887. | RHRLGVNNPKR; |
| 1888. | HHRLGVNNPKR; |
| 1889. | KKRLGVNNPKR; |
| 1890. | RKRLGVNNPKR; |
| 1891. | HKRLGVNNPKR; |
| 1892. | KRRLGVNNPKR; |
| 1893. | RRRLGVNNPKR; |
| 1894. | HRRLGVNNPKR; |
| 1895. | KHHIGVNNPKR; |
| 1896. | RHHIGVNNPKR; |
| 1897. | HHHIGVNNPKR; |
| 1898. | KKHIGVNNPKR; |
| 1899. | RKHIGVNNPKR; |
| 1900. | HKHIGVNNPKR; |
| 1901. | KRHIGVNNPKR; |
| 1902. | RRHIGVNNPKR; |
| 1903. | HRHIGVNNPKR; |
| 1904. | KHKIGVNNPKR; |
| 1905. | RHKIGVNNPKR; |
| 1906. | HHKIGVNNPKR; |
| 1907. | KKKIGVNNPKR; |
| 1908. | RKKIGVNNPKR; |
| 1909. | HKKIGVNNPKR; |
| 1910. | KRKIGVNNPKR; |
| 1911. | RRKIGVNNPKR; |
| 1912. | HRKIGVNNPKR; |
| 1913. | KHRIGVNNPKR; |
| 1914. | RHRIGVNNPKR; |
| 1915. | HHRIGVNNPKR; |
| 1916. | KKRIGVNNPKR; |
| 1917. | RKRIGVNNPKR; |
| 1918. | HKRIGVNNPKR; |
| 1919. | KRRIGVNNPKR; |
| 1920. | RRRIGVNNPKR; |
| 1921. | HRRIGVNNPKR; |

TABLE 7-continued

SEQ ID NO. shown to left of sequence(cont'd)

| | |
|---|---|
| 1922. | KHHVGVNNPKR; |
| 1923. | RHHVGVNNPKR; |
| 1924. | HHHVGVNNPKR; |
| 1925. | KKHVGVNNPKR; |
| 1926. | RKHVGVNNPKR; |
| 1927. | HKHVGVNNPKR; |
| 1928. | KRHVGVNNPKR; |
| 1929. | RRHVGVNNPKR; |
| 1930. | HRHVGVNNPKR; |
| 1931. | KHKVGVNNPKR; |
| 1932. | RHKVGVNNPKR; |
| 1933. | HHKVGVNNPKR; |
| 1934. | KKKVGVNNPKR; |
| 1935. | RKKVGVNNPKR; |
| 1936. | HKKVGVNNPKR; |
| 1937. | KRKVGVNNPKR; |
| 1938. | RRKVGVNNPKR; |
| 1939. | HRKVGVNNPKR; |
| 1940. | KHRVGVNNPKR; |
| 1941. | RHRVGVNNPKR; |
| 1942. | HHRVGVNNPKR; |
| 1943. | KKRVGVNNPKR; |
| 1944. | RKRVGVNNPKR; |
| 1945. | HKRVGVNNPKR; |
| 1946. | KRRVGVNNPKR; |
| 1947. | RRRVGVNNPKR; |
| 1948. | HRRVGVNNPKR; |
| 1949. | KHHLGLEEPKH; |
| 1950. | RHHLGLEEPKH; |
| 1951. | HHHLGLEEPKH; |
| 1952. | KKHLGLEEPKH; |
| 1953. | RKHLGLEEPKH; |
| 1954. | HKHLGLEEPKH; |
| 1955. | KRHLGLEEPKH; |
| 1956. | RRHLGLEEPKH; |
| 1957. | HRHLGLEEPKH; |
| 1958. | KHKLGLEEPKH; |
| 1959. | RHKLGLEEPKH; |
| 1960. | HHKLGLEEPKH; |

TABLE 7-continued

SEQ ID NO. shown to left of sequence(cont'd)

| | |
|---|---|
| 1961. | KKRLGLEEPKH; |
| 1962. | RKKLGLEEPKH; |
| 1963. | HKKLGLEEPKH; |
| 1964. | KRKLGLEEPKH; |
| 1965. | RRKLGLEEPKH; |
| 1966. | HRKLGLEEPKH; |
| 1967. | KHRLGLEEPKH; |
| 1968. | RHRLGLEEPKH; |
| 1969. | HHRLGLEEPKH; |
| 1970. | KKRLGLEEPKH; |
| 1971. | RKRLGLEEPKH; |
| 1972. | HKRLGLEEPKH; |
| 1973. | KRRLGLEEPKH; |
| 1974. | RRRLGLEEPKH; |
| 1975. | HRRLGLEEPKH; |
| 1976. | KHHIGLEEPKH; |
| 1977. | RHHIGLEEPKH; |
| 1978. | HHHIGLEEPKH; |
| 1979. | KKHIGLEEPKH; |
| 1980. | RKHIGLEEPKH; |
| 1981. | HKHIGLEEPKH; |
| 1982. | KRHIGLEEPKH; |
| 1983. | RRHIGLEEPKH; |
| 1984. | HRHIGLEEPKH; |
| 1985. | KHKIGLEEPKH; |
| 1986. | RHKIGLEEPKH; |
| 1987. | HHKIGLEEPKH; |
| 1988. | KKKIGLEEPKH; |
| 1989. | RKKIGLEEPKH; |
| 1990. | HKKIGLEEPKH; |
| 1991. | KRKIGLEEPKH; |
| 1992. | RRKIGLEEPKH; |
| 1993. | HRKIGLEEPKH; |
| 1994. | KHRIGLEEPKH; |
| 1995. | RHRIGLEEPKH; |
| 1996. | HHRIGLEEPKH; |
| 1997. | KKRIGLEEPKH; |
| 1998. | RKRIGLEEPKH; |
| 1999. | HKRIGLEEPKH; |

TABLE 7-continued

SEQ ID NO. shown to left of sequence (cont'd)

| SEQ ID NO. | Sequence |
|---|---|
| 2000. | KRRIGLEEPKH; |
| 2001. | RRRIGLEEPKH; |
| 2002. | HRRIGLEEPKH; |
| 2003. | KHHVGLEEPKH; |
| 2004. | RHHVGLEEPKH; |
| 2005. | HHHVGLEEPKH; |
| 2006. | KKHVGLEEPKH; |
| 2007. | RKHVGLEEPKH; |
| 2008. | HKHVGLEEPKH; |
| 2009. | KRHVGLEEPKH; |
| 2010. | RRHVGLEEPKH; |
| 2011. | HRHVGLEEPKH; |
| 2012. | KHKVGLEEPKH; |
| 2013. | RHKVGLEEPKH; |
| 2014. | HHKVGLEEPKH; |
| 2015. | KKKVGLEEPKH; |
| 2016. | RKKVGLEEPKH; |
| 2017. | HKKVGLEEPKH; |
| 2018. | KRKVGLEEPKH; |
| 2019. | RRKVGLEEPKH; |
| 2020. | HRKVGLEEPKH; |
| 2021. | KHRVGLEEPKH; |
| 2022. | RHRVGLEEPKH; |
| 2023. | HHRVGLEEPKH; |
| 2024. | KKRVGLEEPKH; |
| 2025. | RKRVGLEEPKH; |
| 2026. | HKRVGLEEPKH; |
| 2027. | KRRVGLEEPKH; |
| 2028. | RRRVGLEEPKH; |
| 2029. | HRRVGLEEPKH; |
| 2030. | KHHLGIEEPKH; |
| 2031. | RHHLGIEEPKH; |
| 2032. | HHHLGIEEPKH; |
| 2033. | KKHLGIEEPKH; |
| 2034. | RKHLGIEEPKH; |
| 2035. | HKHLGIEEPKH; |
| 2036. | KRHLGIEEPKH; |
| 2037. | RRHLGIEEPKH; |
| 2038. | HRHLGIEEPKH; |
| 2039. | KHKLGIEEPKH; |
| 2040. | RHKLGIEEPKH; |
| 2041. | HHKLGIEEPKH; |
| 2042. | KKKLGIEEPKH; |
| 2043. | RKKLGIEEPKH; |
| 2044. | HKKLGIEEPKH; |
| 2045. | KRKLGIEEPKH; |
| 2046. | RRKLGIEEPKH; |
| 2047. | HRKLGIEEPKH; |
| 2048. | KHRLGIEEPKH; |
| 2049. | RHRLGIEEPKH; |
| 2050. | HHRLGIEEPKH; |
| 2051. | KKRLGIEEPKH; |
| 2052. | RKRLGIEEPKH; |
| 2053. | HKRLGIEEPKH; |
| 2054. | KRRLGIEEPKH; |
| 2055. | RRRLGIEEPKH; |
| 2056. | HRRLGIEEPKH; |
| 2057. | KHHIGIEEPKH; |
| 2058. | RHHIGIEEPKH; |
| 2059. | HHHIGIEEPKH; |
| 2060. | KKHIGIEEPKH; |
| 2061. | RKHIGIEEPKH; |
| 2062. | HKHIGIEEPKH; |
| 2063. | KRHIGIEEPKH; |
| 2064. | RRHIGIEEPKH; |
| 2065. | HRHIGIEEPKH; |
| 2066. | KHKIGIEEPKH; |
| 2067. | RHKIGIEEPKH; |
| 2068. | HHKIGIEEPKH; |
| 2069. | KKKIGIEEPKH; |
| 2070. | RKKIGIEEPKH; |
| 2071. | HKKIGIEEPKH; |
| 2072. | KRKIGIEEPKH; |
| 2073. | RRKIGIEEPKH; |
| 2074. | HRKIGIEEPKH; |
| 2075. | KHRIGIEEPKH; |
| 2076. | RHRIGIEEPKH; |
| 2077. | HHRIGIEEPKH; |

TABLE 7-continued

| SEQ ID NO. shown to left of sequence(cont'd) | |
|---|---|
| 2078. | KKRIGIEEPKH; |
| 2079. | RKRIGIEEPKH; |
| 2080. | HKRIGIEEPKH; |
| 2081. | KRRIGIEEPKH; |
| 2082. | RRRIGIEEPKH; |
| 2083. | HRRIGIEEPKH; |
| 2084. | KHHVGIEEPKH; |
| 2085. | RHHVGIEEPKH; |
| 2086. | HHHVGIEEPKH; |
| 2087. | KKHVGIEEPKH; |
| 2088. | RKHVGIEEPKH; |
| 2089. | HKHVGIEEPKH; |
| 2090. | KRHVGIEEPKH; |
| 2091. | RRHVGIEEPKH; |
| 2092. | HRHVGIEEPKH; |
| 2093. | KHKVGIEEPKH; |
| 2094. | RHKVGIEEPKH; |
| 2095. | HHKVGIEEPKH; |
| 2096. | KKKVGIEEPKH; |
| 2097. | RKKVGIEEPKH; |
| 2098. | HKKVGIEEPKH; |
| 2099. | KRKVGIEEPKH; |
| 2100. | RRKVGIEEPKH; |
| 2101. | HRKVGIEEPKH; |
| 2102. | KHRVGIEEPKH; |
| 2103. | RHRVGIEEPKH; |
| 2104. | HHRVGIEEPKH; |
| 2105. | KKRVGIEEPKH; |
| 2106. | RKRVGIEEPKH; |
| 2107. | HKRVGIEEPKH; |
| 2108. | KRRVGIEEPKH; |
| 2109. | RRRVGIEEPKH; |
| 2110. | HRRVGIEEPKH; |
| 2111. | KHHLGVEEPKH; |
| 2112. | RHHLGVEEPKH; |
| 2113. | HHHLGVEEPKH; |
| 2114. | KKHLGVEEPKH; |
| 2115. | RKHLGVEEPKH; |
| 2116. | HKHLGVEEPKH; |
| 2117. | KRHLGVEEPKH; |
| 2118. | RRHLGVEEPKH; |
| 2119. | HRHLGVEEPKH; |
| 2120. | KHKLGVEEPKH; |
| 2121. | RHKLGVEEPKH; |
| 2122. | HHKLGVEEPKH; |
| 2123. | KKKLGVEEPKH; |
| 2124. | RKKLGVEEPKH; |
| 2125. | HKKLGVEEPKH; |
| 2126. | KRKLGVEEPKH; |
| 2127. | RRKLGVEEPKH; |
| 2128. | HRKLGVEEPKH; |
| 2129. | KHRLGVEEPKH; |
| 2130. | RHRLGVEEPKH; |
| 2131. | HHRLGVEEPKH; |
| 2132. | KKRLGVEEPKH; |
| 2133. | RKRLGVEEPKH; |
| 2134. | HKRLGVEEPKH; |
| 2135. | KRRLGVEEPKH; |
| 2136. | RRRLGVEEPKH; |
| 2137. | HRRLGVEEPKH; |
| 2138. | KHHIGVEEPKH; |
| 2139. | RHHIGVEEPKH; |
| 2140. | HHHIGVEEPKH; |
| 2141. | KKHIGVEEPKH; |
| 2142. | RKHIGVEEPKH; |
| 2143. | HKHIGVEEPKH; |
| 2144. | KRHIGVEEPKH; |
| 2145. | RRHIGVEEPKH; |
| 2146. | HRHIGVEEPKH; |
| 2147. | KHKIGVEEPKH; |
| 2148. | RHKIGVEEPKH; |
| 2149. | HHKIGVEEPKH; |
| 2150. | KKKIGVEEPKH; |
| 2151. | RKKIGVEEPKH; |
| 2152. | HKKIGVEEPKH; |
| 2153. | KRKIGVEEPKH; |
| 2154. | RRKIGVEEPKH; |
| 2155. | HRKIGVEEPKH; |

TABLE 7-continued

SEQ ID NO. shown to left of sequence(cont'd)

| SEQ ID NO. | Sequence |
|---|---|
| 2156. | KHRIGVEEPKH; |
| 2157. | RHRIGVEEPKH; |
| 2158. | HHRIGVEEPKH; |
| 2159. | KKRIGVEEPKH; |
| 2160. | RKRIGVEEPKH; |
| 2161. | HKRIGVEEPKH; |
| 2162. | KRRIGVEEPKH; |
| 2163. | RRRIGVEEPKH; |
| 2164. | HRRIGVEEPKH; |
| 2165. | KHHVGVEEPKH; |
| 2166. | RHHVGVEEPKH; |
| 2167. | HHHVGVEEPKH; |
| 2168. | KKHVGVEEPKH; |
| 2169. | RKHVGVEEPKH; |
| 2170. | HKHVGVEEPKH; |
| 2171. | KRHVGVEEPKH; |
| 2172. | RRHVGVEEPKH; |
| 2173. | HRHVGVEEPKH; |
| 2174. | KHKVGVEEPKH; |
| 2175. | RHKVGVEEPKH; |
| 2176. | HHKVGVEEPKH; |
| 2177. | KKKVGVEEPKH; |
| 2178. | RKKVGVEEPKH; |
| 2179. | HKKVGVEEPKH; |
| 2180. | KRKVGVEEPKH; |
| 2181. | RRKVGVEEPKH; |
| 2182. | HRKVGVEEPKH; |
| 2183. | KHRVGVEEPKH; |
| 2184. | RHRVGVEEPKH; |
| 2185. | HHRVGVEEPKH; |
| 2186. | KKRVGVEEPKH; |
| 2187. | RKRVGVEEPKH; |
| 2188. | HKRVGVEEPKH; |
| 2189. | KRRVGVEEPKH; |
| 2190. | RRRVGVEEPKH; |
| 2191. | HRRVGVEEPKH; |
| 2192. | KHHLGLNEPKH; |
| 2193. | RHHLGLNEPKH; |
| 2194. | HHHLGLNEPKH; |
| 2195. | KKHLGLNEPKH; |
| 2196. | RKHLGLNEPKH; |
| 2197. | HKHLGLNEPKH; |
| 2198. | KRHLGLNEPKH; |
| 2199. | RRHLGLNEPKH; |
| 2200. | HRHLGLNEPKH; |
| 2201. | KHKLGLNEPKH; |
| 2202. | RHKLGLNEPKH; |
| 2203. | HHKLGLNEPKH; |
| 2204. | KKKLGLNEPKH; |
| 2205. | RKKLGLNEPKH; |
| 2206. | HKKLGLNEPKH; |
| 2207. | KRKLGLNEPKH; |
| 2208. | RRKLGLNEPKH; |
| 2209. | HRKLGLNEPKH; |
| 2210. | KHRLGLNEPKH; |
| 2211. | RHRLGLNEPKH; |
| 2212. | HHRLGLNEPKH; |
| 2213. | KKRLGLNEPKH; |
| 2214. | RKRLGLNEPKH; |
| 2215. | HKRLGLNEPKH; |
| 2216. | KRRLGLNEPKH; |
| 2217. | RRRLGLNEPKH; |
| 2218. | HRRLGLNEPKH; |
| 2219. | KHHIGLNPKH; |
| 2220. | RHHIGLNPKH; |
| 2221. | HHHIGLNPKH; |
| 2222. | KKHIGLNEPKH; |
| 2223. | RKHIGLNEPKH; |
| 2224. | HKHIGLNEPKH; |
| 2225. | KRHIGLNEPKH; |
| 2226. | RRHIGLNEPKH; |
| 2227. | HRHIGLNEPKH; |
| 2228. | KHKIGLNEPKH; |
| 2229. | RHKIGLNEPKH; |
| 2230. | HHKIGLNEPKH; |
| 2231. | KKKIGLNEPKH; |
| 2232. | RKKIGLNEPKH; |
| 2233. | HKKIGLNEPKH; |

TABLE 7-continued

SEQ ID NO. shown to left of sequence(cont'd)

| | |
|---|---|
| 2234. | KRKLGLNEPKH; |
| 2235. | RRKIGLNEPKH; |
| 2236. | HRKIGLNEPKH; |
| 2237. | KHRIGLNEPKH; |
| 2238. | RHRIGLNEPKH; |
| 2239. | HHRIGLNEPKH; |
| 2240. | KKRIGLNEPKH; |
| 2241. | RKRIGLNEPKH; |
| 2242. | HKRIGLNEPKH; |
| 2243. | KRRIGLNEPKH; |
| 2244. | RRRIGLNEPKH; |
| 2245. | HRRIGLNEPKH; |
| 2246. | KHHVGLNEPKH; |
| 2247. | RHHVGLNEPKH; |
| 2248. | HHHVGLNEPKH; |
| 2249. | KKHVGLNEPKH; |
| 2250. | RKHVGLNEPKH; |
| 2251. | HKHVGLNEPKH; |
| 2252. | KRHVGLNEPKH; |
| 2253. | RRHVGLNEPKH; |
| 2254. | HRHVGLNEPKH; |
| 2255. | KHKVGLNEPKH; |
| 2256. | RHKVGLNEPKH; |
| 2257. | HHKVGLNEPKH; |
| 2258. | KKKVGLNEPKH; |
| 2259. | RKKVGLNEPKH; |
| 2260. | HKKVGLNEPKH; |
| 2261. | KRKVGLNEPKH; |
| 2262. | RRKVGLNEPKH; |
| 2263. | HRKVGLNEPKH; |
| 2264. | KHRVGLNEPKH; |
| 2265. | RHRVGLNEPKH; |
| 2266. | HHRVGLNEPKH; |
| 2267. | KKRVGLNEPKH; |
| 2268. | RKRVGLNEPKH; |
| 2269. | HKRVGLNEPKH; |
| 2270. | KRRVGLNEPKH; |
| 2271. | RRRVGLNEPKH; |
| 2272. | HRRVGLNEPKH; |
| 2273. | KHHLGINEPKH; |
| 2274. | RHHLGINEPKH; |
| 2275. | HHHLGINEPKH; |
| 2276. | KKHLGINEPKH; |
| 2277. | RKHLGINEPKH; |
| 2278. | HKHLGINEPKH; |
| 2279. | KRHLGINEPKH; |
| 2280. | RRHLGINEPKH; |
| 2281. | HRHLGINEPKH; |
| 2282. | KHKLGINEPKH; |
| 2283. | RHKLGINEPKH; |
| 2284. | HHKLGINEPKH; |
| 2285. | KKKLGINEPKH; |
| 2286. | RKKLGINEPKH; |
| 2287. | HKKLGINEPKH; |
| 2288. | KRKLGINEPKH; |
| 2289. | RRKLGINEPKH; |
| 2290. | HRKLGINEPKH; |
| 2291. | KHRLGINEPKH; |
| 2292. | RHRLGINEPKH; |
| 2293. | HHRLGINEPKH; |
| 2294. | KKRLGINEPKH; |
| 2295. | RKRLGINEPKH; |
| 2296. | HKRLGINEPKH; |
| 2297. | KRRLGINEPKH; |
| 2298. | RRRLGINEPKH; |
| 2299. | HRRLGINEPKH; |
| 2300. | KHHIGINEPKH; |
| 2301. | RHHIGINEPKH; |
| 2302. | HHHIGINEPKH; |
| 2303. | KKHIGINEPKH; |
| 2304. | RKHIGINEPKH; |
| 2305. | HKHIGINEPKH; |
| 2306. | KRHIGINEPKH; |
| 2307. | RRHIGINEPKH; |
| 2308. | HRHIGINEPKH; |
| 2309. | KHKIGINEPKH; |
| 2310. | RHKIGINEPKH; |
| 2311. | HHKIGINEPKH; |

TABLE 7-continued

SEQ ID NO. shown to left of sequence(cont'd)

| SEQ ID NO. | Sequence |
|---|---|
| 2312. | KKKIGINEPKH; |
| 2313. | RKKIGINEPKH; |
| 2314. | HKKIGINEPKH; |
| 2315. | KRKIGINEPKH; |
| 2316. | RRKIGINEPKH; |
| 2317. | HRKIGINEPKH; |
| 2318. | KHRIGINEPKH; |
| 2319. | RHRIGINEPKH; |
| 2320. | HHRIGINEPKH; |
| 2321. | KKRIGINEPKH; |
| 2322. | RKRIGINEPKH; |
| 2323. | HKRIGINEPKH; |
| 2324. | KRRIGINEPKH; |
| 2325. | RRRIGINEPKH; |
| 2326. | HRRIGINEPKH; |
| 2327. | KHHVGINEPKH; |
| 2328. | RHHVGINEPKH; |
| 2329. | HHHVGINEPKH; |
| 2330. | KKHVGINEPKH; |
| 2331. | RKHVGINEPKH; |
| 2332. | HKHVGINEPKH; |
| 2333. | KRHVGINEPKH; |
| 2334. | RRHVGINEPKH; |
| 2335. | HRHVGINEPKH; |
| 2336. | KHKVGINEPKH; |
| 2337. | RHKVGINEPKH; |
| 2338. | HHKVGINEPKH; |
| 2339. | KKKVGINEPKH; |
| 2340. | RKKVGINEPKH; |
| 2341. | HKKVGINEPKH; |
| 2342. | KRKVGINEPKH; |
| 2343. | RRKVGINEPKH; |
| 2344. | HRKVGINEPKH; |
| 2345. | KHRVGINEPKH; |
| 2346. | RHRVGINEPKH; |
| 2347. | HHRVGINEPKH; |
| 2348. | KKRVGINEPKH; |
| 2349. | RKRVGINEPKH; |
| 2350. | HKRVGINEPKH; |
| 2351. | KRRVGINEPKH; |
| 2352. | RRRVGINEPKH; |
| 2353. | HRRVGINEPKH; |
| 2354. | KHHLGVNEPKH; |
| 2355. | RHHLGVNEPKH; |
| 2356. | HHHLGVNEPKH; |
| 2357. | KKHLGVNEPKH; |
| 2358. | RKHLGVNEPKH; |
| 2359. | HKHLGVNEPKH; |
| 2360. | KRHLGVNEPKH; |
| 2361. | RRHLGVNEPKH; |
| 2362. | HRHLGVNEPKH; |
| 2363. | KHKLGVNEPKH; |
| 2364. | RHKLGVNEPKH; |
| 2365. | HHKLGVNEPKH; |
| 2366. | KKKLGVNEPKH; |
| 2367. | RKKLGVNEPKH; |
| 2368. | HKKLGVNEPKH; |
| 2369. | KRKLGVNEPKH; |
| 2370. | RRKLGVNEPKH; |
| 2371. | HRKLGVNEPKH; |
| 2372. | KHRLGVNEPKH; |
| 2373. | RHRLGVNEPKH; |
| 2374. | HHRLGVNEPKH; |
| 2375. | KKRLGVNEPKH; |
| 2376. | RKRLGVNEPKH; |
| 2377. | HKRLGVNEPKH; |
| 2378. | KRRLGVNEPKH; |
| 2379. | RRRLGVNEPKH; |
| 2380. | HRRLGVNEPKH; |
| 2381. | KHHIGVNEPKH; |
| 2382. | RHHIGVNEPKH; |
| 2383. | HHHIGVNEPKH; |
| 2384. | KKHIGVNEPKH; |
| 2385. | RKHIGVNEPKH; |
| 2386. | HKHIGVNEPKH; |
| 2387. | KRHIGVNEPKH; |
| 2388. | RRHIGVNEPKH; |
| 2389. | HRHIGVNEPKH; |

TABLE 7-continued

SEQ ID NO. shown to left of sequence(cont'd)

| SEQ ID NO. | Sequence |
|---|---|
| 2390. | KHKIGVNEPKH; |
| 2391. | RHKIGVNEPKH; |
| 2392. | HHKIGVNEPKH; |
| 2393. | KKKIGVNEPKH; |
| 2394. | RKKIGVNEPKH; |
| 2395. | HKKIGVNEPKH; |
| 2396. | KRKIGVNEPKH; |
| 2397. | RRKIGVNEPKH; |
| 2398. | HRKIGVNEPKH; |
| 2399. | KHRIGVNEPKH; |
| 2400. | RHRIGVNEPKH; |
| 2401. | HHRIGVNEPKH; |
| 2402. | KKRIGVNEPKH; |
| 2403. | RKRIGVNEPKH; |
| 2404. | HKRIGVNEPKH; |
| 2405. | KRRIGVNEPKH; |
| 2406. | RRRIGVNEPKH; |
| 2407. | HRRIGVNEPKH; |
| 2408. | KHHVGVNEPKH; |
| 2409. | RHHVGVNEPKH; |
| 2410. | HHHVGVNEPKH; |
| 2411. | KKHVGVNEPKH; |
| 2412. | RKHVGVNEPKH; |
| 2413. | HKHVGVNEPKH; |
| 2414. | KRHVGVNEPKH; |
| 2415. | RRHVGVNEPKH; |
| 2416. | HRHVGVNEPKH; |
| 2417. | KHKVGVNEPKH; |
| 2418. | RHKVGVNEPKH; |
| 2419. | HHKVGVNEPKH; |
| 2420. | KKKVGVNEPKH; |
| 2421. | RKKVGVNEPKH; |
| 2422. | HKKVGVNEPKH; |
| 2423. | KRKVGVNEPKH; |
| 2424. | RRKVGVNEPKH; |
| 2425. | HRKVGVNEPKH; |
| 2426. | KHRVGVNEPKH; |
| 2427. | RHRVGVNEPKH; |
| 2428. | HHRVGVNEPKH; |
| 2429. | KKRVGVNEPKH; |
| 2430. | RKRVGVNEPKH; |
| 2431. | HKRVGVNEPKH; |
| 2432. | KRRVGVNEPKH; |
| 2433. | RRRVGVNEPKH; |
| 2434. | HRRVGVNEPKH; |
| 2435. | KHHLGLENPKH; |
| 2436. | RHHLGLENPKH; |
| 2437. | HHHLGLENPKH; |
| 2438. | KKHLGLENPKH; |
| 2439. | RKHLGLENPKH; |
| 2440. | HKHLGLENPKH; |
| 2441. | KRHLGLENPKH; |
| 2442. | RRHLGLENPKH; |
| 2443. | HRHLGLENPKH; |
| 2444. | KHKLGLENPKH; |
| 2445. | RHKLGLENPKH; |
| 2446. | HHKLGLENPKH; |
| 2447. | KKKLGLENPKH; |
| 2448. | RKKLGLENPKH; |
| 2449. | HKKLGLENPKH; |
| 2450. | KRKLGLENPKH; |
| 2451. | RRKLGLENPKH; |
| 2452. | HRKLGLENPKH; |
| 2453. | KHRLGLENPKH; |
| 2454. | RHRLGLENPKH; |
| 2455. | HHRLGLENPKH; |
| 2456. | KKRLGLENPKH; |
| 2457. | RKRLGLENPKH; |
| 2458. | HKRLGLENPKH; |
| 2459. | KRRLGLENPKH; |
| 2460. | RRRLGLENPKH; |
| 2461. | HRRLGLENPKH; |
| 2462. | KHHIGLENPKH; |
| 2463. | RHHIGLENPKH; |
| 2464. | HHHIGLENPKH; |
| 2465. | KKHIGLENPKH; |
| 2466. | RKHIGLENPKH; |
| 2467. | HKHIGLENPKH; |

TABLE 7-continued

SEQ ID NO. shown to left of sequence(cont'd)

| | |
|---|---|
| 2468. | KRHIGLENPKH; |
| 2469. | RRHIGLENPKH; |
| 2470. | HRHIGLENPKH; |
| 2471. | KHKIGLENPKH; |
| 2472. | RHKIGLENPKH; |
| 2473. | HHKIGLENPKH; |
| 2474. | KKKIGLENPKH; |
| 2475. | RKKIGLENPKH; |
| 2476. | HKKIGLENPKH; |
| 2477. | KRKIGLENPKH; |
| 2478. | RRKIGLENPKH; |
| 2479. | HRKIGLENPKH; |
| 2480. | KHRIGLENPKH; |
| 2481. | RHRIGLENPKH; |
| 2482. | HHRIGLENPKH; |
| 2483. | KKRIGLENPKH; |
| 2484. | RKRIGLENPKH; |
| 2485. | HKRIGLENPKH; |
| 2486. | KRRIGLENPKH; |
| 2487. | RRRIGLENPKH; |
| 2488. | HRRIGLENPKH; |
| 2489. | KHHVGLENPKH; |
| 2490. | RHHVGLENPKH; |
| 2491. | HHHVGLENPKH; |
| 2492. | KKHVGLENPKH; |
| 2493. | RKHVGLENPKH; |
| 2494. | HKHVGLENPKH; |
| 2495. | KRHVGLENPKH; |
| 2496. | RRHVGLENPKH; |
| 2497. | HRHVGLENPKH; |
| 2498. | KHKVGLENPKH; |
| 2499. | RHKVGLENPKH; |
| 2500. | HHKVGLENPKH; |
| 2501. | KKKVGLENPKH; |
| 2502. | RKKVGLENPKH; |
| 2503. | HKKVGLENPKH; |
| 2504. | KRKVGLENPKH; |
| 2505. | RRKVGLENPKH; |
| 2506. | HRKVGLENPKH; |

TABLE 7-continued

SEQ ID NO. shown to left of sequence(cont'd)

| | |
|---|---|
| 2507. | KHRVGLENPKH; |
| 2508. | RHRVGLENPKH; |
| 2509. | HHRVGLENPKH; |
| 2510. | KKRVGLENPKH; |
| 2511. | RKRVGLENPKH; |
| 2512. | HKRVGLENPKH; |
| 2513. | KRRVGLENPKH; |
| 2514. | RRRVGLENPKH; |
| 2515. | HRRVGLENPKH; |
| 2516. | KHHLGIENPKH; |
| 2517. | RHHLGIENPKH; |
| 2518. | HHHLGIENPKH; |
| 2519. | KKHLGIENPKH; |
| 2520. | RKHLGIENPKH; |
| 2521. | HKHLGIENPKH; |
| 2522. | KRHLGIENPKH; |
| 2523. | RRHLGIENPKH; |
| 2524. | HRHLGIENPKH; |
| 2525. | KHKLGIENPKH; |
| 2526. | RHKLGIENPKH; |
| 2527. | HHKLGIENPKH; |
| 2528. | KKKLGIENPKH; |
| 2529. | RKKLGIENPKH; |
| 2530. | HKKLGIENPKH; |
| 2531. | KRKLGIENPKH; |
| 2532. | RRKLGIENPKH; |
| 2533. | HRKLGIENPKH; |
| 2534. | KHRLGIENPKH; |
| 2535. | RHRLGIENPKH; |
| 2536. | HHRLGIENPKH; |
| 2537. | KKRLGIENPKH; |
| 2538. | RKRLGIENPKH; |
| 2539. | HKRLGIENPKH; |
| 2540. | KRRLGIENPKH; |
| 2541. | RRRLGIENPKH; |
| 2542. | HRRLGIENPKH; |
| 2543. | KHHIGIENPKH; |
| 2544. | RHHIGIENPKH; |
| 2545. | HHHIGIENPKH; |

TABLE 7-continued

SEQ ID NO. shown to left of sequence(cont'd)

| SEQ ID NO. | Sequence |
|---|---|
| 2546. | KKHIGIENPKH; |
| 2547. | RKHIGIENPKH; |
| 2548. | HKHIGIENPKH; |
| 2549. | KRHIGIENPKH; |
| 2550. | RRHIGIENPKH; |
| 2551. | HRHIGIENPKH; |
| 2552. | KHHIGIENPKH; |
| 2553. | RHKIGIENPKH; |
| 2554. | HHKIGIENPKH; |
| 2555. | KKKIGIENPKH; |
| 2556. | RKKIGIENPKH; |
| 2557. | HKKIGIENPKH; |
| 2558. | KRKIGIENPKH; |
| 2559. | RRKIGIENPKH; |
| 2560. | HRKIGIENPKH; |
| 2561. | KHRIGIENPKH; |
| 2562. | RHRIGIENPKH; |
| 2563. | HHRIGIENPKH; |
| 2564. | KKRIGIENPKH; |
| 2565. | RKRIGIENPKH; |
| 2566. | HKRIGIENPKH; |
| 2567. | KRRIGIENPKH; |
| 2568. | RRRIGIENPKH; |
| 2569. | HRRIGIENPKH; |
| 2570. | KHHVGIENPKH; |
| 2571. | RHHVGIENPKH; |
| 2572. | HHHVGIENPKH; |
| 2571. | KKHVGIENPKH; |
| 2574. | RKHVGIENPKH; |
| 2575. | HKHVGIENPKH; |
| 2576. | KRHVGIENPKH; |
| 2577. | RRHVGIENPKH; |
| 2578. | HRHVGIENPKH; |
| 2579. | KHKVGIENPKH; |
| 2580. | RHKVGIENPKH; |
| 2581. | HHKVGIENPKH; |
| 2582. | KKKVGIENPKH; |
| 2583. | RKKVGIENPKH; |
| 2584. | HKKVGIENPKH; |
| 2585. | KRKVGIENPKH; |
| 2586. | RRKVGIENPKH; |
| 2587. | HRKVGIENPKH; |
| 2588. | KHRVGIENPKH; |
| 2589. | RHRVGIENPKH; |
| 2590. | HHRVGIENPKH; |
| 2591. | KKRVGIENPKH; |
| 2592. | RKRVGIENPKH; |
| 2593. | HKRVGIENPKH; |
| 2594. | KRRVGIENPKH; |
| 2595. | RRRVGIENPKH; |
| 2596. | HRRVGIENPKH; |
| 2597. | KHHLGVENPKH; |
| 2598. | RHHLGVENPKH; |
| 2599. | HHHLGVENPKH; |
| 2600. | KKHLGVENPKH; |
| 2601. | RKHLGVENPKH; |
| 2602. | HKHLGVENPKH; |
| 2603. | KRHLGVENPKH; |
| 2604. | RRHLGVENPKH; |
| 2605. | HRHLGVENPKH; |
| 2606. | KHKLGVENPKH; |
| 2607. | RHKLGVENPKH; |
| 2608. | HHKLGVENPKH; |
| 2609. | KKKLGVENPKH; |
| 2610. | RKKLGVENPKH; |
| 2611. | HKKLGVENPKH; |
| 2612. | KRKLGVENPKH; |
| 2613. | RRKLGVENPKH; |
| 2614. | HRKLGVENPKH; |
| 2615. | KHRLGVENPKH; |
| 2616. | RHRLGVENPKH; |
| 2617. | HHRLGVENPKH; |
| 2618. | KKRLGVENPKH; |
| 2619. | RKRLGVENPKH; |
| 2620. | HKRLGVENPKH; |
| 2621. | KRRLGVENPKH; |
| 2622. | RRRLGVENPKH; |
| 2623. | HRRLGVENPKH; |

TABLE 7-continued

SEQ ID NO. shown to left of sequence(cont'd)

| | |
|---|---|
| 2624. | KHHIGVENPKH; |
| 2625. | RHHIGVEEPKH; |
| 2626. | HHHIGVENPKH; |
| 2627. | KKHIGVENPKH; |
| 2628. | RKHIGVENPKH; |
| 2629. | HKHIGVENPKH; |
| 2630. | KRHIGVENPKH; |
| 2631. | RRHIGVENPKH; |
| 2632. | HRHIGVENPKH; |
| 2633. | KHKIGVENPKH; |
| 2634. | RHKIGVENPKH; |
| 2635. | HHKIGVENPKH; |
| 2636. | KKKIGVENPKH; |
| 2637. | RKKIGVENPKH; |
| 2638. | HKKIGVENPKH; |
| 2639. | KRKIGVENPKH; |
| 2640. | RRKIGVENPKH; |
| 2641. | HRKIGVENPKH; |
| 2642. | KHRIGVENPKH; |
| 2643. | RHRIGVENPKH; |
| 2644. | HHRIGVENPKH; |
| 2645. | KKRIGVENPKH; |
| 2646. | RKRIGVENPKH; |
| 2647. | HKRIGVENPKH; |
| 2648. | KRRIGVENPKH; |
| 2649. | RRRIGVENPKH; |
| 2650. | HRRIGVENPKH; |
| 2651. | KHHVGVENPKH; |
| 2652. | RHHVGVENPKH; |
| 2653. | HHHVGVENPKH; |
| 2654. | KKHVGVENPKH; |
| 2655. | RKHVGVENPKH; |
| 2656. | HKHVGVENPKH; |
| 2657. | KRHVGVENPKH; |
| 2658. | RRHVGVENPKH; |
| 2659. | HRHVGVENPKH; |
| 2660. | KHKVGVENPKH; |
| 2661. | RHKVGVENPKH; |
| 2662. | HHKVGVENPKH; |

TABLE 7-continued

SEQ ID NO. shown to left of sequence(cont'd)

| | |
|---|---|
| 2663. | KKKVGVENPKH; |
| 2664. | RKKVGVENPKH; |
| 2665. | HKKVGVENPKH; |
| 2666. | KRKVGVENPKH; |
| 2667. | RRKVGVEEPKH; |
| 2668. | HRKVGVENPKH; |
| 2669. | KHRVGVENPKH; |
| 2670. | RHRVGVENPKH; |
| 2671. | HHRVGVENPKH; |
| 2672. | KKRVGVENPKH; |
| 2673. | RKRVGVENPKH; |
| 2674. | HKRVGVENPKH; |
| 2675. | KRRVGVENPKH; |
| 2676. | RRRVGVENPKH; |
| 2677. | HRRVGVENPKH; |
| 2678. | KHHLGLNNPKH; |
| 2679. | RHHLGLNNPKH; |
| 2680. | HHHLGLNNPKH; |
| 2681. | KKHLGLNNPKH; |
| 2682. | RKHLGLNNPKH; |
| 2683. | HKHLGLNNPKH; |
| 2684. | KRHLGLNNPKH; |
| 2685. | RRHLGLNNPKH; |
| 2686. | HRHLGLNNPKH; |
| 2687. | KHKLGLNNPKH; |
| 2688. | RHKLGLNNPKH; |
| 2689. | HHKLGLNNPKH; |
| 2690. | KKKLGLNNPKH; |
| 2691. | RKKLGLNNPKH; |
| 2692. | HKKLGLNNPKH; |
| 2693. | KRKLGLNNPKH; |
| 2694. | RRKLGLNNPKH; |
| 2695. | HRKLGLNNPKH; |
| 2696. | KHRLGLNNPKH; |
| 2697. | RHRLGLNNPKH; |
| 2698. | HHRLGLNNPKH; |
| 2699. | KKRLGLNNPKH; |
| 2700. | RKRLGLNNPKH; |
| 2701. | HKRLGLNNPKH; |

TABLE 7-continued

SEQ ID NO. shown to left of sequence(cont'd)

| SEQ ID NO. | Sequence |
|---|---|
| 2702. | KRRLGLNNPKH; |
| 2703. | RRRLGLNNPKH; |
| 2704. | HRRLGLNNPKH; |
| 2705. | KHHIGLNNPKH; |
| 2706. | RHHIGLNNPKH; |
| 2707. | HHHIGLNNPKH; |
| 2708. | KKHIGLNNPKH; |
| 2709. | RKHIGLNNPKH; |
| 2710. | HKHIGLNNPKH; |
| 2711. | KRHIGLNNPKH; |
| 2712. | RRHIGLNNPKH; |
| 2713. | HRHIGLNNPKH; |
| 2714. | KHKIGLNNPKH; |
| 2715. | RHKIGLNNPKH; |
| 2716. | HHKIGLNNPKH; |
| 2717. | KKKIGLNNPKH; |
| 2718. | RKKIGLNNPKH; |
| 2719. | HKKIGLNNPKH; |
| 2720. | KRKIGLNNPKH; |
| 2721. | RRKIGLNNPKH; |
| 2722. | HRKIGLNNPKH; |
| 2723. | KHRIGLNNPKH; |
| 2724. | RHRIGLNNPKH; |
| 2725. | HHRIGLNNPKH; |
| 2726. | KKRIGLNNPKH; |
| 2727. | RKRIGLNNPKH; |
| 2728. | HKRIGLNNPKH; |
| 2729. | KRRIGLNNPKH; |
| 2730. | RRRIGLNNPKH; |
| 2731. | HRRIGLNNPKH; |
| 2732. | KHHVGLNNPKH; |
| 2733. | RHHVGLNNPKH; |
| 2734. | HHHVGLNNPKH; |
| 2735. | KKHVGLNNPKH; |
| 2736. | RKHVGLNNPKH; |
| 2737. | HKHVGLNNPKH; |
| 2738. | KRHVGLNNPKH; |
| 2739. | RRHVGLNNPKH; |
| 2740. | HRHVGLNNPKH; |
| 2741. | KHKVGLNNPKH; |
| 2742. | RHKVGLNNPKH; |
| 2743. | HHKVGLNNPKH; |
| 2744. | KKKVGLNNPKH; |
| 2745. | RKKVGLNNPKH; |
| 2746. | HKKVGLNNPKH; |
| 2747. | KRKVGLNNPKH; |
| 2748. | RRKVGLNNPKH; |
| 2749. | HRKVGLNNPKH; |
| 2750. | KHRVGLNNPKH; |
| 2751. | RHRVGLNNPKH; |
| 2752. | HHRVGLNNPKH; |
| 2753. | KKRVGLNNPKH; |
| 2754. | RKRVGLNNPKH; |
| 2755. | HKRVGLNNPKH; |
| 2756. | KRRVGLNNPKH; |
| 2757. | RRRVGLNNPKH; |
| 2758. | HRRVGLNNPKH; |
| 2759. | KHHLGINNPKH; |
| 2760. | RHHLGINNPKH; |
| 2761. | HHHLGINNPKH; |
| 2762. | KKHLGINNPKH; |
| 2763. | RKHLGINNPKH; |
| 2764. | HKHLGINNPKH; |
| 2765. | KRHLGINNPKH; |
| 2766. | RRHLGINNPKH; |
| 2767. | HRHLGINNPKH; |
| 2768. | KHKLGINNPKH; |
| 2769. | RHKLGINNPKH; |
| 2770. | HHKLGINNPKH; |
| 2771. | KKKLGINNPKH; |
| 2772. | RKKLGINNPKH; |
| 2773. | HKKLGINNPKH; |
| 2774. | KRKLGINNPKH; |
| 2775. | RRKLGINNPKH; |
| 2776. | HRKLGINNPKH; |
| 2777. | KHRLGINNPKH; |
| 2778. | RHRLGINNPKH; |
| 2779. | HHRLGINNPKH; |

TABLE 7-continued

SEQ ID NO. shown to left of sequence (cont'd)

| | |
|---|---|
| 2780. | KKRLGINNPKH; |
| 2781. | RKRLGINNPKH; |
| 2782. | HKRLGINNPKH; |
| 2783. | KRRLGINNPKH; |
| 2784. | RRRLGINNPKH; |
| 2785. | HRRLGINNPKH; |
| 2786. | KHHIGIENPKH; |
| 2787. | RHHIGINNPKH; |
| 2788. | HHHIGINNPKH; |
| 2789. | KKHIGINNPKH; |
| 2790. | RKHIGINNPKH; |
| 2791. | HKHIGINNPKH; |
| 2792. | KRHIGINNPKH; |
| 2793. | RRHIGINNPKH; |
| 2794. | HRHIGINNPKH; |
| 2795. | KHKIGINNPKH; |
| 2796. | RHKIGINNPKH; |
| 2797. | HHKIGINNPKH; |
| 2798. | KKKIGINNPKH; |
| 2799. | RKKIGINNPKH; |
| 2800. | HKKIGINNPKH; |
| 2801. | KRKIGINNPKH; |
| 2802. | RRKIGINNPKH; |
| 2803. | HRKIGINNPKH; |
| 2804. | KHRIGINNPKH; |
| 2805. | RHRIGINNPKH; |
| 2806. | HHRIGINNPKH; |
| 2807. | KKRIGINNPKH; |
| 2808. | RKRIGINNPKH; |
| 2809. | HKRIGINNPKH; |
| 2810. | KRRIGINNPKH; |
| 2811. | RRRIGINNPKH; |
| 2812. | HRRIGINNPKH; |
| 2813. | KHHVGINNPKH; |
| 2814. | RHHVGINNPKH; |
| 2815. | HHHVGINNPKH; |
| 2816. | KKHVGINNPKH; |
| 2817. | RKHVGINNPKH; |
| 2818. | HKHVGINNPKH; |
| 2819. | KRHVGINNPKH; |
| 2820. | RRHVGINNPKH; |
| 2821. | HRHVGINNPKH; |
| 2822. | KHKVGINNPKH; |
| 2823. | RHKVGINNPKH; |
| 2824. | HHKVGINNPKH; |
| 2825. | KKKVGINNPKH; |
| 2826. | RKKVGINNPKH; |
| 2827. | HKKVGINNPKH; |
| 2828. | KRKVGINNPKH; |
| 2829. | RRKVGINNPKH; |
| 2830. | HRKVGINNPKH; |
| 2831. | KHRVGINNPKH; |
| 2832. | RHRVGINNPKH; |
| 2833. | HHRVGINNPKH; |
| 2834. | KKRVGINNPKH; |
| 2835. | RKRVGINNPKH; |
| 2836. | HKRVGINNPKH; |
| 2837. | KRRVGINNPKH; |
| 2838. | RRRVGINNPKH; |
| 2839. | HRRVGINNPKH; |
| 2840. | KHHLGVNNPKH; |
| 2841. | RHHLGVNNPKH; |
| 2842. | HHHLGVNNPKH; |
| 2843. | KKHLGVNNPKH; |
| 2844. | RKHLGVNNPKH; |
| 2845. | HKHLGVNNPKH; |
| 2846. | KRHLGVNNPKH; |
| 2847. | RRHLGVNNPKH; |
| 2848. | HRHLGVNNPKH; |
| 2849. | KHKLGVNNPKH; |
| 2850. | RHKLGVNNPKH; |
| 2851. | HHKLGVNNPKH; |
| 2852. | KKKLGVNNPKH; |
| 2853. | RKKLGVNNPKH; |
| 2854. | HKKLGVNNPKH; |
| 2855. | KRKLGVNNPKH; |
| 2856. | RRKLGVNNPKH; |
| 2857. | HRKLGVNNPKH; |

TABLE 7-continued

SEQ ID NO. shown to left of sequence(cont'd)

| SEQ ID NO. | Sequence |
|---|---|
| 2858. | KHRLGVNNPKH; |
| 2859. | RHRLGVNNPKH; |
| 2860. | HHRLGVNNPKH; |
| 2861. | KKRLGVNNPKH; |
| 2862. | RKRLGVNNPKH; |
| 2863. | HKRLGVNNPKH; |
| 2864. | KRRLGVNNPKH; |
| 2865. | RRRLGVNNPKH; |
| 2866. | HRRLGVNNPKH; |
| 2867. | KHHIGVNNPKH; |
| 2868. | RHHIGVNNPKH; |
| 2869. | HHHIGVNNPKH; |
| 2870. | KKHIGVNNPKH; |
| 2871. | RKHIGVNNPKH; |
| 2872. | HKHIGVNNPKH; |
| 2873. | KRHIGVNNPKH; |
| 2874. | RRHIGVNNPKH; |
| 2875. | HRHIGVNNPKH; |
| 2876. | KHKIGVNNPKH; |
| 2877. | RHKIGVNNPKH; |
| 2878. | HHKIGVNNPKH; |
| 2879. | KKKIGVNNPKH; |
| 2880. | RKKIGVNNPKH; |
| 2881. | HKKIGVNNPKH; |
| 2882. | KRKIGVNNPKH; |
| 2883. | RRKIGVNNPKH; |
| 2884. | HRKIGVNNPKH; |
| 2885. | KHRIGVNNPKH; |
| 2886. | RHRIGVNNPKH; |
| 2887. | HHRIGVNNPKH; |
| 2888. | KKRIGVNNPKH; |
| 2889. | RKRIGVNNPKH; |
| 2890. | HKRIGVNNPKH; |
| 2891. | KRRIGVNNPKH; |
| 2892. | RRRIGVNNPKH; |
| 2893. | HRRIGVNNPKH; |
| 2894. | KHHVGVNNPKH; |
| 2895. | RHHVGVNNPKH; |
| 2896. | HHHVGVNNPKH; |
| 2897. | KKHVGVNNPKH; |
| 2898. | RKHVGVNNPKH; |
| 2899. | HKHVGVNNPKH; |
| 2900. | KRHVGVNNPKH; |
| 2901. | RRHVGVNNPKH; |
| 2902. | HRHVGVNNPKH; |
| 2903. | KHKVGVNNPKH; |
| 2904. | RHKVGVNNPKH; |
| 2905. | HHKVGVNNPKH; |
| 2906. | KKKVGVNNPKH; |
| 2907. | RKKVGVNNPKH; |
| 2908. | HKKVGVNNPKH; |
| 2909. | KRKVGVNNPKH; |
| 2910. | RRKVGVNNPKH; |
| 2911. | HRKVGVNNPKH; |
| 2912. | KHRVGVNNPKH; |
| 2913. | RHRVGVNNPKH; |
| 2914. | HHRVGVNNPKH; |
| 2915. | KKRVGVNNPKH; |
| 2916. | RKRVGVNNPKH; |
| 2917. | HKRVGVNNPKH; |
| 2918. | KRRVGVNNPKH; |
| 2919. | RRRVGVNNPKH; |
| 2920. | HRRVGVNNPKH; |
| 2921. | KHHLGLEEPRK; |
| 2922. | RHHLGLEEPRK; |
| 2923. | HHHLGLEEPRK; |
| 2924. | KKHLGLEEPRK; |
| 2925. | RKHLGLEEPRK; |
| 2926. | HKHLGLEEPRK; |
| 2927. | KRHLGLEEPRK; |
| 2928. | RRHLGLEEPRK; |
| 2929. | HRHLGLEEPRK; |
| 2930. | KHKLGLEEPRK; |
| 2931. | RHKLGLEEPRK; |
| 2932. | HHKLGLEEPRK; |
| 2933. | KKKLGLEEPRK; |
| 2934. | RKKLGLEEPRK; |
| 2935. | HKKLGLEEPRK; |

TABLE 7-continued

| SEQ ID NO. shown to left of sequence(cont'd) | |
|---|---|
| 2936. | KRKLGLEEPRK; |
| 2937. | RRKLGLEEPRK; |
| 2938. | HRKLGLEEPRK; |
| 2939. | KHRLGLEEPRK; |
| 2940. | RHRLGLEEPRK; |
| 2941. | HHRLGLEEPRK; |
| 2942. | KKRLGLEEPRK; |
| 2943. | RKRLGLEEPRK; |
| 2944. | HKRLGLEEPRK; |
| 2945. | KRRLGLEEPRK; |
| 2946. | RRRLGLEEPRK; |
| 2947. | HRRLGLEEPRK; |
| 2948. | KHHIGLEEPRK; |
| 2949. | RHHIGLEEPRK; |
| 2950. | HHHIGLEEPRK; |
| 2951. | KKHIGLEEPRK; |
| 2952. | RKHIGLEEPRK; |
| 2953. | HKHIGLEEPRK; |
| 2954. | KRHIGLEEPRK; |
| 2955. | RRHIGLEEPRK; |
| 2956. | HRHIGLEEPRK; |
| 2957. | KHKIGLEEPRK; |
| 2958. | RHKIGLEEPRK; |
| 2959. | HHKIGLEEPRK; |
| 2960. | KKKIGLEEPRK; |
| 2961. | RKKIGLEEPRK; |
| 2962. | HKKIGLEEPRK; |
| 2963. | KRKIGLEEPRK; |
| 2964. | RRKIGLEEPRK; |
| 2965. | HRKIGLEEPRK; |
| 2966. | KHRIGLEEPRK; |
| 2967. | RHRIGLEEPRK; |
| 2968. | HHRIGLEEPRK; |
| 2969. | KKRIGLEEPRK; |
| 2970. | RKRIGLEEPRK; |
| 2971. | HKRIGLEEPRK; |
| 2972. | KRRIGLEEPRK; |
| 2973. | RRRIGLEEPRK; |
| 2974. | HRRIGLEEPRK; |
| 2975. | KHHVGLEEPRK; |
| 2976. | RHHVGLEEPRK; |
| 2977. | HHHVGLEEPRK; |
| 2978. | KKHVGLEEPRK; |
| 2979. | RHHVGLEEPRK; |
| 2980. | HKHVGLEEPRK; |
| 2981. | KRHVGLEEPRK; |
| 2982. | RRHVGLEEPRK; |
| 2983. | HRHVGLEEPRK; |
| 2984. | KHKVGLEEPRK; |
| 2985. | RHKVGLEEPRK; |
| 2986. | HHKVGLEEPRK; |
| 2987. | KKKVGLEEPRK; |
| 2988. | RKKVGLEEPRK; |
| 2989. | HKKVGLEEPRK; |
| 2990. | KRKVGLEEPRK; |
| 2991. | RRKVGLEEPRK; |
| 2992. | HRKVGLEEPRK; |
| 2993. | KHRVGLEEPRK; |
| 2994. | RHRVGLEEPRK; |
| 2995. | HHRVGLEEPRK; |
| 2996. | KKRVGLEEPRK; |
| 2997. | RKRVGLEEPRK; |
| 2998. | HKRVGLEEPRK; |
| 2999. | KRRVGLEEPRK; |
| 3000. | RRRVGLEEPRK; |
| 3001. | HRRVGLEEPRK; |
| 3002. | KHHLGIEEPRK; |
| 3003. | RHHLGIEEPRK; |
| 3004. | HHHLGIEEPRK; |
| 3005. | KKHLGIEEPRK; |
| 3006. | RKHLGIEEPRK; |
| 3007. | HKHLGIEEPRK; |
| 3008. | KRHLGIEEPRK; |
| 3009. | RRHLGIEEPRK; |
| 3010. | HRHLGIEEPRK; |
| 3011. | KHKLGIEEPRK; |
| 3012. | RHKLGIEEPRK; |
| 3013. | HHKLGIEEPRK; |

TABLE 7-continued

SEQ ID NO. shown to left of sequence(cont'd)

| | |
|---|---|
| 3014. | KKKLGIEEPRK; |
| 3015. | RKKLGIEEPRK; |
| 3016. | HKKLGIEEPRK; |
| 3017. | KRKLGIEEPRK; |
| 3018. | RRKLGIEEPRK; |
| 3019. | HRKLGIEEPRK; |
| 3020. | KHRLGIEEPRK; |
| 3021. | RHRLGIEEPRK; |
| 3022. | HHRLGVEEPRK; |
| 3023. | KKRLGIEEPRK; |
| 3024. | RKRLGVEEPRK; |
| 3025. | HKRLGIEEPRK; |
| 3026. | KRRLGIEEPRK; |
| 3027. | RRRLGIEEPRK; |
| 3028. | HRRLGIEEPRK; |
| 3029. | KHHIGIEEPRK; |
| 3030. | RHHIGIEEPRK; |
| 3031. | HHHIGIEEPRK; |
| 3032. | KKHIGIEEPRK; |
| 3033. | RKHIGIEEPRK; |
| 3034. | HKHIGIEEPRK; |
| 3035. | KRHIGIEEPRK; |
| 3036. | RRHIGIEEPRK; |
| 3037. | HRHIGIEEPRK; |
| 3038. | KHKIGIEEPRK; |
| 3039. | RHKIGIEEPRK; |
| 3040. | HHKIGIEEPRK; |
| 3041. | KKKIGIEEPRK; |
| 3042. | RKKIGIEEPRK; |
| 3043. | HKKIGIEEPRK; |
| 3044. | KRKIGIEEPRK; |
| 3045. | RRKIGIEEPRK; |
| 3046. | HRKIGIEEPRK; |
| 3047. | KHRIGIEEPRK; |
| 3048. | RHRIGIEEPRK; |
| 3049. | HHRIGIEEPRK; |
| 3050. | KKRIGIEEPRK; |
| 3051. | RKRIGIEEPRK; |
| 3052. | HKRIGIEEPRK; |
| 3053. | KRRIGIEEPRK; |
| 3054. | RRRIGIEEPRK; |
| 3055. | HRRIGIEEPRK; |
| 3056. | KHHVGIEEPRK; |
| 3057. | RHHVGIEEPRK; |
| 3058. | HHHVGIEEPRK; |
| 3059. | KKHVGIEEPRK; |
| 3060. | RKHVGIEEPRK; |
| 3061. | HKHVGIEEPRK; |
| 3062. | KRHVGIEEPRK; |
| 3063. | RRHVGIEEPRK; |
| 3064. | HRHVGIEEPRK; |
| 3065. | KHKVGIEEPRK; |
| 3066. | RHKVGIEEPRK; |
| 3067. | HHKVGIEEPRK; |
| 3068. | KKKVGIEEPRK; |
| 3069. | RKKVGIEEPRK; |
| 3070. | HKKVGIEEPRK; |
| 3071. | KRKVGIEEPRK; |
| 3072. | RRKVGIEEPRK; |
| 3073. | HRKVGIEEPRK; |
| 3074. | KHRVGIEEPRK; |
| 3075. | RHRVGIEEPRK; |
| 3076. | HHRVGIEEPRK; |
| 3077. | KKRVGIEEPRK; |
| 3078. | RKRVGIEEPRK; |
| 3079. | HKRVGIEEPRK; |
| 3080. | KRRVGIEEPRK; |
| 3081. | RRRVGIEEPRK; |
| 3082. | HRRVGIEEPRK; |
| 3083. | KHHLGVEEPRK; |
| 3084. | RHHLGVEEPRK; |
| 3085. | HHHLGVEEPRK; |
| 3086. | KKHLGVEEPRK; |
| 3087. | RKHLGVEEPRK; |
| 3088. | HKHLGVEEPRK; |
| 3089. | KRHLGVEEPRK; |
| 3090. | RRHLGVEEPRK; |
| 3091. | HRHLGVEEPRK; |

TABLE 7-continued

SEQ ID NO. shown to left of sequence(cont'd)

| SEQ ID NO. | Sequence |
|---|---|
| 3092. | KHKLGVEEPRK; |
| 3093. | RHKLGVEEPRK; |
| 3094. | HHKLGVEEPRK; |
| 3095. | KKKLGVEEPRK; |
| 3096. | RKKLGVEEPRK; |
| 3097. | HKKLGVEEPRK; |
| 3098. | KRKLGVEEPRK; |
| 3099. | RRKLGVEEPRK; |
| 3100. | HRKLGVEEPRK; |
| 3101. | KHRLGVEEPRK; |
| 3102. | RHRLGVEEPRK; |
| 3103. | HHRLGVEEPRK; |
| 3104. | KKRLGVEEPRK; |
| 3105. | RKRLGVEEPRK; |
| 3106. | HKRLGVEEPRK; |
| 3107. | KRRLGVEEPRK; |
| 3108. | RRRLGVEEPRK; |
| 3109. | HRRLGVEEPRK; |
| 3110. | KHHIGVEEPRK; |
| 3111. | RHHIGVEEPRK; |
| 3112. | HHHIGVEEPRK; |
| 3113. | KKHIGVEEPRK; |
| 3114. | RKHIGVEEPRK; |
| 3115. | HKHIGVEEPRK; |
| 3116. | KRHIGVEEPRK; |
| 3117. | RRHIGVEEPRK; |
| 3118. | HRHIGVEEPRK; |
| 3119. | KHKIGVEEPRK; |
| 3120. | RHKIGVEEPRK; |
| 3121. | HHKIGVEEPRK; |
| 3122. | KKKIGVEEPRK; |
| 3123. | RKKIGVEEPRK; |
| 3124. | HKKIGVEEPRK; |
| 3125. | KRKIGVEEPRK; |
| 3126. | RRKIGVEEPRK; |
| 3127. | HRKIGVEEPRK; |
| 3128. | KHRIGVEEPRK; |
| 3129. | RHRIGVEEPRK; |
| 3130. | HHRIGVEEPRK; |
| 3131. | KKRIGVEEPRK; |
| 3132. | RKRIGVEEPRK; |
| 3133. | HKRIGVEEPRK; |
| 3134. | KRRIGVEEPRK; |
| 3135. | RRRIGVEEPRK; |
| 3136. | HRRIGVEEPRK; |
| 3137. | KHHVGVEEPRK; |
| 3138. | RHHVGVEEPRK; |
| 3139. | HHHVGVEEPRK; |
| 3140. | KKHVGVEEPRK; |
| 3141. | RKHVGVEEPRK; |
| 3142. | HKHVGVEEPRK; |
| 3143. | KRHVGVEEPRK; |
| 3144. | RRHVGVEEPRK; |
| 3145. | HRHVGVEEPRK; |
| 3146. | KHKVGVEEPRK; |
| 3147. | RHKVGVEEPRK; |
| 3148. | HHKVGVEEPRK; |
| 3149. | KKKVGVEEPRK; |
| 3150. | RKKVGVEEPRK; |
| 3151. | HKKVGVEEPRK; |
| 3152. | KRKVGVEEPRK; |
| 3153. | RRKVGVEEPRK; |
| 3154. | HRKVGVEEPRK; |
| 3155. | KHRVGVEEPRK; |
| 3156. | RHRVGVEEPRK; |
| 3157. | HHRVGVEEPRK; |
| 3158. | KKRVGVEEPRK; |
| 3159. | RKRVGVEEPRK; |
| 3160. | HKRVGVEEPRK; |
| 3161. | KRRVGVEEPRK; |
| 3162. | RRRVGVEEPRK; |
| 3163. | HRRVGVEEPRK; |
| 3164. | KHHLGLNEPRK; |
| 3165. | RHHLGLNEPRK; |
| 3166. | HHHLGLNEPRK; |
| 3167. | KKHLGLNEPRK; |
| 3168. | RKHLGLNEPRK; |
| 3169. | HKHLGLNEPRK; |

TABLE 7-continued

SEQ ID NO. shown to left of sequence (cont'd)

| SEQ ID NO. | Sequence |
|---|---|
| 3170. | KRHLGLNEPRK; |
| 3171. | RRHLGLNEPRK; |
| 3172. | HRHLGLNEPRK; |
| 3173. | KHKLGLNEPRK; |
| 3174. | RHKLGLNEPRK; |
| 3175. | HHKLGLNEPRK; |
| 3176. | KKKLGLNEPRK; |
| 3177. | RKKLGLNEPRK; |
| 3178. | HKKLGLNEPRK; |
| 3179. | KRKLGLNEPRK; |
| 3180. | RRKLGLNEPRK; |
| 3181. | HRKLGLNEPRK; |
| 3182. | KHRLGLNEPRK; |
| 3183. | RHRLGLNEPRK; |
| 3184. | HHRLGLNEPRK; |
| 3185. | KKRLGLNEPRK; |
| 3186. | RKRLGLNEPRK; |
| 3187. | HKRLGLNEPRK; |
| 3188. | KRRLGLNEPRK; |
| 3189. | RRRLGLNEPRK; |
| 3190. | HRRLGLNEPRK; |
| 3191. | KHHIGLNPRK; |
| 3192. | RHHIGLNEPRK; |
| 3193. | HHHIGLNEPRK; |
| 3194. | KKHIGLNEPRK; |
| 3195. | RKHIGLNEPRK; |
| 3196. | HKHIGLNEPRK; |
| 3197. | KRHIGLNEPRK; |
| 3198. | RRHIGLNEPRK; |
| 3199. | HRHIGLNEPRK; |
| 3200. | KHKIGLNEPRK; |
| 3201. | RHKIGLNEPRK; |
| 3202. | HHHIGLNEPRK; |
| 3203. | KKKIGLNEPRK; |
| 3204. | RKKIGLNEPRK; |
| 3205. | HKKIGLNEPRK; |
| 3206. | KRKIGLNEPRK; |
| 3207. | RRKIGLNEPRK; |
| 3208. | HRKIGLNEPRK; |
| 3209. | KHRIGLNEPRK; |
| 3210. | RHRIGLNEPRK; |
| 3211. | HHRIGLNEPRK; |
| 3212. | KKRIGLNEPRK; |
| 3213. | RKRIGLNEPRK; |
| 3214. | HKRIGLNEPRK; |
| 3215. | KRRIGLNEPRK; |
| 3216. | RRRIGLNEPRK; |
| 3217. | HRRIGLNEPRK; |
| 3218. | KHHVGLNEPRK; |
| 3219. | RHHVGLNEPRK; |
| 3220. | HHHVGLNEPRK; |
| 3221. | KKHVGLNEPRK; |
| 3222. | RKHVGLNEPRK; |
| 3223. | HKHVGLNEPRK; |
| 3224. | KRHVGLNEPRK; |
| 3225. | RRHVGLNEPRK; |
| 3226. | HRHVGLNEPRK; |
| 3227. | KHKVGLNEPRK; |
| 3228. | RHKVGLNEPRK; |
| 3229. | HHKVGLNEPRK; |
| 3230. | KKKVGLNEPRK; |
| 3231. | RKKVGLNEPRK; |
| 3232. | HKKVGLNEPRK; |
| 3233. | KRKVGLNEPRK; |
| 3234. | RRKVGLNEPRK; |
| 3235. | HRKVGLNEPRK; |
| 3236. | KHRVGLNEPRK; |
| 3237. | RHRVGLNEPRK; |
| 3238. | HHRVGLNEPRK; |
| 3239. | KKRVGLNEPRK; |
| 3240. | RKRVGLNEPRK; |
| 3241. | HKRVGLNEPRK; |
| 3242. | KRRVGLNEPRK; |
| 3243. | RRRVGLNEPRK; |
| 3244. | HRRVGLNEPRK; |
| 3245. | KHHLGINEPRK; |
| 3246. | RHHLGINEPRK; |
| 3247. | HHHLGINEPRK; |

TABLE 7-continued

SEQ ID NO. shown to left of sequence(cont'd)

| SEQ ID NO. | Sequence |
|---|---|
| 3248. | KKHLGINEPRK; |
| 3249. | RKHLGINEPRK; |
| 3250. | HKHLGINEPRK; |
| 3251. | KRHLGINEPRK; |
| 3252. | RRHLGINEPRK; |
| 3253. | HRHLGINEPRK; |
| 3254. | KHKLGINEPRK; |
| 3255. | RHKLGINEPRK; |
| 3256. | HHKLGINEPRK; |
| 3257. | KKKLGINEPRK; |
| 3258. | RKKLGINEPRK; |
| 3259. | HKKLGINEPRK; |
| 3260. | KRKLGINEPRK; |
| 3261. | RRKLGINEPRK; |
| 3262. | HRKLGINEPRK; |
| 3263. | KHRLGINEPRK; |
| 3264. | RHRLGINEPRK; |
| 3265. | HHRLGINEPRK; |
| 3266. | KKRLGINEPRK; |
| 3267. | RKRLGINEPRK; |
| 3268. | HKRLGINEPRK; |
| 3269. | KRRLGINEPRK; |
| 3270. | RRRLGINEPRK; |
| 3271. | HRRLGINEPRK; |
| 3272. | KHHIGIENPRK; |
| 3273. | RHHIGINEPRK; |
| 3274. | HHHIGINEPRK; |
| 3275. | KKHIGINEPRK; |
| 3276. | RKHIGINEPRK; |
| 3277. | HKHIGINEPRK; |
| 3278. | KRHIGINEPRK; |
| 3279. | RRHIGINEPRK; |
| 3280. | HRHIGINEPRK; |
| 3281. | KHKIGINEPRK; |
| 3282. | RHKIGINEPRK; |
| 3283. | HHKIGINEPRK; |
| 3284. | KKKIGINEPRK; |
| 3285. | RKKIGINEPRK; |
| 3286. | HKKIGINEPRK; |
| 3287. | KRKIGINEPRK; |
| 3288. | RRKIGINEPRK; |
| 3289. | HRKIGINEPRK; |
| 3290. | KHRIGINEPRK; |
| 3291. | RHRIGINEPRK; |
| 3292. | HHRIGINEPRK; |
| 3293. | KKRIGINEPRK; |
| 3294. | RKRIGINEPRK; |
| 3295. | HKRIGINEPRK; |
| 3296. | KRRIGINEPRK; |
| 3297. | RRRIGINEPRK; |
| 3298. | HRRIGINEPRK; |
| 3299. | KHHVGINEPRK; |
| 3300. | RHHVGINEPRK; |
| 3301. | HHHVGINEPRK; |
| 3302. | KKHVGINEPRK; |
| 3303. | RKHVGINEPRK; |
| 3304. | HKHVGINEPRK; |
| 3305. | KRHVGINEPRK; |
| 3306. | RRHVGINEPRK; |
| 3307. | HRHVG1NEPRK; |
| 3308. | KHKVGINEPRK; |
| 3309. | RHKVGINEPRK; |
| 3310. | HHKVGINEPRK; |
| 3311. | KKKVGINEPRK; |
| 3312. | RKKVGINEPRK; |
| 3313. | HKKVGINEPRK; |
| 3314. | KRKVGINEPRK; |
| 3315. | RRKVGINEPRK; |
| 3316. | HRKVGINEPRK; |
| 3317. | KHRVGINEPRK; |
| 3318. | RHRVGINEPRK; |
| 3319. | HHRVGINEPRK; |
| 3320. | KKRVGINEPRK; |
| 3321. | RKRVGINEPRK; |
| 3322. | HKRVGINEPRK; |
| 3323. | KRRVGINEPRK; |
| 3324. | RRRVGINEPRK; |
| 3325. | HRRVGINEPRK; |

TABLE 7-continued

SEQ ID NO. shown to left of sequence(cont'd)

| | |
|---|---|
| 3326. | KHHLGVNEPRK; |
| 3327. | RHHLGVNEPRK; |
| 3328. | HHHLGVNEPRK; |
| 3329. | KKHLGVNEPRK; |
| 3330. | RKHLGVNEPRK; |
| 3331. | HKHLGVNEPRK; |
| 3332. | KRHLGVNEPRK; |
| 3333. | RRHLGVNEPRK; |
| 3334. | HRHLGVNEPRK; |
| 3335. | KHKLGVNEPRK; |
| 3336. | RHKLGVNEPRK; |
| 3337. | HHKLGVNEPRK; |
| 3338. | KKKLGVNEPRK; |
| 3339. | RKKLGVNEPRK; |
| 3340. | HKKLGVNEPRK; |
| 3341. | KRKLGVNEPRK; |
| 3342. | RRKLGVNEPRK; |
| 3343. | HRKLGVNEPRK; |
| 3344. | KHRLGVNEPRK; |
| 3345. | RHRLGVNEPRK; |
| 3346. | HHRLGVNEPRK; |
| 3347. | KKRLGVNEPRK; |
| 3348. | RKRLGVNEPRK; |
| 3349. | HKRLGVNEPRK; |
| 3350. | KRRLGVNEPRK; |
| 3351. | RRRLGVNEPRK; |
| 3352. | HRRLGVNEPRK; |
| 3353. | KHHIGVNEPRK; |
| 3354. | RHHIGVNEPRK; |
| 3355. | HHHIGVNEPRK; |
| 3356. | KKHIGVNEPRK; |
| 3357. | RKHIGVNEPRK; |
| 3358. | HKHIGVNEPRK; |
| 3359. | KRHIGVNEPRK; |
| 3360. | RRHIGVNEPRK; |
| 3361. | HRHIGVNEPRK; |
| 3362. | KHKIGVNEPRK; |
| 3363. | RHKIGVNEPRK; |
| 3364. | HHKIGVNEPRK; |
| 3365. | KKKIGVNEPRK; |
| 3366. | RKKIGVNEPRK; |
| 3367. | HKKIGVNEPRK; |
| 3368. | KRKIGVNEPRK; |
| 3369. | RRKIGVNEPRK; |
| 3370. | HRKIGVNEPRK; |
| 3371. | KHRIGVNEPRK; |
| 3372. | RHRIGVNEPRK; |
| 3373. | HHRIGVNEPRK; |
| 3374. | KKRIGVNEPRK; |
| 3375. | RKRIGVNEPRK; |
| 3376. | HKRIGVNEPRK; |
| 3377. | KRRIGVNEPRK; |
| 3378. | RRRIGVNEPRK; |
| 3379. | HRRIGVNEPRK; |
| 3380. | KHHVGVNEPRK; |
| 3381. | RHHVGVNEPRK; |
| 3382. | HHHVGVNEPRK; |
| 3383. | KHHVGVNEPRK; |
| 3384. | RKHVGVNEPRK; |
| 3385. | HKHVGVNEPRK; |
| 3386. | KRHVGVNEPRK; |
| 3387. | RRHVGVNEPRK; |
| 3388. | HRHVGVNEPRK; |
| 3389. | KHKVGVNEPRK; |
| 3390. | RHKVGVNEPRK; |
| 3391. | HHKVGVNEPRK; |
| 3392. | KKKVGVNEPRK; |
| 3393. | RKKVGVNEPRK; |
| 3394. | HKKVGVNEPRK; |
| 3395. | KRKVGVNEPRK; |
| 3396. | RRKVGVNEPRK; |
| 3397. | HRKVGVNEPRK; |
| 3398. | KHRVGVNEPRK; |
| 3399. | RHRVGVNEPRK; |
| 3400. | HHRVGVNEPRK; |
| 3401. | KKRVGVNEPRK; |
| 3402. | RKRVGVNEPRK; |
| 3403. | HKRVGVNEPRK; |

TABLE 7-continued

| SEQ ID NO. shown to left of sequence(cont'd) | |
|---|---|
| 3404. | KRRVGVNEPRK; |
| 3405. | RRRVGVNEPRK; |
| 3406. | HRRVGVNEPRK; |
| 3407. | KHHLGLENPRK; |
| 3408. | RHHLGLENPRK; |
| 3409. | HHHLGLENPRK; |
| 3410. | KKHLGLENPRK; |
| 3411. | RKHLGLENPRK; |
| 3412. | HKHLGLENPRK; |
| 3413. | KRHLGLENPRK; |
| 3414. | RRHLGLENPRK; |
| 3415. | HRHLGLENPRK; |
| 3416. | KHKLGLENPRK; |
| 3417. | RHKLGLENPRK; |
| 3418. | HHKLGLENPRK; |
| 3419. | KKKLGLENPRK; |
| 3420. | RKKLGLENPRK; |
| 3421. | HKKLGLENPRK; |
| 3422. | KRKLGLENPRK; |
| 3423. | RRKLGLENPRK; |
| 3424. | HRKLGLENPRK; |
| 3425. | KHRLGLENPRK; |
| 3426. | RHRLGLENPRK; |
| 3427. | HHRLGLENPRK; |
| 3428. | KKRLGLENPRK; |
| 3429. | RKRLGLENPRK; |
| 3430. | HKRLGLENPRK; |
| 3431. | KRRLGLENPRK; |
| 3432. | RRRLGLENPRK; |
| 3433. | HRRLGLENPRK; |
| 3434. | KHHIGLENPRK; |
| 3435. | RHHIGLENPRK; |
| 3436. | HHHIGLENPRK; |
| 3437. | KKHIGLENPRK; |
| 3438. | RKHIGLENPRK; |
| 3439. | HKHIGLENPRK; |
| 3440. | KRHIGLENPRK; |
| 3441. | RRHIGLENPRK; |
| 3442. | HRHIGLENPRK; |
| 3443. | KHKIGLENPRK; |
| 3444. | RHKIGLENPRK; |
| 3445. | HHKIGLENPRK; |
| 3446. | KKKIGLENPRK; |
| 3447. | RKKIGLENPRK; |
| 3448. | HKKIGLENPRK; |
| 3449. | KRKIGLENPRK; |
| 3450. | RRKIGLENPRK; |
| 3451. | HRKIGLENPRK; |
| 3452. | KHRIGLENPRK; |
| 3453. | RHRIGLENPRK; |
| 3454. | HHRIGLENPRK; |
| 3455. | KKRIGLENPRK; |
| 3456. | RKRIGLENPRK; |
| 3457. | HKRIGLENPRK; |
| 3458. | KRRIGLENPRK; |
| 3459. | RRRIGLENPRK; |
| 3460. | HRRIGLENPRK; |
| 3461. | KHHVGLENPRK; |
| 3462. | RHHVGLENPRK; |
| 3463. | HHHVGLENPRK; |
| 3464. | KKHVGLENPRK; |
| 3465. | RKHVGLENPRK; |
| 3466. | HKHVGLENPRK; |
| 3467. | KRHVGLENPRK; |
| 3468. | RRHVGLENPRK; |
| 3469. | HRHVGLENPRK; |
| 3470. | KHKVGLENPRK; |
| 3471. | RHKVGLENPRK; |
| 3472. | HHKVGLENPRK; |
| 3473. | KKKVGLENPRK; |
| 3474. | RKKVGLENPRK; |
| 3475. | HKKVGLENPRK; |
| 3476. | KRKVGLENPRK; |
| 3477. | RRKVGLENPRK; |
| 3478. | HRKVGLENPRK; |
| 3479. | KHRVGLENPRK; |
| 3480. | RHRVGLENPRK; |
| 3481. | HHRVGLENPRK; |

TABLE 7-continued

SEQ ID NO. shown to left of sequence(cont'd)

| | |
|---|---|
| 3482. | KKRVGLENPRK; |
| 3483. | RKRVGLENPRK; |
| 3484. | HKRVGLENPRK; |
| 3485. | KRRVGLENPRK; |
| 3486. | RRRVGLENPRK; |
| 3487. | HRRVGLENPRK; |
| 3488. | KHHLGIENPRK; |
| 3489. | RHHLGIENPRK; |
| 3490. | HHHLGIENPRK; |
| 3491. | KKHLGIENPRK; |
| 3492. | RKHLGIENPRK; |
| 3493. | HKHLGIENPRK; |
| 3494. | KRHLGIENPRK; |
| 3495. | RRHLGIENPRK; |
| 3496. | HRHLGIENPRK; |
| 3497. | KHKLGIENPRK; |
| 3498. | RHKLGIENPRK; |
| 3499. | HHKLGIENPRK; |
| 3500. | KKKLGIENPRK; |
| 3501. | RKKLGIENPRK; |
| 3502. | HKKLGIENPRK; |
| 3503. | KRKLGIENPRK; |
| 3504. | RRKLGIENPRK; |
| 3505. | HRKLGIENPRK; |
| 3506. | KHRLGIENPRK; |
| 3507. | RHRLGIENPRK; |
| 3508. | HHRLGIENPRK; |
| 3509. | KKRLGIENPRK; |
| 3510. | RKRLGIENPRK; |
| 3511. | HKRLGIENPRK; |
| 3512. | KRRLGIENPRK; |
| 3513. | RRRLGIENPRK; |
| 3514. | HRRLGIENPRK; |
| 3515. | KHHIGIENPRK; |
| 3516. | RHHIGIENPRK; |
| 3517. | HHHIGIENPRK; |
| 3518. | KKHIGIENPRK; |
| 3519. | RKHIGIENPRK; |
| 3520. | HKHIGIENPRK; |

TABLE 7-continued

SEQ ID NO. shown to left of sequence(cont'd)

| | |
|---|---|
| 3521. | KRHIGIENPRK; |
| 3522. | RRHIGIENPRK; |
| 3523. | HRHIGIENPRK; |
| 3524. | KHKIGIENPRK; |
| 3525. | RHKIGIENPRK; |
| 3526. | HHKIGIENPRK; |
| 3527. | KKKIGIENPRK; |
| 3528. | RKKIGIENPRK; |
| 3529. | HKKIGIENPRK; |
| 3530. | KRKIGIENPRK; |
| 3531. | RRKIGIENPRK; |
| 3532. | HRKIGIENPRK; |
| 3533. | KHRIGIENPRK; |
| 3534. | RHRIGIENPRK; |
| 3535. | HHRIGIENPRK; |
| 3536. | KKRIGIENPRK; |
| 3537. | RKRIGIENPRK; |
| 3538. | HKRIGIENPRK; |
| 3539. | KRRIGIENPRK; |
| 3540. | RRRIGIENPRK; |
| 3541. | HRRIGIENPRK; |
| 3542. | KHHVGIENPRK; |
| 3543. | RHHVGIENPRK; |
| 3544. | HHHVGIENPRK; |
| 3545. | KKHVGIENPRK; |
| 3546. | RKHVGIENPRK; |
| 3547. | HKHVGIENPRK; |
| 3548. | KRHVGIENPRK; |
| 3549. | RRHVGIENPRK; |
| 3550. | HRHVGIENPRK; |
| 3551. | KHKVGIENPRK; |
| 3552. | RHKVGIENPRK; |
| 3553. | HHKVGIENPRK; |
| 3554. | KKKVGIENPRK; |
| 3555. | RKKVGIENPRK; |
| 3556. | HKKVGIENPRK; |
| 3557. | KRKVGIENPRK; |
| 3558. | RRKVGIENPRK; |
| 3559. | HRKVGIENPRK; |

TABLE 7-continued

SEQ ID NO. shown to left of sequence(cont'd)

| SEQ ID NO. | Sequence |
|---|---|
| 3560. | KHRVGIENPRK; |
| 3561. | RHRVGIENPRK; |
| 3562. | HHRVGIENPRK; |
| 3563. | KKRVGIENPRK; |
| 3564. | RKRVGIENPRK; |
| 3565. | HKRVGIENPRK; |
| 3566. | KRRVGIENPRK; |
| 3567. | RRRVGIENPRK; |
| 3568. | HRRVGIENPRK; |
| 3569. | KHHLGVENPRK; |
| 3570. | RHHLGVENPRK; |
| 3571. | HHHLGVENPRK; |
| 3572. | KKHLGVENPRK; |
| 3573. | RKHLGVENPRK; |
| 3574. | HKHLGVENPRK; |
| 3575. | KRHLGVENPRK; |
| 3576. | RRHLGVENPRK; |
| 3577. | HRHLGVENPRK; |
| 3578. | KHKLGVENPRK; |
| 3579. | RHKLGVENPRK; |
| 3580. | HHKLGVENPRK; |
| 3581. | KKKLGVENPRK; |
| 3582. | RKKLGVENPRK; |
| 3583. | HKKLGVENPRK; |
| 3584. | KRKLGVENPRK; |
| 3585. | RRKLGVENPRK; |
| 3586. | HRKLGVENPRK; |
| 3587. | KHRLGVENPRK; |
| 3588. | RHRLGVENPRK; |
| 3589. | HHRLGVENPRK; |
| 3590. | KKRLGVENPRK; |
| 3591. | RKRLGVENPRK; |
| 3592. | HKRLGVENPRK; |
| 3593. | KRRLGVENPRK; |
| 3594. | RRRLGVENPRK; |
| 3595. | HRRLGVENPRK; |
| 3596. | KHHIGVENPRK; |
| 3597. | RHHIGVEEPRK; |
| 3598. | HHHIGVENPRK; |
| 3599. | KKHIGVENPRK; |
| 3600. | RKHIGVENPRK; |
| 3601. | HKHIGVENPRK; |
| 3602. | KRHIGVENPRK; |
| 3603. | RRHIGVENPRK; |
| 3604. | HRHIGVENPRK; |
| 3605. | KHKIGVENPRK; |
| 3606. | RHKIGVENPRK; |
| 3607. | HHKIGVENPRK; |
| 3608. | KKKIGVENPRK; |
| 3609. | RKKIGVENPRK; |
| 3610. | HKKIGVENPRK; |
| 3611. | KRKIGVENPRK; |
| 3612. | RRKIGVENPRK; |
| 3613. | HRKIGVENPRK; |
| 3614. | KHRIGVENPRK; |
| 3615. | RHRIGVENPRK; |
| 3616. | HHRIGVENPRK; |
| 3617. | KKRIGVENPRK; |
| 3618. | RKRIGVENPRK; |
| 3619. | HKRIGVENPRK; |
| 3620. | KRRIGVENPRK; |
| 3621. | RRRIGVENPRK; |
| 3622. | HRRIGVENPRK; |
| 3623. | KHHVGVENPRK; |
| 3624. | RHHVGVENPRK; |
| 3625. | HHHVGVENPRK; |
| 3626. | KKHVGVENPRK; |
| 3627. | RKHVGVENPRK; |
| 3628. | HKHVGVENPRK; |
| 3629. | KRHVGVENPRK; |
| 3630. | RRHVGVENPRK; |
| 3631. | HRHVGVENPRK; |
| 3632. | KHKVGVENPRK; |
| 3633. | RHKVGVENPRK; |
| 3634. | HHKVGVENPRK; |
| 3635. | KKKVGVENPRK; |
| 3636. | RKKVGVENPRK; |
| 3637. | HKKVGVENPRK; |

TABLE 7-continued

SEQ ID NO. shown to left of sequence(cont'd)

| SEQ ID | Sequence |
|---|---|
| 3638. | KRKVGVENPRK; |
| 3639. | RRKVGVEEPRK; |
| 3640. | HRKVGVENPRK; |
| 3641. | KHRVGVENPRK; |
| 3642. | RHRVGVENPRK; |
| 3643. | HHRVGVENPRK; |
| 3644. | KKRVGVENPRK; |
| 3645. | RKRVGVENPRK; |
| 3646. | HKRVGVENPRK; |
| 3647. | KRRVGVENPRK; |
| 3648. | RRRVGVENPRK; |
| 3649. | HRRVGVENPRK; |
| 3650. | KHHLGLNNPRK; |
| 3651. | RHHLGLNNPRK; |
| 3652. | HHHLGLNNPRK; |
| 3653. | KKHLGLNNPRK; |
| 3654. | RKHLGLNNPRK; |
| 3655. | HKHLGLNNPRK; |
| 3656. | KRHLGLNNPRK; |
| 3657. | RRHLGLNNPRK; |
| 3658. | HRHLGLNNPRK; |
| 3659. | KHKLGLNNPRK; |
| 3660. | RHKLGLNNPRK; |
| 3661. | HHKLGLNNPRK; |
| 3662. | KKKLGLNNPRK; |
| 3663. | RKKLGLNNPRK; |
| 3664. | HKKLGLNNPRK; |
| 3665. | KRKLGLNNPRK; |
| 3666. | RRKLGLNNPRK; |
| 3667. | HRKLGLNNPRK; |
| 3668. | KHRLGLNNPRK; |
| 3669. | RHRLGLNNPRK; |
| 3670. | HHRLGLNNPRK; |
| 3671. | KKRLGLNNPRK; |
| 3672. | RKRLGLNNPRK; |
| 3673. | HKRLGLNNPRK; |
| 3674. | KRRLGLNNPRK; |
| 3675. | RRRLGLNNPRK; |
| 3676. | HRRLGLNNPRK; |
| 3677. | KHHIGLNNPRK; |
| 3678. | RHHIGLNNPRK; |
| 3679. | HHHIGLNNPRK; |
| 3680. | KKHIGLNNPRK; |
| 3681. | RKHIGLNNPRK; |
| 3682. | HKHIGLNNPRK; |
| 3683. | KRHIGLNNPRK; |
| 3684. | RRHIGLNNPRK; |
| 3685. | HRHIGLNNPRK; |
| 3686. | KHKIGLNNPRK; |
| 3687. | RHKIGLNNPRK; |
| 3688. | HHKIGLNNPRK; |
| 3689. | KKKIGLNNPRK; |
| 3690. | RKKIGLNNPRK; |
| 3691. | HKKIGLNNPRK; |
| 3692. | KRKIGLNNPRK; |
| 3693. | RRKIGLNNPRK; |
| 3694. | HRKIGLNNPRK; |
| 3695. | KHRIGLNNPRK; |
| 3696. | RHRIGLNNPRK; |
| 3697. | HHRIGLNNPRK; |
| 3698. | KKRIGLNNPRK; |
| 3699. | RKRIGLNNPRK; |
| 3700. | HKRIGLNNPRK; |
| 3701. | KRRIGLNNPRK; |
| 3702. | RRRIGLNNPRK; |
| 3703. | HRRIGLNNPRK; |
| 3704. | KHHVGLNNPRK; |
| 3705. | RHHVGLNNPRK; |
| 3706. | HHHVGLNNPRK; |
| 3707. | KKHVGLNNPRK; |
| 3708. | RKHVGLNNPRK; |
| 3709. | HKHVGLNNPRK; |
| 3710. | KRHVGLNNPRK; |
| 3711. | RRHVGLNNPRK; |
| 3712. | HRHVGLNNPRK; |
| 3713. | KHKVGLNNPRK; |
| 3714. | RHKVGLNNPRK; |
| 3715. | HHKVGLNNPRK; |

TABLE 7-continued

SEQ ID NO. shown to left of sequence(cont'd)

| | |
|---|---|
| 3716. | KKKVGLNNPRK; |
| 3717. | RKKVGLNNPRK; |
| 3718. | HKKVGLNNPRK; |
| 3719. | KRKVGLNNPRK; |
| 3720. | RRKVGLNNPRK; |
| 3721. | HRKVGLNNPRK; |
| 3722. | KHRVGLNNPRK; |
| 3723. | RHRVGLNNPRK; |
| 3724. | HHRVGLNNPRK; |
| 3725. | KKRVGLNNPRK; |
| 3726. | RKRVGLNNPRK; |
| 3727. | HKRVGLNNPRK; |
| 3728. | KRRVGLNNPRK; |
| 3729. | RRRVGLNNPRK; |
| 3730. | HRRVGLNNPRK; |
| 3731. | KHHLGINNPRK; |
| 3732. | RHHLGINNPRK; |
| 3733. | HHHLGINNPRK; |
| 3734. | KKHLGINNPRK; |
| 3735. | RKHLGINNPRK; |
| 3736. | HKHLGINNPRK; |
| 3737. | KRHLGINNPRK; |
| 3738. | RRHLGINNPRK; |
| 3739. | HRHLGINNPRK; |
| 3740. | KHKLGINNPRK; |
| 3741. | RHKLGINNPRK; |
| 3742. | HHKLGINNPRK; |
| 3743. | KKKLGINNPRK; |
| 3744. | RKKLGINNPRK; |
| 3745. | HKKLGINNPRK; |
| 3746. | KRKLGINNPRK; |
| 3747. | RRKLGINNPRK; |
| 3748. | HRKLGINNPRK; |
| 3749. | KHRLGINNPRK; |
| 3750. | RHRLGINNPRK; |
| 3751. | HHRLGINNPRK; |
| 3752. | KKRLGINNPRK; |
| 3753. | RKRLGINNPRK; |
| 3754. | HKRLGINNPRK; |

TABLE 7-continued

SEQ ID NO. shown to left of sequence(cont'd)

| | |
|---|---|
| 3755. | KRRLGINNPRK; |
| 3756. | RRRLGINNPRK; |
| 3757. | HRRLGINNPRK; |
| 3758. | KHHIGIENPRK; |
| 3759. | RHHIGINNPRK; |
| 3760. | HHHIGINNPRK; |
| 3761. | KKHIGINNPRK; |
| 3762. | RKHIGINNPRK; |
| 3763. | HKHIGINNPRK; |
| 3764. | KRHIGINNPRK; |
| 3765. | RRHIGINNPRK; |
| 3766. | HRHIGINNPRK; |
| 3767. | KHKIGINNPRK; |
| 3768. | RHKIGINNPRK; |
| 3769. | HHKIGINNPRK; |
| 3770. | KKKIGINNPRK; |
| 3771. | RKKIGINNPRK; |
| 3772. | HKKIGINNPRK; |
| 3773. | KRKIGINNPRK; |
| 3774. | RRKIGINNPRK; |
| 3775. | HRKIGINNPRK; |
| 3776. | KHRIGINNPRK; |
| 3777. | RHRIGINNPRK; |
| 3778. | HHRIGINNPRK; |
| 3779. | KKRIGINNPRK; |
| 3780. | RKRIGINNPRK; |
| 3781. | HKRIGINNPRK; |
| 3782. | KRRIGINNPRK; |
| 3783. | RRRIGINNPRK; |
| 3784. | HRRIGINNPRK; |
| 3785. | KHHVGINNPRK; |
| 3786. | RHHVGINNPRK; |
| 3787. | HHHVGINNPRK; |
| 3788. | KKHVGINNPRK; |
| 3789. | RKHVGINNPRK; |
| 3790. | HKHVGINNPRK; |
| 3791. | KRHVGINNPRK; |
| 3792. | RRHVGINNPRK; |
| 3793. | HRHVGINNPRK; |

TABLE 7-continued

SEQ ID NO. shown to left of sequence(cont'd)

| | |
|---|---|
| 3794. | KHKVGINNPRK; |
| 3795. | RHKVGINNPRK; |
| 3796. | HHKVGINNPRK; |
| 3797. | KKKVGINNPRK; |
| 3798. | RKKVGINNPRK; |
| 3799. | HKKVGINNPRK; |
| 3800. | KRKVGINNPRK; |
| 3801. | RRKVGINNPRK; |
| 3802. | HRKVGINNPRK; |
| 3803. | KHRVGINNPRK; |
| 3804. | RHRVGINNPRK; |
| 3805. | HHRVGINNPRK; |
| 3806. | KKRVGINNPRK; |
| 3807. | RKRVGINNPRK; |
| 3808. | HKRVGINNPRK; |
| 3809. | KRRVGINNPRK; |
| 3810. | RRRVGINNPRK; |
| 3811. | HRRVGINNPRK; |
| 3812. | KHHLGVNNPRK; |
| 3813. | RHHLGVNNPRK; |
| 3814. | HHHLGVNNPRK; |
| 3815. | KKHLGVNNPRK; |
| 3816. | RKHLGVNNPRK; |
| 3817. | HKHLGVNNPRK; |
| 3818. | KRHLGVNNPRK; |
| 3819. | RRHLGVNNPRK; |
| 3820. | HRHLGVNNPRK; |
| 3821. | KHKLGVNNPRK; |
| 3822. | RHKLGVNNPRK; |
| 3823. | HHKLGVNNPRK; |
| 3824. | KKKLGVNNPRK; |
| 3825. | RKKLGVNNPRK; |
| 3826. | HKKLGVNNPRK; |
| 3827. | KRKLGVNNPRK; |
| 3828. | RRKLGVNNPRK; |
| 3829. | HRKLGVNNPRK; |
| 3830. | KHRLGVNNPRK; |
| 3831. | RHRLGVNNPRK; |
| 3832. | HHRLGVNNPRK; |
| 3833. | KKRLGVNNPRK; |
| 3834. | RKRLGVNNPRK; |
| 3835. | HKRLGVNNPRK; |
| 3836. | KRRLGVNNPRK; |
| 3837. | RRRLGVNNPRK; |
| 3838. | HRRLGVNNPRK; |
| 3839. | KHHIGVNNPRK; |
| 3840. | RHHIGVNNPRK; |
| 3841. | HHHIGVNNPRK; |
| 3842. | KKHIGVNNPRK; |
| 3843. | RKHIGVNNPRK; |
| 3844. | HKHIGVNNPRK; |
| 3845. | KRHIGVNNPRK; |
| 3846. | RRHIGVNNPRK; |
| 3847. | HRHIGVNNPRK; |
| 3848. | KHKIGVNNPRK; |
| 3849. | RHKIGVNNPRK; |
| 3850. | HHKIGVNNPRK; |
| 3851. | KKKIGVNNPRK; |
| 3852. | RKKIGVNNPRK; |
| 3853. | HKKIGVNNPRK; |
| 3854. | KRKIGVNNPRK; |
| 3855. | RRKIGVNNPRK; |
| 3856. | HRKIGVNNPRK; |
| 3857. | KHRIGVNNPRK; |
| 3858. | RHRIGVNNPRK; |
| 3859. | HHRIGVNNPRK; |
| 3860. | KKRIGVNNPRK; |
| 3861. | RKRIGVNNPRK; |
| 3862. | HKRIGVNNPRK; |
| 3863. | KRRIGVNNPRK; |
| 3864. | RRRIGVNNPRK; |
| 3865. | HRRIGVNNPRK; |
| 3866. | KHHVGVNNPRK; |
| 3867. | RHHVGVNNPRK; |
| 3868. | HHHVGVNNPRK; |
| 3869. | KKHVGVNNPRK; |
| 3870. | RKHVGVNNPRK; |
| 3871. | HKHVGVNNPRK; |

TABLE 7-continued

SEQ ID NO. shown to left of sequence(cont'd)

| | |
|---|---|
| 3872. | KRHVGVNNPRK; |
| 3873. | RRHVGVNNPRK; |
| 3874. | HRHVGVNNPRK; |
| 3875. | KHKVGVNNPRK; |
| 3876. | RHKVGVNNPRK; |
| 3877. | HHKVGVNNPRK; |
| 3878. | KKKVGVNNPRK; |
| 3879. | RKKVGVNNPRK; |
| 3880. | HKKVGVNNPRK; |
| 3881. | KRKVGVNNPRK; |
| 3882. | RRKVGVNNPRK; |
| 3883. | HRKVGVNNPRK; |
| 3884. | KHRVGVNNPRK; |
| 3885. | RHRVGVNNPRK; |
| 3886. | HHRVGVNNPRK; |
| 3887. | KKRVGVNNPRK; |
| 3888. | RKRVGVNNPRK; |
| 3889. | HKRVGVNNPRK; |
| 3890. | KRRVGVNNPRK; |
| 3891. | RRRVGVNNPRK; |
| 3892. | HRRVGVNNPRK; |
| 3893. | KHHLGLEEPHK; |
| 3894. | RHHLGLEEPHK; |
| 3895. | HHHLGLEEPHK; |
| 3896. | KKHLGLEEPHK; |
| 3897. | RKHLGLEEPHK; |
| 3898. | HKHLGLEEPHK; |
| 3899. | KRHLGLEEPHK; |
| 3900. | RRHLGLEEPHK; |
| 3901. | HRHLGLEEPHK; |
| 3902. | KHKLGLEEPHK; |
| 3903. | RHKLGLEEPHK; |
| 3904. | HHKLGLEEPHK; |
| 3905. | KKKLGLEEPHK; |
| 3906. | RKKLGLEEPHK; |
| 3907. | HKKLGLEEPHK; |
| 3908. | KRKLGLEEPHK; |
| 3909. | RRKLGLEEPHK; |
| 3910. | HRKLGLEEPHK; |
| 3911. | KHRLGLEEPHK; |
| 3912. | RHRLGLEEPHK; |
| 3913. | HHRLGLEEPHK; |
| 3914. | KKRLGLEEPHK; |
| 3915. | RKRLGLEEPHK; |
| 3916. | HKRLGLEEPHK; |
| 3917. | KRRLGLEEPHK; |
| 3918. | RRRLGLEEPHK; |
| 3919. | HRRLGLEEPHK; |
| 3920. | KHHIGLEEPHK; |
| 3921. | RHHIGLEEPHK; |
| 3922. | HHHIGLEEPHK; |
| 3923. | KKHIGLEEPHK; |
| 3924. | RKHIGLEEPHK; |
| 3925. | HKHIGLEEPHK; |
| 3926. | KRHIGLEEPHK; |
| 3927. | RRHIGLEEPHK; |
| 3928. | HRHIGLEEPHK; |
| 3929. | KHKIGLEEPHK; |
| 3930. | RHKIGLEEPHK; |
| 3931. | HHKIGLEEPHK; |
| 3932. | KKKIGLEEPHK; |
| 3933. | RKKIGLEEPHK; |
| 3934. | HKKIGLEEPHK; |
| 3935. | KRKIGLEEPHK; |
| 3936. | RRKIGLEEPHK; |
| 3937. | HRKIGLEEPHK; |
| 3938. | KHRIGLEEPHK; |
| 3939. | RHRIGLEEPHK; |
| 3940. | HHRIGLEEPHK; |
| 3941. | KKRIGLEEPHK; |
| 3942. | RKRIGLEEPHK; |
| 3943. | HKRIGLEEPHK; |
| 3944. | KRRIGLEEPHK; |
| 3945. | RRRIGLEEPHK; |
| 3946. | HRRIGLEEPHK; |
| 3947. | KHHVGLEEPHK; |
| 3948. | RHHVGLEEPHK; |
| 3949. | HHHVGLEEPHK; |

TABLE 7-continued

SEQ ID NO. shown to left of sequence(cont'd)

| | |
|---|---|
| 3950. | KKHVGLEEPHK; |
| 3951. | RKHVGLEEPHK; |
| 3952. | HKHVGLEEPHK; |
| 3953. | KRHVGLEEPHK; |
| 3954. | RRHVGLEEPHK; |
| 3955. | HRHVGLEEPHK; |
| 3956. | KHKVGLEEPHK; |
| 3957. | RHKVGLEEPHK; |
| 3958. | HHKVGLEEPHK; |
| 3959. | KKKVGLEEPHK; |
| 3960. | RKKVGLEEPHK; |
| 3961. | HKKVGLEEPHK; |
| 3962. | KRKVGLEEPHK; |
| 3963. | RRKVGLEEPHK; |
| 3964. | HRKVGLEEPHK; |
| 3965. | KHRVGLEEPHK; |
| 3966. | RHRVGLEEPHK;. |
| 3967. | HHRVGLEEPHK; |
| 3968. | KKRVGLEEPHK; |
| 3969. | RKRVGLEEPHK; |
| 3970. | HKRVGLEEPHK; |
| 3971. | KRRVGLEEPHK; |
| 3972. | RRRVGLEEPHK; |
| 3973. | HRRVGLEEPHK; |
| 3974. | KHHLGIEEPHK; |
| 3975. | RHHLGIEEPHK; |
| 3976. | HHHLGIEEPHK; |
| 3977. | KKHLGIEEPHK; |
| 3978. | RKHLGIEEPHK; |
| 3979. | HKHLGIEEPHK; |
| 3980. | KRHLGIEEPHK; |
| 3981. | RRHLGIEEPHK; |
| 3982. | HRHLGIEEPHK; |
| 3983. | KHKLGIEEPHK; |
| 3984. | RHKLGIEEPHK; |
| 3985. | HHKLGIEEPHK; |
| 3986. | KKKLGIEEPHK; |
| 3987. | RKKLGIEEPHK; |
| 3988. | HKKLGIEEPHK; |
| 3989. | KRKLGIEEPHK; |
| 3990. | RRKLGIEEPHK; |
| 3991. | HRKLGIEEPHK; |
| 3992. | KHRLGIEEPHK; |
| 3993. | RHRLGIEEPHK; |
| 3994. | HHRLGIEEPHK; |
| 3995. | KKRLGIEEPHK; |
| 3996. | RKRLGIEEPHK; |
| 3997. | HKRLGIEEPHK; |
| 3998. | KRRLGIEEPHK; |
| 3999. | RRRLGIEEPHK; |
| 4000. | HRRLGIEEPHK; |
| 4001. | KHHIGIEEPHK; |
| 4002. | RHHIGIEEPHK; |
| 4003. | HHHIGIEEPHK; |
| 4004. | KKHIGIEEPHK; |
| 4005. | RKHIGIEEPHK; |
| 4006. | HKHIGIEEPHK; |
| 4007. | KRHIGIEEPHK; |
| 4008. | RRHIGIEEPHK; |
| 4009. | HRHIGIEEPHK; |
| 4010. | KHKIGIEEPHK; |
| 4011. | RHKIGIEEPHK; |
| 4012. | HHKIGIEEPHK; |
| 4013. | KKKIGIEEPHK; |
| 4014. | RKKIGIEEPHK; |
| 4015. | HKKIGIEEPHK; |
| 4016. | KRKIGIEEPHK; |
| 4017. | RRKIGIEEPHK; |
| 4018. | HRKIGIEEPHK; |
| 4019. | KHRIGIEEPHK; |
| 4020. | RHRIGIEEPHK; |
| 4021. | HHRIGIEEPHK; |
| 4022. | KKRIGIEEPHK; |
| 4023. | RKRIGIEEPHK; |
| 4024. | HKRIGIEEPHK; |
| 4025. | KRRIGIEEPHK; |
| 4026. | RRRIGIEEPHK; |
| 4027. | HRRIGIEEPHK; |

TABLE 7-continued

| SEQ ID NO. shown to left of sequence(cont'd) | |
|---|---|
| 4028. | KHHVGIEEPHK; |
| 4029. | RHHVGIEEPHK; |
| 4030. | HHHVGIEEPHK; |
| 4031. | KKHVGIEEPHK; |
| 4032. | RKHVGIEEPHK; |
| 4033. | HKHVGIEEPHK; |
| 4034. | KRHVGIEEPHK; |
| 4035. | RRHVGIEEPHK; |
| 4036. | HRHVGIEEPHK; |
| 4037. | KHKVGIEEPHK; |
| 4038. | RHKVGIEEPHK; |
| 4039. | HHKVGIEEPHK; |
| 4040. | KKKVGIEEPHK; |
| 4041. | RKKVGIEEPHK; |
| 4042. | HKKVGIEEPHK; |
| 4043. | KRKVGIEEPHK; |
| 4044. | RRKVGIEEPHK; |
| 4045. | HRKVGIEEPHK; |
| 4046. | KHRVGIEEPHK; |
| 4047. | RHRVGIEEPHK; |
| 4048. | HHRVGIEEPHK; |
| 4049. | KKRVGIEEPHK; |
| 4050. | RKRVGIEEPHK; |
| 4051. | HKRVGIEEPHK; |
| 4052. | KRRVGIEEPHK; |
| 4053. | RRRVGIEEPHK; |
| 4054. | HRRVGIEEPHK; |
| 4055. | KHHLGVEEPHK; |
| 4056. | RHHLGVEEPHK; |
| 4057. | HHHLGVEEPHK; |
| 4058. | KKHLGVEEPHK; |
| 4059. | RKHLGVEEPHK; |
| 4060. | HKHLGVEEPHK; |
| 4061. | KRHLGVEEPHK; |
| 4062. | RRHLGVEEPHK; |
| 4063. | HRHLGVEEPHK; |
| 4064. | KHKLGVEEPHK; |
| 4065. | RHKLGVEEPHK; |
| 4066. | HHKLGVEEPHK; |
| 4067. | KKKLGVEEPHK; |
| 4068. | RKKLGVEEPHK; |
| 4069. | HKKLGVEEPHK; |
| 4070. | KRKLGVEEPHK; |
| 4071. | RRKLGVEEPHK; |
| 4072. | HRKLGVEEPHK; |
| 4073. | KHRLGVEEPHK; |
| 4074. | RHRLGVEEPHK; |
| 4075. | HHRLGVEEPHK; |
| 4076. | KKRLGVEEPHK; |
| 4077. | RKRLGVEEPHK; |
| 4078. | HKRLGVEEPHK; |
| 4079. | KRRLGVEEPHK; |
| 4080. | RRRLGVEEPHK; |
| 4081. | HRRLGVEEPHK; |
| 4082. | KHHIGVEEPHK; |
| 4083. | RHHIGVEEPHK; |
| 4084. | HHHIGVEEPHK; |
| 4085. | KKHIGVEEPHK; |
| 4086. | RKHIGVEEPHK; |
| 4087. | HKHIGVEEPHK; |
| 4088. | KRHIGVEEPHK; |
| 4089. | RRHIGVEEPHK; |
| 4090. | HRHIGVEEPHK; |
| 4091. | KHKIGVEEPHK; |
| 4092. | RHKIGVEEPHK; |
| 4093. | HHKIGVEEPHK; |
| 4094. | KKKIGVEEPHK; |
| 4095. | RKKIGVEEPHK; |
| 4096. | HKKIGVEEPHK; |
| 4097. | KRKIGVEEPHK; |
| 4098. | RRKIGVEEPHK; |
| 4099. | HRKIGVEEPHK; |
| 4100. | KHRIGVEEPHK; |
| 4101. | RHRIGVEEPHK; |
| 4102. | HHRIGVEEPHK; |
| 4101. | KKRIGVEEPHK; |
| 4104. | RKRIGVEEPHK; |
| 4105. | HKRIGVEEPHK; |

TABLE 7-continued

SEQ ID NO. shown to left of sequence(cont'd)

| | |
|---|---|
| 4106. | KRRIGVEEPHK; |
| 4107. | RRRIGVEEPHK; |
| 4108. | HRRIGVEEPHK; |
| 4109. | KHHVGVEEPHK; |
| 4110. | RHHVGVEEPHK; |
| 4111. | HHHVGVEEPHK; |
| 4112. | KKHVGVEEPHK; |
| 4113. | RKHVGVEEPHK; |
| 4114. | HKHVGVEEPHK; |
| 4115. | KRHVGVEEPHK; |
| 4116. | RRHVGVEEPHK; |
| 4117. | HRHVGVEEPHK; |
| 4118. | KHKVGVEEPHK; |
| 4119. | RHKVGVEEPHK; |
| 4120. | HHKVGVEEPHK; |
| 4121. | KKKVGVEEPHK; |
| 4122. | RKKVGVEEPHK; |
| 4123. | HKKVGVEEPHK; |
| 4124. | KRKVGVEEPHK; |
| 4125. | RRKVGVEEPHK; |
| 4126. | HRKVGVEEPHK; |
| 4127. | KHRVGVEEPHK; |
| 4128. | RHRVGVEEPHK; |
| 4129. | HHRVGVEEPHK; |
| 4130. | KKRVGVEEPHK; |
| 4131. | RKRVGVEEPHK; |
| 4132. | HKRVGVEEPHK; |
| 4133. | KRRVGVEEPHK; |
| 4134. | RRRVGVEEPHK; |
| 4135. | HRRVGVEEPHK; |
| 4136. | KHHLGLNEPHK; |
| 4137. | RHHLGLNEPHK; |
| 4138. | HHHLGLNEPHK; |
| 4139. | KKHLGLNEPHK; |
| 4140. | RKHLGLNEPHK; |
| 4141. | HKHLGLNEPHK; |
| 4142. | KRHLGLNEPHK; |
| 4143. | RRHLGLNEPHK; |
| 4144. | HRHLGLNEPHK; |

TABLE 7-continued

SEQ ID NO. shown to left of sequence(cont'd)

| | |
|---|---|
| 4145. | KHKLGLNEPHK; |
| 4146. | RHKLGLNEPHK; |
| 4147. | HHKLGLNEPHK; |
| 4148. | KKKLGLNEPHK; |
| 4149. | RKKLGLNEPHK; |
| 4150. | HKKLGLNEPHK; |
| 4151. | KRKLGLNEPHK; |
| 4152. | RRKLGLNEPHK; |
| 4153. | HRKLGLNEPHK; |
| 4154. | KHRLGLNEPHK; |
| 4155. | RHRLGLNEPHK; |
| 4156. | HHRLGLNEPHK; |
| 4157. | KKRLGLNEPHK; |
| 4158. | RKRLGLNEPHK; |
| 4159. | HKRLGLNEPHK; |
| 4160. | KRRLGLNEPHK; |
| 4161. | RRRLGLNEPHK; |
| 4162. | HRRLGLNEPHK; |
| 4163. | KHHIGLNPHK; |
| 4164. | RHHIGLNEPHK; |
| 4165. | HHHIGLNEPHK; |
| 4166. | KKHIGLNEPHK; |
| 4167. | RKHIGLNEPHK; |
| 4168. | HHHIGLNEPHK; |
| 4169. | KRHIGLNEPHK; |
| 4170. | RRHIGLNEPHK; |
| 4171. | HRHIGLNEPHK; |
| 4172. | KHKIGLNEPHK; |
| 4173. | RHKIGLNEPHK; |
| 4174. | HHKIGLNEPHK; |
| 4175. | KKKIGLNEPHK; |
| 4176. | RKKIGLNEPHK; |
| 4177. | HKKIGLNEPHK; |
| 4178. | KRKIGLNEPHK; |
| 4179. | RRKIGLNEPHK; |
| 4180. | HRKIGLNEPHK; |
| 4181. | KHRIGLNEPHK; |
| 4182. | RHRIGLNEPHK; |
| 4183. | HHRIGLNEPHK; |

TABLE 7-continued

SEQ ID NO. shown to left of sequence(cont'd)

| SEQ ID NO. | Sequence |
|---|---|
| 4184. | KKRIGLNEPHK; |
| 4185. | RKRIGLNEPHK; |
| 4186. | HKRIGLNEPHK; |
| 4187. | KRRIGLNEPHK; |
| 4188. | RRRIGLNEPHK; |
| 4189. | HRRIGLNEPHK; |
| 4190. | KHHVGLNEPHK; |
| 4191. | RHHVGLNEPHK; |
| 4192. | HHHVGLNEPHK; |
| 4193. | KKHVGLNEPHK; |
| 4194. | RKHVGLNEPHK; |
| 4195. | HKHVGLNEPHK; |
| 4196. | KRHVGLNEPHK; |
| 4197. | RRHVGLNEPHK; |
| 4198. | HRHVGLNEPHK; |
| 4199. | KHKVGLNEPHK; |
| 4200. | RHKVGLNEPHK; |
| 4201. | HHKVGLNEPHK; |
| 4202. | KKKVGLNEPHK; |
| 4203. | RKKVGLNEPHK; |
| 4204. | HKKVGLNEPHK; |
| 4205. | KRKVGLNEPHK; |
| 4206. | RRKVGLNEPHK; |
| 4207. | HRKVGLNEPHK; |
| 4208. | KHRVGLNEPHK; |
| 4209. | RHRVGLNEPHK; |
| 4210. | HHRVGLNEPHK; |
| 4211. | KKRVGLNEPHK; |
| 4212. | RKRVGLNEPHK; |
| 4213. | HKRVGLNEPHK; |
| 4214. | KRRVGLNEPHK; |
| 4215. | RRRVGLNEPHK; |
| 4216. | HRRVGLNEPHK; |
| 4217. | KHHLGINEPHK; |
| 4218. | RHHLGINEPHK; |
| 4219. | HHHLGINEPHK; |
| 4220. | KKHLGINEPHK; |
| 4221. | RKHLGINEPHK; |
| 4222. | HKHLGINEPHK; |
| 4223. | KRHLGINEPHK; |
| 4224. | RRHLGINEPHK; |
| 4225. | HRHLGINEPHK; |
| 4226. | KHKLGINEPHK; |
| 4227. | RHKLGINEPHK; |
| 4228. | HHKLGINEPHK; |
| 4229. | KKKLGINEPHK; |
| 4230. | RKKLGINEPHK; |
| 4231. | HKKLGINEPHK; |
| 4232. | KRKLGLNEPHK; |
| 4233. | RRKLGINEPHK; |
| 4234. | HRKLGLNEPHK; |
| 4235. | KHRLGINEPHK; |
| 4236. | RHRLGINEPHK; |
| 4237. | HHRLGINEPHK; |
| 4238. | KKRLGINEPHK; |
| 4239. | RKRLGINEPHK; |
| 4240. | HKRLGINEPHK; |
| 4241. | KRRLGINEPHK; |
| 4242. | RRRLGINEPHK; |
| 4243. | HRRLGINEPHK; |
| 4244. | KHHIGIENPHK; |
| 4245. | RHHIGINEPHK; |
| 4246. | HHHIGINEPHK; |
| 4247. | KKHIGINEPHK; |
| 4248. | RKHIGINEPHK; |
| 4249. | HKHIGINEPHK; |
| 4250. | KRHIGINEPHK; |
| 4251. | RRHIGINEPHK; |
| 4252. | HRHIGINEPHK; |
| 4253. | KHKIGINEPHK; |
| 4254. | RHKIGINEPHK; |
| 4255. | HHKIGINEPHK; |
| 4256. | KKKIGINEPHK; |
| 4257. | RKKIGINEPHK; |
| 4258. | HKKIGINEPHK; |
| 4259. | KRKIGLNEPHK; |
| 4260. | RRKIGINEPHK; |
| 4261. | HRKIGINEPHK; |

TABLE 7-continued

SEQ ID NO. shown to left of sequence(cont'd)

| | |
|---|---|
| 4262. | KHRIGINEPHK; |
| 4263. | RHRIGINEPHK; |
| 4264. | HHRIGINEPHK; |
| 4265. | KKRIGINEPHK; |
| 4266. | RKRIGINEPHK; |
| 4267. | HKRIGINEPHK; |
| 4268. | KRRIGINEPHK; |
| 4269. | RRRIGINEPHK; |
| 4270. | HRRIGINEPHK; |
| 4271. | KHHVGINEPHK; |
| 4272. | RHHVGINEPHK; |
| 4273. | HHHVGINEPHK; |
| 4274. | KKHVGINEPHK; |
| 4275. | RKHVGINEPHK; |
| 4276. | HKHVGINEPHK; |
| 4277. | KRHVGINEPHK; |
| 4278. | RRHVGINEPHK; |
| 4279. | HRHVGINEPHK; |
| 4280. | KHKVGINEPHK; |
| 4281. | RHKVGINEPHK; |
| 4282. | HHKVGINEPHK; |
| 4283. | KKHVGINEPHK; |
| 4284. | RKKVGINEPHK; |
| 4285. | HKKVGINEPHK; |
| 4286. | KRKVGINEPHK; |
| 4287. | RRKVGINEPHK; |
| 4288. | HRKVGINEPHK; |
| 4289. | KHRVGINEPHK; |
| 4290. | RHRVGINEPHK; |
| 4291. | HHRVGINEPHK; |
| 4292. | KKRVGINEPHK; |
| 4293. | RKRVGINEPHK; |
| 4294. | HKRVGINEPHK; |
| 4295. | KRRVGINEPHK; |
| 4296. | RRRVGINEPHK; |
| 4297. | HRRVGINEPHK; |
| 4298. | KHHLGVNEPHK; |
| 4299. | RHHLGVNEPHK; |
| 4300. | HHHLGVNEPHK; |
| 4301. | KKHLGVNEPHK; |
| 4302. | RKHLGVNEPHK; |
| 4303. | HKHLGVNEPHK; |
| 4304. | KRHLGVNEPHK; |
| 4305. | RRHLGVNEPHK; |
| 4306. | HRHLGVNEPHK; |
| 4307. | KHKLGVNEPHK; |
| 4308. | RHKLGVNEPHK; |
| 4309. | HHKLGVNEPHK; |
| 4310. | KKKLGVNEPHK; |
| 4311. | RKKLGVNEPHK; |
| 4312. | HKKLGVNEPHK; |
| 4313. | KRKLGVNEPHK; |
| 4314. | RRKLGVNEPHK; |
| 4315. | HRKLGVNEPHK; |
| 4316. | KHRLGVNEPHK; |
| 4317. | RHRLGVNEPHK; |
| 4318. | HHRLGVNEPHK; |
| 4319. | KKRLGVNEPHK; |
| 4320. | RKRLGVNEPHK; |
| 4321. | HKRLGVNEPHK; |
| 4322. | KRRLGVNEPHK; |
| 4323. | RRRLGVNEPHK; |
| 4324. | HRRLGVNEPHK; |
| 4325. | KHHIGVNEPHK; |
| 4326. | RHHIGVNEPHK; |
| 4327. | HHHIGVNEPHK; |
| 4328. | KKHIGVNEPHK; |
| 4329. | RKHIGVNEPHK; |
| 4330. | HKHIGVNEPHK; |
| 4331. | KRHIGVNEPHK; |
| 4332. | RRHIGVNEPHK; |
| 4333. | HRHIGVNEPHK; |
| 4334. | KHKIGVNEPHK; |
| 4335. | RHKIGVNEPHK; |
| 4336. | HHKIGVNEPHK; |
| 4337. | KKKIGVNEPHK; |
| 4338. | RKKIGVNEPHK; |
| 4339. | HKKIGVNEPHK; |

TABLE 7-continued

SEQ ID NO. shown to left of sequence(cont'd)

| | |
|---|---|
| 4340. | KRKIGVNEPHK; |
| 4341. | RRKIGVNEPHK; |
| 4342. | HRKIGVNEPHK; |
| 4343. | KHRIGVNEPHK; |
| 4344. | RHRIGVNEPHK; |
| 4345. | HHRIGVNEPHK; |
| 4346. | KKRIGVNEPHK; |
| 4347. | RKRIGVNEPHK; |
| 4348. | HKRIGVNEPHK; |
| 4349. | KRRIGVNEPHK; |
| 4350. | RRRIGVNEPHK; |
| 4351. | HRRIGVNEPHK; |
| 4352. | KHHVGVNEPHK; |
| 4353. | RHHVGVNEPHK; |
| 4354. | HHHVGVNEPHK; |
| 4355. | KKHVGVNEPHK; |
| 4356. | RKHVGVNEPHK; |
| 4357. | HKHVGVNEPHK; |
| 4358. | KRHVGVNEPHK; |
| 4359. | RRHVGVNEPHK; |
| 4360. | HRHVGVNEPHK; |
| 4361. | KHKVGVNEPHK; |
| 4362. | RHKVGVNEPHK; |
| 4363. | HHKVGVNEPHK; |
| 4364. | KKKVGVNEPHK; |
| 4365. | RKKVGVNEPHK; |
| 4366. | HKKVGVNEPHK; |
| 4367. | KRKVGVNEPHK; |
| 4368. | RRKVGVNEPHK; |
| 4369. | HRKVGVNEPHK; |
| 4370. | KHRVGVNEPHK; |
| 4371. | RHRVGVNEPHK; |
| 4372. | HHRVGVNEPHK; |
| 4373. | KKRVGVNEPHK; |
| 4374. | RKRVGVNEPHK; |
| 4375. | HKRVGVNEPHK; |
| 4376. | KRRVGVNEPHK; |
| 4377. | RRRVGVNEPHK; |
| 4378. | HRRVGVNEPHK; |

TABLE 7-continued

SEQ ID NO. shown to left of sequence(cont'd)

| | |
|---|---|
| 4379. | KHHLGLENPHK; |
| 4380. | RHHLGLENPHK; |
| 4381. | HHHLGLENPHK; |
| 4382. | KKHLGLENPHK; |
| 4383. | RKHLGLENPHK; |
| 4384. | HKHLGLENPHK; |
| 4385. | KRHLGLENPHK; |
| 4386. | RRHLGLENPHK; |
| 4387. | HRHLGLENPHK; |
| 4388. | KHKLGLENPHK; |
| 4389. | RHKLGLENPHK; |
| 4390. | HHKLGLENPHK; |
| 4391. | KKKLGLENPHK; |
| 4392. | RKKLGLENPHK; |
| 4393. | HKKLGLENPHK; |
| 4394. | KRKLGLENPHK; |
| 4395. | RRKLGLENPHK; |
| 4396. | HRKLGLENPHK; |
| 4397. | KHRLGLENPHK; |
| 4398. | RHRLGLENPHK; |
| 4399. | HHRLGLENPHK; |
| 4400. | KKRLGLENPHK; |
| 4401. | RKRLGLENPHK; |
| 4402. | HKRLGLENPHK; |
| 4403. | KRRLGLENPHK; |
| 4404. | RRRLGLENPHK; |
| 4405. | HRRLGLENPHK; |
| 4406. | KHHIGLENPHK; |
| 4407. | RHHIGLENPHK; |
| 4408. | HHHIGLENPHK; |
| 4409. | KKHIGLENPHK; |
| 4410. | RKHIGLENPHK; |
| 4411. | HKHIGLENPHK; |
| 4412. | KRHIGLENPHK; |
| 4413. | RRHIGLENPHK; |
| 4414. | HRHIGLENPHK; |
| 4415. | KHKIGLENPHK; |
| 4416. | RHKIGLENPHK; |
| 4417. | HHKIGLENPHK; |

TABLE 7-continued

SEQ ID NO. shown to left of sequence(cont'd)

| | |
|---|---|
| 4418. | KKKIGLENPHK; |
| 4419. | RKKIGLENPHK; |
| 4420. | HKKIGLENPHK; |
| 4421. | KRKIGLENPHK; |
| 4422. | RRKIGLENPHK; |
| 4423. | HRKIGLENPHK; |
| 4424. | KHRIGLENPHK; |
| 4425. | RHRIGLENPHK; |
| 4426. | HHRIGLENPHK; |
| 4427. | KKRIGLENPHK; |
| 4428. | RKRIGLENPHK; |
| 4429. | HKRIGLENPHK; |
| 4430. | KRRIGLENPHK; |
| 4431. | RRRIGLENPHK; |
| 4432. | HRRIGLENPHK; |
| 4433. | KHHVGLENPHK; |
| 4434. | RHHVGLENPHK; |
| 4435. | HHHVGLENPHK; |
| 4436. | KKHVGLENPHK; |
| 4437. | RKHVGLENPHK; |
| 4438. | HKHVGLENPHK; |
| 4439. | KRHVGLENPHK; |
| 4440. | RRHVGLENPHK; |
| 4441. | HRHVGLENPHK; |
| 4442. | KHKVGLENPHK; |
| 4443. | RHKVGLENPHK; |
| 4444. | HHKVGLENPHK; |
| 4445. | KKKVGLENPHK; |
| 4446. | RKKVGLENPHK; |
| 4447. | HKKVGLENPHK; |
| 4448. | KRKVGLENPHK; |
| 4449. | RRKVGLENPHK; |
| 4450. | HRKVGLENPHK; |
| 4451. | KHRVGLENPHK; |
| 4452. | RHRVGLENPHK; |
| 4453. | HHRVGLENPHK; |
| 4454. | KKRVGLENPHK; |
| 4455. | RKRVGLENPHK; |
| 4456. | HKRVGLENPHK; |

TABLE 7-continued

SEQ ID NO. shown to left of sequence(cont'd)

| | |
|---|---|
| 4457. | KRRVGLENPHK; |
| 4458. | RRRVGLENPHK; |
| 4459. | HRRVGLENPHK; |
| 4460. | KHHLGIENPHK; |
| 4461. | RHHLGIENPHK; |
| 4462. | HHHLGIENPHK; |
| 4463. | KKHLGIENPHK; |
| 4464. | RKHLGIENPHK; |
| 4465. | HKHLGIENPHK; |
| 4466. | KRHLGIENPHK; |
| 4467. | RRHLGIENPHK; |
| 4468. | HRHLGIENPHK; |
| 4469. | KHKLGIENPHK; |
| 4470. | RHKLGIENPHK; |
| 4471. | HHKLGIENPHK; |
| 4472. | KKKLGIENPHK; |
| 4473. | RKKLGIENPHK; |
| 4474. | HKKLGIENPHK; |
| 4475. | KRKLGIENPHK; |
| 4476. | RRKLGIENPHK; |
| 4477. | HRKLGIENPHK; |
| 4478. | KHRLGIENPHK; |
| 4479. | RHRLGIENPHK; |
| 4480. | HHRLGIENPHK; |
| 4481. | KKRLGIENPHK; |
| 4482. | RKRLGIENPHK; |
| 4483. | HKRLGIENPHK; |
| 4484. | KRRLGIENPHK; |
| 4485. | RRRLGIENPHK; |
| 4486. | HRRLGIENPHK; |
| 4487. | KHHIGIENPHK; |
| 4488. | RHHIGIENPHK; |
| 4489. | HHHIGIENPHK; |
| 4490. | KKHIGIENPHK; |
| 4491. | RKHIGIENPHK; |
| 4492. | HKHIGIENPHK; |
| 4493. | KRHIGIENPHK; |
| 4494. | RRHIGIENPHK; |
| 4495. | HRHIGIENPHK; |

TABLE 7-continued

SEQ ID NO. shown to left of sequence(cont'd)

| | |
|---|---|
| 4496. | KHKIGIENPHK; |
| 4497. | RHKIGIENPHK; |
| 4498. | HHKIGIENPHK; |
| 4499. | KKKIGIENPHK; |
| 4500. | RKKIGIENPHK; |
| 4501. | HKKIGIENPHK; |
| 4502. | KRKIGIENPHK; |
| 4503. | RRKIGIENPHK; |
| 4504. | HRKIGIENPHK; |
| 4505. | KHRIGIENPHK; |
| 4506. | RHRIGIENPHK; |
| 4507. | HHRIGIENPHK; |
| 4508. | KKRIGIENPHK; |
| 4509. | RKRIGIENPHK; |
| 4510. | HKRIGIENPHK; |
| 4511. | KRRIGIENPHK; |
| 4512. | RRRIGIENPHK; |
| 4513. | HRRIGIENPHK; |
| 4514. | KHHVGIENPHK; |
| 4515. | RHHVGIENPHK; |
| 4516. | HHHVGIENPHK; |
| 4517. | KKHVGIENPHK; |
| 4518. | RKHVGIENPHK; |
| 4519. | HKHVGIENPHK; |
| 4520. | KRHVGIENPHK; |
| 4521. | RRHVGIENPHK; |
| 4522. | HRHVGIENPHK; |
| 4523. | KHKVGIENPHK; |
| 4524. | RHKVGIENPHK; |
| 4525. | HHKVGIENPHK; |
| 4526. | KKKVGIENPHK; |
| 4527. | RKKVGIENPHK; |
| 4528. | HKKVGIENPHK; |
| 4529. | KRKVGIENPHK; |
| 4530. | RRKVGIENPHK; |
| 4531. | HRKVGIENPHK; |
| 4532. | KHRVGIENPHK; |
| 4533. | RHRVGIENPHK; |
| 4534. | HHRVGIENPHK; |
| 4535. | KKRVGIENPHK; |
| 4536. | RKRVGIENPHK; |
| 4537. | HKRVGIENPHK; |
| 4538. | KRRVGIENPHK; |
| 4539. | RRRVGIENPHK; |
| 4540. | HRRVGIENPHK; |
| 4541. | KHHLGVENPHK; |
| 4542. | RHHLGVENPHK; |
| 4543. | HHHLGVENPHK; |
| 4544. | KKHLGVENPHK; |
| 4545. | RKHLGVENPHK; |
| 4546. | HKHLGVENPHK; |
| 4547. | KRHLGVENPHK; |
| 4548. | RRHLGVENPHK; |
| 4549. | HRHLGVENPHK; |
| 4550. | KHKLGVENPHK; |
| 4551. | RHKLGVENPHK; |
| 4552. | HHKLGVENPHK; |
| 4553. | KKKLGVENPHK; |
| 4554. | RKKLGVENPHK; |
| 4555. | HKKLGVENPHK; |
| 4556. | KRKLGVENPHK; |
| 4557. | RRKLGVENPHK; |
| 4558. | HRKLGVENPHK; |
| 4559. | KHRLGVENPHK; |
| 4560. | RHRLGVENPHK; |
| 4561. | HHRLGVENPHK; |
| 4562. | KKRLGVENPHK; |
| 4563. | RKRLGVENPHK; |
| 4564. | HKRLGVENPHK; |
| 4565. | KRRLGVENPHK; |
| 4566. | RRRLGVENPHK; |
| 4567. | HRRLGVENPHK; |
| 4568. | KHHIGVENPHK; |
| 4569. | RHHIGVEEPHK; |
| 4570. | HHHIGVENPHK; |
| 4571. | KKHIGVENPHK; |
| 4572. | RKHIGVENPHK; |
| 4573. | HKHIGVENPHK; |

TABLE 7-continued

SEQ ID NO. shown to left of sequence(cont'd)

| SEQ ID NO. | Sequence |
|---|---|
| 4574. | KRHIGVENPHK; |
| 4575. | RRHIGVENPHK; |
| 4576. | HRHIGVENPHK; |
| 4577. | KHKIGVENPHK; |
| 4578. | RHKIGVENPHK; |
| 4579. | HHKVGVENPHK; |
| 4580. | KKKIGVENPHK; |
| 4581. | RKKIGVENPHK; |
| 4582. | HKKIGVENPHK; |
| 4583. | KRKIGVENPHK; |
| 4584. | RRKIGVENPHK; |
| 4585. | HRKIGVENPHK; |
| 4586. | KHRIGVENPHK; |
| 4587. | RHRIGVENPHK; |
| 4588. | HHRIGVENPHK; |
| 4589. | KKRIGVENPHK; |
| 4590. | RKRIGVENPHK; |
| 4591. | HKRIGVENPHK; |
| 4592. | KRRIGVENPHK; |
| 4593. | RRRIGVENPHK; |
| 4594. | HRRIGVENPHK; |
| 4595. | KHHVGVENPHK; |
| 4596. | RHHVGVENPHK; |
| 4597. | HHHVGVENPHK; |
| 4598. | KKHVGVENPHK; |
| 4599. | RHHVGVENPHK; |
| 4600. | HKHVGVENPHK; |
| 4601. | KRHVGVENPHK; |
| 4602. | RRHVGVENPHK; |
| 4603. | HRHVGVENPHK; |
| 4604. | KHKVGVENPHK; |
| 4605. | RHKVGVENPHK; |
| 4606. | HHKVGVENPHK; |
| 4607. | KKKVGVENPHK; |
| 4608. | RKKVGVENPHK; |
| 4609. | HKKVGVENPHK; |
| 4610. | KRKVGVENPHK; |
| 4611. | RRKVGVEEPHK; |
| 4612. | HRKVGVENPHK; |
| 4613. | KHRVGVENPHK; |
| 4614. | RHRVGVENPHK; |
| 4615. | HHRVGVENPHK; |
| 4616. | KKRVGVENPHK; |
| 4617. | RKRVGVENPHK; |
| 4618. | HKRVGVENPHK; |
| 4619. | KRRVGVENPHK; |
| 4620. | RRRVGVENPHK; |
| 4621. | HRRVGVENPHK; |
| 4622. | KHHLGLNNPHK; |
| 4623. | RHHLGLNNPHK; |
| 4624. | HHHLGLNNPHK; |
| 4625. | KKHLGLNNPHK; |
| 4626. | RKHLGLNNPHK; |
| 4627. | HKHLGLNNPHK; |
| 4628. | KRHLGLNNPHK; |
| 4629. | RRHLGLNNPHK; |
| 4630. | HRHLGLNNPHK; |
| 4631. | KHKLGLNNPHK; |
| 4632. | RHKLGLNNPHK; |
| 4633. | HHKLGLNNPHK; |
| 4634. | KKKLGLNNPHK; |
| 4635. | RKKLGLNNPHK; |
| 4636. | HKKLGLNNPHK; |
| 4637. | KRKLGLNNPHK; |
| 4638. | RRKLGLNNPHK; |
| 4639. | HRKLGLNNPHK; |
| 4640. | KHRLGLNNPHK; |
| 4641. | RHRLGLNNPHK; |
| 4642. | HHRLGLNNPHK; |
| 4643. | KKRLGLNNPHK; |
| 4644. | RKRLGLNNPHK; |
| 4645. | HKRLGLNNPHK; |
| 4646. | KRRLGLNNPHK; |
| 4647. | RRRLGLNNPHK; |
| 4648. | HRRLGLNNPHK; |
| 4649. | KHHIGLNNPHK; |
| 4650. | RHHIGLNNPHK; |
| 4651. | HHHIGLNNPHK; |

TABLE 7-continued

SEQ ID NO. shown to left of sequence (cont'd)

| SEQ ID NO. | Sequence |
|---|---|
| 4652. | KKHIGLNNPHK; |
| 4653. | RKHIGLNNPHK; |
| 4654. | HKHIGLNNPHK; |
| 4655. | KRHIGLNNPHK; |
| 4656. | RRHIGLNNPHK; |
| 4657. | HRHIGLNNPHK; |
| 4658. | KHKIGLNNPHK; |
| 4659. | RHKIGLNNPHK; |
| 4660. | HHKIGLNNPHK; |
| 4661. | KKKIGLNNPHK; |
| 4662. | RKKIGLNNPHK; |
| 4663. | HKKIGLNNPHK; |
| 4664. | KRKIGLNNPHK; |
| 4665. | RRKIGLNNPHK; |
| 4666. | HRKIGLNNPHK; |
| 4667. | KHRIGLNNPHK; |
| 4668. | RHRIGLNNPHK; |
| 4669. | HHRIGLNNPHK; |
| 4670. | KKRIGLNNPHK; |
| 4671. | RKRIGLNNPHK; |
| 4672. | HKRIGLNNPHK; |
| 4673. | KRRIGLNNPHK; |
| 4674. | RRRIGLNNPHK; |
| 4675. | HRRIGLNNPHK; |
| 4676. | KHHVGLNNPHK; |
| 4677. | RHHVGLNNPHK; |
| 4678. | HHHVGLNNPHK; |
| 4679. | KKHVGLNNPHK; |
| 4680. | RKHVGLNNPHK; |
| 4681. | HKHVGLNNPHK; |
| 4682. | KRHVGLNNPHK; |
| 4683. | RRHVGLNNPHK; |
| 4684. | HRHVGLNNPHK; |
| 4685. | KHKVGLNNPHK; |
| 4686. | RHKVGLNNPHK; |
| 4687. | HHKVGLNNPHK; |
| 4688. | KKKVGLNNPHK; |
| 4689. | RKKVGLNNPHK; |
| 4690. | HKKVGLNNPHK; |
| 4691. | KRKVGLNNPHK; |
| 4692. | RRKVGLNNPHK; |
| 4693. | HRKVGLNNPHK; |
| 4694. | KHRVGLNNPHK; |
| 4695. | RHRVGLNNPHK; |
| 4696. | HHRVGLNNPHK; |
| 4697. | KKRVGLNNPHK; |
| 4698. | RKRVGLNNPHK; |
| 4699. | HKRVGLNNPHK; |
| 4700. | KRRVGLNNPHK; |
| 4701. | RRRVGLNNPHK; |
| 4702. | HRRVGLNNPHK; |
| 4703. | KHHLGINNPHK; |
| 4704. | RHHLGINNPHK; |
| 4705. | HHHLGINNPHK; |
| 4706. | KKHLGINNPHK; |
| 4707. | RKHLGINNPHK; |
| 4708. | HKHLGINNPHK; |
| 4709. | KRHLGINNPHK; |
| 4710. | RRHLGINNPHK; |
| 4711. | HRHLGINNPHK; |
| 4712. | KHKLGINNPHK; |
| 4713. | RHKLGINNPHK; |
| 4714. | HHKLGINNPHK; |
| 4715. | KKKLGINNPHK; |
| 4716. | RHKLGINNPHK; |
| 4717. | HKKLGINNPHK; |
| 4718. | KRKLGINNPHK; |
| 4719. | RRKLGINNPHK; |
| 4720. | HRKLGINNPHK; |
| 4721. | KHRLGINNPHK; |
| 4722. | RHRLGINNPHK; |
| 4723. | HHRLGINNPHK; |
| 4724. | KKRLGINNPHK; |
| 4725. | RKRLGINNPHK; |
| 4726. | HKRLGINNPHK; |
| 4727. | KRRLGINNPHK; |
| 4728. | RRRLGINNPHK; |
| 4729. | HRRLGINNPHK; |

TABLE 7-continued

SEQ ID NO. shown to left of sequence(cont'd)

| | |
|---|---|
| 4730. | KHHIGIENPHK; |
| 4731. | RHHIGINNPHK; |
| 4732. | HHHIGINNPHK; |
| 4733. | KKHIGINNPHK; |
| 4734. | RKHIGINNPHK; |
| 4735. | HKHIGINNPHK; |
| 4736. | KRHIGINNPHK; |
| 4737. | RRHIGINNPHK; |
| 4738. | HRHIGINNPHK; |
| 4739. | KHKIGINNPHK; |
| 4740. | RHKIGVNNPHK; |
| 4741. | HHKIGINNPHK; |
| 4742. | KKKIGINNPHK; |
| 4743. | RKKIGINNPHK; |
| 4744. | HKKIGINNPHK; |
| 4745. | KRKIGINNPHK; |
| 4746. | RRKIGINNPHK; |
| 4747. | HRKIGVNNPHK; |
| 4748. | KHRIGINNPHK; |
| 4749. | RHRIGINNPHK; |
| 4750. | HHRIGINNPHK; |
| 4751. | KKRIGINNPHK; |
| 4752. | RKRIGINNPHK; |
| 4753. | HKRIGINNPHK; |
| 4754. | KRRIGINNPHK; |
| 4755. | RRRIGINNPHK; |
| 4756. | HRRIGINNPHK; |
| 4757. | KHHVGINNPHK; |
| 4758. | RHHVGINNPHK; |
| 4759. | HHHVGINNPHK; |
| 4760. | KKHVGINNPHK; |
| 4761. | RKHVGINNPHK; |
| 4762. | HKHVGINNPHK; |
| 4763. | KRHVGINNPHK; |
| 4764. | RRHVGINNPHK; |
| 4765. | HRHVGINNPHK; |
| 4766. | KHKVGINNPHK; |
| 4767. | RHKVGINNPHK; |
| 4768. | HHKVGINNPHK; |

TABLE 7-continued

SEQ ID NO. shown to left of sequence(cont'd)

| | |
|---|---|
| 4769. | KKKVGINNPHK; |
| 4770. | RKKVGINNPHK; |
| 4771. | HKKVGINNPHK; |
| 4772. | KRKVGINNPHK; |
| 4773. | RRKVGINNPHK; |
| 4774. | HRKVGINNPHK; |
| 4775. | KHRVGINNPHK; |
| 4776. | RHRVGINNPHK; |
| 4777. | HHRVGINNPHK; |
| 4778. | KHRVGINNPHK; |
| 4779. | RKRVGINNPHK; |
| 4780. | HKRVGINNPHK; |
| 4781. | KRRVGINNPHK; |
| 4782. | RRRVGINNPHK; |
| 4783. | HRRVGINNPHK; |
| 4784. | KHHLGVNNPHK; |
| 4785. | RHHLGVNNPHK; |
| 4786. | HHHLGVNNPHK; |
| 4787. | KKHLGVNNPHK; |
| 4788. | RKHLGVNNPHK; |
| 4789. | HKHLGVNNPHK; |
| 4790. | KRHLGVNNPHK; |
| 4791. | RRHLGVNNPHK; |
| 4792. | HRHLGVNNPHK; |
| 4793. | KHKLGVNNPHK; |
| 4794. | RHKLGVNNPHK; |
| 4795. | HHKLGVNNPHK; |
| 4796. | KKKLGVNNPHK; |
| 4797. | RKKLGVNNPHK; |
| 4798. | HKKLGVNNPHK; |
| 4799. | KRKLGVNNPHK; |
| 4800. | RRKLGVNNPHK; |
| 4801. | HRKLGVNNPHK; |
| 4802. | KHRLGVNNPHK; |
| 4803. | RHRLGVNNPHK; |
| 4804. | HHRLGVNNPHK; |
| 4805. | KKRLGVNNPHK; |
| 4806. | RKRLGVNNPHK; |
| 4807. | HKRLGVNNPHK; |

TABLE 7-continued

SEQ ID NO. shown to left of sequence(cont'd)

| | |
|---|---|
| 4808. | KRRLGVNNPHK; |
| 4809. | RRRLGVNNPHK; |
| 4810. | HRRLGVNNPHK; |
| 4811. | KHHIGVNNPHK; |
| 4812. | RHHIGVNNPHK; |
| 4813. | HHHIGVNNPHK; |
| 4814. | KKHIGVNNPHK; |
| 4815. | RKHIGVNNPHK; |
| 4816. | HKHIGVNNPHK; |
| 4817. | KHHIGVNNPHK; |
| 4818. | RRHIGVNNPHK; |
| 4819. | HRHIGVNNPHK; |
| 4820. | KHKIGVNNPHK; |
| 4821. | RHKIGVNNPHK; |
| 4822. | HHKIGVNNPHK; |
| 4823. | KKKIGVNNPHK; |
| 4824. | RKKIGVNNPHK; |
| 4825. | HKKIGVNNPHK; |
| 4826. | KRKIGVNNPHK; |
| 4827. | RRKIGVNNPHK; |
| 4828. | HRKIGVNNPHK; |
| 4829. | KHRIGVNNPHK; |
| 4830. | RHRIGVNNPHK; |
| 4831. | HHRIGVNNPHK; |
| 4832. | KKRIGVNNPHK; |
| 4833. | RKRIGVNNPHK; |
| 4834. | HKRIGVNNPHK; |
| 4835. | KRRIGVNNPHK; |
| 4836. | RRRIGVNNPHK; |
| 4837. | HRRIGVNNPHK; |
| 4838. | KHHVGVNNPHK; |
| 4839. | RHHVGVNNPHK; |
| 4840. | HHHVGVNNPHK; |
| 4841. | KKHVGVNNPHK; |
| 4842. | RKHVGVNNPHK; |
| 4843. | HKHVGVNNPHK; |
| 4844. | KRHVGVNNPHK; |
| 4845. | RRHVGVNNPHK; |
| 4846. | HRHVGVNNPHK; |

TABLE 7-continued

SEQ ID NO. shown to left of sequence(cont'd)

| | |
|---|---|
| 4847. | KHKVGVNNPHK; |
| 4848. | RHKVGVNNPHK; |
| 4849. | HHKVGVNNPHK; |
| 4850. | KKKVGVNNPHK; |
| 4851. | RKKVGVNNPHK; |
| 4852. | HKKVGVNNPHK; |
| 4853. | KRKVGVNNPHK; |
| 4854. | RRKVGVNNPHK; |
| 4855. | HRKVGVNNPHK; |
| 4856. | KHRVGVNNPHK; |
| 4857. | RHRVGVNNPHK; |
| 4858. | HHRVGVNNPHK; |
| 4859. | KKRVGVNNPHK; |
| 4860. | RKRVGVNNPHK; |
| 4861. | HKRVGVNNPHK; |
| 4862. | KRRVGVNNPHK; |
| 4863. | RRRVGVNNPHK; |
| 4864. | HRRVGVNNPHK; |
| 4865. | KHHLGLEEPRR; |
| 4866. | RHHLGLEEPRR; |
| 4867. | HHHLGLEEPRR; |
| 4868. | KKHLGLEEPRR; |
| 4869. | RKHLGLEEPRR; |
| 4870. | HKHLGLEEPRR; |
| 4871. | KRHLGLEEPRR; |
| 4872. | RRHLGLEEPRR; |
| 4873. | HRHLGLEEPRR; |
| 4874. | KHKLGLEEPRR; |
| 4875. | RHKLGLEEPRR; |
| 4876. | HHKLGLEEPRR; |
| 4877. | KKKLGLEEPRR; |
| 4878. | RKKLGLEEPRR; |
| 4879. | HKKLGLEEPRR; |
| 4880. | KRKLGLEEPRR; |
| 4881. | RRKLGLEEPRR; |
| 4882. | HRKLGLEEPRR; |
| 4883. | KHRLGLEEPRR; |
| 4884. | RHRLGLEEPRR; |
| 4885. | HHRLGLEEPRR; |

TABLE 7-continued

SEQ ID NO. shown to left of sequence(cont'd)

| | |
|---|---|
| 4886. | KKRLGLEEPRR; |
| 4887. | RKRLGLEEPRR; |
| 4888. | HKRLGLEEPRR; |
| 4889. | KRRLGLEEPRR; |
| 4890. | RRRLGLEEPRR; |
| 4891. | HRRLGLEEPRR; |
| 4892. | KHHIGLEEPRR; |
| 4893. | RHHIGLEEPRR; |
| 4894. | HHHIGLEEPRR; |
| 4895. | KKHIGLEEPRR; |
| 4896. | RKHIGLEEPRR; |
| 4897. | HKHIGLEEPRR; |
| 4898. | KRHIGLEEPRR; |
| 4899. | RRHIGLEEPRR; |
| 4900. | HRHIGLEEPRR; |
| 4901. | KHKIGLEEPRR; |
| 4902. | RHKIGLEEPRR; |
| 4903. | HHKIGLEEPRR; |
| 4904. | KKKLGLEEPRR; |
| 4905. | RKKIGLEEPRR; |
| 4906. | HKKLGLEEPRR; |
| 4907. | KRKIGLEEPRR; |
| 4908. | RRKIGLEEPRR; |
| 4909. | HRKIGLEEPRR; |
| 4910. | KHRIGLEEPRR; |
| 4911. | RHRIGLEEPRR; |
| 4912. | HHRIGLEEPRR; |
| 4913. | KKRIGLEEPRR; |
| 4914. | RKRIGLEEPRR; |
| 4915. | HKRIGLEEPRR; |
| 4916. | KRRIGLEEPRR; |
| 4917. | RRRIGLEEPRR; |
| 4918. | HRRIGLEEPRR; |
| 4919. | KHHVGLEEPRR; |
| 4920. | RHHVGLEEPRR; |
| 4921. | HHHVGLEEPRR; |
| 4922. | KKHVGLEEPRR; |
| 4923. | RKHVGLEEPRR; |
| 4924. | HKHVGLEEPRR; |
| 4925. | KRHVGLEEPRR; |
| 4926. | RRHVGLEEPRR; |
| 4927. | HRHVGLEEPRR; |
| 4928. | KHKVGLEEPRR; |
| 4929. | RHKVGLEEPRR; |
| 4930. | HHKVGLEEPRR; |
| 4931. | KKKVGLEEPRR; |
| 4932. | RKKVGLEEPRR; |
| 4933. | HKKVGLEEPRR; |
| 4934. | KRKVGLEEPRR; |
| 4935. | RRKVGLEEPRR; |
| 4936. | HRKVGLEEPRR; |
| 4937. | KHRVGLEEPRR; |
| 4938. | RHRVGLEEPRR; |
| 4939. | HHRVGLEEPRR; |
| 4940. | KKRVGLEEPRR; |
| 4941. | RKRVGLEEPRR; |
| 4942. | HKRVGLEEPRR; |
| 4943. | KRRVGLEEPRR; |
| 4944. | RRRVGLEEPRR; |
| 4945. | HRRVGLEEPRR; |
| 4946. | KHHLGIEEPRR; |
| 4947. | RHHLGIEEPRR; |
| 4948. | HHHLGIEEPRR; |
| 4949. | KKHLGIEEPRR; |
| 4950. | RKHLGIEEPRR; |
| 4951. | HKHLGIEEPRR; |
| 4952. | KRHLGIEEPRR; |
| 4953. | RRHLGIEEPRR; |
| 4954. | HRHLGIEEPRR; |
| 4955. | KHKLGIEEPRR; |
| 4956. | RHKLGIEEPRR; |
| 4957. | HHKLGIEEPRR; |
| 4958. | KKKLGIEEPRR; |
| 4959. | RKKLGIEEPRR; |
| 4960. | HKKLGIEEPRR; |
| 4961. | KRKLGIEEPRR; |
| 4962. | RRKLGIEEPRR; |
| 4963. | HRKLGIEEPRR; |

TABLE 7-continued

SEQ ID NO. shown to left of sequence(cont'd)

| | |
|---|---|
| 4964. | KHRLGIEEPRR; |
| 4965. | RHRLGIEEPRR; |
| 4966. | HHRLGIEEPRR; |
| 4967. | KKRLGIEEPRR; |
| 4968. | RKRLGIEEPRR; |
| 4969. | HKRLGIEEPRR; |
| 4970. | KRRLGIEEPRR; |
| 4971. | RRRLGIEEPRR; |
| 4972. | HRRLGIEEPRR; |
| 4973. | KHHIGIEEPRR; |
| 4974. | RHHIGIEEPRR; |
| 4975. | HHHIGIEEPRR; |
| 4976. | KKHIGIEEPRR; |
| 4977. | RKHIGIEEPRR; |
| 4978. | HKHIGIEEPRR; |
| 4979. | KRHIGIEEPRR; |
| 4980. | RRHIGIEEPRR; |
| 4981. | HRHIGIEEPRR; |
| 4982. | KHKIGIEEPRR; |
| 4983. | RHKIGIEEPRR; |
| 4984. | HHKIGIEEPRR; |
| 4985. | KKKIGIEEPRR; |
| 4986. | RKKIGIEEPRR; |
| 4987. | HKKIGIEEPRR; |
| 4988. | KRKIGIEEPRR; |
| 4989. | RRKIGIEEPRR; |
| 4990. | HRKIGIEEPRR; |
| 4991. | KHRIGIEEPRR; |
| 4992. | RHRIGIEEPRR; |
| 4993. | HHRIGIEEPRR; |
| 4994. | KKRIGIEEPRR; |
| 4995. | RKRIGIEEPRR; |
| 4996. | HKRIGIEEPRR; |
| 4997. | KRRIGIEEPRR; |
| 4998. | RRRIGIEEPRR; |
| 4999. | HRRIGIEEPRR; |
| 5000. | KHHVGIEEPRR; |
| 5001. | RHHVGIEEPRR; |
| 5002. | HHHVGIEEPRR; |
| 5003. | KKHVGIEEPRR; |
| 5004. | RKHVGIEEPRR; |
| 5005. | HKHVGIEEPRR; |
| 5006. | KRHVGIEEPRR; |
| 5007. | RRHVGIEEPRR; |
| 5008. | HRHVGIEEPRR; |
| 5009. | KHKVGIEEPRR; |
| 5010. | RHKVGIEEPRR; |
| 5011. | HHKVGIEEPRR; |
| 5012. | KKKVGIEEPRR; |
| 5013. | RKKVGIEEPRR; |
| 5014. | HKKVGIEEPRR; |
| 5015. | KRKVGIEEPRR; |
| 5016. | RRKVGIEEPRR; |
| 5017. | HRKVGIEEPRR; |
| 5018. | KHRVGIEEPRR; |
| 5019. | RHRVGIEEPRR; |
| 5020. | HHRVGIEEPRR; |
| 5021. | KKRVGIEEPRR; |
| 5022. | RKRVGIEEPRR; |
| 5023. | HKRVGIEEPRR; |
| 5024. | KRRVGIEEPRR; |
| 5025. | RRRVGIEEPRR; |
| 5026. | HRRVGIEEPRR; |
| 5027. | KHHLGVEEPRR; |
| 5028. | RHHLGVEEPRR; |
| 5029. | HHHLGVEEPRR; |
| 5030. | KKHLGVEEPRR; |
| 5031. | RKHLGVEEPRR; |
| 5032. | HKHLGVEEPRR; |
| 5033. | KRHLGVEEPRR; |
| 5034. | RRHLGVEEPRR; |
| 5035. | HRHLGVEEPRR; |
| 5036. | KHKLGVEEPRR; |
| 5037. | RHKLGVEEPRR; |
| 5038. | HHKLGVEEPRR; |
| 5039. | KKKLGVEEPRR; |
| 5040. | RKKLGVEEPRR; |
| 5041. | HKKLGVEEPRR; |

TABLE 7-continued

SEQ ID NO. shown to left of sequence(cont'd)

| SEQ ID NO. | Sequence |
|---|---|
| 5042. | KRKLGVEEPRR; |
| 5043. | RRKLGVEEPRR; |
| 5044. | HRKLGVEEPRR; |
| 5045. | KHRLGVEEPRR; |
| 5046. | RHRLGVEEPRR; |
| 5047. | HHRLGVEEPRR; |
| 5048. | KHRLGVEEPRR; |
| 5049. | RKRLGVEEPRR; |
| 5050. | HKRLGVEEPRR; |
| 5051. | KRRLGVEEPRR; |
| 5052. | RRRLGVEEPRR; |
| 5053. | HRRLGVEEPRR; |
| 5054. | KHHIGVEEPRR; |
| 5055. | RHHIGVEEPRR; |
| 5056. | HHHIGVEEPRR; |
| 5057. | KKHIGVEEPRR; |
| 5058. | RKHIGVEEPRR; |
| 5059. | HKHIGVEEPRR; |
| 5060. | KRHIGVEEPRR; |
| 5061. | RRHIGVEEPRR; |
| 5062. | HRHIGVEEPRR; |
| 5063. | KHKIGVEEPRR; |
| 5064. | RHKIGVEEPRR; |
| 5065. | HHKIGVEEPRR; |
| 5066. | KKKIGVEEPRR; |
| 5067. | RKKIGVEEPRR; |
| 5068. | HKKIGVEEPRR; |
| 5069. | KRKIGVEEPRR; |
| 5070. | RRKIGVEEPRR; |
| 5071. | HRKIGVEEPRR; |
| 5072. | KHRIGVEEPRR; |
| 5073. | RHRIGVEEPRR; |
| 5074. | HHRIGVEEPRR; |
| 5075. | KKRIGVEEPRR; |
| 5076. | RKRIGVEEPRR; |
| 5077. | HKRIGVEEPRR; |
| 5078. | KRRIGVEEPRR; |
| 5079. | RRRIGVEEPRR; |
| 5080. | HRRIGVEEPRR; |

TABLE 7-continued

SEQ ID NO. shown to left of sequence(cont'd)

| SEQ ID NO. | Sequence |
|---|---|
| 5081. | KHHVGVEEPRR; |
| 5082. | RHHVGVEEPRR; |
| 5083. | HHHVGVEEPRR; |
| 5084. | KKHVGVEEPRR; |
| 5085. | RKHVGVEEPRR; |
| 5086. | HKHVGVEEPRR; |
| 5087. | KRHVGVEEPRR; |
| 5088. | RRHVGVEEPRR; |
| 5089. | HRHVGVEEPRR; |
| 5090. | KHKVGVEEPRR; |
| 5091. | RHKVGVEEPRR; |
| 5092. | HHKVGVEEPRR; |
| 5093. | KKKVGVEEPRR; |
| 5094. | RKKVGVEEPRR; |
| 5095. | HKKVGVEEPRR; |
| 5096. | KRKVGVEEPRR; |
| 5097. | RRKVGVEEPRR; |
| 5098. | HRKVGVEEPRR; |
| 5099. | KHRVGVEEPRR; |
| 5100. | RHRVGVEEPRR; |
| 5101. | HHRVGVEEPRR; |
| 5102. | KKRVGVEEPRR; |
| 5103. | RKRVGVEEPRR; |
| 5104. | HKRVGVEEPRR; |
| 5105. | KRRVGVEEPRR; |
| 5106. | RRRVGVEEPRR; |
| 5107. | HRRVGVEEPRR; |
| 5108. | KHHLGLNEPRR; |
| 5109. | RHHLGLNEPRR; |
| 5110. | HHHLGLNEPRR; |
| 5111. | KKHLGLNEPRR; |
| 5112. | RKHLGLNEPRR; |
| 5113. | HKHLGLNEPRR; |
| 5114. | KRHLGLNEPRR; |
| 5115. | RRHLGLNEPRR; |
| 5116. | HRHLGLNEPRR; |
| 5117. | KHKLGLNEPRR; |
| 5118. | RHKLGLNEPRR; |
| 5119. | HHKLGLNEPRR; |

TABLE 7-continued

SEQ ID NO. shown to left of sequence(cont'd)

| | |
|---|---|
| 5120. | KKKLGLNEPRR; |
| 5121. | RKKLGLNEPRR; |
| 5122. | HKKLGLNEPRR; |
| 5123. | KRKLGLNEPRR; |
| 5124. | RRKLGLNEPRR; |
| 5125. | HRKLGLNEPRR; |
| 5126. | KHRLGLNEPRR; |
| 5127. | RHRLGLNEPRR; |
| 5128. | HHRLGLNEPRR; |
| 5129. | KKRLGLNEPRR; |
| 5130. | RKRLGLNEPRR; |
| 5131. | HKRLGLNEPRR; |
| 5132. | KRRLGLNEPRR; |
| 5133. | RRRLGLNEPRR; |
| 5134. | HRRLGLNEPRR; |
| 5135. | KHHIGLNPRR; |
| 5136. | RHHIGLNEPRR; |
| 5137. | HHHIGLNEPRR; |
| 5138. | KKHIGLNEPRR; |
| 5139. | RKHIGLNEPRR; |
| 5140. | HKHIGLNEPRR; |
| 5141. | KRHIGLNEPRR; |
| 5142. | RRHIGLNEPRR; |
| 5143. | HRHIGLNEPRR; |
| 5144. | KHKIGLNEPRR; |
| 5145. | RHKIGLNEPRR; |
| 5146. | HHKLGLNEPRR; |
| 5147. | KKKIGLNEPRR; |
| 5148. | RKKIGLNEPRR; |
| 5149. | HKKIGLNEPRR; |
| 5150. | KRKIGLNEPRR; |
| 5151. | RRKIGLNEPRR; |
| 5152. | HRKIGLNEPRR; |
| 5153. | KHRIGLNEPRR; |
| 5154. | RHRIGLNEPRR; |
| 5155. | HHRIGLNEPRR; |
| 5156. | KKRIGLNEPRR; |
| 5157. | RKRIGLNEPRR; |
| 5158. | HKRIGLNEPRR; |

TABLE 7-continued

SEQ ID NO. shown to left of sequence(cont'd)

| | |
|---|---|
| 5159. | KRRIGLNEPRR; |
| 5160. | RRRIGLNEPRR; |
| 5161. | HRRIGLNEPRR; |
| 5162. | KHHVGLNEPRR; |
| 5163. | RHHVGLNEPRR; |
| 5164. | HHHVGLNEPRR; |
| 5165. | KKHVGLNEPRR; |
| 5166. | RKHVGLNEPRR; |
| 5167. | HKHVGLNEPRR; |
| 5168. | KRHVGLNEPRR; |
| 5169. | RRHVGLNEPRR; |
| 5170. | HRHVGLNEPRR; |
| 5171. | KHKVGLNEPRR; |
| 5172. | RHKVGLNEPRR; |
| 5173. | HHKVGLNEPRR; |
| 5174. | KKKVGLNEPRR; |
| 5175. | RKKVGLNEPRR; |
| 5176. | HKKVGLNEPRR; |
| 5177. | KRKVGLNEPRR; |
| 5178. | RRKVGLNEPRR; |
| 5179. | HRKVGLNEPRR; |
| 5180. | KHRVGLNEPRR; |
| 5181. | RHRVGLNEPRR; |
| 5182. | HHRVGLNEPRR; |
| 5183. | KKRVGLNEPRR; |
| 5184. | RKRVGLNEPRR; |
| 5185. | HKRVGLNEPRR; |
| 5186. | KRRVGLNEPRR; |
| 5187. | RRRVGLNEPRR; |
| 5188. | HRRVGLNEPRR; |
| 5189. | KHHLGINEPRR; |
| 5190. | RHHLGINEPRR; |
| 5191. | HHHLGINEPRR; |
| 5192. | KKHLGINEPRR; |
| 5193. | RKHLGINEPRR; |
| 5194. | HKHLGINEPRR; |
| 5195. | KRHLGINEPRR; |
| 5196. | RRHLGINEPRR; |
| 5197. | HRHLGINEPRR; |

TABLE 7-continued

| SEQ ID NO. shown to left of sequence(cont'd) | |
|---|---|
| 5198. | KHKLGINEPRR; |
| 5199. | RHKLGINEPRR; |
| 5200. | HHKLGINEPRR; |
| 5201. | KKKLGINEPRR; |
| 5202. | RKKLGINEPRR; |
| 5203. | HKKLGINEPRR; |
| 5204. | KRKLGINEPRR; |
| 5205. | RRKLGINEPRR; |
| 5206. | HRKLGINEPRR; |
| 5207. | KHRLGINEPRR; |
| 5208. | RHRLGINEPRR; |
| 5209. | HHRLGINEPRR; |
| 5210. | KKRLGINEPRR; |
| 5211. | RKRLGINEPRR; |
| 5212. | HKRLGINEPRR; |
| 5213. | KRRLGINEPRR; |
| 5214. | RRRLGINEPRR; |
| 5215. | HRRLGINEPRR; |
| 5216. | KHHIGIENPRR; |
| 5217. | RHHIGINEPRR; |
| 5218. | HHHIGINEPRR; |
| 5219. | KKHIGINEPRR; |
| 5220. | RKHIGINEPRR; |
| 5221. | HKHIGINEPRR; |
| 5222. | KRHIGINEPRR; |
| 5223. | RRHIGINEPRR; |
| 5224. | HRHIGINEPRR; |
| 5225. | KHKIGINEPRR; |
| 5226. | RHKIGINEPRR; |
| 5227. | HHKIGINEPRR; |
| 5228. | KKKIGINEPRR; |
| 5229. | RKKIGINEPRR; |
| 5230. | HKKIGINEPRR; |
| 5231. | KRKIGINEPRR; |
| 5232. | RRKIGINEPRR; |
| 5233. | HRKIGINEPRR; |
| 5234. | KHRIGINEPRR; |
| 5235. | RHRIGINEPRR; |
| 5236. | HHRIGINEPRR; |
| 5237. | KKHIGINEPRR; |
| 5238. | RKRIGINEPRR; |
| 5239. | HKRIGINEPRR; |
| 5240. | KRRIGINEPRR; |
| 5241. | RRRIGINEPRR; |
| 5242. | HRRIGINEPRR; |
| 5243. | KHHVGINEPRR; |
| 5244. | RHHVGINEPRR; |
| 5245. | HHHVGINEPRR; |
| 5246. | KKHVGINEPRR; |
| 5247. | RKHVGINEPRR; |
| 5248. | HKHVGVNEPRR; |
| 5249. | KRHVGINEPRR; |
| 5250. | RRHVGINEPRR; |
| 5251. | HRHVGINEPRR; |
| 5252. | KHKVGVNEPRR; |
| 5253. | RHKVGINEPRR; |
| 5254. | HHKVGINEPRR; |
| 5255. | KKKVGINEPRR; |
| 5256. | RKKVGINEPRR; |
| 5257. | HKKVGINEPRR; |
| 5258. | KRKVGINEPRR; |
| 5259. | RRKVGINEPRR; |
| 5260. | HRKVGINEPRR; |
| 5261. | KHRVGINEPRR; |
| 5262. | RHRVGINEPRR; |
| 5263. | HHRVGINEPRR; |
| 5264. | KKRVGINEPRR; |
| 5265. | RKRVGINEPRR; |
| 5266. | HKRVGINEPRR; |
| 5267. | KRRVGINEPRR; |
| 5268. | RRRVGINEPRR; |
| 5269. | HRRVGINEPRR; |
| 5270. | KHHLGVNEPRR; |
| 5271. | RHHLGVNEPRR; |
| 5272. | HHHLGVNEPRR; |
| 5273. | KHHLGVNEPRR; |
| 5274. | RKHLGVNEPRR; |
| 5275. | HKHLGVNEPRR; |

TABLE 7-continued

SEQ ID NO. shown to left of sequence(cont'd)

| | |
|---|---|
| 5276. | KRHLGVNEPRR; |
| 5277. | RRHLGVNEPRR; |
| 5278. | HRHLGVNEPRR; |
| 5279. | KHKLGVNEPRR; |
| 5280. | RHKLGVNEPRR; |
| 5281. | HHKLGVNEPRR; |
| 5282. | KKKLGVNEPRR; |
| 5283. | RKKLGVNEPRR; |
| 5284. | HKKLGVNEPRR; |
| 5285. | KRKLGVNEPRR; |
| 5286. | RRKLGVNEPRR; |
| 5287. | HRKLGVNEPRR; |
| 5288. | KHRLGVNEPRR; |
| 5289. | RHRLGVNEPRR; |
| 5290. | HHRLGVNEPRR; |
| 5291. | KKRLGVNEPRR; |
| 5292. | RKRLGVNEPRR; |
| 5293. | HKRLGVNEPRR; |
| 5294. | KRRLGVNEPRR; |
| 5295. | RRRLGVNEPRR; |
| 5296. | HRRLGVNEPRR; |
| 5297. | KHHIGVNEPRR; |
| 5298. | RHHIGVNEPRR; |
| 5299. | HHHIGVNEPRR; |
| 5300. | KKHIGVNEPRR; |
| 5301. | RKHIGVNEPRR; |
| 5302. | HKHIGVNEPRR; |
| 5303. | KRHIGVNEPRR; |
| 5304. | RRHIGVNEPRR; |
| 5305. | HRHIGVNEPRR; |
| 5306. | KHKIGVNEPRR; |
| 5307. | RHKIGVNEPRR; |
| 5308. | HHKIGVNEPRR; |
| 5309. | KKKIGVNEPRR; |
| 5310. | RKKIGVNEPRR; |
| 5311. | HKKIGVNEPRR; |
| 5312. | KRKIGVNEPRR; |
| 5313. | RRKIGVNEPRR; |
| 5314. | HRKIGVNEPRR; |
| 5315. | KHRIGVNEPRR; |
| 5316. | RHRIGVNEPRR; |
| 5317. | HHRIGVNEPRR; |
| 5318. | KKRIGVNEPRR; |
| 5319. | RKRIGVNEPRR; |
| 5320. | HKRIGVNEPRR; |
| 5321. | KRRIGVNEPRR; |
| 5322. | RRRIGVNEPRR; |
| 5323. | HRRIGVNEPRR; |
| 5324. | KHHVGVNEPRR; |
| 5325. | RHHVGVNEPRR; |
| 5326. | HHHVGVNEPRR; |
| 5327. | KKHVGVNEPRR; |
| 5328. | RKHVGVNEPRR; |
| 5329. | HKHVGVNEPRR; |
| 5330. | KRHVGVNEPRR; |
| 5331. | RRHVGVNEPRR; |
| 5332. | HRHVGVNEPRR; |
| 5333. | KHKVGVNEPRR; |
| 5334. | RHKVGVNEPRR; |
| 5335. | HHKVGVNEPRR; |
| 5336. | KKKVGVNEPRR; |
| 5337. | RKKVGVNEPRR; |
| 5338. | HKKVGVNEPRR; |
| 5339. | KRKVGVNEPRR; |
| 5340. | RRKVGVNEPRR; |
| 5341. | HRKVGVNEPRR; |
| 5342. | KHRVGVNEPRR; |
| 5343. | RHRVGVNEPRR; |
| 5344. | HHRVGVNEPRR; |
| 5345. | KKRVGVNEPRR; |
| 5346. | RKRVGVNEPRR; |
| 5347. | HKRVGVNEPRR; |
| 5348. | KRRVGVNEPRR; |
| 5349. | RRRVGVNEPRR; |
| 5350. | HRRVGVNEPRR; |
| 5351. | KHHLGLENPRR; |
| 5352. | RHHLGLENPRR; |
| 5353. | HHHLGLENPRR; |

TABLE 7-continued

SEQ ID NO. shown to left of sequence(cont'd)

| SEQ ID | Sequence |
|---|---|
| 5354. | KKHLGLENPRR; |
| 5355. | RKHLGLENPRR; |
| 5356. | HKHLGLENPRR; |
| 5357. | KRHLGLENPRR; |
| 5358. | RRHLGLENPRR; |
| 5359. | HRHLGLENPRR; |
| 5360. | KHKLGLENPRR; |
| 5361. | RHKLGLENPRR; |
| 5362. | HHKLGLENPRR; |
| 5363. | KKKLGLENPRR; |
| 5364. | RKKLGLENPRR; |
| 5365. | HKKLGLENPRR; |
| 5366. | KRKLGLENPRR; |
| 5367. | RRKLGLENPRR; |
| 5368. | HRKLGLENPRR; |
| 5369. | KHRLGLENPRR; |
| 5370. | RHRLGLENPRR; |
| 5371. | HHRLGLENPRR; |
| 5372. | KKRLGLENPRR; |
| 5373. | RKRLGLENPRR; |
| 5374. | HKRLGLENPRR; |
| 5375. | KRRLGLENPRR; |
| 5376. | RRRLGLENPRR; |
| 5377. | HRRLGLENPRR; |
| 5378. | KHHIGLENPRR; |
| 5379. | RHHIGLENPRR; |
| 5380. | HHHIGLENPRR; |
| 5381. | KKHIGLENPRR; |
| 5382. | RKHIGLENPRR; |
| 5383. | HKHIGLENPRR; |
| 5384. | KRHIGLENPRR; |
| 5385. | RRHIGLENPRR; |
| 5386. | HRHIGLENPRR; |
| 5387. | KHKIGLENPRR; |
| 5388. | RHKIGLENPRR; |
| 5389. | HHKIGLENPRR; |
| 5390. | KKKIGLENPRR; |
| 5391. | RKKIGLENPRR; |
| 5392. | HKKIGLENPRR; |
| 5393. | KRKIGLENPRR; |
| 5394. | RRHIGLENPRR; |
| 5395. | HRKIGLENPRR; |
| 5396. | KKRIGLENPRR; |
| 5397. | RHRIGLENPRR; |
| 5398. | HHRIGLENPRR; |
| 5399. | KKRIGLENPRR; |
| 5400. | RKRIGLENPRR; |
| 5401. | HKRIGLENPRR; |
| 5402. | KRRIGLENPRR; |
| 5403. | RRRIGLENPRR; |
| 5404. | HRRIGLENPRR; |
| 5405. | KHHVGLENPRR; |
| 5406. | RHHVGLENPRR; |
| 5407. | HHHVGLENPRR; |
| 5408. | KKHVGLENPRR; |
| 5409. | RKHVGLENPRR; |
| 5410. | HKHVGLENPRR; |
| 5411. | KRHVGLENPRR; |
| 5412. | RRHVGLENPRR; |
| 5413. | HRHVGLENPRR; |
| 5414. | KHKVGLENPRR; |
| 5415. | RHKVGLENPRR; |
| 5416. | HHKVGLENPRR; |
| 5417. | KKKVGLENPRR; |
| 5418. | RKKVGLENPRR; |
| 5419. | HKKVGLENPRR; |
| 5420. | KRKVGLENPRR; |
| 5421. | RRKVGLENPRR; |
| 5422. | HRKVGLENPRR; |
| 5423. | KHRVGLENPRR; |
| 5424. | RHRVGLENPRR; |
| 5425. | HHRVGLENPRR; |
| 5426. | KKRVGLENPRR; |
| 5427. | RKRVGLENPRR; |
| 5428. | HKRVGLENPRR; |
| 5429. | KRRVGLENPRR; |
| 5430. | RRRVGLENPRR; |
| 5431. | HRRVGLENPRR; |

TABLE 7-continued

| SEQ ID NO. shown to left of sequence(cont'd) | |
|---|---|
| 5432. | KHHLGIENPRR; |
| 5433. | RHHLGIENPRR; |
| 5434. | HHHLGIENPRR; |
| 5435. | KKHLGIENPRR; |
| 5436. | RKHLGIENPRR; |
| 5437. | HKHLGIENPRR; |
| 5438. | KRHLGIENPRR; |
| 5439. | RRHLGIENPRR; |
| 5440. | HRHLGIENPRR; |
| 5441. | KHKLGIENPRR; |
| 5442. | RHKLGIENPRR; |
| 5443. | HHKLGIENPRR; |
| 5444. | KKKLGIENPRR; |
| 5445. | RKKLGIENPRR; |
| 5446. | HKKLGIENPRR; |
| 5447. | KRKLGIENPRR; |
| 5448. | RRKLGIENPRR; |
| 5449. | HRKLGIENPRR; |
| 5450. | KHRLGIENPRR; |
| 5451. | RHRLGIENPRR; |
| 5452. | HHRLGIENPRR; |
| 5453. | KKRLGIENPRR; |
| 5454. | RKRLGIENPRR; |
| 5455. | HKRLGIENPRR; |
| 5456. | KRRLGIENPRR; |
| 5457. | RRRLGIENPRR; |
| 5458. | HRRLGIENPRR; |
| 5459. | KHHIGIENPRR; |
| 5460. | RHHIGIENPRR; |
| 5461. | HHHIGIENPRR; |
| 5462. | KKHIGIENPRR; |
| 5463. | RKHIGIENPRR; |
| 5464. | HKHIGIENPRR; |
| 5465. | KRHIGIENPRR; |
| 5466. | RRHIGIENPRR; |
| 5467. | HRHIGIENPRR; |
| 5468. | KHKIGIENPRR; |
| 5469. | RHKIGIENPRR; |
| 5470. | HHKIGIENPRR; |

TABLE 7-continued

| SEQ ID NO. shown to left of sequence(cont'd) | |
|---|---|
| 5471. | KKKIGIENPRR; |
| 5472. | RKKIGIENPRR; |
| 5473. | HKKIGIENPRR; |
| 5474. | KRKIGIENPRR; |
| 5475. | RRKIGIENPRR; |
| 5476. | HRKIGIENPRR; |
| 5477. | KHRIGIENPRR; |
| 5478. | RHRIGIENPRR; |
| 5479. | HHRIGIENPRR; |
| 5480. | KKRIGIENPRR; |
| 5481. | RKRIGIENPRR; |
| 5482. | HKRIGIENPRR; |
| 5483. | KRRIGIENPRR; |
| 5484. | RRRIGIENPRR; |
| 5485. | HRRIGIENPRR; |
| 5486. | KHHVGIENPRR; |
| 5487. | RHHVGIENPRR; |
| 5488. | HHKVGIENPRR; |
| 5489. | KRHVGIENPRR; |
| 5490. | RKHVGIENPRR; |
| 5491. | HKHVGIENPRR; |
| 5492. | KRHVGIENPRR; |
| 5493. | RRHVGIENPRR; |
| 5494. | HRHVGIENPRR; |
| 5495. | KHKVGIENPRR; |
| 5496. | RHKVGIENPRR; |
| 5497. | HHKVGIENPRR; |
| 5498. | KKKVGIENPRR; |
| 5499. | RKKVGIENPRR; |
| 5500. | HKKVGIENPRR; |
| 5501. | KRKVGIENPRR; |
| 5502. | RRKVGIENPRR; |
| 5503. | HRKVGIENPRR; |
| 5504. | KHRVGIENPRR; |
| 5505. | RHRVGIENPRR; |
| 5506. | HHRVGIENPRR; |
| 5507. | KKRVGIENPRR; |
| 5508. | RKRVGIENPRR; |
| 5509. | HKRVGIENPRR; |

TABLE 7-continued

SEQ ID NO. shown to left of sequence (cont'd)

| SEQ ID NO. | Sequence |
|---|---|
| 5510. | KRRVGIENPRR; |
| 5511. | RRRVGIENPRR; |
| 5512. | HRRVGIENPRR; |
| 5513. | KHHLGVENPRR; |
| 5514. | RHHLGVENPRR; |
| 5515. | HHHLGVENPRR; |
| 5516. | KKHLGVENPRR; |
| 5517. | RKHLGVENPRR; |
| 5518. | HKHLGVENPRR; |
| 5519. | KRHLGVENPRR; |
| 5520. | RRHLGVENPRR; |
| 5521. | HRHLGVENPRR; |
| 5522. | KHKLGVENPRR; |
| 5523. | RHKLGVENPRR; |
| 5524. | HHKLGVENPRR; |
| 5525. | KKKLGVENPRR; |
| 5526. | RKKLGVENPRR; |
| 5527. | HKKLGVENPRR; |
| 5528. | KRKLGVENPRR; |
| 5529. | RRKLGVENPRR; |
| 5530. | HRKLGVENPRR; |
| 5531. | KHRLGVENPRR; |
| 5532. | RHRLGVENPRR; |
| 5533. | HHRLGVENPRR; |
| 5534. | KKRLGVENPRR; |
| 5535. | RKRLGVENPRR; |
| 5536. | HKRLGVENPRR; |
| 5537. | KRRLGVENPRR; |
| 5538. | RRRLGVENPRR; |
| 5539. | HRRLGVENPRR; |
| 5540. | KHHIGVENPRR; |
| 5541. | RHHIGVEEPRR; |
| 5542. | HHHIGVENPRR; |
| 5543. | KKHIGVENPRR; |
| 5544. | RKHIGVENPRR; |
| 5545. | HKHIGVENPRR; |
| 5546. | KRHIGVENPRR; |
| 5547. | RRHIGVENPRR; |
| 5548. | HRHIGVENPRR; |
| 5549. | KHKIGVENPRR; |
| 5550. | RHKIGVENPRR; |
| 5551. | HHKIGVENPRR; |
| 5552. | KKKIGVENPRR; |
| 5553. | RKKIGVENPRR; |
| 5554. | HKKIGVENPRR; |
| 5555. | KRKIGVENPRR; |
| 5556. | RRKIGVENPRR; |
| 5557. | HRKIGVENPRR; |
| 5558. | KHRIGVENPRR; |
| 5559. | RHRIGVENPRR; |
| 5560. | HHRIGVENPRR; |
| 5561. | KKRIGVENPRR; |
| 5562. | RKRIGVENPRR; |
| 5563. | HKRIGVENPRR; |
| 5564. | KRRIGVENPRR; |
| 5565. | RRRIGVENPRR; |
| 5566. | HRRIGVENPRR; |
| 5567. | KHHVGVENPRR; |
| 5568. | RHHVGVENPRR; |
| 5569. | HHHVGVENPRR; |
| 5570. | KKHVGVENPRR; |
| 5571. | RKHVGVENPRR; |
| 5572. | HKHVGVENPRR; |
| 5573. | KRHVGVENPRR; |
| 5574. | RRHVGVENPRR; |
| 5575. | HRHVGVENPRR; |
| 5576. | KHKVGVENPRR; |
| 5577. | RHKVGVENPRR; |
| 5578. | HHKVGVENPRR; |
| 5579. | KKKVGVENPRR; |
| 5580. | RKKVGVENPRR; |
| 5581. | HKKVGVENPRR; |
| 5582. | KRKVGVENPRR; |
| 5583. | RRKVGVEEPRR; |
| 5584. | HRKVGVENPRR; |
| 5585. | KHRVGVENPRR; |
| 5586. | RHRVGVENPRR; |
| 5587. | HHRVGVENPRR; |

TABLE 7-continued

| SEQ ID NO. shown to left of sequence(cont'd) | |
|---|---|
| 5588. | KKRVGVENPRR; |
| 5589. | RKRVGVENPRR; |
| 5590. | HKRVGVENPRR; |
| 5591. | KRRVGVENPRR; |
| 5592. | RRRVGVENPRR; |
| 5593. | HRRVGVENPRR; |
| 5594. | KHHLGLNNPRR; |
| 5595. | RHHLGLNNPRR; |
| 5596. | HHHLGLNNPRR; |
| 5597. | KKHLGLNNPRR; |
| 5598. | RKHLGLNNPRR; |
| 5599. | HKHLGLNNPRR; |
| 5600. | KRHLGLNNPRR; |
| 5601. | RRHLGLNNPRR; |
| 5602. | HRHLGLNNPRR; |
| 5603. | KHKLGLNNPRR; |
| 5604. | RHKLGLNNPRR; |
| 5605. | HHKLGLNNPRR; |
| 5606. | KKKLGLNNPRR; |
| 5607. | RKKLGLNNPRR; |
| 5608. | HKKLGLNNPRR; |
| 5609. | KRKLGLNNPRR; |
| 5610. | RRKLGLNNPRR; |
| 5611. | HRKLGLNNPRR; |
| 5612. | KHRLGLNNPRR; |
| 5613. | RHRLGLNNPRR; |
| 5614. | HHRLGLNNPRR; |
| 5615. | KKRLGLNNPRR; |
| 5616. | RKRLGLNNPRR; |
| 5617. | HKRLGLNNPRR; |
| 5618. | KRRLGLNNPRR; |
| 5619. | RRRLGLNNPRR; |
| 5620. | HRRLGLNNPRR; |
| 5621. | KHHIGLNNPRR; |
| 5622. | RHHIGLNNPRR; |
| 5623. | HHHIGLNNPRR; |
| 5624. | KKHIGLNNPRR; |
| 5625. | RKHIGLNNPRR; |
| 5626. | HKHIGLNNPRR; |
| 5627. | KRHIGLNNPRR; |
| 5628. | RRHIGLNNPRR; |
| 5629. | HRHIGLNNPRR; |
| 5630. | KHKIGLNNPRR; |
| 5631. | RHKIGLNNPRR; |
| 5632. | HHKIGLNNPRR; |
| 5633. | KKKIGLNNPRR; |
| 5634. | RKKIGLNNPRR; |
| 5635. | HKKIGLNNPRR; |
| 5636. | KRKIGLNNPRR; |
| 5637. | RRKIGLNNPRR; |
| 5638. | HRKIGLNNPRR; |
| 5639. | KHRIGLNNPRR; |
| 5640. | RHRIGLNNPRR; |
| 5641. | HHRIGLNNPRR; |
| 5642. | KKRIGLNNPRR; |
| 5643. | RKRIGLNNPRR; |
| 5644. | HKRIGLNNPRR; |
| 5645. | KRRIGLNNPRR; |
| 5646. | RRRIGLNNPRR; |
| 5647. | HRRIGLNNPRR; |
| 5648. | KHHVGLNNPRR; |
| 5649. | RHHVGLNNPRR; |
| 5650. | HHHVGLNNPRR; |
| 5651. | KKHVGLNNPRR; |
| 5652. | RKHVGLNNPRR; |
| 5653. | HKHVGLNNPRR; |
| 5654. | KRHVGLNNPRR; |
| 5655. | RRHVGLNNPRR; |
| 5656. | HRHVGLNNPRR; |
| 5657. | KHKVGLNNPRR; |
| 5658. | RHKVGLNNPRR; |
| 5659. | HHKVGLNNPRR; |
| 5660. | KKKVGLNNPRR; |
| 5661. | RKKVGLNNPRR; |
| 5662. | HKKVGLNNPRR; |
| 5663. | KRKVGLNNPRR; |
| 5664. | RRKVGLNNPRR; |
| 5665. | HRKVGLNNPRR; |

TABLE 7-continued

| SEQ ID NO. shown to left of sequence(cont'd) | |
|---|---|
| 5666. | KHRVGLNNPRR; |
| 5667. | RHRVGLNNPRR; |
| 5668. | HHRVGLNNPRR; |
| 5669. | KKRVGLNNPRR; |
| 5670. | RKRVGLNNPRR; |
| 5671. | HKRVGLNNPRR; |
| 5672. | KRRVGLNNPRR; |
| 5673. | RRRVGLNNPRR; |
| 5674. | HRRVGLNNPRR; |
| 5675. | KHHLGINNPRR; |
| 5676. | RHHLGINNPRR; |
| 5677. | HHHLGINNPRR; |
| 5678. | KKHLGINNPRR; |
| 5679. | RKHLGINNPRR; |
| 5680. | HKHLGINNPRR; |
| 5681. | KRHLGINNPRR; |
| 5682. | RRHLGINNPRR; |
| 5683. | HRHLGINNPRR; |
| 5684. | KHKLGINNPRR; |
| 5685. | RHKLGINNPRR; |
| 5686. | HHKLGINNPRR; |
| 5687. | KKKLGINNPRR; |
| 5688. | RKKLGLNNPRR; |
| 5689. | HKKLGINNPRR; |
| 5690. | KRKLGINNPRR; |
| 5691. | RRKLGINNPRR; |
| 5692. | HRKLGINNPRR; |
| 5693. | KHRLGVNNPRR; |
| 5694. | RHRLGINNPRR; |
| 5695. | HHRLGINNPRR; |
| 5696. | KKRLGINNPRR; |
| 5697. | RKRLGINNPRR; |
| 5698. | HKRLGINNPRR; |
| 5699. | KRRLGINNPRR; |
| 5700. | RRRLGINNPRR; |
| 5701. | HRRLGINNPRR; |
| 5702. | KHHIGIENPRR; |
| 5703. | RHHIGINNPRR; |
| 5704. | HHHIGINNPRR; |
| 5705. | KKHIGINNPRR; |
| 5706. | RKHIGINNPRR; |
| 5707. | HKHIGINNPRR; |
| 5708. | KRHIGINNPRR; |
| 5709. | RRHIGINNPRR; |
| 5710. | HRHIGINNPRR; |
| 5711. | KHKIGINNPRR; |
| 5712. | RHKIGINNPRR; |
| 5713. | HHKIGINNPRR; |
| 5714. | KKKIGINNPRR; |
| 5715. | RKKIGINNPRR; |
| 5716. | HKKIGINNPRR; |
| 5717. | KRKIGINNPRR; |
| 5718. | RRKIGINNPRR; |
| 5719. | HRKIGINNPRR; |
| 5720. | KHRIGINNPRR; |
| 5721. | RHRIGINNPRR; |
| 5722. | HHRIGINNPRR; |
| 5723. | KKRIGINNPRR; |
| 5724. | RKRIGINNPRR; |
| 5725. | HKRIGINNPRR; |
| 5726. | KRRIGINNPRR; |
| 5727. | RRRIGINNPRR; |
| 5728. | HRRIGINNPRR; |
| 5729. | KHHVGINNPRR; |
| 5730. | RHHVGINNPRR; |
| 5731. | HHHVGINNPRR; |
| 5732. | KKHVGINNPRR; |
| 5733. | RKHVGINNPRR; |
| 5734. | HKHVGINNPRR; |
| 5735. | KRHVGINNPRR; |
| 5736. | RRHVGINNPRR; |
| 5737. | HRHVGINNPRR; |
| 5738. | KHKVGINNPRR; |
| 5739. | RHHVGINNPRR; |
| 5740. | HHKVGINNPRR; |
| 5741. | KKKVGLNNPRR; |
| 5742. | RKKVGINNPRR; |
| 5743. | HKKVGINNPRR; |

TABLE 7-continued

SEQ ID NO. shown to left of sequence(cont'd)

| SEQ ID NO. | Sequence |
|---|---|
| 5744. | KRKVGINNPRR; |
| 5745. | RRKVGINNPRR; |
| 5746. | HRKVGINNPRR; |
| 5747. | KHRVGINNPRR; |
| 5748. | RHRVGINNPRR; |
| 5749. | HHRVGINNPRR; |
| 5750. | KKRVGINNPRR; |
| 5751. | RKRVGINNPRR; |
| 5752. | HKRVGINNPRR; |
| 5753. | KRRVGINNPRR; |
| 5754. | RRRVGINNPRR; |
| 5755. | HRRVGINNPRR; |
| 5756. | KHHLGVNNPRR; |
| 5757. | RHHLGVNNPRR; |
| 5758. | HHHLGVNNPRR; |
| 5759. | KKHLGVNNPRR; |
| 5760. | RKHLGVNNPRR; |
| 5761. | HKHLGVNNPRR; |
| 5762. | KRHLGVNNPRR; |
| 5763. | RRHLGVNNPRR; |
| 5764. | HRHLGVNNPRR; |
| 5765. | KHKLGVNNPRR; |
| 5766. | RHKLGVNNPRR; |
| 5767. | HHKLGVNNPRR; |
| 5768. | KKKLGVNNPRR; |
| 5769. | RKKLGVNNPRR; |
| 5770. | HKKLGVNNPRR; |
| 5771. | KRKLGVNNPRR; |
| 5772. | RRKLGVNNPRR; |
| 5773. | HRKLGVNNPRR; |
| 5774. | KHRLGVNNPRR; |
| 5775. | RHRLGVNNPRR; |
| 5776. | HHRLGVNNPRR; |
| 5777. | KKRLGVNNPRR; |
| 5778. | RKRLGVNNPRR; |
| 5779. | HKRLGVNNPRR; |
| 5780. | KRRLGVNNPRR; |
| 5781. | RRRLGVNNPRR; |
| 5782. | HRRLGVNNPRR; |

TABLE 7-continued

SEQ ID NO. shown to left of sequence(cont'd)

| SEQ ID NO. | Sequence |
|---|---|
| 5783. | KHHIGVNNPRR; |
| 5784. | RHHIGVNNPRR; |
| 5785. | HHHIGVNNPRR; |
| 5786. | KKHIGVNNPRR; |
| 5787. | RKHIGVNNPRR; |
| 5788. | HKHIGVNNPRR; |
| 5789. | KRHIGVNNPRR; |
| 5790. | RRHIGVNNPRR; |
| 5791. | HRHIGVNNPRR; |
| 5792. | KHKIGVNNPRR; |
| 5793. | RHKIGVNNPRR; |
| 5794. | HHKIGVNNPRR; |
| 5795. | KKKIGVNNPRR; |
| 5796. | RKHIGVNNPRR; |
| 5797. | HKKIGVNNPRR; |
| 5798. | KRKIGVNNPRR; |
| 5799. | RRKIGVNNPRR; |
| 5800. | HRKIGVNNPRR; |
| 5801. | KHRIGVNNPRR; |
| 5802. | RHRIGVNNPRR; |
| 5803. | HHRIGVNNPRR; |
| 5804. | KKRIGVNNPRR; |
| 5805. | RKRIGVNNPRR; |
| 5806. | HKRIGVNNPRR; |
| 5807. | KRRIGVNNPRR; |
| 5808. | RRRIGVNNPRR; |
| 5809. | HRRLGVNNPRR; |
| 5810. | KHHVGVNNPRR; |
| 5811. | RHHVGVNNPRR; |
| 5812. | HHHVGVNNPRR; |
| 5813. | KKHVGVNNPRR; |
| 5814. | RKHVGVNNPRR; |
| 5815. | HKHVGVNNPRR; |
| 5816. | KRHVGVNNPRR; |
| 5817. | RRHVGVNNPRR; |
| 5818. | HRHVGVNNPRR; |
| 5819. | KHKVGVNNPRR; |
| 5820. | RHKVGVNNPRR; |
| 5821. | HHKVGVNNPRR; |

TABLE 7-continued

SEQ ID NO. shown to left of sequence(cont'd)

| | |
|---|---|
| 5822. | KKKVGVNNPRR; |
| 5823. | RKKVGVNNPRR; |
| 5824. | HKKVGVNNPRR; |
| 5825. | KRKVGVNNPRR; |
| 5826. | RRKVGVNNPRR; |
| 5827. | HRKVGVNNPRR; |
| 5828. | KHRVGVNNPRR; |
| 5829. | RHRVGVNNPRR; |
| 5830. | HHRVGVNNPRR; |
| 5831. | KKRVGVNNPRR; |
| 5832. | RKRVGVNNPRR; |
| 5833. | HKRVGVNNPRR; |
| 5834. | KRRVGVNNPRR; |
| 5835. | RRRVGVNNPRR; |
| 5836. | HRRVGVNNPRR; |
| 5837. | KHHLGLEEPRH; |
| 5838. | RHHLGLEEPRH; |
| 5839. | HHHLGLEEPRH; |
| 5840. | KKHLGLEEPRH; |
| 5841. | RKHLGLEEPRH; |
| 5842. | HKHLGLEEPRH; |
| 5843. | KRHLGLEEPRH; |
| 5844. | RRHLGLEEPRH; |
| 5845. | HRHLGLEEPRH; |
| 5846. | KHKLGLEEPRH; |
| 5847. | RHKLGLEEPRH; |
| 5848. | HHKLGLEEPRH; |
| 5849. | KKKLGLEEPRH; |
| 5850. | RKKLGLEEPRH; |
| 5851. | HKKLGLEEPRH; |
| 5852. | KRKLGLEEPRH; |
| 5853. | RRKLGLEEPRH; |
| 5854. | HRKLGLEEPRH; |
| 5855. | KHRLGLEEPRH; |
| 5856. | RHRLGLEEPRH; |
| 5857. | HHRLGLEEPRH; |
| 5858. | KKRLGLEEPRH; |
| 5859. | RKRLGLEEPRH; |
| 5860. | HKRLGLEEPRH; |

TABLE 7-continued

SEQ ID NO. shown to left of sequence(cont'd)

| | |
|---|---|
| 5861. | KRRLGLEEPRH; |
| 5862. | RRRLGLEEPRH; |
| 5863. | HRRLGLEEPRH; |
| 5864. | KHHIGLEEPRH; |
| 5865. | RHHIGLEEPRH; |
| 5866. | HHHIGLEEPRH; |
| 5867. | KKHIGLEEPRH; |
| 5868. | RKHIGLEEPRH; |
| 5869. | HKHIGLEEPRH; |
| 5870. | KRHIGLEEPRH; |
| 5871. | RRHIGLEEPRH; |
| 5872. | HRHIGLEEPRH; |
| 5873. | KHKIGLEEPRH; |
| 5874. | RHKIGLEEPRH; |
| 5875. | HHKIGLEEPRH; |
| 5876. | KKKIGLEEPRH; |
| 5877. | RKKIGLEEPRH; |
| 5878. | HKKIGLEEPRH; |
| 5879. | KRKIGLEEPRH; |
| 5880. | RRKIGLEEPRH; |
| 5881. | HRKIGLEEPRH; |
| 5882. | KHRIGLEEPRH; |
| 5583. | RHRIGLEEPRH; |
| 5884. | HHRIGLEEPRH; |
| 5885. | KKRIGLEEPRH; |
| 5886. | RKRIGLEEPRH; |
| 5887. | HKRIGLEEPRH; |
| 5888. | KRRIGLEEPRH; |
| 5889. | RRRIGLEEPRH; |
| 5890. | HRRIGLEEPRH; |
| 5891. | KHHVGLEEPRH; |
| 5892. | RHHVGLEEPRH; |
| 5893. | HHHVGLEEPRH; |
| 5894. | KKHVGLEEPRH; |
| 5895. | RKHVGLEEPRH; |
| 5896. | HKHVGLEEPRH; |
| 5897. | KRHVGLEEPRH; |
| 5898. | RRHVGLEEPRH; |
| 5899. | HRHVGLEEPRH; |

TABLE 7-continued

SEQ ID NO. shown to left of sequence(cont'd)

| SEQ ID NO. | Sequence |
|---|---|
| 5900. | KHKVGLEEPRH; |
| 5901. | RHKVGLEEPRH; |
| 5902. | HHKVGLEEPRH; |
| 5903. | KKKVGLEEPRH; |
| 5904. | RKKVGLEEPRH; |
| 5905. | HKKVGLEEPRH; |
| 5906. | KRKVGLEEPRH; |
| 5907. | RRKVGLEEPRH; |
| 5908. | HRKVGLEEPRH; |
| 5909. | KHRVGLEEPRH; |
| 5910. | RHRVGLEEPRH; |
| 5911. | HHRVGLEEPRH; |
| 5912. | KKRVGLEEPRH; |
| 5913. | RKRVGLEEPRH; |
| 5914. | HKRVGLEEPRH; |
| 5915. | KRRVGLEEPRH; |
| 5916. | RRRVGLEEPRH; |
| 5917. | HRRVGLEEPRH; |
| 5918. | KHHLGIEEPRH; |
| 5919. | RHHLGIEEPRH; |
| 5920. | HHHLGIEEPRH; |
| 5921. | KKHLGIEEPRH; |
| 5922. | RKHLGIEEPRH; |
| 5923. | HKHLGIEEPRH; |
| 5924. | KRHLGIEEPRH; |
| 5925. | RRHLGIEEPRH; |
| 5926. | HRHLGIEEPRH; |
| 5927. | KHKLGIEEPRH; |
| 5928. | RHKLGIEEPRH; |
| 5929. | HHKLGIEEPRH; |
| 5930. | KKKLGIEEPRH; |
| 5931. | RKKLGIEEPRH; |
| 5932. | HKKLGIEEPRH; |
| 5933. | KRKLGIEEPRH; |
| 5934. | RRKLGIEEPRH; |
| 5935. | HRKLGIEEPRH; |
| 5936. | KHRLGIEEPRH; |
| 5937. | RHRLGIEEPRH; |
| 5938. | HHRLGIEEPRH; |
| 5939. | KKRLGIEEPRH; |
| 5940. | RKRLGIEEPRH; |
| 5941. | HKRLGIEEPRH; |
| 5942. | KRRLGIEEPRH; |
| 5943. | RRRLGIEEPRH; |
| 5944. | HRRLGIEEPRH; |
| 5945. | KHHIGIEEPRH; |
| 5946. | RHHIGIEEPRH; |
| 5947. | HHHIGIEEPRH; |
| 5948. | KKHIGIEEPRH; |
| 5949. | RKHIGIEEPRH; |
| 5950. | HKHIGIEEPRH; |
| 5951. | KRHIGIEEPRH; |
| 5952. | RRHIGIEEPRH; |
| 5953. | HRHIGIEEPRH; |
| 5954. | KHKIGIEEPRH; |
| 5955. | RHKIGIEEPRH; |
| 5956. | HHKIGIEEPRH; |
| 5957. | KKKIGIEEPRH; |
| 5958. | RKKIGIEEPRH; |
| 5959. | HKKIGIEEPRH; |
| 5960. | KRKIGIEEPRH; |
| 5961. | RRKIGIEEPRH; |
| 5962. | HRKIGIEEPRH; |
| 5963. | KHRIGIEEPRH; |
| 5964. | RHRIGIEEPRH; |
| 5965. | HHRIGIEEPRH; |
| 5966. | KKRIGIEEPRH; |
| 5967. | RKRIGIEEPRH; |
| 5968. | HKRIGIEEPRH; |
| 5969. | KRRIGIEEPRH; |
| 5970. | RRRIGIEEPRH; |
| 5971. | HRRIGIEEPRH; |
| 5972. | KHHVGIEEPRH; |
| 5973. | RHHVGIEEPRH; |
| 5974. | HHHVGIEEPRH; |
| 5975. | KKHVGIEEPRH; |
| 5976. | RKHVGIEEPRH; |
| 5977. | HKHVGIEEPRH; |

TABLE 7-continued

| SEQ ID NO. shown to left of sequence(cont'd) | |
|---|---|
| 5978. | KRHVGIEEPRH; |
| 5979. | RRHVGIEEPRH; |
| 5980. | HRHVGIEEPRH; |
| 5981. | KHKVGIEEPRH; |
| 5982. | RHKVGIEEPRH; |
| 5983. | HHKVGIEEPRH; |
| 5984. | KKKVGIEEPRH; |
| 5985. | RKKVGIEEPRH; |
| 5986. | HKKVGIEEPRH; |
| 5987. | KRKVGIEEPRH; |
| 5988. | RRKVGIEEPRH; |
| 5989. | HRKVGIEEPRH; |
| 5990. | KHRVGIEEPRH; |
| 5991. | RHRVGIEEPRH; |
| 5992. | HHRVGIEEPRH; |
| 5993. | KKRVGIEEPRH; |
| 5994. | RKRVGIEEPRH; |
| 5995. | HKRVGIEEPRH; |
| 5996. | KRRVGIEEPRH; |
| 5997. | RRRVGIEEPRH; |
| 5998. | HRRVGIEEPRH; |
| 5999. | KHHLGVEEPRH; |
| 6000. | RHHLGVEEPRH; |
| 6001. | HHHLGVEEPRH; |
| 6002. | KKHLGVEEPRH; |
| 6003. | RKHLGVEEPRH; |
| 6004. | HKHLGVEEPRH; |
| 6005. | KRHLGVEEPRH; |
| 6006. | RRHLGVEEPRH; |
| 6007. | HRHLGVEEPRH; |
| 6008. | KHKLGVEEPRH; |
| 6009. | RHKLGVEEPRH; |
| 6010. | HHKLGVEEPRH; |
| 6011. | KKKLGVEEPRH; |
| 6012. | RKKLGVEEPRH; |
| 6013. | HKKLGVEEPRH; |
| 6014. | KRKLGVEEPRH; |
| 6015. | RRKLGVEEPRH; |
| 6016. | HRKLGVEEPRH; |
| 6017. | KHRLGVEEPRH; |
| 6018. | RHRLGVEEPRH; |
| 6019. | HHRLGVEEPRH; |
| 6020. | KKRLGVEEPRH; |
| 6021. | RKRLGVEEPRH; |
| 6022. | HKRLGVEEPRH; |
| 6023. | KRRLGVEEPRH; |
| 6024. | RRRLGVEEPRH; |
| 6025. | HRRLGVEEPRH; |
| 6026. | KHHIGVEEPRH; |
| 6027. | RHHIGVEEPRH; |
| 6028. | HHHIGVEEPRH; |
| 6029. | KKHIGVEEPRH; |
| 6030. | RKHIGVEEPRH; |
| 6031. | HKHIGVEEPRH; |
| 6032. | KRHIGVEEPRH; |
| 6033. | RRHIGVEEPRH; |
| 6034. | HRHIGVEEPRH; |
| 6035. | KHKIGVEEPRH; |
| 6036. | RHKIGVEEPRH; |
| 6037. | HHKIGVEEPRH; |
| 6038. | KKKIGVEEPRH; |
| 6039. | RKKIGVEEPRH; |
| 6040. | HKKIGVEEPRH; |
| 6041. | KRKIGVEEPRH; |
| 6042. | RRKIGVEEPRH; |
| 6043. | HRKIGVEEPRH; |
| 6044. | KHRIGVEEPRH; |
| 6045. | RHRIGVEEPRH; |
| 6046. | HHRIGVEEPRH; |
| 6047. | KKRIGVEEPRH; |
| 6048. | RKRIGVEEPRH; |
| 6049. | HKRIGVEEPRH; |
| 6050. | KRRIGVEEPRH; |
| 6051. | RRRIGVEEPRH; |
| 6052. | HRRIGVEEPRH; |
| 6053. | KHHVGVEEPRH; |
| 6054. | RHHVGVEEPRH; |
| 6055. | HHHVGVEEPRH; |

TABLE 7-continued

SEQ ID NO. shown to left of sequence(cont'd)

| | |
|---|---|
| 6056. | KKHVGVEEPRH; |
| 6057. | RKHVGVEEPRH; |
| 6058. | HKHVGVEEPRH; |
| 6059. | KRHVGVEEPRH; |
| 6060. | RRHVGVEEPRH; |
| 6061. | HRHVGVEEPRH; |
| 6062. | KHKVGVEEPRH; |
| 6063. | RHKVGVEEPRH; |
| 6064. | HHKVGVEEPRH; |
| 6065. | KKKVGVEEPRH; |
| 6066. | RKKVGVEEPRH; |
| 6067. | HKKVGVEEPRH; |
| 6068. | KRKVGVEEPRH; |
| 6069. | RRKVGVEEPRH; |
| 6070. | HRKVGVEEPRH; |
| 6071. | KHRVGVEEPRH; |
| 6072. | RHRVGVEEPRH; |
| 6073. | HHRVGVEEPRH; |
| 6074. | KKRVGVEEPRH; |
| 6075. | RKRVGVEEPRH; |
| 6076. | HKRVGVEEPRH; |
| 6077. | KRRVGVEEPRH; |
| 6078. | RRRVGVEEPRH; |
| 6079. | HRRVGVEEPRH; |
| 6080. | KHHLGLNEPRH; |
| 6081. | RHHLGLNEPRH; |
| 6082. | HHHLGLNEPRH; |
| 6083. | KKHLGLNEPRH; |
| 6084. | RKHLGLNEPRH; |
| 6085. | HKHLGLNEPRH; |
| 6086. | KRHLGLNEPRH; |
| 6087. | RRHLGLNEPRH; |
| 6088. | HRHLGLNEPRH; |
| 6089. | KHKLGLNEPRH; |
| 6090. | RHKLGLNEPRH; |
| 6091. | HHKLGLNEPRH; |
| 6092. | KKKLGLNEPRH; |
| 6093. | RKKLGLNEPRH; |
| 6094. | HKKLGLNEPRH; |
| 6095. | KRKLGLNEPRH; |
| 6096. | RRKLGLNEPRH; |
| 6097. | HRKLGLNEPRH; |
| 6098. | KHRLGLNEPRH; |
| 6099. | RHRLGLNEPRH; |
| 6100. | HHRLGLNEPRH; |
| 6101. | KKRLGLNEPRH; |
| 6102. | RKRLGLNEPRH; |
| 6103. | HKRLGLNEPRH; |
| 6104. | KRRLGLNEPRH; |
| 6105. | RRRLGLNEPRH; |
| 6106. | HRRLGLNEPRH; |
| 6107. | KHHIGLNPRH; |
| 6108. | RHHIGLNEPRH; |
| 6109. | HHHIGLNEPRH; |
| 6110. | KKHIGLNEPRH; |
| 6111. | RKHIGLNEPRH; |
| 6112. | HKHIGLNEPRH; |
| 6113. | KRHIGLNEPRH; |
| 6114. | RRHIGLNEPRH; |
| 6115. | HRHIGLNEPRH; |
| 6116. | KHKIGLNEPRH; |
| 6117. | RHKIGLNEPRH; |
| 6118. | HHKIGLNEPRH; |
| 6119. | KKKIGLNEPRH; |
| 6120. | RKKIGLNEPRH; |
| 6121. | HKKIGLNEPRH; |
| 6122. | KRKIGLNEPRH; |
| 6123. | RRKIGLNEPRH; |
| 6124. | HRKIGLNEPRH; |
| 6125. | KHRIGLNEPRH; |
| 6126. | RHRIGLNEPRH; |
| 6127. | HHRIGLNEPRH; |
| 6128. | KKRIGLNEPRH; |
| 6129. | RKRIGLNEPRH; |
| 6130. | HKRIGLNEPRH; |
| 6131. | KRRIGLNEPRH; |
| 6132. | RRRIGLNEPRH; |
| 6133. | HRRIGLNEPRH; |

TABLE 7-continued

SEQ ID NO. shown to left of sequence(cont'd)

| | |
|---|---|
| 6134. | KHHVGLNEPRH; |
| 6135. | RHHVGLNEPRH; |
| 6136. | HHHVGLNEPRH; |
| 6137. | KKHVGLNEPRH; |
| 6138. | RKHVGLNEPRH; |
| 6139. | HKHVGLNEPRH; |
| 6140. | KRHVGLNEPRH; |
| 6141. | RRHVGLNEPRH; |
| 6142. | HRHVGLNEPRH; |
| 6143. | KHKVGLNEPRH; |
| 6144. | RHKVGLNEPRH; |
| 6145. | HHKVGLNEPRH; |
| 6146. | KKKVGLNEPRH; |
| 6147. | RKKVGLNEPRH; |
| 6148. | HKKVGLNEPRH; |
| 6149. | KRKVGLNEPRH; |
| 6150. | RRKVGLNEPRH; |
| 6151. | HRKVGLNEPRH; |
| 6152. | KHRVGLNEPRH; |
| 6153. | RHRVGLNEPRH; |
| 6154. | HHRVGLNEPRH; |
| 6155. | KKRVGLNEPRH; |
| 6156. | RKRVGLNEPRH; |
| 6157. | HKRVGLNEPRH; |
| 6158. | KRRVGLNEPRH; |
| 6159. | RRRVGLNEPRH; |
| 6160. | HRRVGLNEPRH; |
| 6161. | KHHLGINEPRH; |
| 6162. | RHHLGINEPRH; |
| 6163. | HHHLGINEPRH; |
| 6164. | KKHLGINEPRH; |
| 6165. | RKHLGINEPRH; |
| 6166. | HKHLGINEPRH; |
| 6167. | KRHLGINEPRH; |
| 6168. | RRHLGINEPRH; |
| 6169. | HRHLGINEPRH; |
| 6170. | KHKLGINEPRH; |
| 6171. | RHKLGINEPRH; |
| 6172. | HHKLGINEPRH; |

TABLE 7-continued

SEQ ID NO. shown to left of sequence(cont'd)

| | |
|---|---|
| 6173. | KKKLGINEPRH; |
| 6174. | RKKLGINEPRH; |
| 6175. | HKKLGINEPRH; |
| 6176. | KRKLGINEPRH; |
| 6177. | RRKLGINEPRH; |
| 6178. | HRKLGINEPRH; |
| 6179. | KHRLGINEPRH; |
| 6180. | RHRLGINEPRH; |
| 6181. | HHRLGINEPRH; |
| 6182. | KKRLGINEPRH; |
| 6183. | RKRLGINEPRH; |
| 6184. | HKRLGINEPRH; |
| 6185. | KRRLGINEPRH; |
| 6186. | RRRLGINEPRH; |
| 6187. | HRRLGINEPRH; |
| 6188. | KHHIGIENPRH; |
| 6189. | RHHIGINEPRH; |
| 6190. | HHHIGINEPRH; |
| 6191. | KKHIGINEPRH; |
| 6192. | RKHIGINEPRH; |
| 6193. | HKHIGINEPRH; |
| 6194. | KRHIGINEPRH; |
| 6195. | RRHIGINEPRH; |
| 6196. | HRHIGINEPRH; |
| 6197. | KHKIGINEPRH; |
| 6198. | RHKIGINEPRH; |
| 6199. | HHKIGINEPRH; |
| 6200. | KKKIGINEPRH; |
| 6201. | RKKIGINEPRH; |
| 6202. | HKKIGINEPRH; |
| 6203. | KRKIGINEPRH; |
| 6204. | RRKIGINEPRH; |
| 6205. | HRKIGINEPRH; |
| 6206. | KHRIGINEPRH; |
| 6207. | RHRIGINEPRH; |
| 6208. | HHRIGINEPRH; |
| 6209. | KKRIGINEPRH; |
| 6210. | RKRIGINEPRH; |
| 6211. | HKRIGINEPRH; |

TABLE 7-continued

SEQ ID NO. shown to left of sequence(cont'd)

| SEQ ID NO. | Sequence |
|---|---|
| 6212. | KRRIGINEPRH; |
| 6213. | RRRIGINEPRH; |
| 6214. | HRRIGINEPRH; |
| 6215. | KHHVGINEPRH; |
| 6216. | RHHVGINEPRH; |
| 6217. | HHHVGINEPRH; |
| 6218. | KKHVGINEPRH; |
| 6219. | RKHVGINEPRH; |
| 6220. | HKHVGINEPRH; |
| 6221. | KRHVGINEPRH; |
| 6222. | RRHVGINEPRH; |
| 6223. | HRHVGINEPRH; |
| 6224. | KHKVGINEPRH; |
| 6225. | RHKVGINEPRH; |
| 6226. | HHKVGINEPRH; |
| 6227. | KKKVGINEPRH; |
| 6228. | RKKVGINEPRH; |
| 6229. | HKKVGINEPRH; |
| 6230. | KRKVGINEPRH; |
| 6231. | RRKVGINEPRH; |
| 6232. | HRKVGINEPRH; |
| 6233. | KHRVGINEPRH; |
| 6234. | RHRVGINEPRH; |
| 6235. | HHRVGINEPRH; |
| 6236. | KKRVGINEPRH; |
| 6237. | RKRVGINEPRH; |
| 6238. | HKRVGINEPRH; |
| 6239. | KRRVGINEPRH; |
| 6240. | RRRVGINEPRH; |
| 6241. | HRRVGINEPRH; |
| 6242. | KHHLGVNEPRH; |
| 6243. | RHHLGVNEPRH; |
| 6244. | HHHLGVNEPRH; |
| 6245. | KKHLGVNEPRH; |
| 6246. | RHHLGVNEPRH; |
| 6247. | HKHLGVNEPRH; |
| 6248. | KRHLGVNEPRH; |
| 6249. | RRHLGVNEPRH; |
| 6250. | HRHLGVNEPRH; |
| 6251. | KHKLGVNEPRH; |
| 6252. | RHKLGVNEPRH; |
| 6253. | HHKLGVNEPRH; |
| 6254. | KKKLGVNEPRH; |
| 6255. | RKKLGVNEPRH; |
| 6256. | HKKLGVNEPRH; |
| 6257. | KRKLGVNEPRH; |
| 6258. | RRKLGVNEPRH; |
| 6259. | HRKLGVNEPRH; |
| 6260. | KHRLGVNEPRH; |
| 6261. | RHRLGVNEPRH; |
| 6262. | HHRLGVNEPRH; |
| 6263. | KKRLGVNEPRH; |
| 6264. | RKRLGVNEPRH; |
| 6265. | HKRLGVNEPRH; |
| 6266. | KRRLGVNEPRH; |
| 6267. | RRRLGVNEPRH; |
| 6268. | HRRLGVNEPRH; |
| 6269. | KHHIGVNEPRH; |
| 6270. | RHHIGVNEPRH; |
| 6271. | HHHIGVNEPRH; |
| 6272. | KKHIGVNEPRH; |
| 6273. | RKHIGVNEPRH; |
| 6274. | HKHIGVNEPRH; |
| 6275. | KRHIGVNEPRH; |
| 6276. | RRHIGVNEPRH; |
| 6277. | HRHIGVNEPRH; |
| 6278. | KHKIGVNEPRH; |
| 6279. | RHKIGVNEPRH; |
| 6280. | HHKIGVNEPRH; |
| 6281. | KKKIGVNEPRH; |
| 6282. | RKKIGVNEPRH; |
| 6283. | HKKIGVNEPRH; |
| 6284. | KRKIGVNEPRH; |
| 6285. | RRKIGVNEPRH; |
| 6286. | HRKIGVNEPRH; |
| 6287. | KHRIGVNEPRH; |
| 6288. | RHRIGVNEPRH; |
| 6289. | HHRIGVNEPRH; |

TABLE 7-continued

SEQ ID NO. shown to left of sequence (cont'd)

| SEQ ID NO. | Sequence |
|---|---|
| 6290. | KKRIGVNEPRH; |
| 6291. | RKRIGVNEPRH; |
| 6292. | HKRIGVNEPRH; |
| 6293. | KRRIGVNEPRH; |
| 6294. | RRRIGVNEPRH; |
| 6295. | HRRIGVNEPRH; |
| 6296. | KHHVGVNEPRH; |
| 6297. | RHHVGVNEPRH; |
| 6298. | HHHVGVNEPRH; |
| 6299. | KKHVGVNEPRH; |
| 6300. | RKHVGVNEPRH; |
| 6301. | HKHVGVNEPRH; |
| 6302. | KRHVGVNEPRH; |
| 6303. | RRHVGVNEPRH; |
| 6304. | HRHVGVNEPRH; |
| 6305. | KHKVGVNEPRH; |
| 6306. | RHKVGVNEPRH; |
| 6307. | HHKVGVNEPRH; |
| 6308. | KKKVGVNEPRH; |
| 6309. | RKKVGVNEPRH; |
| 6310. | HKKVGVNEPRH; |
| 6311. | KRKVGVNEPRH; |
| 6312. | RRKVGVNEPRH; |
| 6313. | HRKVGVNEPRH; |
| 6314. | KHRVGVNEPRH; |
| 6315. | RHRVGVNEPRH; |
| 6316. | HHRVGVNEPRH; |
| 6317. | KKRVGVNEPRH; |
| 6318. | RKRVGVNEPRH; |
| 6319. | HKRVGVNEPRH; |
| 6320. | KRRVGVNEPRH; |
| 6321. | RRRVGVNEPRH; |
| 6322. | HRRVGVNEPRH; |
| 6323. | KHHLGLENPRH; |
| 6324. | RHHLGLENPRH; |
| 6325. | HHHLGLENPRH; |
| 6326. | KKHLGLENPRH; |
| 6327. | RKHLGLENPRH; |
| 6328. | HKHLGLENPRH; |
| 6329. | KRHLGLENPRH; |
| 6330. | RRHLGLENPRH; |
| 6331. | HRHLGLENPRH; |
| 6332. | KHKLGLENPRH; |
| 6333. | RHKLGLENPRH; |
| 6334. | HHKLGLENPRH; |
| 6335. | KKKLGLENPRH; |
| 6336. | RKKLGLENPRH; |
| 6337. | HKKLGLENPRH; |
| 6338. | KRKLGLENPRH; |
| 6339. | RRKLGLENPRH; |
| 6340. | HRKLGLENPRH; |
| 6341. | KHRLGLENPRH; |
| 6342. | RHRLGLENPRH; |
| 6343. | HHRLGLENPRH; |
| 6344. | KKRLGLENPRH; |
| 6345. | RKRLGLENPRH; |
| 6346. | HKRLGLENPRH; |
| 6347. | KRRLGLENPRH; |
| 6348. | RRRLGLENPRH; |
| 6349. | HRRLGLENPRH; |
| 6350. | KHHIGLENPRH; |
| 6351. | RHHIGLENPRH; |
| 6352. | HHHIGLENPRH; |
| 6353. | KKHIGLENPRH; |
| 6354. | RKHIGLENPRH; |
| 6355. | HKHIGLENPRH; |
| 6356. | KRHIGLENPRH; |
| 6357. | RRHIGLENPRH; |
| 6358. | HRHIGLENPRH; |
| 6359. | KHKIGLENPRH; |
| 6360. | RHKIGLENPRH; |
| 6361. | HHKIGLENPRH; |
| 6362. | KKKIGLENPRH; |
| 6363. | RKKIGLENPRH; |
| 6364. | HKKIGLENPRH; |
| 6365. | KRKIGLENPRH; |
| 6366. | RRKIGLENPRH; |
| 6367. | HRKIGLENPRH; |

TABLE 7-continued

SEQ ID NO. shown to left of sequence(cont'd)

| | |
|---|---|
| 6368. | KHRIGLENPRH; |
| 6369. | RHRIGLENPRH; |
| 6370. | HHRIGLENPRH; |
| 6371. | KKRIGLENPRH; |
| 6372. | RKRIGLENPRH; |
| 6373. | HKRIGLENPRH; |
| 6374. | KRRIGLENPRH; |
| 6375. | RRRIGLENPRH; |
| 6376. | HRRIGLENPRH; |
| 6377. | KHHVGLENPRH; |
| 6378. | RHHVGLENPRH; |
| 6379. | HHHVGLENPRH; |
| 6380. | KKHVGLENPRH; |
| 6381. | RKHVGLENPRH; |
| 6382. | HKHVGLENPRH; |
| 6383. | KRHVGLENPRH; |
| 6384. | RRHVGLENPRH; |
| 6385. | HRHVGLENPRH; |
| 6386. | KHKVGLENPRH; |
| 6387. | RHKVGLENPRH; |
| 6388. | HHKVGLENPRH; |
| 6389. | KKKVGLENPRH; |
| 6390. | RKKVGLENPRH; |
| 6391. | HKKVGLENPRH; |
| 6392. | KRKVGLENPRH; |
| 6393. | RRKVGLENPRH; |
| 6394. | HRKVGLENPRH; |
| 6395. | KHRVGLENPRH; |
| 6396. | RHRVGLENPRH; |
| 6397. | HHRVGLENPRH; |
| 6398. | KKRVGLENPRH; |
| 6399. | RKRVGLENPRH; |
| 6400. | HKRVGLENPRH; |
| 6401. | KRRVGLENPRH; |
| 6402. | RRRVGLENPRH; |
| 6403. | HRRVGLENPRH; |
| 6404. | KHHLGIENPRH; |
| 6405. | RHHLGIENPRH; |
| 6406. | HHHLGIENPRH; |

TABLE 7-continued

SEQ ID NO. shown to left of sequence(cont'd)

| | |
|---|---|
| 6407. | KKHLGIENPRH; |
| 6408. | RKHLGIENPRH; |
| 6409. | HKHLGIENPRH; |
| 6410. | KRHLGIENPRH; |
| 6411. | RRHLGIENPRH; |
| 6412. | HRHLGIENPRH; |
| 6413. | KHKLGIENPRH; |
| 6414. | RHKLGIENPRH; |
| 6415. | HHKLGIENPRH; |
| 6416. | KKKLGIENPRH; |
| 6417. | RKKLGIENPRH; |
| 6418. | HKKLGIENPRH; |
| 6419. | KRKLGIENPRH; |
| 6420. | RRKLGIENPRH; |
| 6421. | HRKLGIENPRH; |
| 6422. | KHRLGIENPRH; |
| 6423. | RHRLGIENPRH; |
| 6424. | HHRLGIENPRH; |
| 6425. | KKRLGIENPRH; |
| 6426. | RKRLGIENPRH; |
| 6427. | HKRLGIENPRH; |
| 6428. | KRRLGIENPRH; |
| 6429. | RRRLGIENPRH; |
| 6430. | HRRLGIENPRH; |
| 6431. | KHHIGIENPRH; |
| 6432. | RHHIGIENPRH; |
| 6433. | HHHIGIENPRH; |
| 6434. | KKHIGIENPRH; |
| 6435. | RKHIGIENPRH; |
| 6436. | HKHIGIENPRH; |
| 6437. | KRHIGIENPRH; |
| 6438. | RRHIGIENPRH; |
| 6439. | HRHIGIENPRH; |
| 6440. | KHKIGIENPRH; |
| 6441. | RHKIGIENPRH; |
| 6442. | HHKIGIENPRH; |
| 6443. | KKKIGIENPRH; |
| 6444. | RKKIGIENPRH; |
| 6445. | HKKIGIENPRH; |

TABLE 7-continued

SEQ ID NO. shown to left of sequence (cont'd)

| | |
|---|---|
| 6446. | KRKIGIENPRH; |
| 6447. | RRKIGIENPRH; |
| 6448. | HRKIGIENPRH; |
| 6449. | KHRIGIENPRH; |
| 6450. | RHRIGIENPRH; |
| 6451. | HHRIGIENPRH; |
| 6452. | KKRIGIENPRH; |
| 6453. | RKRIGIENPRH; |
| 6454. | HKRIGIENPRH; |
| 6455. | KRRIGIENPRH; |
| 6456. | RRRIGIENPRH; |
| 6457. | HRRIGIENPRH; |
| 6458. | KHHVGIENPRH; |
| 6459. | RHHVGIENPRH; |
| 6460. | HHHVGIENPRH; |
| 6461. | KKHVGIENPRH; |
| 6462. | RKHVGIENPRH; |
| 6463. | HKHVGIENPRH; |
| 6464. | KRHVGIENPRH; |
| 6465. | RRHVGIENPRH; |
| 6466. | HRHVGIENPRH; |
| 6467. | KHKVGIENPRH; |
| 6468. | RHKVGIENPRH; |
| 6469. | HHKVGIENPRH; |
| 6470. | KKKVGIENPRH; |
| 6471. | RKKVGIENPRH; |
| 6472. | HKKVGIENPRH; |
| 6473. | KRKVGIENPRH; |
| 6474. | RRKVGIENPRH; |
| 6475. | HRKVGIENPRH; |
| 6476. | KHRVGIENPRH; |
| 6477. | RHRVGIENPRH; |
| 6478. | HHRVGIENPRH; |
| 6479. | KKRVGIENPRH; |
| 6480. | RKRVGIENPRH; |
| 6481. | HKRVGIENPRH; |
| 6482. | KRRVGIENPRH; |
| 6483. | RRRVGIENPRH; |
| 6484. | HRRVGIENPRH; |

TABLE 7-continued

SEQ ID NO. shown to left of sequence (cont'd)

| | |
|---|---|
| 6485. | KHHLGVENPRH; |
| 6486. | RHHLGVENPRH; |
| 6487. | HHHLGVENPRH; |
| 6488. | KKHLGVENPRH; |
| 6489. | RKHLGVENPRH; |
| 6490. | HKHLGVENPRH; |
| 6491. | KRHLGVENPRH; |
| 6492. | RRHLGVENPRH; |
| 6493. | HRHLGVENPRH; |
| 6494. | KHKLGVENPRH; |
| 6495. | RHKLGVENPRH; |
| 6496. | HHKLGVENPRH; |
| 6497. | KKKLGVENPRH; |
| 6498. | RKKLGVENPRH; |
| 6499. | HKKLGVENPRH; |
| 6500. | KRKLGVENPRH; |
| 6501. | RRKLGVENPRH; |
| 6502. | HRKLGVENPRH; |
| 6503. | KHRLGVENPRH; |
| 6504. | RHRLGVENPRH; |
| 6505. | HHRLGVENPRH; |
| 6506. | KKRLGVENPRH; |
| 6507. | RKRLGVENPRH; |
| 6508. | HKRLGVENPRH; |
| 6509. | KRRLGVENPRH; |
| 6510. | RRRLGVENPRH; |
| 6511. | HRRLGVENPRH; |
| 6512. | KHHIGVENPRH; |
| 6513. | RHHIGVEEPRH; |
| 6514. | HHHIGVENPRH; |
| 6515. | KKHIGVENPRH; |
| 6516. | RKHIGVENPRH; |
| 6517. | HKHIGVENPRH; |
| 6518. | KRHIGVENPRH; |
| 6519. | RRHIGVENPRH; |
| 6520. | HRHIGVENPRH; |
| 6521. | KHKIGVENPRH; |
| 6522. | RHKIGVENPRH; |
| 6523. | HHKIGVENPRH; |

TABLE 7-continued

SEQ ID NO. shown to left of sequence(cont'd)

| | |
|---|---|
| 6524. | KKKIGVENPRH; |
| 6525. | RKKIGVENPRH; |
| 6526. | HKKIGVENPRH; |
| 6527. | KRKIGVENPRH; |
| 6528. | RRKIGVENPRH; |
| 6529. | HRKIGVENPRH; |
| 6530. | KHRIGVENPRH; |
| 6531. | RHRIGVENPRH; |
| 6532. | HHRIGVENPRH; |
| 6533. | KKRIGVENPRH; |
| 6534. | RKRIGVENPRH; |
| 6535. | HKRIGVENPRH; |
| 6536. | KRRIGVENPRH; |
| 6537. | RRRIGVENPRH; |
| 6538. | HRRIGVENPRH; |
| 6539. | KHHVGVENPRH; |
| 6540. | RHHVGVENPRH; |
| 6541. | HHHVGVENPRH; |
| 6542. | KKHVGVENPRH; |
| 6543. | RKHVGVENPRH; |
| 6544. | HKHVGVENPRH; |
| 6545. | KRHVGVENPRH; |
| 6546. | RRRVGVENPRH; |
| 6547. | HRHVGVENPRH; |
| 6548. | KHKVGVENPRH; |
| 6549. | RHKVGVENPRH; |
| 6550. | HHKVGVENPRH; |
| 6551. | KKKVGVENPRH; |
| 6552. | RKKVGVENPRH; |
| 6553. | HKKVGVENPRH; |
| 6554. | KRKVGVENPRH; |
| 6555. | RRKVGVEEPRH; |
| 6556. | HRKVGVENPRH; |
| 6557. | KHRVGVENPRH; |
| 6558. | RHRVGVENPRH; |
| 6559. | HHRVGVENPRH; |
| 6560. | KKRVGVENPRH; |
| 6561. | RKRVGVENPRH; |
| 6562. | HKRVGVENPRH; |

TABLE 7-continued

SEQ ID NO. shown to left of sequence(cont'd)

| | |
|---|---|
| 6563. | KRRVGVENPRH; |
| 6564. | RRRVGVENPRH; |
| 6565. | HRRVGVENPRH; |
| 6566. | KHHLGLNNPRH; |
| 6567. | RHHLGLNNPRH; |
| 6568. | HHHLGLNNPRH; |
| 6569. | KKHLGLNNPRH; |
| 6570. | RKHLGLNNPRH; |
| 6571. | HKHLGLNNPRH; |
| 6572. | KRHLGLNNPRH; |
| 6573. | RRHLGLNNPRH; |
| 6574. | HRHLGLNNPRH; |
| 6575. | KHKLGLNNPRH; |
| 6576. | RHKLGLNNPRH; |
| 6577. | HHKLGLNNPRH; |
| 6578. | KKKLGLNNPRH; |
| 6579. | RKKLGLNNPRH; |
| 6580. | HKKLGLNNPRH; |
| 6581. | KRKLGLNNPRH; |
| 6582. | RRKLGLNNPRH; |
| 6583. | HRKLGLNNPRH; |
| 6584. | KHRLGLNNPRH; |
| 6585. | RHRLGLNNPRH; |
| 6586. | HHRLGLNNPRH; |
| 6587. | KKRLGLNNPRH; |
| 6588. | RKRLGLNNPRH; |
| 6589. | HKRLGLNNPRH; |
| 6590. | KRRLGLNNPRH; |
| 6591. | RRRLGLNNPRH; |
| 6592. | HRRLGLNNPRH; |
| 6593. | KHHIGLNNPRH; |
| 6594. | RHHIGLNNPRH; |
| 6595. | HHHIGLNNPRH; |
| 6596. | KKHIGLNNPRH; |
| 6597. | RKHIGLNNPRH; |
| 6598. | HKHIGLNNPRH; |
| 6599. | KRHIGLNNPRH; |
| 6600. | RRHIGLNNPRH; |
| 6601. | HRHIGLNNPRH; |

TABLE 7-continued

SEQ ID NO. shown to left of sequence (cont'd)

| SEQ ID NO. | Sequence |
|---|---|
| 6602. | KHKIGLNNPRH; |
| 6603. | RHKIGLNNPRH; |
| 6604. | HHKIGLNNPRH; |
| 6605. | KKKIGLNNPRH; |
| 6606. | RKKIGLNNPRH; |
| 6607. | HKKIGLNNPRH; |
| 6608. | KRKIGLNNPRH; |
| 6609. | RRKIGLNNPRH; |
| 6610. | HRKIGLNNPRH; |
| 6611. | KHRIGLNNPRH; |
| 6612. | RHRIGLNNPRH; |
| 6613. | HHRIGLNNPRH; |
| 6614. | KKRIGLNNPRH; |
| 6615. | RKRIGLNNPRH; |
| 6616. | HKRIGLNNPRH; |
| 6617. | KRRIGLNNPRH; |
| 6618. | RRRIGLNNPRH; |
| 6619. | HRRIGLNNPRH; |
| 6620. | KHHVGLNNPRH; |
| 6621. | RHHVGLNNPRH; |
| 6622. | HHHVGLNNPRH; |
| 6623. | KKHVGLNNPRH; |
| 6624. | RKHVGLNNPRH; |
| 6625. | HKHVGLNNPRH; |
| 6626. | KRHVGLNNPRH; |
| 6627. | RRHVGLNNPRH; |
| 6628. | HRHVGLNNPRH; |
| 6629. | KHKVGLNNPRH; |
| 6630. | RHKVGLNNPRH; |
| 6631. | HHKVGLNNPRH; |
| 6632. | KKKVGLNNPRH; |
| 6633. | RKKVGLNNPRH; |
| 6634. | HKKVGLNNPRH; |
| 6635. | KRKVGLNNPRH; |
| 6636. | RRKVGLNNPRH; |
| 6637. | HRKVGLNNPRH; |
| 6638. | KHRVGLNNPRH; |
| 6639. | RHRVGLNNPRH; |
| 6640. | HHRVGLNNPRH; |
| 6641. | KKRVGLNNPRH; |
| 6642. | RKRVGLNNPRH; |
| 6643. | HKRVGLNNPRH; |
| 6644. | KRRVGLNNPRH; |
| 6645. | RRRVGLNNPRH; |
| 6646. | HRRVGLNNPRH; |
| 6647. | KHHLGLNNPRH; |
| 6648. | RHHLGINNPRH; |
| 6649. | HHHLGINNPRH; |
| 6650. | KKHLGINNPRH; |
| 6651. | RKHLGINNPRH; |
| 6652. | HKHLGINNPRH; |
| 6653. | KRHLGINNPRH; |
| 6654. | RRHLGINNPRH; |
| 6655. | HRHLGINNPRH; |
| 6656. | KHKLGINNPRH; |
| 6657. | RHKLGINNPRH; |
| 6658. | HHKLGINNPRH; |
| 6659. | KKKLGINNPRH; |
| 6660. | RKKLGINNPRH; |
| 6661. | HKKLGINNPRH; |
| 6662. | KRKLGINNPRH; |
| 6663. | RRKLGINNPRH; |
| 6664. | HRKLGINNPRH; |
| 6665. | KHRLGINNPRH; |
| 6666. | RHRLGINNPRH; |
| 6667. | HHRLGINNPRH; |
| 6668. | KKRLGINNPRH; |
| 6669. | RKRLGINNPRH; |
| 6670. | HKRLGINNPRH; |
| 6671. | KRRLGINNPRH; |
| 6672. | RRRLGINNPRH; |
| 6673. | HRRLGINNPRH; |
| 6674. | KHHIGIENPRH; |
| 6675. | RHHIGINNPRH; |
| 6676. | HHHIGINNPRH; |
| 6677. | KKHIGINNPRH; |
| 6678. | RKHIGINNPRH; |
| 6679. | HKHIGINNPRH; |

TABLE 7-continued

SEQ ID NO. shown to left of sequence(cont'd)

| | |
|---|---|
| 6680. | KRHIGINNPRH; |
| 6681. | RRHIGINNPRH; |
| 6682. | HRHIGINNPRH; |
| 6683. | KHKIGINNPRH; |
| 6684. | RHKIGINNPRH; |
| 6685. | HHKIGINNPRH; |
| 6686. | KKKIGINNPRH; |
| 6687. | RKKIGINNPRH; |
| 6688. | HKKIGINNPRH; |
| 6689. | KRKIGINNPRH; |
| 6690. | RRKIGINNPRH; |
| 6691. | HRKIGINNPRH; |
| 6692. | KHRIGINNPRH; |
| 6693. | RHRIGINNPRH; |
| 6694. | HHRIGINNPRH; |
| 6695. | KKRIGINNPRH; |
| 6696. | RKRIGINNPRH; |
| 6697. | HKRIGINNPRH; |
| 6698. | KRRIGINNPRH; |
| 6699. | RRRIGINNPRH; |
| 6700. | HRRIGINNPRH; |
| 6701. | KHHVGINNPRH; |
| 6702. | RHHVGINNPRH; |
| 6703. | HHHVGINNPRH; |
| 6704. | KKHVGINNPRH; |
| 6705. | RKHVGLNNPRH; |
| 6706. | HKHVGINNPRH; |
| 6707. | KRHVGINNPRH; |
| 6708. | RRHVGINNPRH; |
| 6709. | HRHVGINNPRH; |
| 6710. | KHKVGINNPRH; |
| 6711. | RHKVGINNPRH; |
| 6712. | HHKVGINNPRH; |
| 6713. | KKKVGINNPRH; |
| 6714. | RKKVGINNPRH; |
| 6715. | HKKVGINNPRH; |
| 6716. | KRKVGINNPRH; |
| 6717. | RRKVGINNPRH; |
| 6718. | HRKVGINNPRH; |

TABLE 7-continued

SEQ ID NO. shown to left of sequence(cont'd)

| | |
|---|---|
| 6719. | KHRVGINNPRH; |
| 6720. | RHRVGINNPRH; |
| 6721. | HHRVGINNPRH; |
| 6722. | KKRVGINNPRH; |
| 6723. | RKRVGINNPRH; |
| 6724. | HKRVGINNPRH; |
| 6725. | KRRVGINNPRH; |
| 6726. | RRRVGINNPRH; |
| 6727. | HRRVGINNPRH; |
| 6728. | KHHLGVNNPRH; |
| 6729. | RHHLGVNNPRH; |
| 6730. | HHHLGVNNPRH; |
| 6731. | KKHLGVNNPRH; |
| 6732. | RKHLGVNNPRH; |
| 6733. | HHHLGVNNPRH; |
| 6734. | KRHLGVNNPRH; |
| 6735. | RRHLGVNNPRH; |
| 6736. | HRHLGVNNPRH; |
| 6737. | KHKLGVNNPRH; |
| 6738. | RHKLGVNNPRH; |
| 6739. | HHKLGVNNPRH; |
| 6740. | KKKLGVNNPRH; |
| 6741. | RKKLGVNNPRH; |
| 6742. | HKKLGVNNPRH; |
| 6743. | KRKLGVNNPRH; |
| 6744. | RRKLGVNNPRH; |
| 6745. | HRKLGVNNPRH; |
| 6746. | KHRLGVNNPRH; |
| 6747. | RHRLGVNNPRH; |
| 6748. | HHRLGVNNPRH; |
| 6749. | KKRLGVNNPRH; |
| 6750. | RKRLGVNNPRH; |
| 6751. | HKRLGVNNPRH; |
| 6752. | KRRLGVNNPRH; |
| 6753. | RRRLGVNNPRH; |
| 6754. | HRRLGVNNPRH; |
| 6755. | KHHIGVNNPRH; |
| 6756. | RHHIGVNNPRH; |
| 6757. | HHHIGVNNPRH; |

TABLE 7-continued

SEQ ID NO. shown to left of sequence(cont'd)

| SEQ ID NO. | Sequence |
|---|---|
| 6758. | KKHIGVNNPRH; |
| 6759. | RKHIGVNNPRH; |
| 6760. | HKHIGVNNPRH; |
| 6761. | KRHIGVNNPRH; |
| 6762. | RRHIGVNNPRH; |
| 6763. | HRHIGVNNPRH; |
| 6764. | KHKIGVNNPRH; |
| 6765. | RHKIGVNNPRH; |
| 6766. | HHKIGVNNPRH; |
| 6767. | KKKIGVNNPRH; |
| 6768. | RKKIGVNNPRH; |
| 6769. | HKKIGVNNPRH; |
| 6770. | KRKIGVNNPRH; |
| 6771. | RRKIGVNNPRH; |
| 6772. | HRKIGVNNPRH; |
| 6773. | KHRIGVNNPRH; |
| 6774. | RHRIGVNNPRH; |
| 6775. | HHRIGVNNPRH; |
| 6776. | KKRIGVNNPRH; |
| 6777. | RKRIGVNNPRH; |
| 6778. | HKRIGVNNPRH; |
| 6779. | KRRIGVNNPRH; |
| 6780. | RRRIGVNNPRH; |
| 6781. | HRRIGVNNPRH; |
| 6782. | KHHVGVNNPRH; |
| 6783. | RHHVGVNNPRH; |
| 6784. | HHHVGVNNPRH; |
| 6785. | KKHVGVNNPRH; |
| 6786. | RKHVGVNNPRH; |
| 6787. | HKHVGVNNPRH; |
| 6788. | KRHVGVNNPRH; |
| 6789. | RRHVGVNNPRH; |
| 6790. | HRHVGVNNPRH; |
| 6791. | KHKVGVNNPRH; |
| 6792. | RHKVGVNNPRH; |
| 6793. | HHKVGVNNPRH; |
| 6794. | KKKVGVNNPRH; |
| 6795. | RKKVGVNNPRH; |
| 6796. | HKKVGVNNPRH; |
| 6797. | KRKVGVNNPRH; |
| 6798. | RRKVGVNNPRH; |
| 6799. | HRKVGVNNPRH; |
| 6800. | KHRVGVNNPRH; |
| 6801. | RHRVGVNNPRH; |
| 6802. | HHRVGVNNPRH; |
| 6803. | KKRVGVNNPRH; |
| 6804. | RKRVGVNNPRH; |
| 6805. | HKRVGVNNPRH; |
| 6806. | KRRVGVNNPRH; |
| 6807. | RRRVGVNNPRH; |
| 6808. | HRRVGVNNPRH; |
| 6809. | KHHLGLEEPHR; |
| 6810. | RHHLGLEEPHR; |
| 6811. | HHHLGLEEPHR; |
| 6812. | KKHLGLEEPHR; |
| 6813. | RKHLGLEEPHR; |
| 6814. | HKHLGLEEPHR; |
| 6815. | KRHLGLEEPHR; |
| 6816. | RRHLGLEEPHR; |
| 6817. | HRHLGLEEPHR; |
| 6818. | KHKLGLEEPHR; |
| 6819. | RHKLGLEEPHR; |
| 6820. | HHKLGLEEPHR; |
| 6821. | KKKLGLEEPHR; |
| 6822. | RKKLGLEEPHR; |
| 6823. | HKKLGLEEPHR; |
| 6824. | KRKLGLEEPHR; |
| 6825. | RRKLGLEEPHR; |
| 6826. | HRKLGLEEPHR; |
| 6827. | KHRLGLEEPHR; |
| 6828. | RHRLGLEEPHR; |
| 6829. | HHRLGLEEPHR; |
| 6830. | KKRLGLEEPHR; |
| 6831. | RKRLGLEEPHR; |
| 6832. | HKRLGLEEPHR; |
| 6833. | KRRLGLEEPHR; |
| 6834. | RRRLGLEEPHR; |
| 6835. | HRRLGLEEPHR; |

TABLE 7-continued

SEQ ID NO. shown to left of sequence(cont'd)

| | |
|---|---|
| 6836. | KHHIGLEEPHR; |
| 6837. | RHHIGLEEPHR; |
| 6838. | HHHIGLEEPHR; |
| 6839. | KKHIGLEEPHR; |
| 6840. | RKHIGLEEPHR; |
| 6841. | HKHIGLEEPHR; |
| 6842. | KRHIGLEEPHR; |
| 6843. | RRHIGLEEPHR; |
| 6844. | HRHIGLEEPHR; |
| 6845. | KHKIGLEEPHR; |
| 6846. | RHKIGLEEPHR; |
| 6847. | HHKIGLEEPHR; |
| 6848. | KKKIGLEEPHR; |
| 6849. | RKKIGLEEPHR; |
| 6850. | HKKIGLEEPHR; |
| 6851. | KRKIGLEEPHR; |
| 6852. | RRKIGLEEPHR; |
| 6853. | HRKIGLEEPHR; |
| 6854. | KHRIGLEEPHR; |
| 6855. | RHRIGLEEPHR; |
| 6856. | HHRIGLEEPHR; |
| 6857. | KKRIGLEEPHR; |
| 6858. | RKRIGLEEPHR; |
| 6859. | HKRIGLEEPHR; |
| 6860. | KRRIGLEEPHR; |
| 6861. | RRRIGLEEPHR; |
| 6862. | HRRIGLEEPHR; |
| 6863. | KHHVGLEEPHR; |
| 6864. | RHHVGLEEPHR; |
| 6865. | HHHVGLEEPHR; |
| 6866. | KKHVGLEEPHR; |
| 6867. | RKHVGLEEPHR; |
| 6868. | HKHVGLEEPHR; |
| 6869. | KRHVGLEEPHR; |
| 6870. | RRHVGLEEPHR; |
| 6871. | HRHVGLEEPHR; |
| 6872. | KHKVGLEEPHR; |
| 6873. | RHKVGLEEPHR; |
| 6874. | HHKVGLEEPHR; |

TABLE 7-continued

SEQ ID NO. shown to left of sequence(cont'd)

| | |
|---|---|
| 6875. | KKKVGLEEPHR; |
| 6876. | RKKVGLEEPHR; |
| 6877. | HKKVGLEEPHR; |
| 6878. | KRKVGLEEPHR; |
| 6879. | RRKVGLEEPHR; |
| 6880. | HRKVGLEEPHR; |
| 6881. | KHRVGLEEPHR; |
| 6882. | RHRVGLEEPHR; |
| 6883. | HHRVGLEEPHR; |
| 6884. | KKRVGLEEPHR; |
| 6885. | RKRVGLEEPHR; |
| 6886. | HKRVGLEEPHR; |
| 6887. | KRRVGLEEPHR; |
| 6888. | RRRVGLEEPHR; |
| 6889. | HRRVGLEEPHR; |
| 6890. | KHHLGIEEPHR; |
| 6891. | RHHLGIEEPHR; |
| 6892. | HHHLGIEEPHR; |
| 6893. | KKHLGIEEPHR; |
| 6894. | RKHLGIEEPHR; |
| 6895. | HKHLGIEEPHR; |
| 6896. | KRHLGIEEPHR; |
| 6897. | RRHLGIEEPHR; |
| 6898. | HRHLGIEEPHR; |
| 6899. | KHKLGIEEPHR; |
| 6900. | RHKLGIEEPHR; |
| 6901. | HHKLGIEEPHR; |
| 6902. | KKKLGIEEPHR; |
| 6903. | RKKLGIEEPHR; |
| 6904. | HKKLGIEEPHR; |
| 6905. | KRKLGIEEPHR; |
| 6906. | RRKLGIEEPHR; |
| 6907. | HRKLGIEEPHR; |
| 6908. | KHRLGIEEPHR; |
| 6909. | RHRLGIEEPHR; |
| 6910. | HHRLGIEEPHR; |
| 6911. | KKRLGIEEPHR; |
| 6912. | RKRLGIEEPHR; |
| 6913. | HKRLGIEEPHR; |

TABLE 7-continued

SEQ ID NO. shown to left of sequence(cont'd)

| | |
|---|---|
| 6914. | KRRLGIEEPHR; |
| 6915. | RRRLGIEEPHR; |
| 6916. | HRRLGIEEPHR; |
| 6917. | KHHIGIEEPHR; |
| 6918. | RHHIGIEEPHR; |
| 6919. | HHHIGIEEPHR; |
| 6920. | KKHIGIEEPHR; |
| 6921. | RKHIGIEEPHR; |
| 6922. | HKHIGIEEPHR; |
| 6923. | KRHIGIEEPHR; |
| 6924. | RRHIGIEEPHR; |
| 6925. | HRHIGIEEPHR; |
| 6926. | KHKIGIEEPHR; |
| 6927. | RHKIGIEEPHR; |
| 6928. | HHKIGIEEPHR; |
| 6929. | KKKIGIEEPHR; |
| 6930. | RKKIGIEEPHR; |
| 6931. | HKKIGIEEPHR; |
| 6932. | KRKIGIEEPHR; |
| 6933. | RRKIGIEEPHR; |
| 6934. | HRKIGIEEPHR; |
| 6935. | KHRIGIEEPHR; |
| 6936. | RHRIGIEEPHR; |
| 6937. | HHRIGIEEPHR; |
| 6938. | KKRIGIEEPHR; |
| 6939. | RKRIGIEEPHR; |
| 6940. | HKRIGIEEPHR; |
| 6941. | KRRIGIEEPHR; |
| 6942. | RRRIGIEEPHR; |
| 6943. | HRRIGIEEPHR; |
| 6944. | KHHVGIEEPHR; |
| 6945. | RHHVGIEEPHR; |
| 6946. | HHHVGIEEPHR; |
| 6947. | KKHVGIEEPHR; |
| 6948. | RKHVGIEEPHR; |
| 6949. | HKHVGIEEPHR; |
| 6950. | KRHVGIEEPHR; |
| 6951. | RRHVGIEEPHR; |
| 6952. | HRHVGIEEPHR; |

TABLE 7-continued

SEQ ID NO. shown to left of sequence(cont'd)

| | |
|---|---|
| 6953. | KHKVGIEEPHR; |
| 6954. | RHKVGIEEPHR; |
| 6955. | HHKVGIEEPHR; |
| 6956. | KKKVGIEEPHR; |
| 6957. | RKKVGIEEPHR; |
| 6958. | HKKVGIEEPHR; |
| 6959. | KRKVGIEEPHR; |
| 6960. | RRKVGIEEPHR; |
| 6961. | HRKVGIEEPHR; |
| 6962. | KHRVGIEEPHR; |
| 6963. | RHRVGIEEPHR; |
| 6964. | HHRVGIEEPHR; |
| 6965. | KKRVGIEEPHR; |
| 6966. | RKRVGIEEPHR; |
| 6967. | HKRVGIEEPHR; |
| 6968. | KRRVGIEEPHR; |
| 6969. | RRRVGIEEPHR; |
| 6970. | HRRVGIEEPHR; |
| 6971. | KHHLGVEEPHR; |
| 6972. | RHHLGVEEPHR; |
| 6973. | HHHLGVEEPHR; |
| 6974. | KKHLGVEEPHR; |
| 6975. | RKHLGVEEPHR; |
| 6976. | HKHLGVEEPHR; |
| 6977. | KRHLGVEEPHR; |
| 6978. | RRHLGVEEPHR; |
| 6979. | HRHLGVEEPHR; |
| 6980. | KHKLGVEEPHR; |
| 6981. | RHKLGVEEPHR; |
| 6982. | HHKLGVEEPHR; |
| 6983. | KKKLGVEEPHR; |
| 6984. | RKKLGVEEPHR; |
| 6985. | HKKLGVEEPHR; |
| 6986. | KRKLGVEEPHR; |
| 6987. | RRKLGVEEPHR; |
| 6988. | HRKLGVEEPHR; |
| 6989. | KHRLGVEEPHR; |
| 6990. | RHRLGVEEPHR; |
| 6991. | HHRLGVEEPHR; |

TABLE 7-continued

SEQ ID NO. shown to left of sequence(cont'd)

| | |
|---|---|
| 6992. | KKRLGVEEPHR; |
| 6993. | RKRLGVEEPHR; |
| 6994. | HKRLGVEEPHR; |
| 6995. | KRRLGVEEPHR; |
| 6996. | RRRLGVEEPHR; |
| 6997. | HRRLGVEEPHR; |
| 6998. | KHHIGVEEPHR; |
| 6999. | RHHIGVEEPHR; |
| 7000. | HHHIGVEEPHR; |
| 7001. | KKHIGVEEPHR; |
| 7002. | RKHIGVEEPHR; |
| 7003. | HKHIGVEEPHR; |
| 7004. | KRHIGVEEPHR; |
| 7005. | RRHIGVEEPHR; |
| 7006. | HRHIGVEEPHR; |
| 7007. | KHKIGVEEPHR; |
| 7008. | RHKIGVEEPHR; |
| 7009. | HHKIGVEEPHR; |
| 7010. | KKKIGVEEPHR; |
| 7011. | RKKIGVEEPHR; |
| 7012. | HKKIGVEEPHR; |
| 7013. | KRKIGVEEPHR; |
| 7014. | RRKIGVEEPHR; |
| 7015. | HRKIGVEEPHR; |
| 7016. | KHRIGVEEPHR; |
| 7017. | RHRIGVEEPHR; |
| 7018. | HHRIGVEEPHR; |
| 7019. | KKRIGVEEPHR; |
| 7020. | RKRIGVEEPHR; |
| 7021. | HKRIGVEEPHR; |
| 7022. | KRRIGVEEPHR; |
| 7023. | RRRIGVEEPHR; |
| 7024. | HRRIGVEEPHR; |
| 7025. | KHHVGVEEPHR; |
| 7026. | RHHVGVEEPHR; |
| 7027. | HHHVGVEEPHR; |
| 7028. | KKHVGVEEPHR; |
| 7029. | RKHVGVEEPHR; |
| 7030. | HKHVGVEEPHR; |

TABLE 7-continued

SEQ ID NO. shown to left of sequence(cont'd)

| | |
|---|---|
| 7031. | KRHVGVEEPHR; |
| 7032. | RRHVGVEEPHR; |
| 7033. | HRHVGVEEPHR; |
| 7034. | KHKVGVEEPHR; |
| 7035. | RHKVGVEEPHR; |
| 7036. | HHKVGVEEPHR; |
| 7037. | KKKVGVEEPHR; |
| 7038. | RKKVGVEEPHR; |
| 7039. | HKKVGVEEPHR; |
| 7040. | KRKVGVEEPHR; |
| 7041. | RRKVGVEEPHR; |
| 7042. | HRKVGVEEPHR; |
| 7043. | KHRVGVEEPHR; |
| 7044. | RHRVGVEEPHR; |
| 7045. | HHRVGVEEPHR; |
| 7046. | KKRVGVEEPHR; |
| 7047. | RKRVGVEEPHR; |
| 7048. | HKRVGVEEPHR; |
| 7049. | KRRVGVEEPHR; |
| 7050. | RRRVGVEEPHR; |
| 7051. | HRRVGVEEPHR; |
| 7052. | KHHLGLNEPHR; |
| 7053. | RHHLGLNEPHR; |
| 7054. | HHHLGLNEPHR; |
| 7055. | KKHLGLNEPHR; |
| 7056. | RKHLGLNEPHR; |
| 7057. | HKHLGLNEPHR; |
| 7058. | KRHLGLNEPHR; |
| 7059. | RRHLGLNEPHR; |
| 7060. | HRHLGLNEPHR; |
| 7061. | KHKLGLNEPHR; |
| 7062. | RHKLGLNEPHR; |
| 7063. | HHKLGLNEPHR; |
| 7064. | KKKLGLNEPHR; |
| 7065. | RKKLGLNEPHR; |
| 7066. | HKKLGLNEPHR; |
| 7067. | KRKLGLNEPHR; |
| 7068. | RRKLGLNEPHR; |
| 7069. | HRKLGLNEPHR; |

TABLE 7-continued

SEQ ID NO. shown to left of sequence(cont'd)

| SEQ ID NO. | Sequence |
|---|---|
| 7070. | KHRLGLNEPHR; |
| 7071. | RHRLGLNEPHR; |
| 7072. | HHRLGLNEPHR; |
| 7073. | KKRLGLNEPHR; |
| 7074. | RKRLGLNEPHR; |
| 7075. | HKRLGLNEPHR; |
| 7076. | KRRLGLNEPHR; |
| 7077. | RRRLGLNEPHR; |
| 7078. | HRRLGLNEPHR; |
| 7079. | KHHIGLNPHR; |
| 7080. | RHHIGLNEPHR; |
| 7081. | HHHIGLNEPHR; |
| 7082. | KKHIGLNEPHR; |
| 7083. | RKHIGLNEPHR; |
| 7084. | HKHIGLNEPHR; |
| 7085. | KRHIGLNEPHR; |
| 7086. | RRHIGLNEPHR; |
| 7087. | HRHIGLNEPHR; |
| 7088. | KHKIGLNEPHR; |
| 7089. | RHKIGLNEPHR; |
| 7090. | HHKIGLNEPHR; |
| 7091. | KKKIGLNEPHR; |
| 7092. | RKKIGLNEPHR; |
| 7093. | HKKIGLNEPHR; |
| 7094. | KRKIGLNEPHR; |
| 7095. | RRKIGLNEPHR; |
| 7096. | HRKIGLNEPHR; |
| 7097. | KHRIGLNEPHR; |
| 7098. | RHRIGLNEPHR; |
| 7099. | HHRIGLNEPHR; |
| 7100. | KKRIGLNEPHR; |
| 7101. | RKRIGLNEPHR; |
| 7102. | HKRIGLNEPHR; |
| 7103. | KRRIGLNEPHR; |
| 7104. | RRRIGLNEPHR; |
| 7105. | HRRIGLNEPHR; |
| 7106. | KHHVGLNEPHR; |
| 7107. | RHHVGLNEPHR; |
| 7108. | HHHVGLNEPHR; |
| 7109. | KKHVGLNEPHR; |
| 7110. | RKHVGLNEPHR; |
| 7111. | HKHVGLNEPHR; |
| 7112. | KRHVGLNEPHR; |
| 7113. | RRHVGLNEPHR; |
| 7114. | HRHVGLNEPHR; |
| 7115. | KHKVGLNEPHR; |
| 7116. | RHKVGLNEPHR; |
| 7117. | HHKVGLNEPHR; |
| 7118. | KKKVGLNEPHR; |
| 7119. | RKKVGLNEPHR; |
| 7120. | HKKVGLNEPHR; |
| 7121. | KRKVGLNEPHR; |
| 7122. | RRKVGLNEPHR; |
| 7123. | HRKVGLNEPHR; |
| 7124. | KHRVGLNEPHR; |
| 7125. | RHRVGLNEPHR; |
| 7126. | HHRVGLNEPHR; |
| 7127. | KKRVGLNEPHR; |
| 7128. | RKRVGLNEPHR; |
| 7129. | HKRVGLNEPHR; |
| 7130. | KRRVGLNEPHR; |
| 7131. | RRRVGLNEPHR; |
| 7132. | HRRVGLNEPHR; |
| 7133. | KHHLGINEPHR; |
| 7134. | RHHLGINEPHR; |
| 7135. | HHHLGINEPHR; |
| 7136. | KKHLGINEPHR; |
| 7137. | RKHLGINEPHR; |
| 7138. | HKHLGINEPHR; |
| 7139. | KRHLGINEPHR; |
| 7140. | RRHLGINEPHR; |
| 7141. | HRHLGINEPHR; |
| 7142. | KHKLGINEPHR; |
| 7143. | RHKLGINEPHR; |
| 7144. | HHKLGINEPHR; |
| 7145. | KKKLGINEPHR; |
| 7146. | RKKLGINEPHR; |
| 7147. | HKKLGINEPHR; |

TABLE 7-continued

SEQ ID NO. shown to left of sequence (cont'd)

| | |
|---|---|
| 7148. | KRKLGINEPHR; |
| 7149. | RRKLGINEPHR; |
| 7150. | HRKLGINEPHR; |
| 7151. | KHRLGINEPHR; |
| 7152. | RHRLGINEPHR; |
| 7153. | HHRLGINEPHR; |
| 7154. | KKRLGINEPHR; |
| 7155. | RKRLGINEPHR; |
| 7156. | HKRLGLNEPHR; |
| 7157. | KRRLGINEPHR; |
| 7158. | RRRLGINEPHR; |
| 7159. | HRRLGINEPHR; |
| 7160. | KHHIGIENPHR; |
| 7161. | RHHIGINEPHR; |
| 7162. | HHHIGINEPHR; |
| 7163. | KKHIGINEPHR; |
| 7164. | RKHIGLNEPHR; |
| 7165. | HKHIGINEPHR; |
| 7166. | KRHLGINEPHR; |
| 7167. | RRHIGINEPHR; |
| 7168. | HRHIGINEPHR; |
| 7169. | KHKIGINEPHR; |
| 7170. | RHKIGINEPHR; |
| 7171. | HHKIGINEPHR; |
| 7172. | KKKIGINEPHR; |
| 7173. | RKKIGINEPHR; |
| 7174. | HKKIGINEPHR; |
| 7175. | KRKIGINEPHR; |
| 7176. | RRKIGINEPHR; |
| 7177. | HRKIGINEPHR; |
| 7178. | KHRIGINEPHR; |
| 7179. | RHRIGINEPHR; |
| 7180. | HHRIGINEPHR; |
| 7181. | KKRIGINEPHR; |
| 7182. | RKRIGINEPHR; |
| 7183. | HKRIGINEPHR; |
| 7184. | KRRIGINEPHR; |
| 7185. | RRRIGINEPHR; |
| 7186. | HRRIGINEPHR; |

TABLE 7-continued

SEQ ID NO. shown to left of sequence (cont'd)

| | |
|---|---|
| 7187. | KHHVGINEPHR; |
| 7188. | RHHVGINEPHR; |
| 7189. | HHHVGINEPHR; |
| 7190. | KKHVGINEPHR; |
| 7191. | RKHVGINEPHR; |
| 7192. | HKHVGINEPHR; |
| 7193. | KRHVGINEPHR; |
| 7194. | RRHVGINEPHR; |
| 7195. | HRHVGINEPHR; |
| 7196. | KHKVGINEPHR; |
| 7197. | RHKVGINEPHR; |
| 7198. | HHKVGINEPHR; |
| 7199. | KKKVGINEPHR; |
| 7200. | RKHVGINEPHR; |
| 7201. | HKKVGINEPHR; |
| 7202. | KRKVGINEPHR; |
| 7203. | RRKVGINEPHR; |
| 7204. | HRKVGINEPHR; |
| 7205. | KHRVGINEPHR; |
| 7206. | RHRVGINEPHR; |
| 7207. | HHRVGINEPHR; |
| 7208. | KKRVGINEPHR; |
| 7209. | RKRVGINEPHR; |
| 7210. | HKRVGINEPHR; |
| 7211. | KRRVGINEPHR; |
| 7212. | RRRVGINEPHR; |
| 7213. | HRRVGINEPHR; |
| 7214. | KHHLGVNEPHR; |
| 7215. | RHHLGVNEPHR; |
| 7216. | HHHLGVNEPHR; |
| 7217. | KKHLGVNEPHR; |
| 7218. | RKHLGVNEPHR; |
| 7219. | HKHLGVNEPHR; |
| 7220. | KRHLGVNEPHR; |
| 7221. | RRHLGVNEPHR; |
| 7222. | HRHLGVNEPHR; |
| 7223. | KHKLGVNEPHR; |
| 7224. | RHKLGVNEPHR; |
| 7225. | HHKLGVNEPHR; |

TABLE 7-continued

SEQ ID NO. shown to left of sequence(cont'd)

| | |
|---|---|
| 7226. | KKKLGVNEPHR; |
| 7227. | RKKLGVNEPHR; |
| 7228. | HKKLGVNEPHR; |
| 7229. | KRKLGVNEPHR; |
| 7230. | RRKLGVNEPHR; |
| 7231. | HRKLGVNEPHR; |
| 7232. | KHRLGVNEPHR; |
| 7233. | RHRLGVNEPHR; |
| 7234. | HHRLGVNEPHR; |
| 7235. | KKRLGVNEPHR; |
| 7236. | RKRLGVNEPHR; |
| 7237. | HKRLGVNEPHR; |
| 7238. | KRRLGVNEPHR; |
| 7239. | RRRLGVNEPHR; |
| 7240. | HRRLGVNEPHR; |
| 7241. | KHHIGVNEPHR; |
| 7242. | RHHIGVNEPHR; |
| 7243. | HHHIGVNEPHR; |
| 7244. | KKHIGVNEPHR; |
| 7245. | RKHIGVNEPHR; |
| 7246. | HKHIGVNEPHR; |
| 7247. | KRHIGVNEPHR; |
| 7248. | RRHIGVNEPHR; |
| 7249. | HRHIGVNEPHR; |
| 7250. | KHKIGVNEPHR; |
| 7251. | RHKIGVNEPHR; |
| 7252. | HHKIGVNEPHR; |
| 7253. | KKKIGVNEPHR; |
| 7254. | RKKIGVNEPHR; |
| 7255. | HKKIGVNEPHR; |
| 7256. | KRKIGVNEPHR; |
| 7257. | RRKIGVNEPHR; |
| 7258. | HRKIGVNEPHR; |
| 7259. | KHRIGVNEPHR; |
| 7260. | RHRIGVNEPHR; |
| 7261. | HHRIGVNEPHR; |
| 7262. | KKRIGVNEPHR; |
| 7263. | RKRIGVNEPHR; |
| 7264. | HKRIGVNEPHR; |
| 7265. | KRRIGVNEPHR; |
| 7266. | RRRIGVNEPHR; |
| 7267. | HRRIGVNEPHR; |
| 7268. | KHHVGVNEPHR; |
| 7269. | RHHVGVNEPHR; |
| 7270. | HHHVGVNEPHR; |
| 7271. | KKHVGVNEPHR; |
| 7272. | RKHVGVNEPHR; |
| 7273. | HKHVGVNEPHR; |
| 7274. | KRHVGVNEPHR; |
| 7275. | RRHVGVNEPHR; |
| 7276. | HRHVGVNEPHR; |
| 7277. | KHKVGVNEPHR; |
| 7278. | RHKVGVNEPHR; |
| 7279. | HHKVGVNEPHR; |
| 7280. | KKKVGVNEPHR; |
| 7281. | RKKVGVNEPHR; |
| 7282. | HKKVGVNEPHR; |
| 7283. | KRKVGVNEPHR; |
| 7284. | RRKVGVNEPHR; |
| 7285. | HRKVGVNEPHR; |
| 7286. | KHRVGVNEPHR; |
| 7287. | RHRVGVNEPHR; |
| 7288. | HHRVGVNEPHR; |
| 7289. | KKRVGVNEPHR; |
| 7290. | RKRVGVNEPHR; |
| 7291. | HKRVGVNEPHR; |
| 7292. | KRRVGVNEPHR; |
| 7293. | RRRVGVNEPHR; |
| 7294. | HRRVGVNEPHR; |
| 7295. | KHHLGLENPHR; |
| 7296. | RHHLGLENPHR; |
| 7297. | HHHLGLENPHR; |
| 7298. | KKHLGLENPHR; |
| 7299. | RKHLGLENPHR; |
| 7300. | HKHLGLENPHR; |
| 7301. | KRHLGLENPHR; |
| 7302. | RRHLGLENPHR; |
| 7303. | HRHLGLENPHR; |

TABLE 7-continued

SEQ ID NO. shown to left of sequence(cont'd)

| | |
|---|---|
| 7304. | KHKLGLENPHR; |
| 7305. | RHKLGLENPHR; |
| 7306. | HHKLGLENPHR; |
| 7307. | KKKLGLENPHR; |
| 7308. | RKKLGLENPHR; |
| 7309. | HKKLGLENPHR; |
| 7310. | KRKLGLENPHR; |
| 7311. | RRKLGLENPHR; |
| 7312. | HRKLGLENPHR; |
| 7313. | KHRLGLENPHR; |
| 7314. | RHRLGLENPHR; |
| 7315. | HHRLGLENPHR; |
| 7316. | KKRLGLENPHR; |
| 7317. | RKRLGLENPHR; |
| 7318. | HKRLGLENPHR; |
| 7319. | KRRLGLENPHR; |
| 7320. | RRRLGLENPHR; |
| 7321. | HRRLGLENPHR; |
| 7322. | KHHIGLENPHR; |
| 7323. | RHHIGLENPHR; |
| 7324. | HHHIGLENPHR; |
| 7325. | KKHIGLENPHR; |
| 7326. | RKHIGLENPHR; |
| 7327. | HKHIGLENPHR; |
| 7328. | KRHIGLENPHR; |
| 7329. | RRHIGLENPHR; |
| 7330. | HRHIGLENPHR; |
| 7331. | KHKIGLENPHR; |
| 7332. | RHKIGLENPHR; |
| 7333. | HHKIGLENPHR; |
| 7334. | KKKIGLENPHR; |
| 7335. | RKKIGLENPHR; |
| 7336. | HKKIGLENPHR; |
| 7337. | KRKIGLENPHR; |
| 7338. | RRKIGLENPHR; |
| 7339. | HRKIGLENPHR; |
| 7340. | KHRIGLENPHR; |
| 7341. | RHRIGLENPHR; |
| 7342. | HHRIGLENPHR; |
| 7343. | KKRIGLENPHR; |
| 7344. | RKRIGLENPHR; |
| 7345. | HKRIGLENPHR; |
| 7346. | KRRIGLENPHR; |
| 7347. | RRRIGLENPHR; |
| 7348. | HRRIGLENPHR; |
| 7349. | KHHVGLENPHR; |
| 7350. | RHHVGLENPHR; |
| 7351. | HHHVGLENPHR; |
| 7352. | KKHVGLENPHR; |
| 7353. | RKHVGLENPHR; |
| 7354. | HKHVGLENPHR; |
| 7355. | KRHVGLENPHR; |
| 7356. | RRHVGLENPHR; |
| 7357. | HRHVGLENPHR; |
| 7358. | KHKVGLENPHR; |
| 7359. | RHKVGLENPHR; |
| 7360. | HHKVGLENPHR; |
| 7361. | KKKVGLENPHR; |
| 7362. | RKKVGLENPHR; |
| 7363. | HKKVGLENPHR; |
| 7364. | KRKVGLENPHR; |
| 7365. | RRKVGLENPHR; |
| 7366. | HRKVGLENPHR; |
| 7367. | KHRVGLENPHR; |
| 7368. | RHRVGLENPHR; |
| 7369. | HHRVGLENPHR; |
| 7370. | KKRVGLENPHR; |
| 7371. | RKRVGLENPHR; |
| 7372. | HKRVGLENPHR; |
| 7373. | KRRVGLENPHR; |
| 7374. | RRRVGLENPHR; |
| 7375. | HRRVGLENPHR; |
| 7376. | KHHLGIENPHR; |
| 7377. | RHHLGIENPHR; |
| 7378. | HHHLGIENPHR; |
| 7379. | KKHLGIENPHR; |
| 7380. | RKHLGIENPHR; |
| 7381. | HKHLGIENPHR; |

TABLE 7-continued

SEQ ID NO. shown to left of sequence(cont'd)

| SEQ ID NO. | Sequence |
|---|---|
| 7382. | KRHLGIENPHR; |
| 7383. | RRHLGIENPHR; |
| 7384. | HRHLGIENPHR; |
| 7385. | KHKLGIENPHR; |
| 7386. | RHKLGIENPHR; |
| 7387. | HHKLGIENPHR; |
| 7388. | KKKLGIENPHR; |
| 7389. | RKKLGIENPHR; |
| 7390. | HKKLGIENPHR; |
| 7391. | KRKLGIENPHR; |
| 7392. | RRKLGIENPHR; |
| 7393. | HRKLGIENPHR; |
| 7394. | KHRLGIENPHR; |
| 7395. | RHRLGIENPHR; |
| 7396. | HHRLGIENPHR; |
| 7397. | KKRLGIENPHR; |
| 7398. | RKRLGIENPHR; |
| 7399. | HKRLGIENPHR; |
| 7400. | KRRLGIENPHR; |
| 7401. | RRRLGIENPHR; |
| 7402. | HRRLGIENPHR; |
| 7403. | KHHIGIENPHR; |
| 7404. | RHHIGIENPHR; |
| 7405. | HHHIGIENPHR; |
| 7406. | KKHIGIENPHR; |
| 7407. | RKHIGIENPHR; |
| 7408. | HKHIGIENPHR; |
| 7409. | KRHIGIENPHR; |
| 7410. | RRHIGIENPHR; |
| 7411. | HRHIGIENPHR; |
| 7412. | KHKIGIENPHR; |
| 7413. | RHKIGIENPHR; |
| 7414. | HHKIGIENPHR; |
| 7415. | KKKIGIENPHR; |
| 7416. | RKKIGIENPHR; |
| 7417. | HKKIGIENPHR; |
| 7418. | KRKIGIENPHR; |
| 7419. | RKKIGIENPHR; |
| 7420. | HRKIGIENPHR; |
| 7421. | KHRIGIENPHR; |
| 7422. | RHRIGIENPHR; |
| 7423. | HHRIGIENPHR; |
| 7424. | KKRIGIENPHR; |
| 7425. | RKRIGIENPHR; |
| 7426. | HKRIGIENPHR; |
| 7427. | KRRIGIENPHR; |
| 7428. | RRRIGIENPHR; |
| 7429. | HRRIGIENPHR; |
| 7430. | KHHVGIENPHR; |
| 7431. | RHHVGIENPHR; |
| 7432. | HHHVGIENPHR; |
| 7433. | KKHVGIENPHR; |
| 7434. | RKHVGIENPHR; |
| 7435. | HKHVGIENPHR; |
| 7436. | KRHVGIENPHR; |
| 7437. | RRHVGIENPHR; |
| 7438. | HRHVGIENPHR; |
| 7439. | KHKVGIENPHR; |
| 7440. | RHKVGIENPHR; |
| 7441. | HHKVGIENPHR; |
| 7442. | KKKVGIENPHR; |
| 7443. | RKKVGIENPHR; |
| 7444. | HKKVGIENPHR; |
| 7445. | KRKVGIENPHR; |
| 7446. | RRKVGIENPHR; |
| 7447. | HRKVGIENPHR; |
| 7448. | KHRVGIENPHR; |
| 7449. | RHRVGIENPHR; |
| 7450. | HHRVGIENPHR; |
| 7451. | KKRVGIENPHR; |
| 7452. | RKRVGIENPHR; |
| 7453. | HKRVGIENPHR; |
| 7454. | KRRVGIENPHR; |
| 7455. | RRRVGIENPHR; |
| 7456. | HRRVGIENPHR; |
| 7457. | KHHLGVENPHR; |
| 7458. | RHHLGVENPHR; |
| 7459. | HHHLGVENPHR; |

TABLE 7-continued

SEQ ID NO. shown to left of sequence(cont'd)

| SEQ ID NO. | Sequence |
|---|---|
| 7460. | KKHLGVENPHR; |
| 7461. | RKHLGVENPHR; |
| 7462. | HKHLGVENPHR; |
| 7463. | KRHLGVENPHR; |
| 7464. | RRHLGVENPHR; |
| 7465. | HRHLGVENPHR; |
| 7466. | KHKLGVENPHR; |
| 7467. | RHKLGVENPHR; |
| 7468. | HHKLGVENPHR; |
| 7469. | KKKLGVENPHR; |
| 7470. | RKKLGVENPHR; |
| 7471. | HKKLGVENPHR; |
| 7472. | KRKLGVENPHR; |
| 7473. | RRKLGVENPHR; |
| 7474. | HRKLGVENPHR; |
| 7475. | KHRLGVENPHR; |
| 7476. | RHRLGVENPHR; |
| 7477. | HHRLGVENPHR; |
| 7478. | KKRLGVENPHR; |
| 7479. | RKRLGVENPHR; |
| 7480. | HKRLGVENPHR; |
| 7481. | KRRLGVENPHR; |
| 7482. | RRRLGVENPHR; |
| 7483. | HRRLGVENPHR; |
| 7484. | KHHIGVENPHR; |
| 7485. | RHHIGVEEPHR; |
| 7486. | HHHIGVENPHR; |
| 7487. | KKHIGVENPHR; |
| 7488. | RKHIGVENPHR; |
| 7489. | HKHIGVENPHR; |
| 7490. | KRHIGVENPHR; |
| 7491. | RRHIGVENPHR; |
| 7492. | HRHIGVENPHR; |
| 7493. | KHKIGVENPHR; |
| 7494. | RHKIGVENPHR; |
| 7495. | HHKIGVENPHR; |
| 7496. | KKKIGVENPHR; |
| 7497. | RKKVGVENPHR; |
| 7498. | HKKIGVENPHR; |
| 7499. | KRKIGVENPHR; |
| 7500. | RRKIGVENPHR; |
| 7501. | HRKIGVENPHR; |
| 7502. | KHRIGVENPHR; |
| 7503. | RHRIGVENPHR; |
| 7504. | HHRIGVENPHR; |
| 7505. | KKRIGVENPHR; |
| 7506. | RKRIGVENPHR; |
| 7507. | HKRIGVENPHR; |
| 7508. | KRRIGVENPHR; |
| 7509. | RRRIGVENPHR; |
| 7510. | HRRIGVENPHR; |
| 7511. | KHHVGVENPHR; |
| 7512. | RHHVGVENPHR; |
| 7513. | HHHVGVENPHR; |
| 7514. | KKHVGVENPHR; |
| 7515. | RKHVGVENPHR; |
| 7516. | HKHVGVENPHR; |
| 7517. | KRHVGVENPHR; |
| 7518. | RRHVGVENPHR; |
| 7519. | HRHVGVENPHR; |
| 7520. | KHKVGVENPHR; |
| 7521. | RHKVGVENPHR; |
| 7522. | HHKVGVENPHR; |
| 7523. | KKKVGVENPHR; |
| 7524. | RKKVGVENPHR; |
| 7525. | HKKVGVENPHR; |
| 7526. | KRKVGVENPHR; |
| 7527. | RRKVGVEEPHR; |
| 7528. | HRKVGVENPHR; |
| 7529. | KHRVGVENPHR; |
| 7530. | RHRVGVENPHR; |
| 7531. | HHRVGVENPHR; |
| 7532. | KKRVGVENPHR; |
| 7533. | RKRVGVENPHR; |
| 7534. | HKRVGVENPHR; |
| 7535. | KRRVGVENPHR; |
| 7536. | RRRVGVENPHR; |
| 7537. | HRRVGVENPHR; |

TABLE 7-continued

SEQ ID NO. shown to left of sequence(cont'd)

| SEQ ID NO. | Sequence |
|---|---|
| 7538. | KHHLGLNNPHR; |
| 7539. | RHHLGLNNPHR; |
| 7540. | HHHLGLNNPHR; |
| 7541. | KKHLGLNNPHR; |
| 7542. | RKHLGLNNPHR; |
| 7543. | HKHLGLNNPHR; |
| 7544. | KRHLGLNNPHR; |
| 7545. | RRHLGLNNPHR; |
| 7546. | HRHLGLNNPHR; |
| 7547. | KHKLGLNNPHR; |
| 7548. | RHKLGLNNPHR; |
| 7549. | HHKLGLNNPHR; |
| 7550. | KKKLGLNNPHR; |
| 7551. | RKKLGLNNPHR; |
| 7552. | HKKLGLNNPHR; |
| 7553. | KRKLGLNNPHR; |
| 7554. | RRKLGLNNPHR; |
| 7555. | HRKLGLNNPHR; |
| 7556. | KHRLGLNNPHR; |
| 7557. | RHRLGLNNPHR; |
| 7558. | HHRLGLNNPHR; |
| 7559. | KKRLGLNNPHR; |
| 7560. | RKRLGLNNPHR; |
| 7561. | HKRLGLNNPHR; |
| 7562. | KRRLGLNNPHR; |
| 7563. | RRRLGLNNPHR; |
| 7564. | HRRLGLNNPHR; |
| 7565. | KHHIGLNNPHR; |
| 7566. | RHHIGLNNPHR; |
| 7567. | HHHIGLNNPHR; |
| 7568. | KKHIGLNNPHR; |
| 7569. | RKHIGLNNPHR; |
| 7570. | HKHIGLNNPHR; |
| 7571. | KRHIGLNNPHR; |
| 7572. | RRHIGLNNPHR; |
| 7573. | HRHIGLNNPHR; |
| 7574. | KHKIGLNNPHR; |
| 7575. | RHKIGLNNPHR; |
| 7576. | HHKIGLNNPHR; |
| 7577. | KKKIGLNNPHR; |
| 7578. | RKKIGLNNPHR; |
| 7579. | HKKIGLNNPHR; |
| 7580. | KRKIGLNNPHR; |
| 7581. | RRKIGLNNPHR; |
| 7582. | HRKIGLNNPHR; |
| 7583. | KHRIGLNNPHR; |
| 7584. | RHRIGLNNPHR; |
| 7585. | HHRIGLNNPHR; |
| 7586. | KKRIGLNNPHR; |
| 7587. | RKRIGLNNPHR; |
| 7588. | HKRIGLNNPHR; |
| 7589. | KRRIGLNNPHR; |
| 7590. | RRRIGLNNPHR; |
| 7591. | HRRIGLNNPHR; |
| 7592. | KHHVGLNNPHR; |
| 7593. | RHHVGLNNPHR; |
| 7594. | HHHVGLNNPHR; |
| 7595. | KKHVGLNNPHR; |
| 7596. | RKHVGLNNPHR; |
| 7597. | HKHVGLNNPHR; |
| 7598. | KRHVGLNNPHR; |
| 7599. | RRHVGLNNPHR; |
| 7600. | HRHVGLNNPHR; |
| 7601. | KHKVGLNNPHR; |
| 7602. | RHKVGLNNPHR; |
| 7603. | HHKVGLNNPHR; |
| 7604. | KKKVGLNNPHR; |
| 7605. | RKKVGLNNPHR; |
| 7606. | HKKVGLNNPHR; |
| 7607. | KRKVGLNNPHR; |
| 7608. | RRKVGLNNPHR; |
| 7609. | HRKVGLNNPHR; |
| 7610. | KHRVGLNNPHR; |
| 7611. | RHRVGLNNPHR; |
| 7612. | HHRVGLNNPHR; |
| 7613. | KKRVGLNNPHR; |
| 7614. | RKRVGLNNPHR; |
| 7615. | HKRVGLNNPHR; |

TABLE 7-continued

SEQ ID NO. shown to left of sequence(cont'd)

| | |
|---|---|
| 7616. | KRRVGLNNPHR; |
| 7617. | RRRVGLNNPHR; |
| 7618. | HRRVGLNNPHR; |
| 7619. | KHHLGINNPHR; |
| 7620. | RHHLGINNPHR; |
| 7621. | HHHLGINNPHR; |
| 7622. | KKHLGINNPHR; |
| 7623. | RKHLGINNPHR; |
| 7624. | HKHLGINNPHR; |
| 7625. | KRHLGINNPHR; |
| 7626. | RRHLGINNPHR; |
| 7627. | HRHLGINNPHR; |
| 7628. | KHKLGINNPHR; |
| 7629. | RHKLGINNPHR; |
| 7630. | HHKLGINNPHR; |
| 7631. | KKKLGINNPHR; |
| 7632. | RKKLGINNPHR; |
| 7633. | HKKLGINNPHR; |
| 7634. | KRKLGINNPHR; |
| 7635. | RRKLGINNPHR; |
| 7636. | HRKLGINNPHR; |
| 7637. | KHRLGINNPHR; |
| 7638. | RHRLGINNPHR; |
| 7639. | HHRLGINNPHR; |
| 7640. | KKRLGINNPHR; |
| 7641. | RKRLGINNPHR; |
| 7642. | HKRLGINNPHR; |
| 7643. | KRRLGINNPHR; |
| 7644. | RRRLGINNPHR; |
| 7645. | HRRLGINNPHR; |
| 7646. | KHHIGIENPHR; |
| 7647. | RHHIGINNPHR; |
| 7648. | HHHIGINNPHR; |
| 7649. | KKHIGINNPHR; |
| 7650. | RKHIGINNPHR; |
| 7651. | HKHIGINNPHR; |
| 7652. | KRHIGINNPHR; |
| 7653. | RRHIGVNNPHR; |
| 7654. | HRHIGINNPHR; |
| 7655. | KHKIGINNPHR; |
| 7656. | RHKIGINNPHR; |
| 7657. | HHKIGINNPHR; |
| 7658. | KKKIGINNPHR; |
| 7659. | RKKIGINNPHR; |
| 7660. | HKKIGINNPHR; |
| 7661. | KRKIGINNPHR; |
| 7662. | RRKIGINNPHR; |
| 7663. | HRKIGVNNPHR; |
| 7664. | KHRIGINNPHR; |
| 7665. | RHRIGINNPHR; |
| 7666. | HHRIGINNPHR; |
| 7667. | KKRIGINNPHR; |
| 7668. | RKRIGINNPHR; |
| 7669. | HKRIGINNPHR; |
| 7670. | KRRIGINNPHR; |
| 7671. | RRRIGINNPHR; |
| 7672. | HRRIGINNPHR; |
| 7673. | KHHVGINNPHR; |
| 7674. | RHHVGINNPHR; |
| 7675. | HHHVGINNPHR; |
| 7676. | KKHVGINNPHR; |
| 7677. | RKHVGINNPHR; |
| 7678. | HKHVGINNPHR; |
| 7679. | KRHVGINNPHR; |
| 7680. | RRHVGINNPHR; |
| 7681. | HRHVGINNPHR; |
| 7682. | KHKVGINNPHR; |
| 7683. | RHKVGINNPHR; |
| 7684. | HHKVGINNPHR; |
| 7685. | KKKVGINNPHR; |
| 7686. | RKKVGINNPHR; |
| 7687. | HKKVGINNPHR; |
| 7688. | KRKVGINNPHR; |
| 7689. | RRKVGINNPHR; |
| 7690. | HRKVGINNPHR; |
| 7691. | KHRVGINNPHR; |
| 7692. | RHRVGINNPHR; |
| 7693. | HHRVGINNPHR; |

TABLE 7-continued

SEQ ID NO. shown to left of sequence(cont'd)

| | |
|---|---|
| 7694. | KKRVGINNPHR; |
| 7695. | RKRVGINNPHR; |
| 7696. | HKRVGINNPHR; |
| 7697. | KRRVGINNPHR; |
| 7698. | RRRVGINNPHR; |
| 7699. | HRHVGINNPHR; |
| 7700. | KHHLGVNNPHR; |
| 7701. | RHHLGVNNPHR; |
| 7702. | HHHLGVNNPHR; |
| 7703. | KKHLGVNNPHR; |
| 7704. | RKHLGVNNPHR; |
| 7705. | HKHLGVNNPHR; |
| 7706. | KRHLGVNNPHR; |
| 7707. | RRHLGVNNPHR; |
| 7708. | HRHLGVNNPHR; |
| 7709. | KHKLGVNNPHR; |
| 7710. | RHKLGVNNPHR; |
| 7711. | HHKLGVNNPHR; |
| 7712. | KKKLGVNNPHR; |
| 7713. | RKKLGVNNPHR; |
| 7714. | HKKLGVNNPHR; |
| 7715. | KRKLGVNNPHR; |
| 7716. | RRKLGVNNPHR; |
| 7717. | HRKLGVNNPHR; |
| 7718. | KHRLGVNNPHR; |
| 7719. | RHRLGVNNPHR; |
| 7720. | HHRLGVNNPHR; |
| 7721. | KKRLGVNNPHR; |
| 7722. | RKRLGVNNPHR; |
| 7723. | HKRLGVNNPHR; |
| 7724. | KRRLGVNNPHR; |
| 7725. | RRRLGVNNPHR; |
| 7726. | HRRLGVNNPHR; |
| 7727. | KHHIGVNNPHR; |
| 7728. | RHHIGVNNPHR; |
| 7729. | HHHIGVNNPHR; |
| 7730. | KKHIGVNNPHR; |
| 7731. | RKHIGVNNPHR; |
| 7732. | HKHIGVNNPHR; |
| 7733. | KRHIGVNNPHR; |
| 7734. | RRHIGVNNPHR; |
| 7735. | HRHIGVNNPHR; |
| 7736. | KHKIGVNNPHR; |
| 7737. | RHKIGVNNPHR; |
| 7738. | HHKIGVNNPHR; |
| 7739. | KKKIGVNNPHR; |
| 7740. | RKKIGVNNPHR; |
| 7741. | HKKIGVNNPHR; |
| 7742. | KRKIGVNNPHR; |
| 7743. | RRHIGVNNPHR; |
| 7744. | HRKIGVNNPHR; |
| 7745. | KHRIGVNNPHR; |
| 7746. | RHRIGVNNPHR; |
| 7747. | HHRIGVNNPHR; |
| 7748. | KKRIGVNNPHR; |
| 7749. | RKRIGVNNPHR; |
| 7750. | HKRIGVNNPHR; |
| 7751. | KRRIGVNNPHR; |
| 7752. | RRRIGVNNPHR; |
| 7753. | HRRIGVNNPHR; |
| 7754. | KHHVGVNNPHR; |
| 7755. | RHHVGVNNPHR; |
| 7756. | HHHVGVNNPHR; |
| 7757. | KKHVGVNNPHR; |
| 7758. | RKHVGVNNPHR; |
| 7759. | HKHVGVNNPHR; |
| 7760. | KRHVGVNNPHR; |
| 7761. | RRHVGVNNPHR; |
| 7762. | HRHVGVNNPHR; |
| 7763. | KHKVGVNNPHR; |
| 7764. | RHKVGVNNPHR; |
| 7765. | HHKVGVNNPHR; |
| 7766. | KKKVGVNNPHR; |
| 7767. | RKKVGVNNPHR; |
| 7768. | HKKVGVNNPHR; |
| 7769. | KRKVGVNNPHR; |
| 7770. | RRKVGVNNPHR; |
| 7771. | HRKVGVNNPHR; |

TABLE 7-continued

SEQ ID NO. shown to left of sequence(cont'd)

| SEQ ID | Sequence |
|---|---|
| 7772. | KHRVGVNNPHR; |
| 7773. | RHRVGVNNPHR; |
| 7774. | HHRVGVNNPHR; |
| 7775. | KKRVGVNNPHR; |
| 7776. | RKRVGVNNPHR; |
| 7777. | HKRVGVNNPHR; |
| 7778. | KRRVGVNNPHR; |
| 7779. | RRRVGVNNPHR; |
| 7780. | HRRVGVNNPHR; |
| 7781. | KHHLGLEEPHH; |
| 7782. | RHHLGLEEPHH; |
| 7783. | HHHLGLEEPHH; |
| 7784. | KKHLGLEEPHH; |
| 7785. | RKHLGLEEPHH; |
| 7786. | HKHLGLEEPHH; |
| 7787. | KRHLGLEEPHH; |
| 7788. | RRHLGLEEPHH; |
| 7789. | HRHLGLEEPHH; |
| 7790. | KHKLGLEEPHH; |
| 7791. | RHKLGLEEPHH; |
| 7792. | HHKLGLEEPHH; |
| 7793. | KKKLGLEEPHH; |
| 7794. | RKKLGLEEPHH; |
| 7795. | HKKLGLEEPHH; |
| 7796. | KRKLGLEEPHH; |
| 7797. | RRHLGLEEPHH; |
| 7798. | HRKLGLEEPHH; |
| 7799. | KHRLGLEEPHH; |
| 7800. | RHRLGLEEPHH; |
| 7801. | HHRLGLEEPHH; |
| 7802. | KKRLGLEEPHH; |
| 7803. | RKRLGLEEPHH; |
| 7804. | HKRLGLEEPHH; |
| 7805. | KRRLGLEEPHH; |
| 7806. | RRRLGLEEPHH; |
| 7807. | HRRLGLEEPHH; |
| 7808. | KHHIGLEEPHH; |
| 7809. | RHHIGLEEPHH; |
| 7810. | HHHIGLEEPHH; |
| 7811. | KKHIGLEEPHH; |
| 7812. | RKHIGLEEPHH; |
| 7813. | HKHIGLEEPHH; |
| 7814. | KRHIGLEEPHH; |
| 7815. | RRHIGLEEPHH; |
| 7816. | HRHIGLEEPHH; |
| 7817. | KHKIGLEEPHH; |
| 7818. | RHKIGLEEPHH; |
| 7819. | HHKIGLEEPHH; |
| 7820. | KKKIGLEEPHH; |
| 7821. | RKKIGLEEPHH; |
| 7822. | HKKIGLEEPHH; |
| 7823. | KRKIGLEEPHH; |
| 7824. | RRKIGLEEPHH; |
| 7825. | HRKIGLEEPHH; |
| 7826. | KHRIGLEEPHH; |
| 7827. | RHRIGLEEPHH; |
| 7828. | HHRIGLEEPHH; |
| 7829. | KKRIGLEEPHH; |
| 7830. | RKRIGLEEPHH; |
| 7831. | HKRIGLEEPHH; |
| 7832. | KRRIGLEEPHH; |
| 7833. | RRRIGLEEPHH; |
| 7834. | HRHIGLEEPHH; |
| 7835. | KHHVGLEEPHH; |
| 7836. | RHHVGLEEPHH; |
| 7837. | HHHVGLEEPHH; |
| 7838. | KKHVGLEEPHH; |
| 7839. | RKHVGLEEPHH; |
| 7840. | HKHVGLEEPHH; |
| 7841. | KRHVGLEEPHH; |
| 7842. | RRHVGLEEPHH; |
| 7843. | HRHVGLEEPHH; |
| 7844. | KHKVGLEEPHH; |
| 7845. | RHKVGLEEPHH; |
| 7846. | HHKVGLEEPHH; |
| 7847. | KKKVGLEEPHH; |
| 7848. | RKKVGLEEPHH; |
| 7849. | HKKVGLEEPHH; |

TABLE 7-continued

SEQ ID NO. shown to left of sequence(cont'd)

| SEQ ID NO. | Sequence |
|---|---|
| 7850. | KRKVGLEEPHH; |
| 7851. | RRKVGLEEPHH; |
| 7852. | HRKVGLEEPHH; |
| 7853. | KHRVGLEEPHH; |
| 7854. | RHRVGLEEPHH; |
| 7855. | HHRVGLEEPHH; |
| 7856. | KKRVGLEEPHH; |
| 7857. | RKRVGLEEPHH; |
| 7858. | HKRVGLEEPHH; |
| 7859. | KRRVGLEEPHH; |
| 7860. | RRRVGLEEPHH; |
| 7861. | HRRVGLEEPHH; |
| 7862. | KHHLGIEEPHH; |
| 7863. | RHHLGIEEPHH; |
| 7864. | HHHLGIEEPHH; |
| 7865. | KKHLGIEEPHH; |
| 7866. | RKHLGIEEPHH; |
| 7867. | HKHLGIEEPHH; |
| 7868. | KRHLGIEEPHH; |
| 7869. | RRHLGIEEPHH; |
| 7870. | HRHLGIEEPHH; |
| 7871. | KHKLGIEEPHH; |
| 7872. | RHKLGIEEPHH; |
| 7873. | HHKLGIEEPHH; |
| 7874. | KKKLGIEEPHH; |
| 7875. | RKKLGIEEPHH; |
| 7876. | HKKLGIEEPHH; |
| 7877. | KRKLGIEEPHH; |
| 7878. | RRKLGIEEPHH; |
| 7879. | HRKLGIEEPHH; |
| 7880. | KHRLGIEEPHH; |
| 7881. | RHRLGIEEPHH; |
| 7882. | HHRLGIEEPHH; |
| 7883. | KKRLGIEEPHH; |
| 7884. | RKRLGIEEPHH; |
| 7885. | HKRLGIEEPHH; |
| 7886. | KRRLGIEEPHH; |
| 7887. | RRRLGIEEPHH; |
| 7888. | HRRLGIEEPHH; |
| 7889. | KHHIGIEEPHH; |
| 7890. | RHHIGIEEPHH; |
| 7891. | HHHIGIEEPHH; |
| 7892. | KKHIGIEEPHH; |
| 7893. | RKHIGIEEPHH; |
| 7894. | HKHIGIEEPHH; |
| 7895. | KRHIGIEEPHH; |
| 7896. | RRHIGIEEPHH; |
| 7897. | HRHIGIEEPHH; |
| 7898. | KHKIGIEEPHH; |
| 7899. | RHKIGIEEPHH; |
| 7900. | HHKIGIEEPHH; |
| 7901. | KKKIGIEEPHH; |
| 7902. | RKKIGIEEPHH; |
| 7903. | HKKIGIEEPHH; |
| 7904. | KRKIGIEEPHH; |
| 7905. | RRKIGIEEPHH; |
| 7906. | HRKIGIEEPHH; |
| 7907. | KHRIGIEEPHH; |
| 7908. | RHRIGIEEPHH; |
| 7909. | HHRIGIEEPHH; |
| 7910. | KKRIGIEEPHH; |
| 7911. | RKKIGIEEPHH; |
| 7912. | HKRIGIEEPHH; |
| 7913. | KRRIGIEEPHH; |
| 7914. | RRRIGIEEPHH; |
| 7915. | HRRIGIEEPHH; |
| 7916. | KHHVGIEEPHH; |
| 7917. | RHHVGIEEPHH; |
| 7918. | HHHVGIEEPHH; |
| 7919. | KKHVGIEEPHH; |
| 7920. | RKHVGIEEPHH; |
| 7921. | HKHVGIEEPHH; |
| 7922. | KRHVGIEEPHH; |
| 7923. | RRHVGIEEPHH; |
| 7924. | HRHVGIEEPHH; |
| 7925. | KHKVGIEEPHH; |
| 7926. | RHKVGIEEPHH; |
| 7927. | HHKVGIEEPHH; |

TABLE 7-continued

SEQ ID NO. shown to left of sequence(cont'd)

| SEQ ID NO. | Sequence |
|---|---|
| 7928. | KKKVGIEEPHH; |
| 7929. | RKKVGIEEPHH; |
| 7930. | HKKVGIEEPHH; |
| 7931. | KRKVGIEEPHH; |
| 7932. | RRKVGIEEPHH; |
| 7933. | HRKVGIEEPHH; |
| 7934. | KHRVGIEEPHH; |
| 7935. | RHRVGIEEPHH; |
| 7936. | HHRVGIEEPHH; |
| 7937. | KKRVGIEEPHH; |
| 7938. | RKRVGIEEPHH; |
| 7939. | HKRVGIEEPHH; |
| 7940. | KRRVGIEEPHH; |
| 7941. | RRRVGIEEPHH; |
| 7942. | HRRVGIEEPHH; |
| 7943. | KHHLGVEEPHH; |
| 7944. | RHHLGVEEPHH; |
| 7945. | HHRLGVEEPHH; |
| 7946. | KKHLGVEEPHH; |
| 7947. | RKKLGVEEPHH; |
| 7948. | HKHLGVEEPHH; |
| 7949. | KRHLGVEEPHH; |
| 7950. | RRHLGVEEPHH; |
| 7951. | HRHLGVEEPHH; |
| 7952. | KHKLGVEEPHH; |
| 7953. | RHKLGVEEPHH; |
| 7954. | HHKLGVEEPHH; |
| 7955. | KKKLGVEEPHH; |
| 7956. | RKKLGVEEPHH; |
| 7957. | HKKLGVEEPHH; |
| 7958. | KRKLGVEEPHH; |
| 7959. | RRKLGVEEPHH; |
| 7960. | HRKLGVEEPHH; |
| 7961. | KHRLGVEEPHH; |
| 7962. | RHRLGVEEPHH; |
| 7963. | HHRLGVEEPHH; |
| 7964. | KKRLGVEEPHH; |
| 7965. | RKRLGVEEPHH; |
| 7966. | HKRLGVEEPHH; |
| 7967. | KRRLGVEEPHH; |
| 7968. | RRRLGVEEPHH; |
| 7969. | HRRLGVEEPHH; |
| 7970. | KHHIGVEEPHH; |
| 7971. | RHHIGVEEPHH; |
| 7972. | HHHIGVEEPHH; |
| 7973. | KKHIGVEEPHH; |
| 7974. | RKHIGVEEPHH; |
| 7975. | HKHIGVEEPHH; |
| 7976. | KRHIGVEEPHH; |
| 7977. | RRHIGVEEPHH; |
| 7978. | HRHIGVEEPHH; |
| 7979. | KHKIGVEEPHH; |
| 7980. | RHKIGVEEPHH; |
| 7981. | HHKIGVEEPHH; |
| 7982. | KKKIGVEEPHH; |
| 7983. | RKKIGVEEPHH; |
| 7984. | HKKIGVEEPHH; |
| 7985. | KRKIGVEEPHH; |
| 7986. | RRKIGVEEPHH; |
| 7987. | HRKIGVEEPHH; |
| 7988. | KHRIGVEEPHH; |
| 7989. | RHRIGVEEPHH; |
| 7990. | HHRIGVEEPHH; |
| 7991. | KKRIGVEEPHH; |
| 7992. | RKRIGVEEPHH; |
| 7993. | HKRIGVEEPHH; |
| 7994. | KRRIGVEEPHH; |
| 7995. | RRRIGVEEPHH; |
| 7996. | HRRIGVEEPHH; |
| 7997. | KHHVGVEEPHH; |
| 7998. | RHHVGVEEPHH; |
| 7999. | HHHVGVEEPHH; |
| 8000. | KKHVGVEEPHH; |
| 8001. | RKKVGVEEPHH; |
| 8002. | HKHVGVEEPHH; |
| 8003. | KRHVGVEEPHH; |
| 8004. | RRHVGVEEPHH; |
| 8005. | HRHVGVEEPHH; |

TABLE 7-continued

SEQ ID NO. shown to left of sequence(cont'd)

| SEQ ID | Sequence |
|---|---|
| 8006. | KHKVGVEEPHH; |
| 8007. | RHKVGVEEPHH; |
| 8008. | HHKVGVEEPHH; |
| 8009. | KKKVGVEEPHH; |
| 8010. | RKKVGVEEPHH; |
| 8011. | HKKVGVEEPHH; |
| 8012. | KRKVGVEEPHH; |
| 8013. | RRKVGVEEPHH; |
| 8014. | HRKVGVEEPHH; |
| 8015. | KHRVGVEEPHH; |
| 8016. | RHRVGVEEPHH; |
| 8017. | HHRVGVEEPHH; |
| 8018. | KKRVGVEEPHH; |
| 8019. | RKRVGVEEPHH; |
| 8020. | HKRVGVEEPHH; |
| 8021. | KRRVGVEEPHH; |
| 8022. | RRRVGVEEPHH; |
| 8023. | HRRVGVEEPHH; |
| 8024. | KHHLGLNEPHH; |
| 8025. | RHHLGLNEPHH; |
| 8026. | HHHLGLNEPHH; |
| 8027. | KKHLGLNEPHH; |
| 8028. | RKHLGLNEPHH; |
| 8029. | HKHLGLNEPHH; |
| 8030. | KRHLGLNEPHH; |
| 8031. | RRHLGLNEPHH; |
| 8032. | HRHLGLNEPHH; |
| 8033. | KHKLGLNEPHH; |
| 8034. | RHKLGLNEPHH; |
| 8035. | HHKLGLNEPHH; |
| 8036. | KKKLGLNEPHH; |
| 8037. | RKKLGLNEPHH; |
| 8038. | HKKLGLNEPHH; |
| 8039. | KRKLGLNEPHH; |
| 8040. | RRKLGLNEPHH; |
| 8041. | HRKLGLNEPHH; |
| 8042. | KHRLGLNEPHH; |
| 8043. | RHRLGLNEPHH; |
| 8044. | HHRLGLNEPHH; |
| 8045. | KKRLGLNEPHH; |
| 8046. | RKRLGLNEPHH; |
| 8047. | HKRLGLNEPHH; |
| 8048. | KRRLGLNEPHH; |
| 8049. | RRRLGLNEPHH; |
| 8050. | HRRLGLNEPHH; |
| 8051. | KHHIGLNPHH; |
| 8052. | RHHLGLNEPHH; |
| 8053. | HHHIGLNEPHH; |
| 8054. | KKHIGLNEPHH; |
| 8055. | RKHIGLNEPHH; |
| 8056. | HKHIGLNEPHH; |
| 8057. | KRHIGLNEPHH; |
| 8058. | RRHIGLNEPHH; |
| 8059. | HRHIGLNEPHH; |
| 8060. | KHKLGLNEPHH; |
| 8061. | RHKIGLNEPHH; |
| 8062. | HHKIGLNEPHH; |
| 8063. | KKKIGLNEPHH; |
| 8064. | RKKIGLNEPHH; |
| 8065. | HKKIGLNEPHH; |
| 8066. | KRKIGLNEPHH; |
| 8067. | RRKIGLNEPHH; |
| 8068. | HRKIGLNEPHH; |
| 8069. | KHRIGLNEPHH; |
| 8070. | RHRIGLNEPHH; |
| 8071. | HHRIGLNEPHH; |
| 8072. | KKRIGLNEPHH; |
| 8073. | RKRIGLNEPHH; |
| 8074. | HKRIGLNEPHH; |
| 8075. | KRRIGLNEPHH; |
| 8076. | RRRIGLNEPHH; |
| 8077. | HRRIGLNEPHH; |
| 8078. | KHHVGLNEPHH; |
| 8079. | RHHVGLNEPHH; |
| 8080. | HHHVGLNEPHH; |
| 8081. | KKHVGLNEPHH; |
| 8082. | RKHVGLNEPHH; |
| 8083. | HKHVGLNEPHH; |

TABLE 7-continued

SEQ ID NO. shown to left of sequence(cont'd)

| | |
|---|---|
| 8084. | KRHVGLNEPHH; |
| 8085. | RRHVGLNEPHH; |
| 8086. | HRHVGLNEPHH; |
| 8087. | KHKVGLNEPHH; |
| 8088. | RHKVGLNEPHH; |
| 8089. | HHKVGLNEPHH; |
| 8090. | KKKVGLNEPHH; |
| 8091. | RKKVGLNEPHH; |
| 8092. | HKKVGLNEPHH; |
| 8093. | KRKVGLNEPHH; |
| 8094. | RRKVGLNEPHH; |
| 8095. | HRKVGLNEPHH; |
| 8096. | KHRVGLNEPHH; |
| 8097. | RHRVGLNEPHH; |
| 8098. | HHRVGLNEPHH; |
| 8099. | KKRVGLNEPHH; |
| 8100. | RKRVGLNEPHH; |
| 8101. | HKRVGLNEPHH; |
| 8102. | KRRVGLNEPHH; |
| 8103. | RRRVGLNEPHH; |
| 8104. | HRRVGLNEPHH; |
| 8105. | KHHLGINEPHH; |
| 8106. | RHHLGINEPHH; |
| 8107. | HHHLGINEPHH; |
| 8108. | KKHLGVNEPHH; |
| 8109. | RKHLGINEPHH; |
| 8110. | HKHLGINEPHH; |
| 8111. | KRHLGINEPHH; |
| 8112. | RRHLGINEPHH; |
| 8113. | HRHLGINEPHH; |
| 8114. | KHKLGINEPHH; |
| 8115. | RHKLGINEPHH; |
| 8116. | HHKLGINEPHH; |
| 8117. | KKKLGINEPHH; |
| 8118. | RKKLGINEPHH; |
| 8119. | HKKLGINEPHH; |
| 8120. | KRKLGINEPHH; |
| 8121. | RHKLGINEPHH; |
| 8122. | HRKLGINEPHH; |

TABLE 7-continued

SEQ ID NO. shown to left of sequence(cont'd)

| | |
|---|---|
| 8123. | KHRLGINEPHH; |
| 8124. | RHRLGINEPHH; |
| 8125. | HHRLGINEPHH; |
| 8126. | KKRLGINEPHH; |
| 8127. | RKRLGINEPHH; |
| 8128. | HKRLGINEPHH; |
| 8129. | KRRLGINEPHH; |
| 8130. | RRRLGINEPHH; |
| 8131. | HRRLGINEPHH; |
| 8132. | KHHIGIENPHH; |
| 8133. | RHHIGINEPHH; |
| 8134. | HHHIGINEPHH; |
| 8135. | KKHIGINEPHH; |
| 8136. | RKHIGINEPHH; |
| 8137. | HKHIGINEPHH; |
| 8138. | KRHIGINEPHH; |
| 8139. | RRHIGINEPHH; |
| 8140. | HRHIGINEPHH; |
| 8141. | KHKIGINEPHH; |
| 8142. | RHKIGINEPHH; |
| 8143. | HHKIGINEPHH; |
| 8144. | KKKIGINEPHH; |
| 8145. | RKKIGINEPHH; |
| 8146. | HKKIGINEPHH; |
| 8147. | KRKIGINEPHH; |
| 8148. | RRKIGINEPHH; |
| 8149. | HRKIGINEPHH; |
| 8150. | KHRIGINEPHH; |
| 8151. | RHRIGINEPHH; |
| 8152. | HHRIGINEPHH; |
| 8153. | KKRIGINEPHH; |
| 8154. | RKRIGINEPHH; |
| 8155. | HKRIGINEPHH; |
| 8156. | KRRIGINEPHH; |
| 8157. | RRRIGINEPHH; |
| 8158. | HRHIGINEPHH; |
| 8159. | KHHVGINEPHH; |
| 8160. | RHHVGINEPHH; |
| 8161. | HHHVGINEPHH; |

TABLE 7-continued

SEQ ID NO. shown to left of sequence(cont'd)

| | |
|---|---|
| 8162. | KKHVGINEPHH; |
| 8163. | RKHVGINEPHH; |
| 8164. | HKHVGINEPHH; |
| 8165. | KRHVGINEPHH; |
| 8166. | RRHVGINEPHH; |
| 8167. | HRHVGINEPHH; |
| 8168. | KHKVGINEPHH; |
| 8169. | RHKVGINEPHH; |
| 8170. | HHKVGINEPHH; |
| 8171. | KKKVGINEPHH; |
| 8172. | RKKVGINEPHH; |
| 8173. | HKKVGINEPHH; |
| 8174. | KRKVGINEPHH; |
| 8175. | RRKVGINEPHH; |
| 8176. | HRKVGINEPHH; |
| 8177. | KHRVGINEPHH; |
| 8178. | RHRVGINEPHH; |
| 8179. | HHRVGINEPHH; |
| 8180. | KKRVGINEPHH; |
| 8181. | RKRVGINEPHH; |
| 8182. | HKRVGINEPHH; |
| 8183. | KRRVGINEPHH; |
| 8184. | RRRVGINEPHH; |
| 8185. | HRRVGINEPHH; |
| 8186. | KHHLGVNEPHH; |
| 8187. | RHHLGVNEPHH; |
| 8188. | HHHLGVNEPHH; |
| 8189. | KKHLGVNEPHH; |
| 8190. | RKHLGVNEPHH; |
| 8191. | HKHLGVNEPHH; |
| 8192. | KRHLGVNEPHH; |
| 8193. | RRHLGVNEPHH; |
| 8194. | HRHLGVNEPHH; |
| 8195. | KHKLGVNEPHH; |
| 8196. | RHKLGVNEPHH; |
| 8197. | HHKLGVNEPHH; |
| 8198. | KKKLGVNEPHH; |
| 8199. | RKKLGVNEPHH; |
| 8200. | HKKLGVNEPHH; |
| 8201. | KRKLGVNEPHH; |
| 8202. | RRKLGVNEPHH; |
| 8203. | HRKLGVNEPHH; |
| 8204. | KHHLGVNEPHH; |
| 8205. | RHRLGVNEPHH; |
| 8206. | HHRLGVNEPHH; |
| 8207. | KKRLGVNEPHH; |
| 8208. | RKRLGVNEPHH; |
| 8209. | HKRLGVNEPHH; |
| 8210. | KRRLGVNEPHH; |
| 8211. | RRRLGVNEPHH; |
| 8212. | HRRLGVNEPHH; |
| 8213. | KHHIGVNEPHH; |
| 8214. | RHHIGVNEPHH; |
| 8215. | HHHIGVNEPHH; |
| 8216. | KKHIGVNEPHH; |
| 8217. | RKHIGVNEPHH; |
| 8218. | HKHIGVNEPHH; |
| 8219. | KRHIGVNEPHH; |
| 8220. | RRHIGVNEPHH; |
| 8221. | HRHIGVNEPHH; |
| 8222. | KHKIGVNEPHH; |
| 8223. | RHKIGVNEPHH; |
| 8224. | HHKIGVNEPHH; |
| 8225. | KKKIGVNEPHH; |
| 8226. | RKKIGVNEPHH; |
| 8227. | HKKIGVNEPHH; |
| 8228. | KRKIGVNEPHH; |
| 8229. | RRKIGVNEPHH; |
| 8230. | HRKIGVNEPHH; |
| 8231. | KHRIGVNEPHH; |
| 8232. | RHRIGVNEPHH; |
| 8233. | HHRIGVNEPHH; |
| 8234. | KKRIGVNEPHH; |
| 8235. | RKRIGVNEPHH; |
| 8236. | HKRIGVNEPHH; |
| 8237. | KRRIGVNEPHH; |
| 8238. | RRRIGVNEPHH; |
| 8239. | HRRIGVNEPHH; |

TABLE 7-continued

SEQ ID NO. shown to left of sequence(cont'd)

| SEQ ID NO. | Sequence |
|---|---|
| 8240. | KHHVGVNEPHH; |
| 8241. | RHHVGVNEPHH; |
| 8242. | HHHVGVNEPHH; |
| 8243. | KKHVGVNEPHH; |
| 8244. | RKHVGVNEPHH; |
| 8245. | HKHVGVNEPHH; |
| 8246. | KRHVGVNEPHH; |
| 8247. | RRHVGVNEPHH; |
| 8248. | HRHVGVNEPHH; |
| 8249. | KKKVGVNEPHH; |
| 8250. | RHKVGVNEPHH; |
| 8251. | HHKVGVNEPHH; |
| 8252. | KKKVGVNEPHH; |
| 8253. | RKKVGVNEPHH; |
| 8254. | HKKVGVNEPHH; |
| 8255. | KRKVGVNEPHH; |
| 8256. | RRKVGVNEPHH; |
| 8257. | HRKVGVNEPHH; |
| 8258. | KHRVGVNEPHH; |
| 8259. | RHRVGVNEPHH; |
| 8260. | HHRVGVNEPHH; |
| 8261. | KKRVGVNEPHH; |
| 8262. | RKRVGVNEPHH; |
| 8263. | HKRVGVNEPHH; |
| 8264. | KRRVGVNEPHH; |
| 8265. | RRRVGVNEPHH; |
| 8266. | HRRVGVNEPHH; |
| 8267. | KHHLGLENPHH; |
| 8268. | RHHLGLENPHH; |
| 8269. | HHHLGLENPHH; |
| 8270. | KKHLGLENPHH; |
| 8271. | RKHLGLENPHH; |
| 8272. | HKHLGLENPHH; |
| 8273. | KRHLGLENPHH; |
| 8274. | RRHLGLENPHH; |
| 8275. | HRHLGLENPHH; |
| 8276. | KHKLGLENPHH; |
| 8277. | RHKLGLENPHH; |
| 8278. | HHKLGLENPHH; |
| 8279. | KKKLGLENPHH; |
| 8280. | RKKLGLENPHH; |
| 8281. | HKKLGLENPHH; |
| 8282. | KRKLGLENPHH; |
| 8283. | RRKLGLENPHH; |
| 8284. | HRKLGLENPHH; |
| 8285. | KHRLGLENPHH; |
| 8286. | RHRLGLENPHH; |
| 8287. | HHRLGLENPHH; |
| 8288. | KKRLGLENPHH; |
| 8289. | RKRLGLENPHH; |
| 8290. | HKRLGLENPHH; |
| 8291. | KRRLGLENPHH; |
| 8292. | RRRLGLENPHH; |
| 8293. | HRRLGLENPHH; |
| 8294. | KHHIGLENPHH; |
| 8295. | RHHIGLENPHH; |
| 8296. | HHHIGLENPHH; |
| 8297. | KKHIGLENPHH; |
| 8298. | RKHIGLENPHH; |
| 8299. | HKHIGLENPHH; |
| 8300. | KRHIGLENPHH; |
| 8301. | RRHIGLENPHH; |
| 8302. | HRHIGLENPHH; |
| 8303. | KHKIGLENPHH; |
| 8304. | RHKIGLENPHH; |
| 8305. | HHKIGLENPHH; |
| 8306. | KKKIGLENPHH; |
| 8307. | RKKIGLENPHH; |
| 8308. | HKKIGLENPHH; |
| 8309. | KRKIGLENPHH; |
| 8310. | RRKIGLENPHH; |
| 8311. | HRKIGLENPHH; |
| 8312. | KHRIGLENPHH; |
| 8313. | RHRIGLENPHH; |
| 8314. | HHRIGLENPHH; |
| 8315. | KKRIGLENPHH; |
| 8316. | RKRIGLENPHH; |
| 8317. | HKRIGLENPHH; |

TABLE 7-continued

SEQ ID NO. shown to left of sequence(cont'd)

| | |
|---|---|
| 8318. | KRRIGLENPHH; |
| 8319. | RRRIGLENPHH; |
| 8320. | HRRIGLENPHH; |
| 8321. | KHHVGLENPHH; |
| 8322. | RHHVGLENPHH; |
| 8323. | HHHVGLENPHH; |
| 8324. | KKHVGLENPHH; |
| 8325. | RKHVGLENPHH; |
| 8326. | HKHVGLENPHH; |
| 8327. | KRHVGLENPHH; |
| 8328. | RRHVGLENPHH; |
| 8329. | HRHVGLENPHH; |
| 8330. | KHKVGLENPHH; |
| 8331. | RHKVGLENPHH; |
| 8332. | HHKVGLENPHH; |
| 8333. | KKKVGLENPHH; |
| 8334. | RKKVGLENPHH; |
| 8335. | HKKVGLENPHH; |
| 8336. | KRKVGLENPHH; |
| 8337. | RRKVGLENPHH; |
| 8338. | HRKVGLENPHH; |
| 8339. | KHRVGLENPHH; |
| 8340. | RHRVGLENPHH; |
| 8341. | HHRVGLENPHH; |
| 8342. | KKRVGLENPHH; |
| 8343. | RKRVGLENPHH; |
| 8344. | HKRVGLENPHH; |
| 8345. | KRRVGLENPHH; |
| 8346. | RRRVGLENPHH; |
| 8347. | HRRVGLENPHH; |
| 8348. | KHHLGIENPHH; |
| 8349. | RHHLGIENPHH; |
| 8350. | HHHLGIENPHH; |
| 8351. | KKHLGIENPHH; |
| 8352. | RKHLGIENPHH; |
| 8353. | HKHLGIENPHH; |
| 8354. | KRHLGIENPHH; |
| 8355. | RRHLGIENPHH; |
| 8356. | HRHLGIENPHH; |
| 8357. | KHKLGIENPHH; |
| 8358. | RHKLGIENPHH; |
| 8359. | HHKLGIENPHH; |
| 8360. | KKKLGIENPHH; |
| 8361. | RKKLGIENPHH; |
| 8362. | HKKLGIENPHH; |
| 8363. | KRKLGIENPHH; |
| 8364. | RRKLGIENPHH; |
| 8365. | HRKLGIENPHH; |
| 8366. | KHRLGIENPHH; |
| 8367. | RHRLGIENPHH; |
| 8368. | HHRLGIENPHH; |
| 8369. | KKRLGIENPHH; |
| 8370. | RKRLGIENPHH; |
| 8371. | HKRLGIENPHH; |
| 8372. | KRRLGIENPHH; |
| 8373. | RRRLGIENPHH; |
| 8374. | HRRLGIENPHH; |
| 8375. | KHHIGIENPHH; |
| 8376. | RHHIGIENPHH; |
| 8377. | HHHIGIENPHH; |
| 8378. | KKHIGIENPHH; |
| 8379. | RKHIGIENPHH; |
| 8380. | HKHIGIENPHH; |
| 8381. | KRHIGIENPHH; |
| 8382. | RRHIGIENPHH; |
| 8383. | HRHIGIENPHH; |
| 8384. | KHKIGIENPHH; |
| 8385. | RHKIGIENPHH; |
| 8386. | HHKIGIENPHH; |
| 8387. | KKKIGIENPHH; |
| 8388. | RKKIGIENPHH; |
| 8389. | HKKIGIENPHH; |
| 8390. | KRKIGIENPHH; |
| 8391. | RRKIGIENPHH; |
| 8392. | HRKIGIENPHH; |
| 8393. | KHRIGIENPHH; |
| 8394. | RHRIGIENPHH; |
| 8395. | HHRIGIENPHH; |

TABLE 7-continued

SEQ ID NO. shown to left of sequence (cont'd)

| | |
|---|---|
| 8396. | KKRIGIENPHH; |
| 8397. | RKRIGIENPHH; |
| 8398. | HKRIGIENPHH; |
| 8399. | KRRIGIENPHH; |
| 8400. | RRRIGIENPHH; |
| 8401. | HRRIGIENPHH; |
| 8402. | KHHVGIENPHH; |
| 8403. | RHHVGIENPHH; |
| 8404. | HHHVGIENPHH; |
| 8405. | KKHVGIENPHH; |
| 8406. | RKHVGIENPHH; |
| 8407. | HKHVGIENPHH; |
| 8408. | KRHVGIENPHH; |
| 8409. | RRHVGIENPHH; |
| 8410. | HRHVGIENPHH; |
| 8411. | KHKVGIENPHH; |
| 8412. | RHKVGIENPHH; |
| 8413. | HHKVGIENPHH; |
| 8414. | KKKVGIENPHH; |
| 8415. | RKKVGIENPHH; |
| 8416. | HKKVGIENPHH; |
| 8417. | KRKVGIENPHH; |
| 8418. | RRKVGIENPHH; |
| 8419. | HRKVGIENPHH; |
| 8420. | KHRVGIENPHH; |
| 8421. | RHRVGIENPHH; |
| 8422. | HHRVGIENPHH; |
| 8423. | KKRVGIENPHH; |
| 8424. | RKRVGIENPHH; |
| 8425. | HKRVGIENPHH; |
| 8426. | KRRVGIENPHH; |
| 8427. | RRRVGIENPHH; |
| 8428. | HRRVGIENPHH; |
| 8429. | KHHLGVENPHH; |
| 8430. | RHHLGVENPHH; |
| 8431. | HHHLGVENPHH; |
| 8432. | KKHLGVENPHH; |
| 8433. | RKHLGVENPHH; |
| 8434. | HKHLGVENPHH; |
| 8435. | KRHLGVENPHH; |
| 8436. | RRHLGVENPHH; |
| 8437. | HRHLGVENPHH; |
| 8438. | KHKLGVENPHH; |
| 8439. | RHKLGVENPHH; |
| 8440. | HHKLGVENPHH; |
| 8441. | KKKLGVENPHH; |
| 8442. | RKKLGVENPHH; |
| 8443. | HKKLGVENPHH; |
| 8444. | KRKLGVENPHH; |
| 8445. | RRKLGVENPHH; |
| 8446. | HRKLGVENPHH; |
| 8447. | KHRLGVENPHH; |
| 8448. | RHRLGVENPHH; |
| 8449. | HHRLGVENPHH; |
| 8450. | KKRLGVENPHH; |
| 8451. | RKRLGVENPHH; |
| 8452. | HKRLGVENPHH; |
| 8453. | KRRLGVENPHH; |
| 8454. | RRRLGVENPHH; |
| 8455. | HRRLGVENPHH; |
| 8456. | KHHIGVENPHH; |
| 8457. | RHHIGVEEPHH; |
| 8458. | HHHIGVENPHH; |
| 8459. | KKHIGVENPHH; |
| 8460. | RKHIGVENPHH; |
| 8461. | HKHIGVENPHH; |
| 8462. | KRHIGVENPHH; |
| 8463. | RRHIGVENPHH; |
| 8464. | HRHIGVENPHH; |
| 8465. | KHKIGVENPHH; |
| 8466. | RHKIGVENPHH; |
| 8467. | HHKIGVENPHH; |
| 8468. | KKKIGVENPHH; |
| 8469. | RKKIGVENPHH; |
| 8470. | HKKIGVENPHH; |
| 8471. | KRKIGVENPHH; |
| 8472. | RRKIGVENPHH; |
| 8473. | HRKIGVENPHH; |

TABLE 7-continued

SEQ ID NO. shown to left of sequence(cont'd)

| | |
|---|---|
| 8474. | KHRIGVENPHH; |
| 8475. | RHRIGVENPHH; |
| 8476. | HKRIGVENPHH; |
| 8477. | KKRIGVENPHH; |
| 8478. | RKRIGVENPHH; |
| 8479. | HKRIGVENPHH; |
| 8480. | KRRIGVENPHH; |
| 8481. | RRRIGVENPHH; |
| 8482. | HRRIGVENPHH; |
| 8483. | KHHVGVENPHH; |
| 8484. | RHHVGVENPHH; |
| 8485. | HHHVGVENPHH; |
| 8486. | KKHVGVENPHH; |
| 8487. | RKHVGVENPHH; |
| 8488. | HKHVGVENPHH; |
| 8489. | KRHVGVENPHH; |
| 8490. | RRHVGVENPHH; |
| 8491. | HRHVGVENPHH; |
| 8492. | KHKVGVENPHH; |
| 8493. | RHKVGVENPHH; |
| 8494. | HHKVGVENPHH; |
| 8495. | KKKVGVENPHH; |
| 8496. | RKKVGVENPHH; |
| 8497. | HKKVGVENPHH; |
| 8498. | KRKVGVENPHH; |
| 8499. | RRKVGVEEPHH; |
| 8500. | HRKVGVENPHH; |
| 8501. | KHRVGVENPHH; |
| 8501. | RHRVGVENPHH; |
| 8503. | HHRVGVENPHH; |
| 8504. | KKRVGVENPHH; |
| 8505. | RKRVGVENPHH; |
| 8506. | HKRVGVENPHH; |
| 8507. | KRRVGVENPHH; |
| 8508. | RRRVGVENPHH; |
| 8509. | HRRVGVENPHH; |
| 8510. | KHHLGLNNPHH; |
| 8511. | RHHLGLNNPHH; |
| 8512. | HHHLGLNNPHH; |

TABLE 7-continued

SEQ ID NO. shown to left of sequence(cont'd)

| | |
|---|---|
| 8513. | KKHLGLNNPHH; |
| 8514. | RKHLGLNNPHH; |
| 8515. | HKHLGLNNPHH; |
| 8516. | KRHLGLNNPHH; |
| 8517. | RRHLGLNNPHH; |
| 8518. | HRHLGLNNPHH; |
| 8519. | KHKLGLNNPHH; |
| 8520. | RHKLGLNNPHH; |
| 8521. | HHKLGLNNPHH; |
| 8522. | KKKLGLNNPHH; |
| 8523. | RKKLGLNNPHH; |
| 8524. | HKKLGLNNPHH; |
| 8525. | KRKLGLNNPHH; |
| 8526. | RRKLGLNNPHH; |
| 8527. | HRKLGLNNPHH; |
| 8528. | KHRLGLNNPHH; |
| 8529. | RHRLGLNNPHH; |
| 8530. | HHRLGLNNPHH; |
| 8531. | KKRLGLNNPHH; |
| 8532. | RKRLGLNNPHH; |
| 8533. | HKRLGLNNPHH; |
| 8534. | KRRLGLNNPHH; |
| 8535. | RRRLGLNNPHH; |
| 8536. | HRRLGLNNPHH; |
| 8537. | KHHIGLNNPHH; |
| 8538. | RHHIGLNNPHH; |
| 8539. | HHHIGLNNPHH; |
| 8540. | KKHIGLNNPHH; |
| 8541. | RKHIGLNNPHH; |
| 8542. | HKHIGLNNPHH; |
| 8543. | KRHIGLNNPHH; |
| 8544. | RRHIGLNNPHH; |
| 8545. | HRHIGLNNPHH; |
| 8546. | KHKIGLNNPHH; |
| 8547. | RHKIGLNNPHH; |
| 8548. | HHKIGLNNPHH; |
| 8549. | KKKIGLNNPHH; |
| 8550. | RKKIGLNNPHH; |
| 8551. | HKKIGLNNPHH; |

TABLE 7-continued

SEQ ID NO. shown to left of sequence(cont'd)

| SEQ ID NO. | Sequence |
|---|---|
| 8552. | KRKIGLNNPHH; |
| 8553. | RRKIGLNNPHH; |
| 8554. | HRKIGLNNPHH; |
| 8555. | KHRIGLNNPHH; |
| 8556. | RHRIGLNNPHH; |
| 8557. | HHRIGLNNPHH; |
| 8558. | KKRIGLNNPHH; |
| 8559. | RKRIGLNNPHH; |
| 8560. | HKRIGLNNPHH; |
| 8561. | KRRIGLNNPHH; |
| 8562. | RRRIGLNNPHH; |
| 8563. | HRRIGLNNPHH; |
| 8564. | KHHVGLNNPHH; |
| 8565. | RHHVGLNNPHH; |
| 8566. | HHHVGLNNPHH; |
| 8567. | KKHVGLNNPHH; |
| 8568. | RKHVGLNNPHH; |
| 8569. | HKHVGLNNPHH; |
| 8570. | KRHVGLNNPHH; |
| 8571. | RRHVGLNNPHH; |
| 8572. | HRHVGLNNPHH; |
| 8573. | KHKVGLNNPHH; |
| 8574. | RHKVGLNNPHH; |
| 8575. | HHKVGLNNPHH; |
| 8576. | KKKVGLNNPHH; |
| 8577. | RKKVGLNNPHH; |
| 8578. | HKKVGLNNPHH; |
| 8579. | KRKVGLNNPHH; |
| 8580. | RRKVGLNNPHH; |
| 8581. | HRKVGLNNPHH; |
| 8582. | KHRVGLNNPHH; |
| 8583. | RHRVGLNNPHH; |
| 8584. | HHRVGLNNPHH; |
| 8585. | KKRVGLNNPHH; |
| 8586. | RKRVGLNNPHH; |
| 8587. | HKRVGLNNPHH; |
| 8588. | KRRVGLNNPHH; |
| 8589. | RRRVGLNNPHH; |
| 8590. | HRRVGLNNPHH; |
| 8591. | KHHLGINNPHH; |
| 8592. | RHHLGINNPHH; |
| 8593. | HHHLGINNPHH; |
| 8594. | KKHLGINNPHH; |
| 8595. | RKHLGINNPHH; |
| 8596. | HKHLGINNPHH; |
| 8597. | KRHLGINNPHH; |
| 8598. | RRHLGINNPHH; |
| 8599. | HRHLGINNPHH; |
| 8600. | KHKLGINNPHH; |
| 8601. | RHKLGINNPHH; |
| 8602. | HHKLGINNPHH; |
| 8603. | KKKLGINNPHH; |
| 8604. | RKKLGINNPHH; |
| 8605. | HKKLGINNPHH; |
| 8606. | KRKLGINNPHH; |
| 8607. | RRKLGINNPHH; |
| 8608. | HRKLGINNPHH; |
| 8609. | KHRLGINNPHH; |
| 8610. | RHRLGINNPHH; |
| 8611. | HHRLGINNPHH; |
| 8612. | KKRLGINNPHH; |
| 8613. | RKRLGINNPHH; |
| 8614. | HKRLGINNPHH; |
| 8615. | KRRLGINNPHH; |
| 8616. | RRRLGINNPHH; |
| 8617. | HRRLGINNPHH; |
| 8618. | KHHIGIENPHH; |
| 8619. | RHHIGINNPHH; |
| 8620. | HHHIGINNPHH; |
| 8621. | KKHIGINNPHH; |
| 8622. | RKHIGINNPHH; |
| 8623. | HKHIGINNPHH; |
| 8624. | KRHIGINNPHH; |
| 8625. | RRHIGINNPHH; |
| 8626. | HRHIGINNPHH; |
| 8627. | KHKIGINNPHH; |
| 8628. | RHKIGINNPHH; |
| 8629. | HHKIGINNPHH; |

TABLE 7-continued

SEQ ID NO. shown to left of sequence (cont'd)

| SEQ ID NO. | Sequence |
|---|---|
| 8630. | KKKIGINNPHH; |
| 8631. | RKKIGINNPHH; |
| 8632. | HKKIGINNPHH; |
| 8633. | KRKIGINNPHH; |
| 8634. | RRKIGINNPHH; |
| 8635. | HRKIGINNPHH; |
| 8636. | KHRIGINNPHH; |
| 8637. | RHRIGINNPHH; |
| 8638. | HHRIGINNPHH; |
| 8639. | KKRIGINNPHH; |
| 8640. | RKRIGINNPHH; |
| 8641. | HHRIGINNPHH; |
| 8642. | KRRIGINNPHH; |
| 8643. | RRRIGINNPHH; |
| 8644. | HRRIGINNPHH; |
| 8645. | KHHVGINNPHH; |
| 8646. | RHHVGINNPHH; |
| 8647. | HHHVGINNPHH; |
| 8648. | KKHVGINNPHH; |
| 8649. | RKHVGINNPHH; |
| 8650. | HKHVGINNPHH; |
| 8651. | KRHVGINNPHH; |
| 8652. | RRHVGINNPHH; |
| 8653. | HRHVGINNPHH; |
| 8654. | KHKVGINNPHH; |
| 8655. | RHKVGINNPHH; |
| 8656. | HHKVGINNPHH; |
| 8657. | KKKVGINNPHH; |
| 8658. | RKKVGINNPHH; |
| 8659. | HKKVGINNPHH; |
| 8660. | KRKVGINNPHH; |
| 8661. | RRKVGINNPHH; |
| 8662. | HRKVGINNPHH; |
| 8663. | KHRVGINNPHH; |
| 8664. | RHRVGINNPHH; |
| 8665. | HHRVGINNPHH; |
| 8666. | KKRVGINNPHH; |
| 8667. | RKRVGINNPHH; |
| 8668. | HKRVGINNPHH; |

TABLE 7-continued

SEQ ID NO. shown to left of sequence (cont'd)

| SEQ ID NO. | Sequence |
|---|---|
| 8669. | KRRVGINNPHH; |
| 8670. | RRRVGINNPHH; |
| 8671. | HRRVGINNPHH; |
| 8672. | KHHLGVNNPHH; |
| 8673. | RHHLGVNNPHH; |
| 8674. | HHHLGVNNPHH; |
| 8675. | KKHLGVNNPHH; |
| 8676. | RKHLGVNNPHH; |
| 8677. | HKHLGVNNPHH; |
| 8678. | KRHLGVNNPHH; |
| 8679. | RRHLGVNNPHH; |
| 8680. | HRHLGVNNPHH; |
| 8681. | KHKLGVNNPHH; |
| 8682. | RHKLGVNNPHH; |
| 8683. | HHKLGVNNPHH; |
| 8684. | KKKLGVNNPHH; |
| 8685. | RKKLGVNNPHH; |
| 8686. | HKKLGVNNPHH; |
| 8687. | KRKLGVNNPHH; |
| 8688. | RRKLGVNNPHH; |
| 8689. | HRKLGVNNPHH; |
| 8690. | KHRLGVNNPHH; |
| 8691. | RHRLGVNNPHH; |
| 8692. | HHRLGVNNPHH; |
| 8693. | KKRLGVNNPHH; |
| 8694. | RKRLGVNNPHH; |
| 8695. | HKRLGVNNPHH; |
| 8696. | KRRLGVNNPHH; |
| 8697. | RRRLGVNNPHH; |
| 8698. | HRRLGVNNPHH; |
| 8699. | KHHIGVNNPHH; |
| 8700. | RHHIGVNNPHH; |
| 8701. | HHHIGVNNPHH; |
| 8702. | KKHIGVNNPHH; |
| 8703. | RKHIGVNNPHH; |
| 8704. | HKHIGVNNPHH; |
| 8705. | KRHIGVNNPHH; |
| 8706. | RRHIGVNNPHH; |
| 8707. | HRHIGVNNPHH; |

TABLE 7-continued

SEQ ID NO. shown to left of sequence (cont'd)

| SEQ ID NO. | Sequence |
|---|---|
| 8708. | KHKIGVNNPHH; |
| 8709. | RHKIGVNNPHH; |
| 8710. | HHKIGVNNPHH; |
| 8711. | KKKIGVNNPHH; |
| 8712. | RKKIGVNNPHH; |
| 8713. | HKKIGVNNPHH; |
| 8714. | KRKIGVNNPHH; |
| 8715. | RRKIGVNNPHH; |
| 8716. | HRKIGVNNPHH; |
| 8717. | KHRIGVNNPHH; |
| 8718. | RHRIGVNNPHH; |
| 8719. | HHRIGVNNPHH; |
| 8720. | KKRIGVNNPHH; |
| 8721. | RKRIGVNNPHH; |
| 8722. | HKRIGVNNPHH; |
| 8723. | KRRIGVNNPHH; |
| 8724. | RRRIGVNNPHH; |
| 8725. | HRRIGVNNPHH; |
| 8726. | KHHVGVNNPHH; |
| 8727. | RHHVGVNNPHH; |
| 8728. | HHHVGVNNPHH; |
| 8729. | KKHVGVNNPHH; |
| 8730. | RKHVGVNNPHH; |
| 8731. | HKHVGVNNPHH; |
| 8732. | KRHVGVNNPHH; |
| 8733. | RRHVGVNNPHH; |
| 8734. | HRHVGVNNPHH; |
| 8735. | KHKVGVNNPHH; |
| 8736. | RHKVGVNNPHH; |
| 8737. | HHKVGVNNPHH; |
| 8738. | KKKVGVNNPHH; |
| 8739. | RKKVGVNNPHH; |
| 8740. | HKKVGVNNPHH; |
| 8741. | KRKVGVNNPHH; |
| 8742. | RRKVGVNNPHH; |
| 8743. | HRKVGVNNPHH; |
| 8744. | KHRVGVNNPHH; |
| 8745. | RHRVGVNNPHH; |
| 8746. | HHRVGVNNPHH; |
| 8747. | KKRVGVNNPHH; |
| 8748. | RKRVGVNNPHH; |
| 8749. | HKRVGVNNPHH; |
| 8750. | KRRVGVNNPHH; |
| 8751. | RRRVGVNNPHH; |
| 8752. | HRRVGVNNPHH |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09220746B2). An electronic copy of the "Sequence Listing" will also be available from the USPTO upon request and payment of the fee set forth in 37 CFR 1.19(b)(3).

That which is claimed is:

1. A method for enhancing bone formation and inhibiting bone resorption simultaneously in a subject in need thereof, comprising administering to the subject a peptide selected from the group consisting of:

a) a peptide consisting of the amino acid sequence KHHLGLEEPKKLR (SEQ ID NO:1), plus an additional 0, 1, 2 or 3 amino acid residues at the carboxy terminus;

b) a peptide consisting of the amino acid sequence KHHLGLEEPKK (SEQ ID NO:2), plus an additional 0, 1, 2 or 3 amino acid residues at the carboxy terminus;

c) a peptide consisting of the amino acid sequence HLGLEEPKKLR (SEQ ID NO:3), plus an additional 0, 1, 2 or 3 amino acid residues at the carboxy terminus;

d) a peptide consisting of the amino acid sequence KHHLGLEEPKKLR (SEQ ID NO:1), wherein the K or H at positions 1, 2, or 3 is substituted with arginine or lysine, the L at positions 4 or 6 is substituted with I or V, the K at positions 10 or 11 is substituted with H or R, the L at position 12 is substituted with I or V and/or the R at position 13 is substituted with K or H, plus an additional 0, 1, 2 or 3 amino acid residues at the carboxy terminus;

e) a pharmaceutically acceptable salt of any of the peptides of (a) through (d); and f) any combination of (a) through (e) above, in an amount effective to enhance bone formation and inhibit bone resorption simultaneously in said subject.

2. The method of claim 1, wherein the peptide has a polyethylene glycol (PEG) moiety coupled to either terminus thereof.

3. The method of claim 2, wherein the PEG moiety is coupled to a cysteine residue.

4. The method of claim 1, wherein said administration is selected from the group consisting of subcutaneous administration, oral administration, intravenous administration, intraperitoneal administration, intramuscular administration, administration via an implant, administration via a matrix, administration via a gel, and any combination thereof.

5. A method for inducing deposition and maturation of bone in a subject having a compromised bone condition, comprising administering to said subject a peptide selected from the group consisting of:

a) a peptide consisting of the amino acid sequence KHHLGLEEPKKLR (SEQ ID NO:1), plus an additional 0, 1, 2, or 3 amino acid residues at the carboxy terminus;

b) a peptide consisting of the amino acid sequence KHHLGLEEPKK (SEQ ID NO:2), plus an additional 0, 1, 2, or 3 amino acid residues at the carboxy terminus;

c) a peptide consisting of the amino acid sequence HLGLEEPKKLR (SEQ ID NO:3), plus an additional 0, 1, 2, or 3 amino acid residues at the carboxy terminus;

d) a peptide consisting of the amino acid sequence KHHLGLEEPKKLR (SEQ ID NO:1), wherein the K or H at positions 1, 2, or 3 is substituted with arginine or lysine, the L at positions 4 or 6 is substituted with I or V, the K at positions 10 or 11 is substituted with H or R, the L at position 12 is substituted with I or V and/or the R at position 13 is substituted with K or H, plus an additional 0, 1, 2, or 3 amino acid residues at the carboxy terminus;

e) a pharmaceutically acceptable salt of any of the peptides (a) through (d); and f) any combination of (a) through (e) above, in an amount effective to induce deposition and maturation of bone in said subject.

6. The method of claim 5, wherein the peptide has a polyethylene glycol (PEG) moiety coupled to either terminus thereof.

7. The method of claim 6, wherein the PEG moiety is coupled to a cysteine residue.

8. The method of claim 5, wherein said compromised bone condition is at a targeted site of said subject.

9. The method of claim 8, wherein the targeted site is selected from the group consisting of an intervertebral space, a facet joint, a site of a bone fracture, a bone of the mouth, a bone of the chin, a bone of the jaw, an implant site and any combination thereof.

10. The method of claim 5, wherein the condition is selected from the group consisting of a broken bone, a bone defect, a bone transplant, a bone graft, bone cancer, a joint replacement, a joint repair, a fusion, a facet repair, a bone degeneration, a dental implant, a dental repair, a bone marrow deficit and any combination thereof.

11. The method of claim 10, wherein the bone defect is a gap, deformation or a nonunion fracture in a bone.

12. The method of claim 10, wherein the bone defect is due to dwarfism.

13. The method of claim 10, wherein the bone degeneration is due to osteopenia or osteoporosis.

14. The method of claim 10, wherein the joint replacement is of a joint selected from the group consisting of a vertebral joint, a knee joint, a hip joint, a tarsal joint, a phalangeal joint, an elbow joint, a shoulder joint, an ankle joint, a wrist joint, a sacroiliac joint and any combination thereof.

15. The method of claim 10, wherein the joint repair is of a joint selected from the group consisting of a vertebral joint, a knee joint, a hip joint, a tarsal joint, a phalangeal joint, an elbow joint, a shoulder joint, an ankle joint, a wrist joint, a sacroiliac joint and any combination thereof.

16. The method of claim 10, further comprising administering a bone resorption inhibitor to said subject in an effective amount.

17. A method for enhancing bone formation and inhibiting bone resorption simultaneously in a subject in need thereof, comprising administering to the subject:

a) a peptide consisting of a fragment of insulin-like growth factor binding protein-2 (IGFBP-2), said fragment being between 11 and 16 amino acid residues in length and comprising the amino acid sequence:

i) KHHLGLEEPKKLR (SEQ ID NO: 1);

ii) KHHLGLEEPKK (SEQ ID NO: 2);

iii) HLGLEEPKKLR (SEQ ID NO: 3); or iv) KHHLGLEEPKKLR (SEQ ID NO: 1), wherein the K or H at positions 1, 2, or 3 is substituted with arginine or lysine, the L at positions 4 or 6 is substituted with I or V, the K at positions 10 or 11 is substituted with H or R, the L at position 12 is substituted with I or V and/or the R at position 13 is substituted with K or H; or b) a pharmaceutically acceptable salt of a);

in an amount effective to enhance bone formation and inhibit bone resorption simultaneously in said subject.

18. The method of claim 17, wherein the peptide has a polyethylene glycol (PEG) moiety coupled to the N- or to the C-terminal thereof.

19. The method of claim 18, wherein the PEG moiety is coupled to a cysteine residue.

* * * * *